US011083806B2

(12) United States Patent
Boyd et al.

(10) Patent No.: US 11,083,806 B2
(45) Date of Patent: Aug. 10, 2021

(54) RADIOEMBOLIC PARTICLES

(71) Applicant: ABK BIOMEDICAL INC., Halifax (CA)

(72) Inventors: Daniel Boyd, Upper Tantallon (CA); Robert Joseph Abraham, Hammonds Plains (CA); Xiaofang Zhang, Dalian (CN); Sharon Legere, Bedford (CA); James Clarke, Halifax (CA)

(73) Assignee: ABK Biomedical Incorporated, Halifax (CA)

( * ) Notice: Subject to any disclaimer, the term of this patent is extended or adjusted under 35 U.S.C. 154(b) by 0 days.

(21) Appl. No.: 15/528,264

(22) PCT Filed: Nov. 26, 2015

(86) PCT No.: PCT/CA2015/051239
§ 371 (c)(1),
(2) Date: May 19, 2017

(87) PCT Pub. No.: WO2016/082045
PCT Pub. Date: Jun. 2, 2016

(65) Prior Publication Data
US 2017/0360968 A1 Dec. 21, 2017

Related U.S. Application Data

(60) Provisional application No. 62/085,213, filed on Nov. 26, 2014.

(51) Int. Cl.
*A61K 51/12* (2006.01)
*A61K 9/00* (2006.01)

(52) U.S. Cl.
CPC ........ *A61K 51/1244* (2013.01); *A61K 9/0019* (2013.01)

(58) Field of Classification Search
CPC .......................... A61K 51/1244; A61K 9/0019
USPC .......................................... 424/400, 1.11, 9.1
See application file for complete search history.

(56) References Cited

U.S. PATENT DOCUMENTS

| | | |
|---|---|---|
| 4,789,501 A | 12/1988 | Day et al. |
| 5,302,369 A | 4/1994 | Day et al. |
| 5,618,763 A | 4/1997 | Frank et al. |
| 6,054,400 A | 4/2000 | Brink et al. |
| 6,335,384 B1 | 1/2002 | Evans et al. |
| 2001/0024662 A1 | 9/2001 | Yang |
| 2002/0119202 A1 | 8/2002 | Hunter et al. |
| 2004/0247849 A1 | 12/2004 | Truckai |
| 2007/0262702 A1 | 11/2007 | Fujita et al. |
| 2008/0068703 A1* | 3/2008 | Nakatsuka ............ C03C 3/095 359/341.5 |
| 2008/0255265 A1 | 10/2008 | Hoescheler et al. |
| 2010/0021550 A1 | 1/2010 | Li et al. |
| 2016/0289116 A1 | 10/2016 | Langner et al. |

FOREIGN PATENT DOCUMENTS

| | | | |
|---|---|---|---|
| CA | 2154990 A1 | 2/1996 | |
| CA | 2825512 A1 | 8/2012 | |
| CN | 1128246 A | 8/1996 | |
| CN | 1241169 A | 1/2000 | |
| CN | 101484396 A | 7/2009 | |
| CN | 102225846 A | 10/2011 | |
| EP | 0695726 A1 | 2/1996 | |
| EP | 0802890 A1 | 10/1997 | |
| EP | 0802890 B1 | 9/2001 | |
| EP | 1547572 B1 * | 8/2007 | .......... A61K 6/0088 |
| FR | 2908891 A1 | 5/2008 | |
| JP | H10512227 A | 11/1998 | |
| JP | 2005350325 A | 12/2005 | |
| JP | 2007515450 A | 6/2007 | |
| JP | 2007-197249 A | 8/2007 | |
| JP | 2007526202 A | 9/2007 | |
| WO | 8603124 A1 | 6/1986 | |
| WO | 9937287 A1 | 7/1999 | |
| WO | 0158720 A1 | 8/2001 | |
| WO | 2004074199 A1 | 9/2004 | |
| WO | 2005/097938 A1 | 10/2005 | |
| WO | 2007048856 A1 | 5/2007 | |
| WO | 2010044413 A1 | 4/2010 | |
| WO | 2014/147062 A1 | 9/2014 | |
| WO | 2014159759 A1 | 10/2014 | |

OTHER PUBLICATIONS

International Patent Application No. PCT/CA2015/051239, International Search Report and Written Opinion dated Feb. 8, 2016.
Jones., "Review of Bioactive Glass: From Hench to Hybrids", Acta Biomaterialia, Jan. 2013, vol. 9 (1), pp. 4457-4486.
Kehoe et al., "Effects of γ-Irradiation and Accelerated Aging on Composition-Structure-Property Relationships for Radiopaque Embolic Microspheres", Journal of Non-Crystalline Solids, Oct. 2014, vol. 402, pp. 84-90.
Kehoe et al., "Mixture Designs to Assess Composition-Structure-Property Relationships in SiO2—CaO—ZnO—La2O3—TiO2—MgO—SrO—Na2O Glasses: Potential Materials for Embolization", Journal of Biomaterials Applications, Sep. 2013, vol. 28 (3), pp. 416-433.
Kehoe et al., "Preliminary Investigation of the Dissolution Behavior, Cytocompatibility, Effects of Fibrinogen Conformation and Platelet Adhesion for Radiopaque Embolic Particles", Journal of Functional Biomaterials, Jul. 2013, 4, pp. 89-113.

(Continued)

*Primary Examiner* — Robert S Cabral
(74) *Attorney, Agent, or Firm* — Borden Ladner Gervais LLP; David Nauman

(57) ABSTRACT

Provided are radiopaque compositions comprising one or more of yttrium (Y), strontium (Sr), gallium (Ga), and silicon, or oxides and salts thereof. The composition can comprise a combination of $Y_2O_3$, SrO, $Ga_2O_3$, and $SiO_2$, and optionally $MnO_2$, and $TiO_2$. Other compositions comprise SrO, $Ga_2O_3$, $TiO_2$, $MnO_2$, and $SiO_2$. The composition can be a particulate material. The compositions are useful for radioembolization to treat tumors.

15 Claims, 49 Drawing Sheets

(56) References Cited

OTHER PUBLICATIONS

Extended European Search Report issued on the corresponding European Patent Application No. 15862703.4, dated Aug. 29, 2018.
Cimek et al., "Experimental Investigation of Nonlinear Refractive Index of Various Soft Glasses dedicated for Development of Nonlinear Photonic Crystal Fibers," Optical Materials Express, Oct. 2017, vol. 7 (10), pp. 3471-3483.
Saralidze et al., "New Acrylic Microspheres for Arterial Embolization: Combining Radiopacity for Precise Localization With Immobilized Thrombin to Trigger Local Blood Coagulation," Biomaterials, May 2007, vol. 28 (15), pp. 2457-2464.
Wu et al., "Melt-derived Bioactive Glass Scaffolds Produced by a Gel-cast Foaming Technique," Acta Biomaterialia, Apr. 2011, vol. 7 (4), pp. 1807-1816.
Japanese Patent Application No. 2017-547031, Notification of Reasons for Refusal and English Translation dated Sep. 6, 2019.
Chinese Patent Application No. 201580074596.2, Office Action dated Dec. 18, 2019 and English Translation.
European Patent Application No. 15862703.4, Office Action dated Feb. 17, 2020.
Japanese Patent Application No. JP2017-547031, Notification of Reasons for Refusal dated Jul. 10, 2020 and English translation.

* cited by examiner

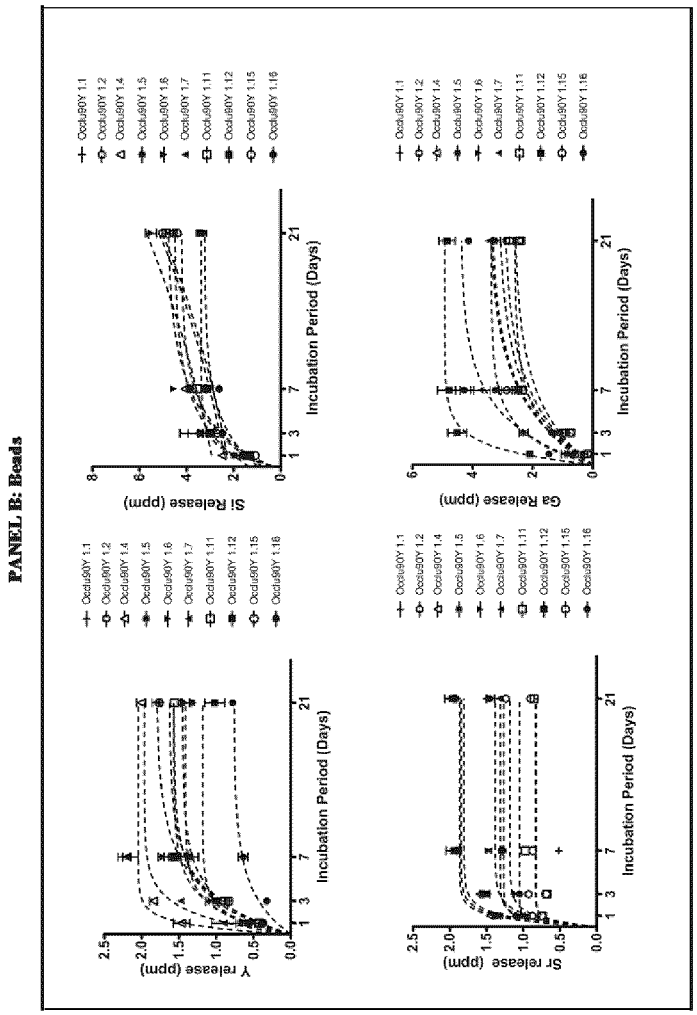
Fig. 8 (con't)

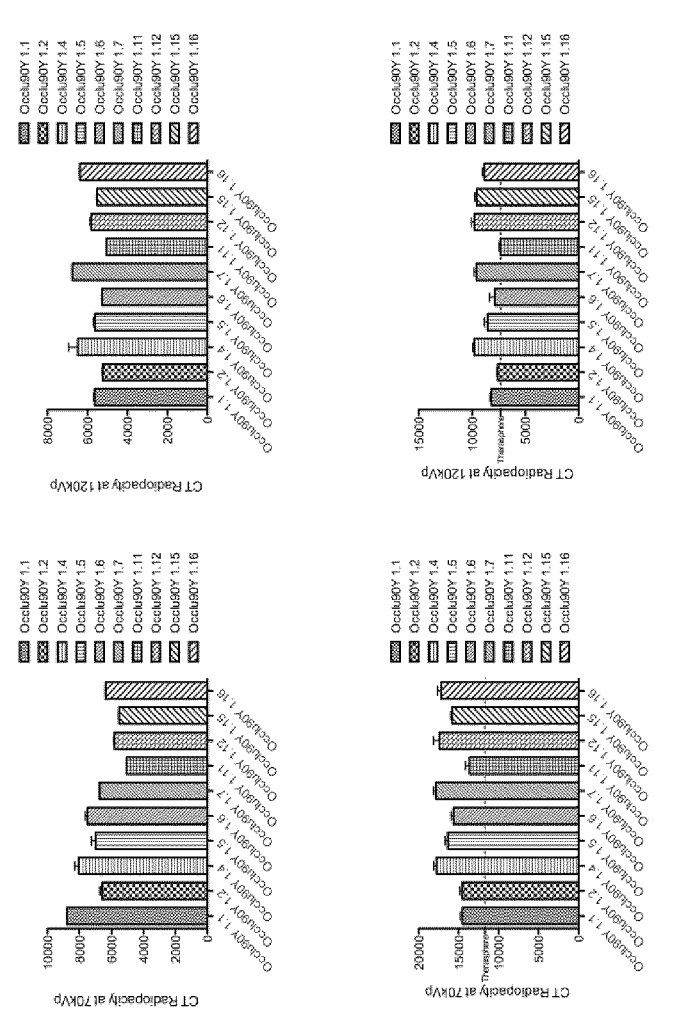
Fig. 9 (con't)

RADIOEMBOLIC PARTICLES

The present application claims the benefit of priority to U.S. Provisional Application No. 62/085,213, filed Nov. 26, 2014, the entire contents of which are incorporated by reference herein.

FIELD OF THE INVENTION

The invention relates to particulate material that is radiopaque and suited for performing embolization.

BACKGROUND OF THE INVENTION

Radioactive polymeric and glass particles (radioembolic agents) are frequently employed by interventional radiologists for the selective internal treatment of tumors. This treatment involves the injection of these radioactive particles through small catheters positioned in the arteries feeding these tumors allowing for the radiation to treat the tumors internally thereby minimizing damage to normal surrounding tissue. Current state of the art regarding radioembolic particles are beset with numerous drawbacks, including the fact that the particles are not radiopaque and are thus invisible on imaging that is used to monitor the procedure (X-ray) and to follow and understand the effect of the particles on the tumor (using imaging modalities including but not limited to CT and MM).

The inability to accurately monitor embolic microspheres during transarterial embolization (TAE) is limited by the imprecise assessment of their terminal locations within target tissues. However, the design of intrinsically radiopaque embolic particles for $^{90}Y$ therapy is not a trivial matter and presents significant design challenges. Firstly, it must be recognized that materials in contact with the body elicit multifactorial responses, which include the generation of dissolution by-products. One design requirement for $^{90}Y$ glass microsphere is that it be durable enough to limit the release of $^{90}Y$ in vivo. Intersecting with this design requirement is the necessity that the material be made radiopaque via the addition of appropriate radio-pacifying elements. However, many elements that are typically appropriate for enhancing biomaterials radiopacity are contraindicated for the synthesis of $^{90}Y$ glass microspheres because their neutron activation by products are extremely hazardous. This design challenge is further complicated by the fact that many elements have inappropriate cross-sections for neutron activation and may act to capture neutrons rather than enable activation of all isotopes within the glass network.

The production of radioisotopes, and radiation sources is a crucial component in the provision of modern healthcare services. Exposing target materials to a neutron flux over an appropriate timeframe produces radioisotopes, including those used in medicine. The interaction of this neutron flux with the nucleus of the target material can be expressed quantitatively in terms of the nuclear cross-section. The cross section is expressed in terms of an imaginary cross-sectional area presented by the nucleus to the beam of neutrons (perpendicular to the beam) such that if neutrons pass through this area, a nuclear reaction occurs. Once neutron capture is achieved, new nuclides with varying radioactive decay characteristics are generated. Many elements, which may intuitively come to mind as radio-pacifying components suitable for the synthesis of imageable glass microspheres (e.g. La and Ta), are contraindicated for neutron activation based on their cross section, nuclides generated and their contiguous decay by-products and half-lives. As described herein, the instant inventors have successfully designed durable and imageable $^{90}Y$ glass compositions.

BRIEF SUMMARY OF THE INVENTION

Described herein are compositions that are useful in medical procedures. In one aspect, the composition comprises one or more of, or a combination of yttrium (Y), strontium (Sr), gallium (Ga), and silicon, or oxides and salts thereof. For example, in some embodiments, the composition comprises a combination or mixture of $Y_2O_3$, SrO, $Ga_2O_3$, and $SiO_2$. In some embodiments, the composition is a particulate material composition. In some embodiments, the particulate material composition is a bead. In some embodiments, the composition comprises radiopaque radioembolic particles.

In another aspect, the composition comprises yttrium (Y), strontium (Sr), gallium (Ga), manganese (Mn), titanium (Ti), and silicon, or oxides and salts thereof. For example, in some embodiments, the composition comprises $Y_2O_3$, SrO, $Ga_2O_3$, $MnO_2$, $TiO_2$, and $SiO_2$.

In another aspect, the composition comprises manganese (Mn), titanium (Ti) and silicon, or oxides and salts thereof. For example, in some embodiments, the composition comprises $MnO_2$, $TiO_2$, and $SiO_2$.

In some embodiments, the composition comprises or consists of about 0.10 to about 0.17 mole fraction of $Y_2O_3$, about 0.02 to about 0.15 mole fraction of SrO, about 0.05 to about 0.30 mole fraction of $Ga_2O_3$, and about 0.5 to about 0.8 mole fraction of $SiO_2$.

In one embodiment, the composition comprises or consists of about 0.10 to about 0.17 mole fraction of $Y_2O_3$, about 0.02 to about 0.05 mole fraction of SrO, about 0.10 to about 0.30 mole fraction of $Ga_2O_3$, and about 0.5 to about 0.8 mole fraction of $SiO_2$. In one embodiment, the composition comprises or consists of about 0.10 to about 0.17 mole fraction of $Y_2O_3$, about 0.025 to about mole fraction of 0.05 SrO, about 0.10 to about mole fraction of 0.30 $Ga_2O_3$, and about 0.5 to about 0.75 mole fraction of $SiO_2$.

In some embodiments, the composition comprises or consists of from about 0.10 to about 0.17 mole fraction of $Y_2O_3$, about 0.02 to about 0.15 mole fraction of SrO, about 0.05 to about 0.30 mole fraction of $Ga_2O_3$, about 0.5 to about 0.8 mole fraction of $SiO_2$, about 0.00 to about 0.350 mole fraction of of $MnO_2$, and about 0.00 to about 0.10 mole fraction of $TiO_2$.

In some embodiments, the composition comprises or consists of from about 0.10 to about 0.17 mole fraction of $Y_2O_3$, about 0.025 to about 0.15 mole fraction of SrO, about 0.1 to about 0.30 mole fraction of $Ga_2O_3$, about 0.5 to about 0.75 mole fraction of $SiO_2$, about 0.00 to about 0.05 mole fraction of of $MnO_2$, and about 0.00 to about 0.10 mole fraction of $TiO_2$.

In some embodiments, the composition comprises or consists of about 0.10 to about 0.17 mole fraction of $Y_2O_3$, about 0.02 to about 0.05 mole fraction of SrO, about 0.10 to about 0.30 mole fraction of $Ga_2O_3$, about 0.5 to about 0.8 mole fraction of $SiO_2$, about 0.00 to about 0.350 mole fraction of $MnO_2$, and about 0.00 to about 0.10 mole fraction of $TiO_2$.

In some embodiments, the composition comprises or consists of about 0.10 to about 0.17 mole fraction of $Y_2O_3$; about 0.025 to about 0.05 mole fraction of SrO; about 0.1 to about 0.30 mole fraction of $Ga_2O_3$; about 0.5 to about 0.75 mole fraction of $SiO_2$, about 0.00 to about 0.05 mole fraction of of $MnO_2$; and about 0.00 to about 0.10 mole fraction of $TiO_2$.

In another aspect, the composition comprises strontium (Sr), gallium (Ga), titanium (Ti), manganese (Mn), and silicon, or oxides and salts thereof. For example, in some embodiments, the composition comprises SrO, $Ga_2O_3$, $TiO_2$, $MnO_2$, and $SiO_2$. In one embodiment of this aspect, the composition comprises or consists of about 0.05 to about 0.15 mole fraction of SrO, about 0.10 to about 0.30 mole fraction of $Ga_2O_3$, about 0.000 to about 0.005 mole fraction of $MnO_2$, about 0.00 to about 0.10 mole fraction of $TiO_2$, and about 0.5 to about 0.8 mole fraction of $SiO_2$. In some embodiments, the composition comprises or consists of about 0.05 to about 0.15 mole fraction of SrO, about 0.10 to about 0.30 mole fraction of $Ga_2O_3$, about 0.000 to about 0.005 mole fraction of $MnO_2$, about 0.00 to about 0.10 mole fraction of $TiO_2$, and about 0.5 to about 0.75 mole fraction of $SiO_2$.

In some aspects, the composition is radiopaque to allow visualization of the particles during a medical procedure, for example, during or after an embolization procedure. In some embodiments, the composition is visible via other imaging modalities (for example, CT or MRI scan).

In some aspects, the composition is biocompatible.

In some embodiments, the composition is non-degradable or non-resorbable in vivo.

In one aspect, the composition (e.g., a particulate material) is comprises particle sizes useful used for TAE. The TAE may be for treatment of tumors and/or for organ ablation. In some embodiments, the composition is useful for radioembolization, for example, for treating a tumor in a human or animal subject.

In another aspect, the compositions described herein are irradiated. Thus, described herein are irradiated compositions produced by or arising from the irradiation of a composition described herein. In some embodiments, the irradiated composition comprises or consists of the radiation or neutron activation by-products of the unirradiated compositions described herein.

In another aspect, the compositions described herein are for use in the treatment of a medical condition. In some embodiments, the irradiated compositions described herein are for use in the treatment of a medical condition. In some embodiments, the medical condition is cancer, and the compositions are for use in the treatment of tumors. In some embodiments, compositions are for use in tumor radioembolization. Examples of tumors include but are not limited to kidney and liver tumors, or other tumors that metastasize to the kidney and liver, such as colorectal cancer, carcinoid tumors, breast cancer and renal cell carcinomas, etc.

In some embodiments, a method of treating a disease or medical condition in a subject in need thereof is provided, the method comprising: administering an irradiated composition described herein to the subject. In some embodiments, the irradiated composition is administered via injection of the composition into a blood vessel of the subject. In some embodiments, the disclosure provides for the use of an irradiated composition described herein for treatment of a tumor.

DEFINITIONS

Figure 1:
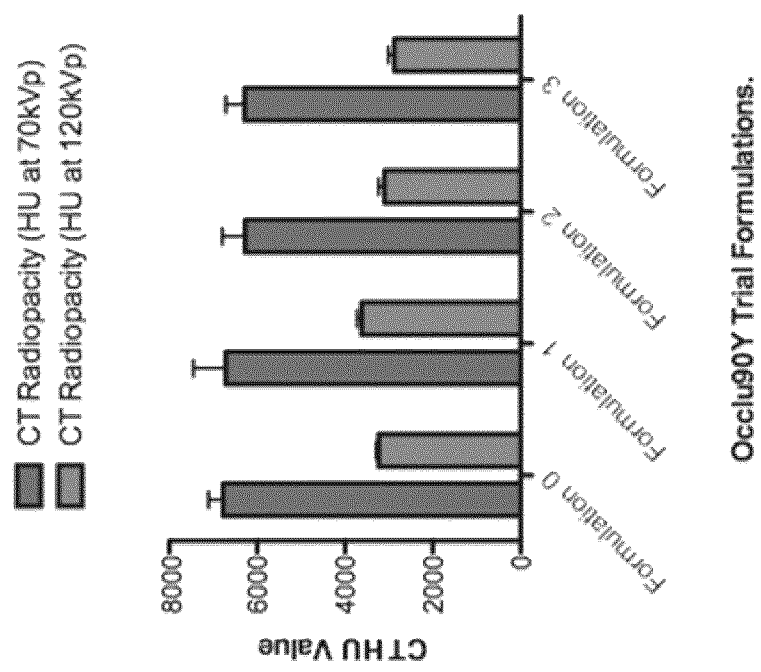
FIG. 1 shows CT radiopacity of compositions described herein.
Figure 2A:
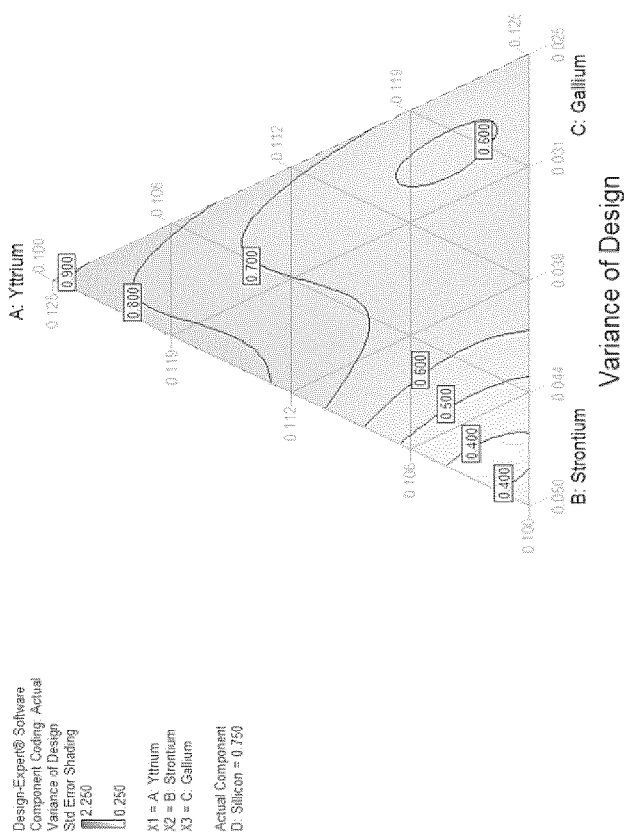
FIG. 2 shows variance of Design for Designs #1 (A), #2 (B), and #3 (C) and #4 (D).
Figure 2B:
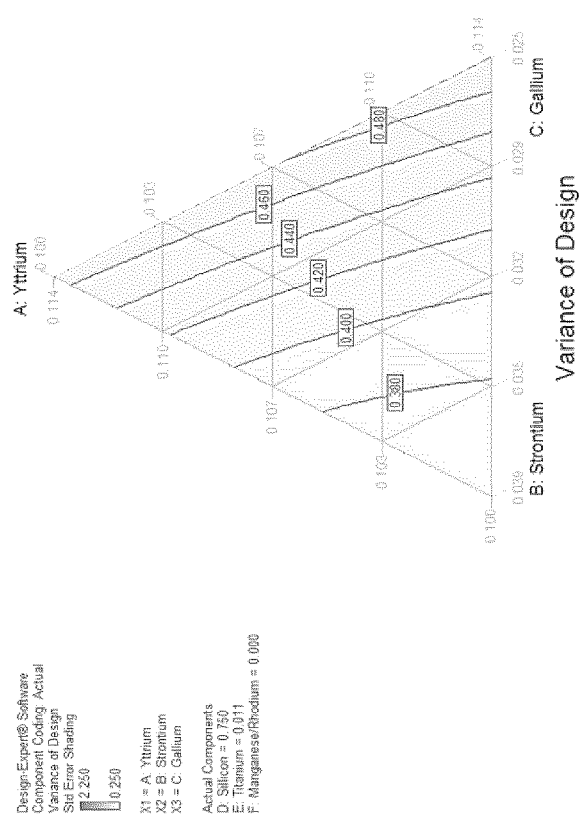
Figure 2C:
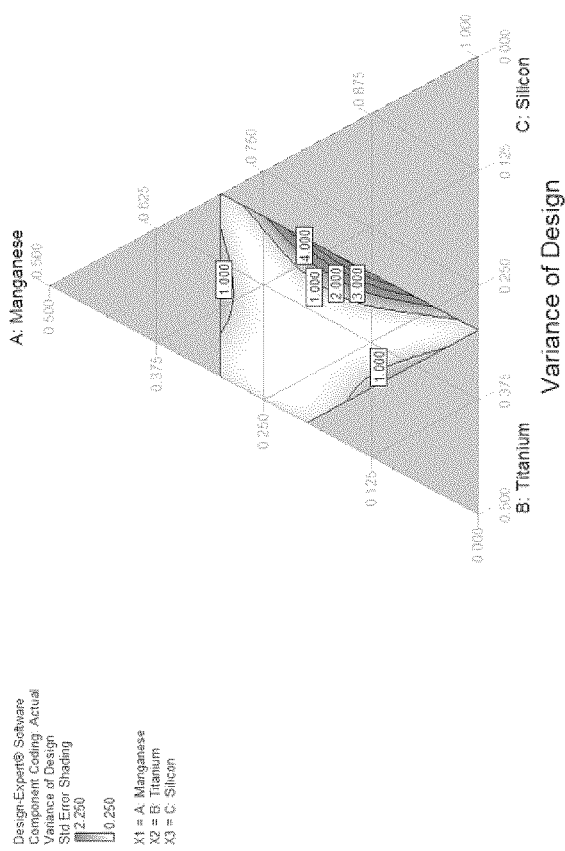
Figure 2D:
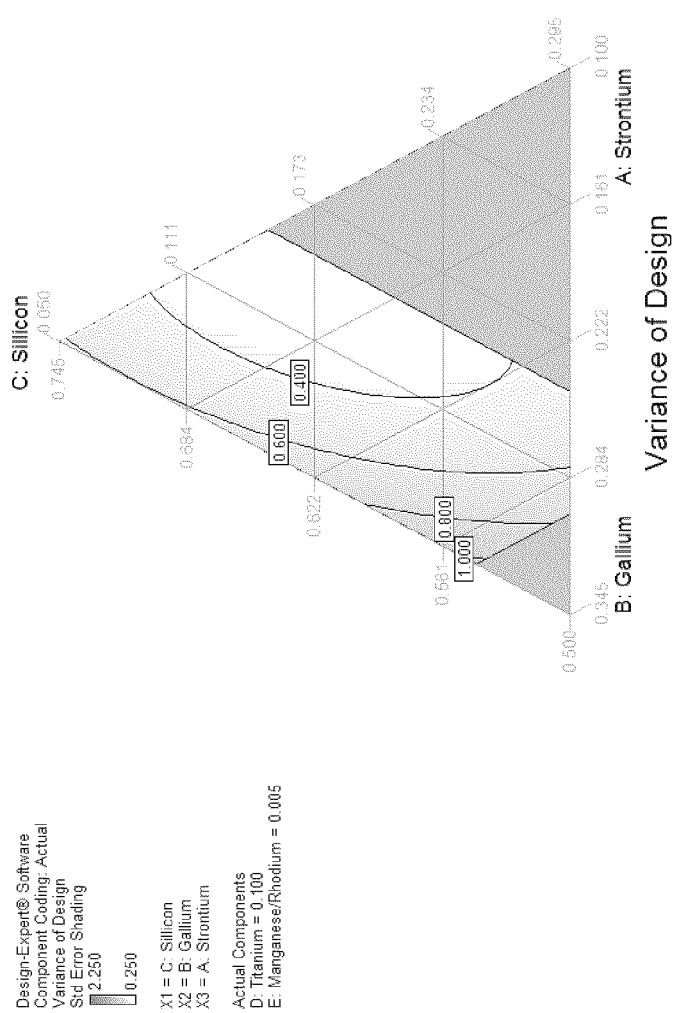

As used herein, the term "about," when modifying any amount, refers to the variation in that amount typically encountered by one of skill in the art, i.e., in the manufacture of compostions suitable for embolization. For example, the term "about" refers to the normal variation encountered in measurements for a given analytical technique, both within and between batches or samples. Thus, the term about can include variation of 1-10% of the measured value, such as 1%, 2%, 3%, 4%, 5%, 6%, 7%, 8%, 9% or 10% variation. The amounts disclosed herein include equivalents to those amounts, including amounts modified or not modified by the term "about."

The term "mole fraction" refers to the number of molecules of a given component in a composition divided by the total number of moles in the composition.

The term "weight percentage" refers to the percentages of each component by weight (wt %) which can easily be derived from the composition's molarities matrices using the appropriate molar masses.

The term "irregular particles" refers to glass frit ground to the appropriate particle size range.

The term "bead" refers to the final spherical-shaped glass product obtained post-spherodization.

DETAILED DESCRIPTION OF THE INVENTION

Described herein are radiopaque compositions that are useful in medical procedures. In one aspect, the composition comprises one or more of yttrium (Y), strontium (Sr), gallium (Ga), and silicon, or oxides and salts thereof. The compositions provide the unexpected advantage of enhanced radiopacity and biocompatibility coupled with chemical durability and non-hazardous neutron activation by-products. For example, in some embodiments, the composition comprises a combination or mixture of two, three, or four of $Y_2O_3$, SrO, $Ga_2O_3$, and $SiO_2$. In some embodiments, the composition is a particulate material composition. In some embodiments, the particulate material composition is a microsphere or bead. In some embodiments, the composition comprises radiopaque radioembolic particles.

Compositions

In some embodiments, the composition comprises from about 0.05 to about 0.20 mole fraction of $Y_2O_3$, e.g., about 0.05, 0.06, 0.07, 0.08, 0.09, 0.10, 0.11, 0.12, 0.13, 0.14, 0.15, 0.16, 0.17, 0.18, 0.19 or 0.20 mole fraction of $Y_2O_3$.

In some embodiments, the composition comprises from about 0.020 to about 0.160 mole fraction of SrO, e.g., about 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.052, 0.054, 0.056, 0.058, 0.060, 0.070, 0.080, 0.090, 0.10, 0.11, 0.12, 0.13, 0.14, 0.15, or 0.16 mole fraction of SrO. In some embodiments, the composition comprises from about 0.020 to about 0.060 mole fraction of SrO, e.g., about 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.052, 0.054, 0.056, 0.058, or 0.060 mole fraction of SrO. In some embodiments, the composition comprises from about 0.050 to about 0.160 mole fraction of SrO, e.g., about 0.050, 0.060, 0.070, 0.080, 0.090, 0.10, 0.11, 0.12, 0.13, 0.14, 0.15, or 0.16 mole fraction of SrO.

In some embodiments, the composition comprises from about 0.05 to about 0.35 mole fraction of $Ga_2O_3$, e.g., about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, or 0.35 mole fraction of $Ga_2O_3$.

In some embodiments, the comprises from about 0.40 to about 0.80 mole fraction of $SiO_2$, e.g., about 0.40, 0.42, 0.44, 0.46, 0.48, 0.50, 0.52, 0.54, 0.56, 0.57, 0.58, 0.594, 0.60, 0.62, 0.64, 0.66. 0.67, 0.68, 0.70, 0.72, 0.74, 0.75, 0.76, 0.78, or 0.80 mole fraction of $SiO_2$.

In some embodiments, the composition comprises or consists of a combination or mixture of $Y_2O_3$, SrO, $Ga_2O_3$, and $SiO_2$ in amounts selected from the range of values for each compound listed herein. Thus, in one embodiment, the composition comprises or consists of from about 0.10 to about 0.17 mole fraction of $Y_2O_3$, about 0.02 to about 0.15 mole fraction of SrO, about 0.05 to about 0.30 mole fraction of $Ga_2O_3$, and/or about 0.5 to about 0.8 mole fraction of $SiO_2$. In one embodiment, the composition comprises or consists of from about 0.10 to about 0.17 mole fraction of $Y_2O_3$, about 0.02 to about 0.15 mole fraction of SrO, about 0.05 to about 0.30 mole fraction of $Ga_2O_3$, and about 0.5 to about 0.75 mole fraction of $SiO_2$.

In one embodiment, the composition comprises or consists of from about 0.10 to about 0.17 mole fraction of $Y_2O_3$, about 0.02 to about 0.05 SrO, about 0.10 to about 0.30 $Ga_2O_3$, and about 0.5 to about 0.8 $SiO_2$.

In one embodiment, the composition comprises or consists of from about 0.10 to about 0.17 mole fraction of $Y_2O_3$, about 0.025 to about 0.05 mole fraction of SrO, about 0.10 to about 0.30 mole fraction of $Ga_2O_3$, and about 0.5 to about 0.75 mole fraction of $SiO_2$.

In some embodiments, the composition comprises from about 0.000 to about 0.350 mole fraction of $MnO_2$, e.g., about 0.0 0.100, 0.110, 0.120, 0.130, 0.140, 0.150, 0.160, 0.170, 0.180, 0.190, 0.200, 0.210, 0.220, 0.230, 0.240, 0.250, 0.260, 0.270, 0.280, 0.290, 0.300, 0.310, 0.320, 0.330. 0.340 or 0.350 mole fraction of $MnO_2$. In one embodiment, the composition comprises or consists of from about 0.0 to about 0.006 mole fraction of $MnO_2$, e.g., about 0.000, 0.001, 0.002, 0.003, 0.004, 0.005 or 0.006 mole fraction of $MnO_2$. In one embodiment, the composition comprises or consists of from about 0.100 to about 0.300 mole fraction of $MnO_2$, e.g., about 0.100, 0.110, 0.120, 0.130, 0.140, 0.150, 0.160, 0.170, 0.180, 0.190, 0.200, 0.210, 0.220, 0.230, 0.240, 0.250, 0.260, 0.270, 0.280, 0.290, or 0.300 mole fraction of $MnO_2$.

In some embodiments, the composition comprises from about 0.00 to about 0.11 mole fraction of $TiO_2$, e.g. from about 0.00, 0.01, 0.02, 0.03, 0.04, 0.05, 0.06, 0.07, 0.08, 0.10, and 0.11 mole fraction of $TiO_2$.

In some embodiments, the composition comprises or consists of from about 0.10 to about 0.17 mole fraction of $Y_2O_3$, about 0.02 to about 0.15 mole fraction of SrO, about 0.05 to about 0.30 mole fraction of $Ga_2O_3$, about 0.5 to about 0.8 mole fraction of $SiO_2$, about 0.00 to about 0.350 mole fraction of of $MnO_2$, and about 0.00 to about 0.10 mole fraction of $TiO_2$.

In some embodiments, the composition comprises or consists of from about 0.10 to about 0.17 mole fraction of $Y_2O_3$, about 0.025 to about 0.15 mole fraction of SrO, about 0.1 to about 0.30 mole fraction of $Ga_2O_3$, about 0.5 to about 0.75 mole fraction of $SiO_2$, about 0.00 to about 0.350 mole fraction of of $MnO_2$, and about 0.00 to about 0.10 mole fraction of $TiO_2$.

In some embodiments, the composition comprises or consists of from about 0.10 to about 0.17 mole fraction of $Y_2O_3$, about 0.025 to about 0.15 mole fraction of SrO, about 0.1 to about 0.30 mole fraction of $Ga_2O_3$, about 0.5 to about 0.75 mole fraction of $SiO_2$, about 0.00 to about 0.05 mole fraction of of $MnO_2$, and about 0.00 to about 0.10 mole fraction of $TiO_2$.

In some embodiments, the composition comprises or consists of from about 0.10 to about 0.17 mole fraction of $Y_2O_3$, about 0.02 to about 0.05 mole fraction of SrO, about 0.10 to about 0.30 mole fraction of $Ga_2O_3$, about 0.5 to about 0.8 mole fraction of $SiO_2$, about 0.00 to about 0.350 mole fraction of of $MnO_2$, and about 0.00 to about 0.10 mole fraction of $TiO_2$.

In some embodiments, the composition comprises or consists of from about 0.1 to about 0.3 mole fraction of $MnO_2$, from about 0.0 to about 0.3 mole fraction of $TiO_2$, and from about 0.5 to about 0.7 mole fraction of $SiO_2$. In some embodiments, the total mole fraction for $MnO_2+TiO_2+SiO_2=1.0$.

In some embodiments, the composition comprises or consists of strontium (Sr), gallium (Ga), titanium (Ti), manganese (Mn), and silicon, or oxides and salts thereof. In some embodiments, the composition comprises or consists of a combination or mixture of two, three, four, or five of SrO, $Ga_2O_3$, $TiO_2$, $MnO_2$, and $SiO_2$. For example, in some embodiments, the composition comprises SrO, $Ga_2O_3$, $TiO_2$, $MnO_2$, and $SiO_2$. In some embodiments, the composition comprises or consists of a combination or mixture of SrO, $Ga_2O_3$, $TiO_2$, $MnO_2$, and $SiO_2$ in amounts selected from the range of values for each compound described herein. In one embodiment, the composition comprises or consists of about 0.05 to about 0.15 mole fraction of SrO, about 0.10 to about 0.30 mole fraction of $Ga_2O_3$, about 0.000 to about 0.005 mole fraction of $MnO_2$, about 0.00 to about 0.10 mole fraction of $TiO_2$, and about 0.5 to about 0.8 mole fraction of $SiO_2$. In some embodiments, the composition comprises or consists of about 0.05 to about 0.15 mole fraction of SrO, about 0.10 to about 0.30 mole fraction of $Ga_2O_3$, about 0.000 to about 0.005 mole fraction of $MnO_2$, about 0.00 to about 0.10 mole fraction of $TiO_2$, and about 0.5 to about 0.75 mole fraction of $SiO_2$.

In some embodiments, the compositions comprise or consist of the formulations described in the Examples.

Core

In some embodiments, the particles of the composition comprise a core. In some embodiments, the core comprises one or more of, or a combination of $Y_2O_3$, SrO, $Ga_2O_3$, and SiO$_2$. In some embodiments, the core comprises one or more of, or a combination of Y$_2$O$_3$, SrO, Ga$_2$O$_3$, MnO$_2$, TiO$_2$, and/or SiO$_2$.

In one embodiment, the composition particulate material has the properties of a glass ceramic. In such an embodiment, the components make up a network, which can be amorphous or crystalline. In some embodiments, the components include one or more of, or a combination of Y$_2$O$_3$, SrO, Ga$_2$O$_3$, SiO$_2$, and optionally MnO$_2$ and/or TiO$_2$. Modifying the amounts of the various core components (as well as the ratios of components to each other) allows for tuning the characteristics of the material to its intended use.

Radiopaque

In some embodiments, the particulate materials, beads, and nanospheres described herein are radiopaque. Thus, the compositions can be visualized, for example, using X-rays, MRI, and CT scans, and are therefore useful in medical procedures where radiopacity is desired, such as embolization procedures.

The compositions described herein will be designed with the following properties.

Particle Size

The individual particles of the composition will be between about 10 and about 80 micrometers, e.g., between about 10 and about 70, between about 10 and about 60, between about 10 and about 50, between about 15 and about 80, between about 15 and about 70, between about 15 and about 60, between about 15 and about 50, between about 15 and about 40, between about 15 and about 30, between about 20 and about 80, between about 20 and about 70, between about 20 and about 60, between about 20 and about 50, between about 20 and about 40, or between about 20 and about 30 micrometers (microns=μm) in diameter. The ranges described herein include all endpoints and sub-ranges between the end points, and all integer values between the endpoints. In some embodiments, the individual particles of the composition are, e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 μm in diameter. In some embodiments, the particle size comprises: $D_0$=15 μm; $D_{50}$=25 μm, and $D_{95}$=35 μm. The particle size can be determined using methods known in the art, for example, laser diffraction according to ISO13320 standard (2009).

Activation Data

The composition will produce radioisotopes (for example Y$^{90}$ or Sr$^{89}$) with a level of therapeutic emissions within regulatory guidelines, and may contain decay products (for example gamma emitters) with an acceptable half-life that meets regulatory guidelines. The type and amount of radioisotopes produced can be determined using methods known in the art and as described in the Examples.

Clinical Radiopacity

The compositions described herein will have a clinical radiopacity sufficient to visualize the particulate materials (e.g., beads or microspheres) during in vivo delivery to a human or animal subject. In some embodiments, the radiopacity is determined by cone-beam and conventional CT evaluation (see S. Kehoe, M. Looney, N. Kilcup, E. Tonkopi, C. Daly, R. J. Abraham, D. Boyd). Effects of γ-irradiation and accelerated aging on composition-structure-property relationships for radiopaque embolic microspheres. Journal of Non-Crystalline Solids 402, 2014, 84-90.10.1016/j.jnoncrysol.2014.05.016.). In some embodiments, the radiopacity is determined as described in Example 1. In some embodiments, the average CT radiopacity is between 6000 and 8000 Housefield Units (HU) at an energy of 70 kVp, and the average CT radiopacity is between about 2000 and 4000 HU at an energy of 120 kVp.

Resorbability

In some embodiments, the compositions described herein are non-resorbable to ensure the microspheres provide for permanent embolization effectiveness. The resorbability can be determined, in part, as described in ISO10993-14 (Biological evaluation of medical devices—Part 14: Identification and quantification of degradation products).

Morphology

In some embodiments, the compositions described herein have a spherical morphology for enhanced flow properties to prevent undesirable catheter clogging. In one embodiment, the composition comprises at least 90% spherical particles. The morphology can be determined using methods known in the art, e.g., visual inspection and quantification of spherical volume testing using scanning electron microscopy.

Catheter Compatibility

In some embodiments, the compositions described herein will not clog or block a microcatheter (0.021" ID). The catheter compatibility and deliverability testing can be determined using methods known in the art.

Non-Compressibility

In some embodiments, the compositions described herein are designed to be non-compressible, providing for mechanical vessel occlusion. Compressibility can be determined using methods known in the art, e.g., by using a mechanical test system.

Density

In some embodiments, the density of the compositions described herein will not exceed 4 g/cc. Density can be determined using methods known in the art, e.g., per ASTM B29.

Biocompatibility

In some embodiments, the compositions described herein comprise a base material (prior to neutron irradiation) that is biocompatible. Biocompatibility refers to the ability of a material to perform with an appropriate host response in a specific indication.

Cytotoxicity

In some embodiments, the compositions described herein comprise a base material (prior to neutron irradiation) that comprises non-toxic materials. In some embodiments, the compositions described herein comprise known biocompatible materials in the embolization device; ensuring cytocompatibility of the base material exceeds 70%. Cytotoxicity can be determined using methods known in the art, e.g., per ISO10993-5 (Biological evaluation of medical devices—Part 5: Tests for in vitro cytotoxicity.).

Sterility

In some embodiments, the compositions described herein comprise a base material (prior to neutron irradiation) that remains un-affected by 1 and 2 doses of Gamma sterilization. In some embodiments, the base material is sterilized by 1 and 2 doses of Gamma Irradiation (25-45 kGy). The sterilization dose can be validated using methods known in the art, e.g., per the ISO11137 standard.

Base Material

The compositional analysis of the base material can be determined using methods known in the art, e.g., per ASTM E1479.

Shelf Life

In some embodiments, the compositions described herein will have a shelf-life of at least one year, for example at least about 1, 2, 3, 4, or 5 years. The shelf life can be determined using methods known in the art, e.g., per ASTM F1980 (accelerated age testing).

Irradiated Compositions

The compositions described herein will produce radioisotopes when irradiated with with neutrons. Neutron activation is a consistent and highly predictable phenomenon. The quantity of radioisotope produced upon irradiation in a neutron flux can be accurately predicted using the equation shown below. The number of atoms N is determined by the sample mass; the neutron flux φ and irradiation time t are selected by the nuclear scientist; the neutron absorbance cross-section σ is a fixed value that is unique to each stable isotope; the decay constant λ is a physical property of the radioisotope being formed.

$$A = N\varphi\sigma(1-e^{-\lambda t})$$

A=activity produced
N=number of atoms
φ=neutron flux
σ=neutron absorbance cross-section
λ=decay constant
t=irradiation time For clarity, radioisotope scientists generally differentiate between radionuclidic impurities—radioisotopes that form unexpectedly due to impurities in the sample—and incidental activation products, which are radioisotopes other than the desired species that will form due to the sample composition. Radionuclidic impurities can be minimized (or eliminated) by careful preparation of the sample material, use of high purity reagents, and so on. Neutron Activation Analysis (NAA) can be used to determine whether there are any impurities in the compositions described herein.

After irradiation, the irradiated composition will comprise the radioisotopes described in Example 3. In some embodiments, the irradiated composition comprises Sr-89, Ga-72, and $^{90}$Y. Sr-89 is a therapeutic beta-emitter, and therefore is expected to act synergistically with $^{90}$Y, which is also a beta-emitter, in radioembolization therapy.

EXAMPLES

Example 1

This example describes radiopacity of trial formulations of the compositions described herein (see Table 1).

Methods: Axial CT scans (1 mm through glass vials containing each trial formulation material) were taken on a Siemens 128 Somatom flash definition scanner at energies of 70 and 120 kVp. Quantitative data was expressed as average Hounsfield Unit (HU) values±SD (n=4).

FIG. 1 shows CT radiopacity data for the trial formulations. All formulations tested were radiopaque. Further, formulations 1-3 melted to different degrees, which indicates that the formulations may be suitable for forming amorphous compositions.

Example 2

Microsphere Preparation

A mixture design of experiments (Design Expert 8.0.4, Stat-Ease Inc.) was carried out to evaluate the effect of various ranges of components within a $SrO$—$Y_2O_3$—$Ga_2O_3$—$SiO_2$ quaternary glass system. The ranges for the individual components investigated were set to the following constraints (in mol. fraction):

Constraint 1: $0.10 \leq Y_2O_3 \leq 0.17$
Constraint 2: $0.025 \leq SrO \leq 0.050$
Constraint 3: $0.10 \leq Ga_2O_3 \leq 0.30$
Constraint 4: $0.50 \leq SiO_2 \leq 0.75$ Material compositions denoted Occlu90Y 1.1 to Occlu90Y 1.16 (per Table 2) were synthesized for this work. Analytical grade reagents: strontium carbonate (Sigma-Aldrich, Milwaukee, US), yttrium oxide, gallium oxide and silicon dioxide (Sigma-Aldrich, Oakville, CAN) were weighed using an analytical balance (ABT 320-4M, Kern & Sohn GmbH, Germany) and homogeneously mixed in a rugged rotator (099A RD9912, Glas-Col, Atlanta, Ga., USA) for 1 h. Each composition was packed into 50 mL or 60 mL platinum crucibles (Alpha Aesar, USA), then fired (1550° C., 3 h) using a high temperature furnace (Carbolite RHF 1600, UK) and shock quenched into distilled water at ambient temperature. The resulting glass irregular particles was dried in an oven (100° C., 24 h), pulverized in an agate planetary mill (Pulverisette 7; Laval Labs Inc., Canada) and sieved to retrieve irregular particulates in the size range of 20-75 μm.

The particles retrieved were subsequently formed into glass microspheres by introducing the irregular particles into a gas/oxygen flame where they were melted and a spherical liquid droplet formed by surface tension. The droplet rapidly cooled before it touched any solid object so that its spherical shape was retained in the solid. Prior to spheroidization, the irregular particles were placed in a vibratory feeder located above the gas/oxygen burner and slowly vibrated into a vertical glass tube guiding the powder particles directly into the hot flame of the gas/oxygen burner at a powder feed rate 5 to 25 g/hr. The flame of the burner was directed into a stainless steel container, which collected the small glass beads as they were expelled from the flame, and subsequently screened with a sonic sifter.

TABLE 1

Occlu90Y trial formulations and ease of melt.

| Trial Formulation # | Y2O3 | SrO | Ga2O3 | SiO2 | La2O3 | TiO2 | ZnO | Ease of Melt |
|---|---|---|---|---|---|---|---|---|
| Trial Formulation 0 | 0.170 | — | — | 0.562 | 0.068 | 0.012 | 0.188 | Did not melt |
| Trial Formulation 1 | 0.100 | 0.05 | 0.21 | 0.640 | — | — | — | Easy |
| Trial Formulation 2 | 0.170 | 0.05 | 0.14 | 0.640 | — | — | — | Viscous |
| Trial Formulation 3 | 0.170 | 0.14 | 0.05 | 0.640 | — | — | — | Viscous |

TABLE 2

16 compositions (in mol. fraction) formulated using a quadratic IV-Optimal mixture design #1.

| Formulation | Y2O3 | SrO | Ga2O3 | SiO2 | Ease of Melt |
|---|---|---|---|---|---|
| Occlu90Y_1.1 | 0.102 | 0.039 | 0.214 | 0.646 | Viscous |
| Occlu90Y_1.2 | 0.100 | 0.025 | 0.300 | 0.575 | Easy |
| Occlu90Y_1.3 | 0.138 | 0.039 | 0.100 | 0.723 | Did not melt |
| Occlu90Y_1.4 | 0.170 | 0.035 | 0.295 | 0.500 | Easy |
| Occlu90Y_1.5 | 0.140 | 0.047 | 0.249 | 0.564 | Easy |
| Occlu90Y_1.6 | 0.100 | 0.025 | 0.300 | 0.575 | Easy |
| Occlu90Y_1.7 | 0.170 | 0.035 | 0.295 | 0.500 | Easy |
| Occlu90Y_1.8 | 0.170 | 0.025 | 0.100 | 0.705 | Did not melt |
| Occlu90Y_1.9 | 0.100 | 0.025 | 0.172 | 0.703 | Did not melt |
| Occlu90Y_1.10 | 0.100 | 0.050 | 0.100 | 0.750 | Did not melt |
| Occlu90Y_1.11 | 0.153 | 0.025 | 0.152 | 0.670 | Viscous |
| Occlu90Y_1.12 | 0.127 | 0.050 | 0.300 | 0.523 | Easy |
| Occlu90Y_1.13 | 0.100 | 0.025 | 0.125 | 0.750 | Did not melt |
| Occlu90Y_1.14 | 0.100 | 0.050 | 0.100 | 0.750 | Did not melt |
| Occlu90Y_1.15 | 0.141 | 0.026 | 0.215 | 0.617 | Viscous |
| Occlu90Y_1.16 | 0.170 | 0.050 | 0.167 | 0.613 | Easy |

X-Ray Diffraction

X-ray diffraction (XRD) measurements for each material composition in the form of both irregular particles and bead were performed using a Bruker D8 Advance XRD system with a high speed LynxEye™ detector coupled to an X-ray generator (40 kV, 40 mA) and equipped with a Cu target X-ray tube. Specimens of each experimental glass were prepared by pressing the materials (Ø8.5 mm) into Poly (methyl methacrylate) (PMMA) holder rings. The detector collected all scattered X-rays in the scan angle range $10°<2\theta<100°$. The handling station in the system allowed measurement and move operations to sequentially analyze up to nine different specimens in an automated, unattended manner.

Particle Size Analysis

The particle size distribution for each glass bead formulation (20-75 μm) was determined using the Mastersizer 3000 (Malvern, UK). Bead suspensions in deionized were prepared to get the obscuration value to range between 6-8%. Suspensions were then measured (n=5) using both a blue (λ=470 nm) and red (λ=632.8 nm) laser with values reported as the mean diameter d90, d50 and d10; representative of particle diameters at 90, 50 and 10% cumulative size, respectively.

Helium Pycnometry

The true density of each material composition (0.75 cc of glass in the particle size range of 20-75 μm) in the form of both irregular particles and beads were measured using helium pycnometry (AccuPyc 1340, Micromeritics) with results representative of an average of 10 measurements per composition.

Differential Scanning Calorimetry

A Differential Scanning calorimeter (DSC) 404 F1 Pegasus (404 F1 Pegasus, Netzsch) was used to measure the glass transition temperature ($T_g$) for each material composition in the form of both irregular particles and bead inside platinum crucibles over the temperature range of 20 to 1000° C. The heating profile used followed the order of heating to 500° C. at a heating rate of 30° C./min up to prior to heating from 500° C. to 1000° C. a rate of 10° C./min. Measurements were conducted under flowing Argon (99.999%, Air Liquide, Canada) at a rate of 50 mL/min. The DSC was calibrated using melting points for pure In, Al, Sn, Au and Ag. $T_g$ at the inflection point for the step change in the heat flow curve, was determined using Proteus Analysis software (Version 6.1).

Scanning Electron Microscopy

Carbon coated morphologies for each bead composition was examined using a Hitachi S-4700 Scanning Electron Microscope (SEM), operating at an accelerating voltage of 3 KV accelerating voltage, 15.5 pA emission current, and 12.2 mm working distance. The average percentage sphericity was calculated from three separate images obtained at 150×. Magnifications using the following equation:

$$\% \text{ Sphericity} = \text{No. Spherical Beads/Total No. Beads} * 100\% \quad \text{Equation 1}$$

Extracts were prepared according to ISO 10993-12. 0.5 g of each glass composition (25-75 μm) was immersed in 2.5 mL deionized water (0.2 g/mL ratio) in 15 mL polypropylene BD Falcon® tubes (n=3). Subsequently, specimens were incubated at 37° C. in a shaking water-bath (Model BS-11, Jeio Tech, Seoul, Korea) agitated at 2 Hz (longitudinal movement) over periods of 1, 3, 7 and 14 days for the irregular particles and at 1, 3, 7 and 21 days for the bead composition. After each incubation period, the extracts derived from the experimental materials were separated via sterile 0.20 μm filter with 3 mL syringe (Sarstedt, Canada). Then 0.5 mL extracts were take out and diluted with 4.5 mL 2% nitric acid solution to a factor of 9 (1:9) and stored at 4° C. for subsequent ionic content analysis.

Chemical Durability Measurements

The Y, Sr, Ga, and Si concentrations for each extract were quantified using inductively coupled plasma-atomic emission spectroscopy (ICP-AES, Perkin Elmer Optima 8000, MA, USA). Before each cycle of measurement, calibration curves were obtained by preparing standard solutions containing Y, Sr, Ga, and Si (Perkin Elmer, USA) at concentrations 0, 0.1, 0.5, 1.0, 2.0 and 5.0 ppm in 2% $HNO_3$ in DI water. Standard sample concentrations were measured periodically to ensure the accuracy of the calibration curve. ICP-AES analyses for each extract were performed in triplicate (n=3 extracts per variable).

CT Radiopacity Evaluation

To evaluate for CT radiopacity, quantitative measurements were determined by taking axial CT scans (1 mm slice thickness, pitch=0.5, 70 kVp and 120 kVp) through glass vials using a Siemens Somatom Definition AS+ Scanner (Siemens Healthcare, Erlangen, Germany), comprising of (i) irregular particles or beads in air and (ii) beads in saline. HU values reported were based on separate measurements ±standard deviation (SD). Extended HU range option was employed for scanning.

Biocompatibility Evaluation

For cytotoxicity evaluations, cultures of L-929 (mouse fibroblast) cells were obtained from American Type Culture Collection (ATCC #CCL-1). *Mycoplasma*-free cell lines were purchased from the vendor and kept frozen in the lab until used. To maintain sensitivity, the cells were only sub-cultured for up to 15 passages and then discarded. The cultures were grown and used as monolayers in disposable tissue culture labware at 37±10° C. in a humidified atmosphere of 5±1% $CO_2$ in air. The media used for growth of cells and preparation of extracts was Eagle's minimal essential medium (E-MEM) supplemented with 10% (v/v) fetal calf serum (FCS). The medium was also supplemented with the following: 2.0% L-glutamine, 1.0% penicillin, and 1.0% streptomycin. The cytotoxicity assay was based on the measurement of the viability of cells via metabolic activity. Yellow water-soluble MTT (3-(4,5-dimethylthiazol2-ul)-2, 5-diphenyltetrazoliumbromid) was metabolically reduced in viable cells to a blue-violet insoluble formazan. The number of viable cells correlated to the color intensity determined by photometric measurements after dissolving the formazan in alcohol.

The bead compositions were placed into extraction vessels, and prepared at a ratio of 0.2 g to 20 mL of extraction vehicle. A negative, positive, vehicle control (VC), and blank were run in parallel. A negative control (high density polyethylene (HDPE)) known to be non-toxic under the test conditions was prepared at a ratio of 60 cm$^2$ to 20 mL of extraction vehicle. A positive control, 0.25% zinc dibutyldithiocarbamate (ZDBC) known to be toxic under the test conditions was prepared at a ratio of 60 cm$^2$ to 10 mL of extraction vehicle. A vehicle control (MTT assay medium) was incubated in parallel with the test sample and controls. Untreated MTT assay medium was also plated in the peripheral wells to serve as a baseline control. One day prior to use (24±2 h), the assay plates were created. Cells were suspended in fresh MTT assay medium at a concentration of 1×105 cells/mL. The outside wells of a 96-well plate were filled with 100 μL of MTT assay medium only. 100μL of the cell suspension was dispensed into each remaining well of a 96-well tissue culture plate. The bead compositions and ZDBC extracts were tested in four concentrations (neat, 75%, 50%, and 25%). HDPE was only tested neat. The expended culture media was removed from all wells. 100 μL of blank (untreated MTT assay media) or extract was added to the wells in triplicate.

The plates were incubated for 24±2 h at 37±10° C. in a humidified atmosphere of 5±1% CO2 in air. After incubation, the extracts were removed and MTT solution was added to each well. The plates were incubated at 37±10° C. in a humidified incubator for 2 h. After incubation, the MTT solution was removed from each well and isopropanol was added to each well. Once all the MTT crystals had dissolved, the absorbance reading for each test well was determined after approximately 30 min. and within 1 h after the addition of the isopropanol using an automated microplate reader. Final evaluation of the validity of the assay and test article results was based upon the criteria listed below and scientific judgment:
1. The mean $OD_{570}$ of vehicle control must be >0.2.
2. The left and the right mean of the vehicle control should not differ by more than 15% from the mean of all vehicle control wells.
3. The positive controls should induce≥30%) reduction in viability.
4. The negative controls should induce≤30% reduction in viability.

The following equation was used as applicable to analyze data:

$$\text{Viability} = 100 \times (\text{mean } OD_{sample})/(\text{mean } OD_{vc}) \quad \text{Equation 2}$$

Statistics

One-way ANOVA was employed for density, Tg and percentage sphericity followed by a Neuman-Keuls test to compare the mean values. Data was considered significant when p≤0.5. All calculations were done using Prism 6 for Mac OS X (GraphPad Software Inc., La Jolla, USA).

Design of Mixtures—Experimental Design Approach

Using a DOM experimental design approach, linear, linear plus squared, quadratic and cubic polynomial mixture equations were fitted to the density, $T_g$, percentage sphericity, CT radiopacity (70 kVp and 120 kVp), cell viability (25% and 50%) and yttrium release (1, 3, 7 and 21 d) responses for each glass based experimental irregular particle and bead. Mixture DOM regression models were developed to relate the response to proportions of pseudo-components. For component proportions (xi) with lower bounds (Li), pseudo-component proportions (zi) were calculated as:

$$zi = (xi - Li)/(1 - \Sigma L) \quad \text{Equation 3}$$

where xi stands for the original component proportions, $L_i$ stands for the lower bound constraint (limit) for the i$^{th}$ component, L stands for the sum of all lower bound constraints (limits) for all components in the design, and 1 represents the mixture total. The pseudo-components are combinations of the original (actual) components, which rescale the constrained composition region so that the minimum allowable proportion of each pseudo-component is zero. This transformation may provide for more precisely estimating model coefficients compared to using the actual component system, and as such the coefficients derived based on the pseudo-component scaling is referred to in the context of the discussion to follow. The test for significance of the polynomial mixture regression models (density and radiopacity) along with each of the coefficients (compositional variants) was carried out using Design-Expert 8.0.4; with either the backward or stepwise regression method selected to determine the significant model coefficient terms automatically. When several response characteristics $y_1$, $y_2$, ... $y_n$ have been modeled in the proportions of the same set of q components, the question that naturally arises is where in the composition space might the best overall set of properties be obtained. In this case, the desirability function approach is implemented.

X-Ray Diffraction

Figure 3:
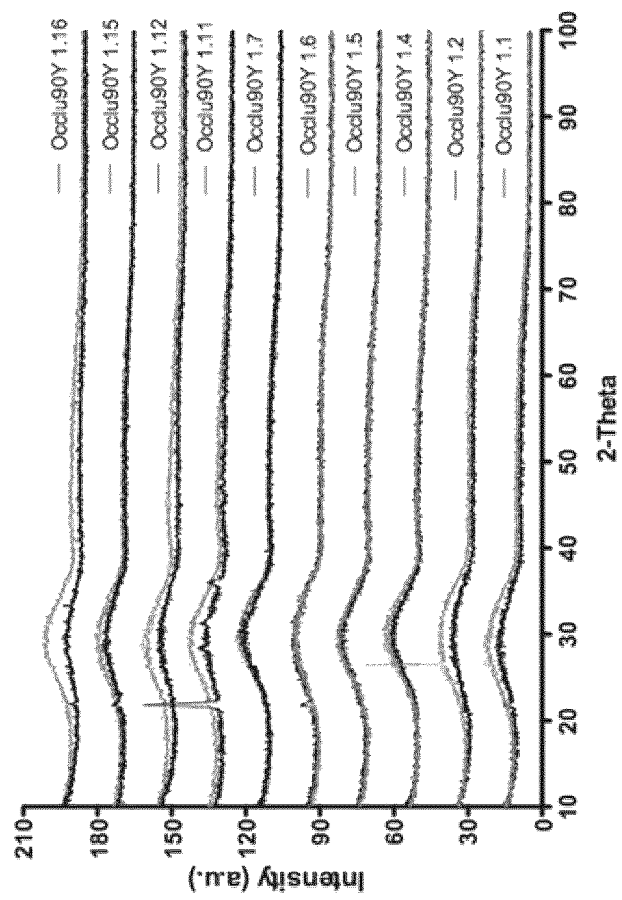
FIG. 3 shows XRD-spectra for each composition pre- (Irregular particles (grey colored spectra)) and post- (Bead) spherodization for Occlu90Y design space #1.

All compositions from design space #1 that permitted either a viscous or easy 'ease of melt' (as shown in Table 2) were subjected to X-ray diffraction (XRD) for confirmation of their amorphous nature. The spectra for all compositions (as shown in FIG. 3) were shown to be fully amorphous with the exceptions of Occlu90Y 1.2 and Occlu90Y 1.11 (in the form of irregular particles and beads, respectively), which contained sharp intense peaks that appeared as potentially crystalline phases; yet were not identifiable against JCPDS standards. This observation for Occlu90Y 1.2 was surprising and unexpected, given that the melt was easy to pour versus the viscous melts which all exhibited broad amorphous humps in their respective spectra. From an ease of melt standpoint, compositions comprising of >0.667 mol. fraction of $SiO_2$ were observed to fail in producing any quality of a melt (ie. Occlu90Y 1.3, Occlu90Y 1.8, Occlu90Y1.9, Occlu90Y 1.10, Occlu90Y 1.13 and Occlu90Y 1.14).

Helium Pycnometry

Figure 4:
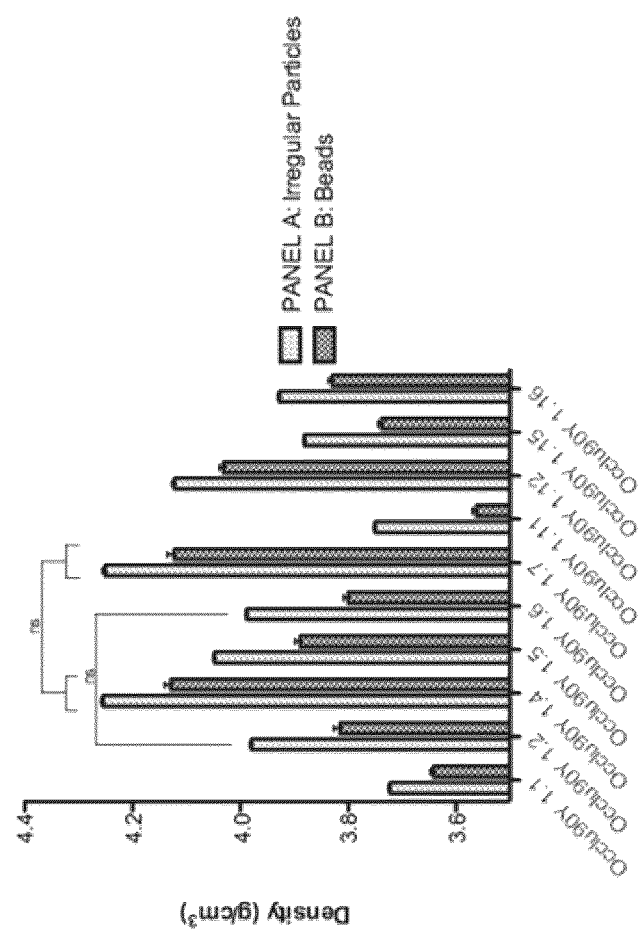
FIG. 4 shows summary of densities for irregular particles versus bead Occlu90Y compositions for design space #1.

The associated density for the materials that could be synthesized is provided. In total 10 of the 16 formulations formed glass irregular particles with mean densities ranging from 3.7 to 4.3 g/cm$^3$, which were subsequently transformed to beads with mean densities ranging from 3.6 to 4.1 g/cm$^3$ (refer to FIG. 4).

Table 3 shows the actual regression models (in terms of L-pseudo and actual component coding) validity, additional adequacy measures, and ANOVA such as $R^2$, adjusted $R^2$, and predicted $R^2$. All adequacy values are in excess of 0.9 indicating significant regression models have been realized. A tabulated comparison between observed and calculated behaviors of material compositions in the form of irregular particles versus beads is also presented in Table 4 (as based on the regression models using L-pseudo coding).

TABLE 3

Regression output for the density models.

| | PANEL A: Irregular Particles | | PANEL B: Beads | |
|---|---|---|---|---|
| Term | L-Pseudo Coefficient | Actual Coefficient | L-Pseudo Coefficient | Actual Coefficient |
| $Y_2O_3$ | +4.83 | +8.68535 | +4.32 | +6.41508 |
| SrO | +3.83 | +4.35939 | +4.52 | +7.14838 |
| $Ga_2O_3$ | +4.24 | +6.52782 | +4.03 | +5.35402 |
| $SiO_2$ | +3.31 | +2.27561 | +3.22 | +2.40147 |
| $Y_2O_3 * Ga_2O_3$ | −0.66 | −8.74815 | | |
| R-squared | | 0.9972 | | 0.9930 |
| Adjusted R-squared | | 0.9950 | | 0.9896 |
| Predicted R-squared | | 0.9913 | | 0.9794 |
| Model F Statistic | | 446.44 | | 285.61 |
| Model Standard Deviation | | 0.013 | | 0.020 |
| Model p-value | | <0.0001 | | <0.0001 |

TABLE 4

Density residuals for each glass model.

| | PANEL A: Irregular particles Density (g/cm³) | | | PANEL B: Beads Density (g/cm³) | | |
|---|---|---|---|---|---|---|
| Glass Designation | Predicted | Experimental | Residual | Predicted | Experimental | Residual |
| Occlu90Y1.1 | 3.723 ± 0.013 | 3.727 ± 0.003 | −0.004 | 3.626 ± 0.020 | 3.642 ± 0.006 | −0.016 |
| Occlu90Y1.2 | 3.980 ± 0.013 | 3.982 ± 0.003 | −0.002 | 3.807 ± 0.020 | 3.815 ± 0.012 | −0.008 |
| Occlu90Y1.4 | 4.254 ± 0.013 | 4.255 ± 0.003 | −0.001 | 4.120 ± 0.020 | 4.129 ± 0.011 | −0.009 |
| Occlu90Y1.5 | 4.025 ± 0.013 | 4.048 ± 0.003 | −0.023 | 3.921 ± 0.020 | 3.889 ± 0.010 | 0.032 |
| Occlu90Y1.6 | 3.988 ± 0.013 | 3.982 ± 0.002 | 0.006 | 3.807 ± 0.020 | 3.801 ± 0.009 | 0.006 |
| Occlu90Y1.7 | 4.254 ± 0.013 | 4.251 ± 0.006 | 0.003 | 4.120 ± 0.020 | 4.123 ± 0.013 | −0.003 |
| Occlu90Y1.11 | 3.750 ± 0.013 | 3.752 ± 0.003 | −0.002 | 3.583 ± 0.020 | 3.563 ± 0.007 | 0.020 |
| Occlu90Y1.12 | 4.137 ± 0.013 | 4.123 ± 0.005 | 0.014 | 4.036 ± 0.020 | 4.031 ± 0.008 | 0.005 |
| Occlu90Y1.15 | 3.881 ± 0.013 | 3.885 ± 0.002 | −0.004 | 3.728 ± 0.020 | 3.738 ± 0.007 | −0.010 |
| Occlu90Y1.16 | 3.928 ± 0.013 | 3.930 ± 0.003 | −0.002 | 3.813 ± 0.020 | 3.830 ± 0.007 | −0.017 |

Table 5 provides a ranked summary of the key compositional elements; which provide for key structure and property responses from the data.

TABLE 5

Summary of the significant (positive and negative), individual and interaction effects (in terms of L-Pseudo co-efficients, as shown in parentheses) associated with compositional elements (order of significant effects: highest to lowest, ↑ represents positive effects, and ↓ represents negative effects).

| PANEL A: Irregular particles Density (g/cm³) Ranking Effect | PANEL B: Beads Density (g/cm³) Ranking Effect |
|---|---|
| ↑ $Y_2O_3$ | ↑ SrO |
| ↑ $Ga_2O_3$ | ↓ $Y_2O_3$ |
| ↑ SrO | ↑ $Ga_2O_3$ |
| ↑ $SiO_2$ | ↑ $SiO_2$ |
| ↓ $Y_2O_3 * Ga_2O_3$ | |

Differential Scanning Calorimetry

Figure 5:
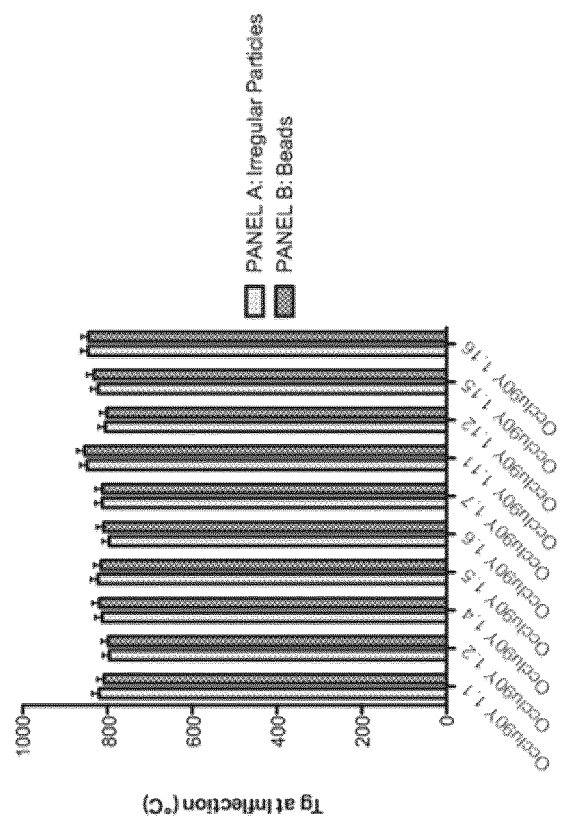
FIG. 5 shows summary of glass transition temperatures for irregular particles versus bead Occlu90Y compositions for design space #1.

The associated $T_g$ for the materials that could be synthesized is provided. In total 10 of the 16 formulations formed glass irregular particles with mean $T_g$ ranging from 796 to 848° C., which were subsequently transformed to beads with mean $T_g$ ranging from 798 to 854° C. (refer to FIG. 5).

Table 6 shows the actual regression models (in terms of L-pseudo and actual component coding) validity, additional adequacy measures, and ANOVA such as $R^2$, adjusted $R^2$, and predicted $R^2$. All adequacy values are in excess of 0.9 indicating significant regression models have been realized. A tabulated comparison between observed and calculated behaviors of material compositions in the form of irregular particles versus beads is also presented in Table 7 (as based on the regression models using L-pseudo coding).

TABLE 6

Regression output for the $T_g$ models.

| | PANEL A: Irregular particles | | PANEL B: Beads | |
|---|---|---|---|---|
| Term | L-Pseudo Coefficient | Actual Coefficient | L-Pseudo Coefficient | Actual Coefficient |
| $Y_2O_3$ | +902.65 | +1050.2640 | +882.35 | −154.53359 |
| SrO | +885.72 | +988.72036 | +726.44 | +599.74074 |
| $Ga_2O_3$ | +776.65 | +592.07433 | +795.87 | +852.19982 |
| $SiO_2$ | +847.51 | +849.74815 | +823.72 | +689.25707 |
| $Y_2O_3 * SiO_2$ | | | +199.83 | +2642.42826 |
| R-squared | | 0.9877 | | 0.9714 |
| Adjusted R-squared | | 0.9816 | | 0.9485 |
| Predicted R-squared | | 0.9601 | | 0.9032 |
| Model F Statistic | | 160.99 | | 42.42 |
| Model Standard Deviation | | 2.45 | | 4.17 |
| Model p-value | | <0.0001 | | 0.0005 |

TABLE 7

$T_g$ residuals for each glass model.

| Glass Designation | PANEL A: Irregular particles $T_g$ (° C.) | | | PANEL B: Beads $T_g$ (° C.) | | |
|---|---|---|---|---|---|---|
| | Predicted | Experimental | Residual | Predicted | Experimental | Residual |
| Occlu90Y1.1 | 820.478 ± 2 | 819.800 ± 16 | 0.678 | 808.092 ± 4 | 808.200 ± 16 | 0.892 |
| Occlu90Y1.2 | 795.972 ± 2 | 795.500 ± 16 | 0.472 | 803.463 ± 4 | 798.400 ± 16 | 0.506 |
| Occlu90Y1.4 | 812.557 ± 2 | 812.500 ± 16 | 0.057 | 815.436 ± 4 | 819.200 ± 16 | −0.376 |
| Occlu90Y1.5 | 820.033 ± 2 | 822.900 ± 16 | −2.867 | 816.299 ± 4 | 815.600 ± 16 | 0.699 |
| Occlu90Y1.6 | 795.972 ± 2 | 796.200 ± 16 | −0.228 | 803.463 ± 4 | 809.200 ± 16 | −5.737 |
| Occlu90Y1.7 | 812.557 ± 2 | 812.500 ± 16 | 0.057 | 815.436 ± 4 | 812.000 ± 16 | 3.436 |
| Occlu90Y1.11 | 844.876 ± 2 | 848.200 ± 17 | −3.324 | 853.795 ± 4 | 854.200 ± 17 | −3.324 |
| Occlu90Y1.12 | 804.924 ± 2 | 805.300 ± 16 | −0.376 | 802.079 ± 4 | 802.000 ± 16 | 0.079 |
| Occlu90Y1.15 | 826.155 ± 2 | 822.900 ± 16 | 3.255 | 833.184 ± 4 | 831.900 ± 17 | 1.284 |
| Occlu90Y1.16 | 847.877 ± 2 | 845.600 ± 17 | 2.277 | 844.053 ± 4 | 844.600 ± 17 | −0.547 |

Table 8 provides a ranked summary of the key compositional elements; which provide for key structure and property responses from the data.

TABLE 8

Summary of the significant (positive and negative), individual and interaction effects (in terms of L-Pseudo co-efficients, as shown in parentheses) associated with compositional elements (order of significant effects: highest to lowest, ↑ represents positive effects, and ↓ represents negative effects).

| PANEL A: Irregular particles Tg (° C.) Ranking Effect | PANEL B: Beads Tg (° C.) Ranking Effect |
|---|---|
| ↑ $Y_2O_3$ | ↓ $Y_2O_3$ |
| ↑ SrO | ↑ $SiO_2$ |
| ↑ $SiO_2$ | ↑ $Ga_2O_3$ |
| ↑ $Ga_2O_3$ | ↑ SrO |
| | ↑ $Y_2O_3$ * $SiO_2$ |

No significant differences were observed for $T_g$ of each composition in the form of irregular particles versus bead. However, the order of influence for the compositional elements with respect to its $T_g$ varied significantly as follows:

1. Irregular particles: $Y_2O_3$>SrO>$SiO_2$>$Ga_2O_3$
2. Bead: $Y_2O_3$>$SiO_2$>$Ga_2O_3$>SrO Furthermore, the order of influence is different to density and not readily apparent. To have high $T_g$ (stability) a maximum loading of $SiO_2$ is warranted, whereas to reduce its level of density, a maximum loading of SrO is required.

Scanning Electron Microscopy

Figure 6:
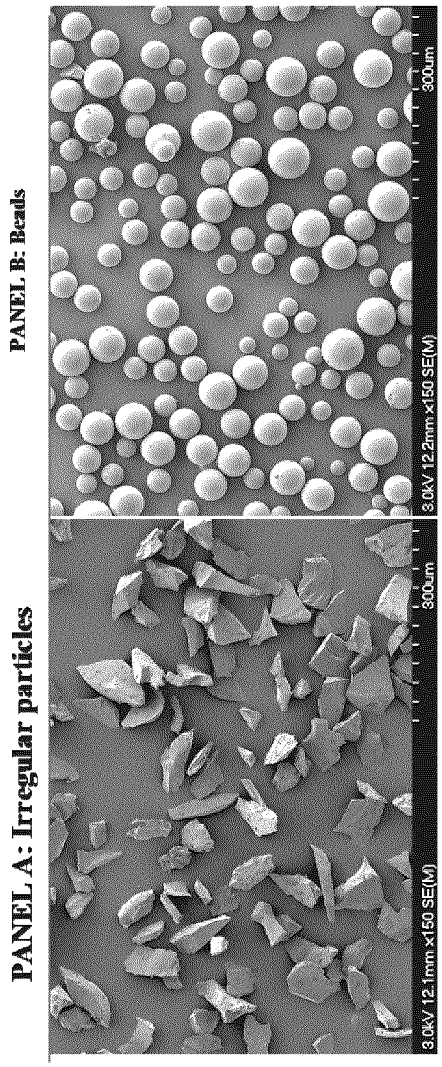
FIG. 6 shows representative SEM images of glass pre- (PANEL A) and post-(PANEL B) spherodization for all compositional design spaces (ie. #s Occlu90Y1, Occlu90Y2 and Occ1u89Sr4).

The associated morphologies for the materials that could be synthesized are provided in the form of SEM images (as shown in FIG. 6) and their relative percentage sphericity. In total 10 of the 16 formulations formed beads with mean percentage sphericity ranging from 90 to 98% (refer to FIGS. 6 and 7).

Table 9 shows the actual regression model (in terms of L-pseudo and actual component coding) validity, additional adequacy measures, and ANOVA such as $R^2$, adjusted $R^2$, and predicted $R^2$. All adequacy values are in excess of 0.8 indicating significant regression models have been realized. A tabulated comparison between observed and calculated behaviors of material compositions in the form of irregular particles versus beads is also presented in Table 10 (as based on the regression models using L-pseudo coding).

TABLE 9

Regression output for the sphericity model.

PANEL B: Beads

| Term | L-Pseudo Coefficient | Actual Coefficient |
|---|---|---|
| $Y_2O_3$ | +100.83 | +128.06495 |
| SrO | +118.68 | +192.98256 |
| $Ga_2O_3$ | +96.08 | +110.81734 |
| $SiO_2$ | +85.90 | +73.79329 |
| R-squared | 0.9311 | |
| Adjusted R-squared | 0.8966 | |
| Predicted R-squared | 0.8290 | |
| Model F Statistic | 27.01 | |
| Model Standard Deviation | 0.91 | |
| Model p-value | 0.0007 | |

TABLE 10

Sphericity residuals for each glass.

PANEL B: Beads Sphericity (%)

| Glass Designation | Predicted | Experimental | Residual |
|---|---|---|---|
| Occlu90Y1.1 | 91.886 ± 0.91 | 92.000 ± 3 | −0.114 |
| Occlu90Y1.2 | 93.307 ± 0.91 | 94.000 ± 2 | −0.693 |
| Occlu90Y1.4 | 98.086 ± 0.91 | 98.000 ± 1 | 0.086 |
| Occlu90Y1.5 | 96.169 ± 0.91 | 96.000 ± 2 | 0.169 |
| Occlu90Y1.6 | 93.307 ± 0.91 | 92.000 ± 3 | 1.307 |
| Occlu90Y1.7 | 98.086 ± 0.91 | 98.000 ± 2 | 0.086 |
| Occlu90Y1.11 | 90.709 ± 0.91 | 90.000 ± 2 | 0.709 |
| Occlu90Y1.12 | 97.770 ± 0.91 | 98.000 ± 1 | −0.230 |
| Occlu90Y1.15 | 92.534 ± 0.91 | 94.000 ± 3 | −1.466 |
| Occlu90Y1.16 | 95.144 ± 0.91 | 95.000 ± 2 | 0.144 |

Table 11 provides a ranked summary of the key compositional elements; which provide for key structure and property responses from the data.

TABLE 11

Summary of the significant (positive and negative), individual effects (in terms of L-Pseudo co-efficients, as shown in parentheses) associated with compositional elements (order of significant effects: highest to lowest, ↑ represents positive effects, and ↓ represents negative effects).

PANEL B: Beads Sphericity (%) Ranking Effect

↑ SrO
↑ $Y_2O_3$
↑ $Ga_2O_3$
↑ $SiO_2$

Based on SEM imaging, no significant differences were observed for sphericity between each composition in the form of the final bead product.

There are various compositions however that were shown to provide for enhanced levels of sphericity in terms of its subsequent morphological quality. The order of influence for the compositional elements with respect to obtaining enhanced levels of sphericity followed the order: $SrO > Y_2O_3 > Ga_2O_3 > SiO_2$. This order of influence is non-obvious, yet critical to producing high quality shaped beads. As previously shown for density, the order of influence is surprising given the minimal loading of SrO in the glasses and unexpectedly is observed to follow the same sequential order as bead density.

Figure 7:
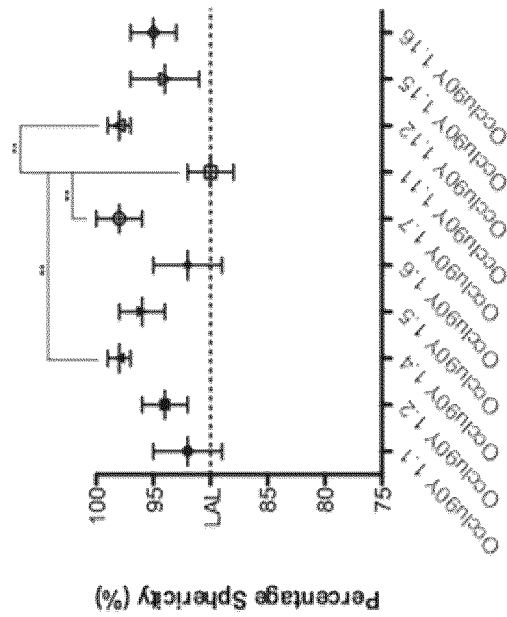
FIG. 7 shows summary of percentage sphericity for Occlu90Y compositions in the form of bead (design space #1).

FIG. 7. Summary of percentage sphericity for Occlu90Y compositions in the form of bead (design space #1).

Chemical Durability Measurements

The associated yttrium release for the materials that could be synthesized is provided. In total 10 of the 16 formulations formed glass irregular particles with mean yttrium release levels ranging from 0 to 0.5 ppm over a 1 d period, and 0.32 to 1.84 ppm, 0.64 to 2.20 ppm and 0.78 to 2.00 ppm for the materials transformed into beads (refer to FIG. 8).

Table 12 shows the actual regression models (in terms of L-pseudo and actual component coding) validity, additional adequacy measures, and ANOVA such as $R^2$, adjusted $R^2$, and predicted $R^2$. All adequacy values are in excess of 0.7 indicating significant regression models have been realized. A tabulated comparison between observed and calculated behaviors of material compositions in the form of irregular particles versus beads is also presented in Table 13 and 14, respectively (as based on the regression models using L-pseudo coding).

TABLE 12

Regression output for the Yttrium release models.

| | PANEL A: Irregular particles | | PANEL B: Beads | | | | | |
| --- | --- | --- | --- | --- | --- | --- | --- | --- |
| | 1 d Yttrium Release | | 3 d Yttrium Release | | 7 d Yttrium Release | | 21 d Yttrium Release | |
| Term | L-Pseudo Coefficient | Actual Coefficient | L-Pseudo Coefficient | Actual Coefficient | L-Pseudo Coefficient | Actual Coefficient | L-Pseudo Coefficient | Actual Coefficient |
| $Y_2O_3$ | −0.081 | −5.07943 | −2.39 | −20.84846 | −3.30 | −28.89815 | −2.02 | −22.44178 |
| SrO | −5.61 | −42.62738 | −2.61 | −9.44744 | −4.33 | −17.02263 | −5.39 | −21.52157 |
| $Ga_2O_3$ | +0.64 | +3.35230 | +0.96 | −8.65269 | +1.46 | −11.58406 | +1.15 | −10.91497 |
| $SiO_2$ | −0.079 | +0.74485 | +1.06 | +3.90069 | +2.14 | +6.52107 | +2.23 | +6.17459 |
| $Y_2O_3$ * SrO | +17.60 | +232.71900 | — | — | — | — | — | — |
| $Y_2O_3$ * $Ga_2O_3$ | — | — | +9.23 | +122.09527 | +11.82 | +156.28167 | +9.96 | +131.74347 |
| R-squared | 0.9485 | | 0.9138 | | 0.9369 | | 0.9670 | |
| Adjusted R-squared | 0.9073 | | 0.8449 | | 0.8864 | | 0.9407 | |
| Predicted R-squared | 0.8227 | | 0.6627 | | 0.7366 | | 0.8467 | |
| Model F Statistic | 23.02 | | 13.26 | | 18.56 | | 36.68 | |
| Model Standard Deviation | 0.20 | | 0.16 | | 0.15 | | 0.089 | |
| Model p-value | 0.0020 | | 0.0072 | | 0.0033 | | 0.0007 | |

TABLE 13

Yttrium release residuals for each glass.

PANEL A: Irregular particles
1 d Yttrium Release

| Glass Designation | Pred. | Exp. | Residual |
| --- | --- | --- | --- |
| Occlu90Y1.1 | −0.063 ± 0.20 | 0.000 ± 0.000 | −0.063 |
| Occlu90Y1.2 | 0.442 ± 0.20 | 0.410 ± 0.010 | −0.128 |
| Occlu90Y1.4 | 0.393 ± 0.20 | 0.457 ± 0.015 | −0.064 |
| Occlu90Y1.5 | 0.078 ± 0.20 | 0.067 ± 0.012 | 0.011 |
| Occlu90Y1.6 | 0.442 ± 0.20 | 0.477 ± 0.006 | −0.035 |
| Occlu90Y1.7 | 0.393 ± 0.20 | 0.390 ± 0.017 | 0.003 |
| Occlu90Y1.11 | 0.055 ± 0.20 | 0.063 ± 0.031 | 0.048 |
| Occlu90Y1.12 | 0.098 ± 0.20 | 0.050 ± 0.017 | 0.048 |
| Occlu90Y1.15 | 0.210 ± 0.20 | 0.133 ± 0.023 | 0.077 |
| Occlu90Y1.16 | −0.002 ± 0.20 | 0.000 ± 0.000 | −0.002 |

TABLE 14

Yttrium release residuals for each model.

PANEL B: Beads

| Glass Designation | 3 d Yttrium Release | | | 7 d Yttrium Release | | | 21 d Yttrium Release | | |
| --- | --- | --- | --- | --- | --- | --- | --- | --- | --- |
| | Pred. | Exp. | Residual | Pred. | Exp. | Residual | Pred. | Exp. | Residual |
| Occlu90Y1.1 | 0.831 ± 0.16 | 0.823 ± 0.035 | 0.008 | 1.524 ± 0.15 | 1.507 ± 0.023 | 0.017 | 1.390 ± 0.089 | 1.353 ± 0.042 | 0.037 |
| Occlu90Y1.2 | 0.989 ± 0.16 | 0.910 ± 0.026 | 0.079 | 1.647 ± 0.15 | 1.600 ± 0.020 | 0.047 | 1.446 ± 0.089 | 1.470 ± 0.046 | −0.024 |

TABLE 14-continued

Yttrium release residuals for each model.

PANEL B: Beads

| Glass Designation | 3 d Yttrium Release | | | 7 d Yttrium Release | | | 21 d Yttrium Release | | |
|---|---|---|---|---|---|---|---|---|---|
| | Pred. | Exp. | Residual | Pred. | Exp. | Residual | Pred. | Exp. | Residual |
| Occlu90Y1.4 | 1.653 ± 0.16 | 1.840 ± 0.053 | −0.187 | 2.183 ± 0.15 | 2.200 ± 0.056 | −0.017 | 1.917 ± 0.089 | 2.007 ± 0.060 | −0.090 |
| Occlu90Y1.5 | 0.947 ± 0.16 | 1.007 ± 0.050 | −0.06 | 1.409 ± 0.15 | 1.547 ± 0.035 | −0.138 | 1.218 ± 0.089 | 1.323 ± 0.040 | −0.105 |
| Occlu90Y1.6 | 0.989 ± 0.16 | 1.067 ± 0.045 | −0.078 | 1.647 ± 0.15 | 1.710 ± 0.070 | −0.063 | 1.446 ± 0.089 | 1.420 ± 0.060 | 0.026 |
| Occlu90Y1.7 | 1.653 ± 0.16 | 1.480 ± 0.026 | 0.173 | 2.183 ± 0.15 | 2.183 ± 0.133 | 0.000 | 1.917 ± 0.089 | 1.793 ± 0.067 | 0.124 |
| Occlu90Y1.11 | 0.708 ± 0.16 | 0.840 ± 0.035 | −0.132 | 1.391 ± 0.15 | 1.557 ± 0.143 | −0.166 | 1.563 ± 0.089 | 1.567 ± 0.031 | −0.004 |
| Occlu90Y1.12 | 0.980 ± 0.16 | 1.003 ± 0.140 | −0.023 | 1.372 ± 0.15 | 1.357 ± 0.117 | 0.015 | 1.052 ± 0.089 | 1.023 ± 0.133 | 0.029 |
| Occlu90Y1.15 | 1.068 ± 0.16 | 0.917 ± 0.049 | 0.151 | 1.760 ± 0.15 | 1.547 ± 0.006 | 0.213 | 1.738 ± 0.089 | 1.767 ± 0.031 | −0.029 |
| Occlu90Y1.16 | 0.392 ± 0.16 | 0.323 ± 0.015 | 0.069 | 0.732 ± 0.15 | 0.640 ± 0.066 | 0.092 | 0.809 ± 0.089 | 0.780 ± 0.046 | 0.029 |

Table 15 provides a ranked summary of the key compositional elements; which provide for key structure and property responses from the data.

TABLE 15

Summary of the top significant (positive and negative), individual and interaction effects (in terms of L-Pseudo co-efficients, as shown in parentheses) associated with compositional elements (order of significant effects: highest to lowest, ↑ represents positive effects, and ↓ represents negative effects).

| PANEL A: Irregular particles 1 d Yttrium Release | 3 d Yttrium Release | PANEL B: Beads 7 d Yttrium Release | 21 d Yttrium Release |
|---|---|---|---|
| ↑ $Y_2O_3$ * SrO | ↑ $Y_2O_3$ * $Ga_2O_3$ | ↑ $Y_2O_3$ * $Ga_2O_3$ | ↑ $Y_2O_3$ * $Ga_2O_3$ |
| ↓ SrO | ↓ SrO | ↓ SrO | ↓ SrO |
| ↑ $Ga_2O_3$ | ↓ $Y_2O_3$ | ↓ $Y_2O_3$ | ↓ $Y_2O_3$ |
| ↓ $Y_2O_3$ | ↑ $SiO_2$ | ↑ $SiO_2$ | ↑ $SiO_2$ |
| ↓ $SiO_2$ | ↑ $Ga_2O_3$ | ↑ $Ga_2O_3$ | ↑ $Ga_2O_3$ |

The chemical durability for the glasses evaluated in this design space with respect to controlling the $Y_2O_3$ release, were shown to crucially be dependent upon both SrO and $Ga_2O_3$. Such trends are unknown in the art, particularly as both compositional elements are known to act as either network modifier or intermediate in the glass matrix to potentially open out its network, thus reducing its stability.

Figure 8:
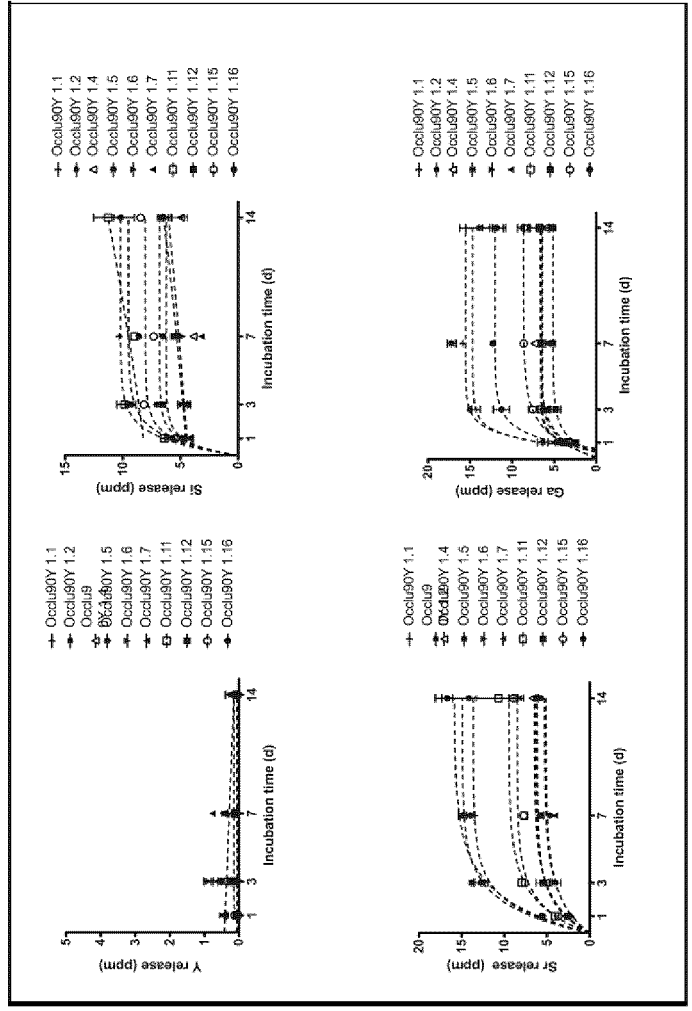
FIG. 8 shows ion release levels for Y, Si, Sr and Ga release for each glass composition produced as irregular particles (PANEL A) in design space #1 with respect of time at 1, 3, 7 and 14 days and comparative release levels for the same glass composition produced as beads (PANEL B) with respect of time 5 at 1, 3, 7 and 21 days.

FIG. 8. Ion release levels for Y, Si, Sr and Ga release for each glass composition produced as irregular particles (PANEL A) in design space #1 with respect of time at 1, 3, 7 and 14 days and comparative release levels for the same glass composition produced as beads (PANEL B) with respect of time at 1, 3, 7 and 21 days.

Ct Radiopacity Evaluation

Figure 9:
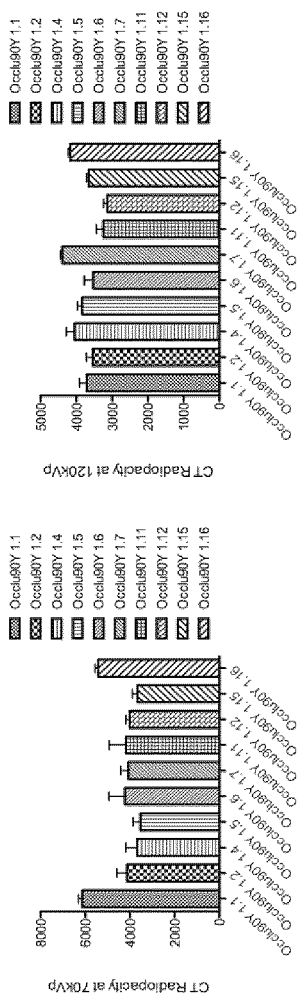
FIG. 9 shows CT radiopacity levels (70 kVp and 120 kVp) for irregular particles (PANEL A: upper row) versus beads (PANEL B: middle row) evaluated in air and compared against beads evaluated in saline (PANEL B: lowest row).
Figure 10:
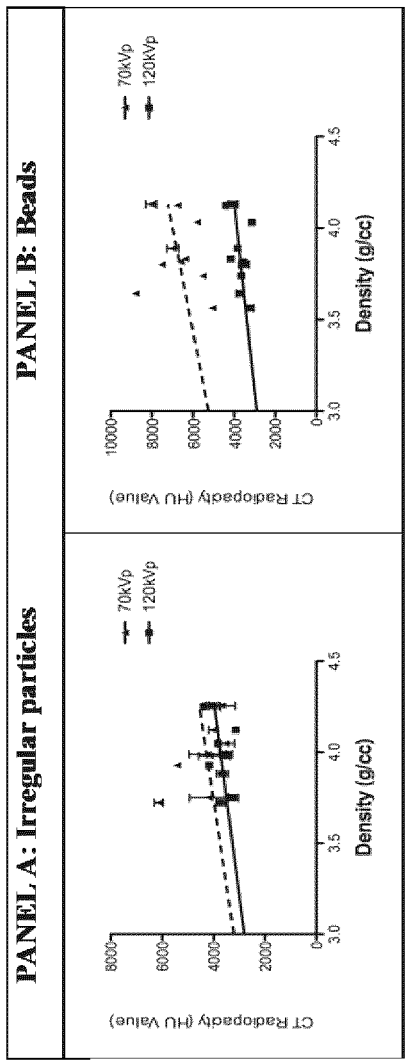
FIG. 10 shows CT radiopacity levels (70 kVp and 120 kVp) for irregular particles (PANEL A) versus beads (PANEL B) evaluated in air.

The associated CT radiopacity for the materials that could be synthesized is provided (refer to FIGS. 9 and 10). In total 10 of the 16 formulations formed glass irregular particles with mean CT radiopacity levels (measured in air) ranging from 3532 HU to 6132 HU and 3141 to 4393 HU at 70 kVp and 120 kVp, respectively. By comparison, the beads were shown to exhibit mean CT radiopacity levels (measured in air) ranging from 5066 HU to 8043 HU and 5066 HU to 6761 HU at 70 kVp and 120 kVp, respectively. The glass beads as measured in saline however, were shown to exhibit significantly higher mean CT radiopacity levels ranging from 13,664 HU to 17,835 HU and 7,341 HU to 9,776 HU at 70 kVp and 120 kVp, respectively.

TABLE 16

Regression output for the CT radiopacity models.

| | PANEL A: Irregular particles | | | | PANEL B: Beads | | | |
|---|---|---|---|---|---|---|---|---|
| | CT Radiopacity at 70 kVp | | CT Radiopacity at 120 kVp | | CT Radopacity 70 kVp | | CT Radiopacity at 120 kVp | |
| Term | L-Pseudo Coefficient | Actual Coefficient | L-Pseudo Coefficient | Actual Coefficient | L-Pseudo Coefficient | Actual Coefficient | L-Pseudo Coefficient | Actual Coefficient |
| $Y_2O_3$ | −37685.54 | −3.64462E+05 | −9740.29 | −1.11400E+05 | +20832.09 | +38288.34673 | +1.446E+5 | +6.18672E+5 |
| SrO | −78097.67 | −8.35217E+05 | −12420.46 | −2.30330E+05 | +28398.52 | +65892.65504 | +1.209E+6 | +1.17478E+7 |
| $Ga_2O_3$ | +30631.19 | +3.30300E+5 | +2544.78 | −20400.01951 | +16275.54 | +21718.34241 | +40081.29 | +6.86601E+5 |
| $SiO_2$ | −12516.75 | −2.34358E+05 | +6168.80 | +22573.92548 | +11764.15 | −5314.11681 | −78536.3 | −6.65952E+05 |
| $(Y_2O_3)^2$ | +1.376E+5 | +1.81907E+6 | — | — | — | — | — | — |
| $(SrO)^2$ | +1.040E+6 | +1.37523E+7 | — | — | — | — | — | — |
| $(Ga_2O_3)^2$ | −31203.83 | −4.12613E+05 | — | — | — | — | — | — |
| $(SiO_2)^2$ | +24595.77 | +3.25233E+5 | — | — | — | — | — | — |
| $Y_2O_3$ * SrO | — | — | +1.401E+5 | +1.85307E+6 | — | — | −4.271E+06 | −5.64729E+07 |
| $Y_2O_3$ * $Ga_2O_3$ | — | — | +22533.00 | +2.97957E+5 | — | — | −1.430E+05 | −1.89037E+06 |
| $Y_2O_3$ * $SiO_2$ | — | — | — | — | — | — | +2.132E+5 | +2.81894E+6 |
| SrO * $Ga_2O_3$ | — | — | — | — | — | — | +1.362E+6 | −1.80114E+07 |
| R-squared | 0.9865 | | 0.9570 | | 0.8861 | | 0.9923 | |
| Adjusted R-squared | 0.9394 | | 0.9033 | | 0.8292 | | 0.9653 | |
| Predicted R-squared | — | | 0.8111 | | 0.6505 | | — | |
| Model F Statistic | 20.92 | | 17.82 | | 15.56 | | 36.74 | |

TABLE 16-continued

Regression output for the CT radiopacity models.

| | PANEL A: Irregular particles | | | | PANEL B: Beads | | | |
|---|---|---|---|---|---|---|---|---|
| | CT Radiopacity at 70 kVp | | CT Radiopacity at 120 kVp | | CT Radoacity 70 kVp | | CT Radiopacity at 120 kVp | |
| Term | L-Pseudo Coefficient | Actual Coefficient | L-Pseudo Coefficient | Actual Coefficient | L-Pseudo Coefficient | Actual Coefficient | L-Pseudo Coefficient | Actual Coefficient |
| Model Standard Deviation | 204.14 | | 123.31 | | 614.41 | | 175.01 | |
| Model p-value | 0.0464 | | 0.0077 | | 0.0031 | | 0.0267 | |

Table 16 shows the actual regression models (in terms of L-pseudo and actual component coding) validity, additional adequacy measures, and ANOVA such as $R^2$, adjusted $R^2$, and predicted $R^2$. All adequacy values are in excess of 0.6 indicating significant regression models have been realized. A tabulated comparison between observed and calculated behaviors of material compositions in the form of irregular particles versus beads is also presented in Table 17 (as based on the regression models using L-pseudo coding).

TABLE 17

CT radiopacity residuals for each glass.

| | PANEL A: Irregular particles | | | | | | PANEL B: Beads | | | | | |
|---|---|---|---|---|---|---|---|---|---|---|---|---|
| Glass | CT Radiopacity at 70 kVp | | | CT Radiopacity at 120 kVp | | | CT Radioacity at 70 kVp | | | CT Radiopacity at 120 kVp | | |
| Designation | Pred. | Exp. | Resid. | Pred. | Exp. | Resid. | Pred. | Exp. | Resid. | Pred. | Exp. | Resid. |
| Occlu90Y1.1 | 6132 ± 204 | 6132 ± 172 | 0.000 | 3714.817 ± 123 | 3714 ± 199 | −0.810 | 14537.785 ± 614 | 14511 ± 270 | 26.700 | 8206 ± 175 | 8206 ± 120 | 0.000 |
| Occlu90Y1.2 | 4188.5 ± 204 | 4143 ± 443 | 45.500 | 3533.147 ± 123 | 3543 ± 187 | −9.860 | 15045.021 ± 614 | 14537 ± 348 | 508.000 | 7731 ± 175 | 7586 ± 111 | 145.000 |
| Occlu90Y1.4 | 3875 ± 204 | 3676 ± 514 | 199.000 | 4222.02 ± 123 | 4052 ± 235 | 170.020 | 17861.731 ± 614 | 17774 ± 354 | 87.700 | 9692 ± 175 | 9790 ± 157 | −98.000 |
| Occlu90Y1.5 | 3532 ± 204 | 3532 ± 338 | 0.000 | 3807.904 ± 123 | 3836 ± 138 | −28.100 | 16835.536 ± 614 | 16336 ± 393 | 499.500 | 8541 ± 175 | 8541 ± 319 | 0.000 |
| Occlu90Y1.6 | 4188 ± 204 | 4234 ± 720 | −46.000 | 3537 ± 123 | 3531 ± 249 | 6.000 | 15045.021 ± 614 | 15682 ± 288 | −637.000 | 7731 ± 175 | 7786 ± 495 | −55.000 |
| Occlu90Y1.7 | 3875 ± 204 | 4074 ± 337 | −199.000 | 4222.02 ± 123 | 4393 ± 53 | −170.980 | 17861.731 ± 614 | 17835 ± 355 | 26.7000 | 9692 ± 175 | 9594 ± 240 | 98.000 |
| Occlu90Y1.11 | 4181 ± 204 | 4181 ± 758 | 0.000 | 3224.963 ± 123 | 3243 ± 198 | −18.040 | 14369.664 ± 614 | 13664 ± 516 | 705.600 | 7341 ± 175 | 7341 ± 112 | 0.000 |
| Occlu90Y1.12 | 4017 ± 204 | 4017 ± 175 | 0.000 | 3156.259 ± 123 | 3141 ± 104 | 15.250 | 17457.991 ± 614 | 17402 ± 792 | 55.900 | 9776 ± 175 | 9776 ± 275 | 0.000 |
| Occlu90Y1.15 | 3656 ± 204 | 3656 ± 233 | 0.000 | 3691.779 ± 123 | 3658 ± 65 | 33.770 | 15077.721 ± 614 | 15838 ± 165 | −760.300 | 9559 ± 175 | 9559 ± 183 | 0.000 |
| Occlu90Y1.16 | 5423 ± 204 | 5423 ± 139 | 0.000 | 4182.943 ± 123 | 4174 ± 52 | 8.940 | 16675.798 ± 614 | 17189 ± 446 | −513.300 | 8846 ± 175 | 8846 ± 167 | 0.000 |

Table 18 provides a ranked summary of the key compositional elements; which provide for key structure and property responses from the data.

TABLE 18

Summary of the top significant (positive and negative) interaction effects (in terms of L-Pseudo co-efficients, as shown in parentheses) associated with compositional elements (order of significant effects: highest to lowest, ↑ represents positive effects, and ↓ represents negative effects).

| PANEL A: Irregular particles | | PANEL B: Beads | |
|---|---|---|---|
| CT Radiopacity at 70 kVp | CT Radiopacity at 120 kVp | CT Radiopacity at 70 kVp | CT Radiopacity at 120 kVp |
| ↓ SrO ↓ $Y_2O_3$ | ↓ SrO ↓ $Y_2O_3$ | ↑ SrO ↑ $Y_2O_3$ | ↑ SrO ↑ $Y_2O_3$ |
| ↑ $Ga_2O_3$ ↓ $SiO_2$ | ↑ $SiO_2$ ↑ $Ga_2O_3$ | ↑ $Ga_2O_3$ ↑ $SiO_2$ | ↑ $Ga_2O_3$ ↓ $SiO_2$ |

The observed variation between composition and radiopacity at varying kVp values is explained by examining the K-absorption edge of each element. The elements considered in this work have K-absorption edges at the following photon energies: 2.14 keV (Si), 11.12 (Ga), 17.04 (Sr), 17.99 (Y). At 70 kVp, the effective energy of the x-ray spectrum is closer to the K-absorption edge energies; therefore the attenuation properties of the embolic particles are more sensitive to compositional change than at 120 kVp.

No quantitative measure for CT Radiopacity of $Y_2O_3$—SrO—$Ga_2O_3$—$SiO_2$ glass systems currently exists in the literature.

Surprisingly, the CT radiopacity levels of the materials produced exceeded that of the clinical contrast agent (50:50) Isovue contrast media at 2455 HU value (Kilcup et al., 2015). It was determined that at both 70 kVp and 120 kVp, the impact of the compositional elements on enhancing radiopacity for the final beads were in the order SrO>$Y_2O_3$>$Ga_2O_3$. Therefore, to increase radiopacity further, increasing the loading of SrO, $Y_2O_3$ and $Ga_2O_3$ within the glass matrix is warranted.

While the CT radiopacity levels were shown to be substantially higher for the beads evaluated in saline versus the irregular particles and beads evaluated in air (refer to FIG. 10), all material in the form of bead were observed to be significantly higher than the conventional YAS glass at 70 kVp, with 7/10 materials evaluated significantly higher than the same YAS glass at 120 kVp. While the increase in CT radiopacity for materials evaluated in saline versus air is expected (since air has a negative HU value with HU values for saline by comparison at c.0 HU), these observations were unexpected.

Surprisingly, CT radiopacity levels for the materials evaluated in air were observed to be significantly higher for the bead versus irregular particles (at both 70 kVp and 120 kVp as shown in the Figure below), even though their densities were shown to be reduced post-spherodization; a desirable feature for bead product development currently not known in the art.

Biocompatibility Evaluation

Figure 11:
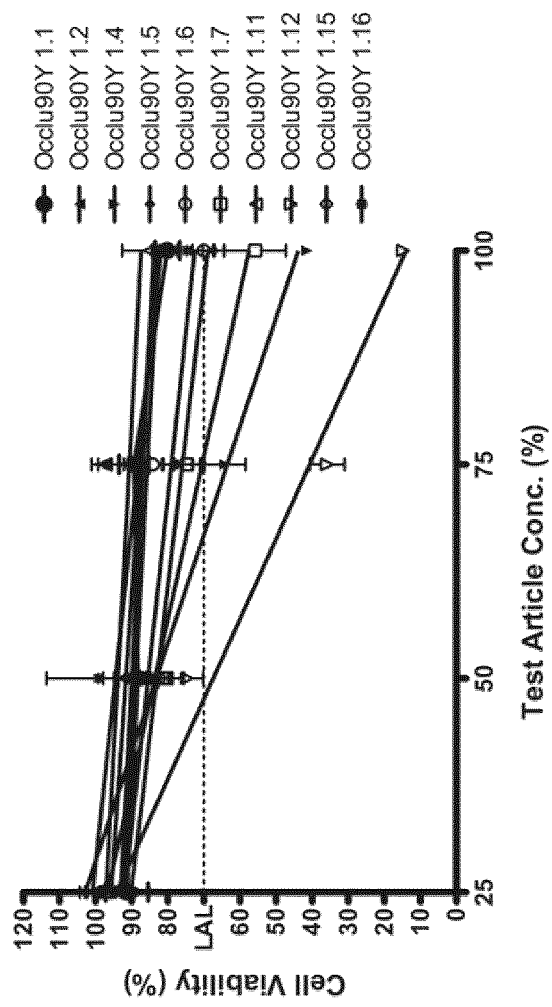
FIG. 11 shows Summary of cell viabilities for Occlu90Y compositions in design space #1 at 25, 50, 75 and 100% concentrations.

The associated cell viabilities for the beads that could be synthesized are provided (refer to FIG. 11). In summary, cell viabilities for compositions satisfying the minimum criterion per ISO10993-5 at all tested concentrations were Occlu90Y 1.1, Occlu90Y 1.2, Occlu90Y 1.6, Occlu90Y 1.11, Occlu90Y 1.5 and Occlu90Y 1.16 with cell viabilities ranging from 75% (for Occlu90Y 1.16 at 100% conc.) to 99.777% (for Occlu90Y 1.11 at 25% conc.). Occlu90Y 1.12 was deemed the most cytotoxic of the 10 bead compositions evaluated with cell viability as low as 14.8% at 25% conc.

In terms of assay validity, the mean OD of vehicle controls was >0.2 and the variance between vehicle controls was ≤15%. The positive controls induced >30% reduction in viability and the negative control induced ≤30% reduction in viability. Therefore, the test system was responding normally and met the criteria for a valid assay. Negative and positive controls were run concurrently with the test article to provide ranges of viability. The positive controls induced a >99% reduction in viability and the negative controls induced 0% reduction in viability. The vehicle control wells had a variance of less than 15%. The mean OD of all vehicle control wells ranged from 0.7805 to 1.187. Therefore, the criteria for a valid assay were met.

TABLE 19

Regression output for the cell viability models.

| | PANEL B: Bead | | | | | |
|---|---|---|---|---|---|---|
| | 25% Conc. | | 50% Conc. | | 75% Conc. | 100% Conc. |
| Term | L-Pseudo Coefficient | Actual Coefficient | L-Pseudo Coefficient | Actual Coefficient | L-Pseudo Coefficient | L-Pseudo Coefficient |
| $Y_2O_3$ | +116.94 | +325.52088 | +95.35 | +73.97431 | +113.47 | +92.92 |
| SrO | +48.60 | +77.03992 | +329.10 | +1650.87426 | −255.34 | −862.36 |
| $Ga_2O_3$ | +93.64 | +240.79606 | +88.60 | +231.15765 | +83.79 | +72.26 |
| $SiO_2$ | +74.45 | −295.57809 | +86.78 | +42.79126 | +94.89 | +88.17 |
| $(SiO_2)^2$ | +35.29 | +466.59957 | — | — | — | — |
| $Y_2O_3$ * $SiO_2$ | — | — | — | — | — | — |
| SrO * $Ga_2O_3$ | — | — | −549.72 | −7268.97643 | +2014.80 | +4422.07 |
| SrO * $Ga_2O_3$ * (SrO—$Ga_2O_3$) | — | — | — | — | +3640.85 | +63559.25 |
| R-squared | | 0.9207 | | 0.7627 | 0.9720 | 0.9603 |
| Adjusted R-squared | | 0.8573 | | 0.5728 | 0.9370 | 0.9106 |
| Predicted R-squared | | 0.6612 | | 0.2308 | 0.7655 | 0.7614 |
| Model F Statistic | | 14.52 | | 14.52 | 27.79 | 19.34 |
| Model Standard Deviation | | 1.40 | | 4.53 | 4.65 | 6.67 |
| Model p-value | | 0.0058 | | 0.9750 | 0.0033 | 0.0066 |

Table 19 shows the actual regression models (in terms of L-pseudo and actual component coding) validity, additional adequacy measures, and ANOVA such as $R^2$, adjusted $R^2$, and predicted $R^2$. All adequacy values are in excess of 0.7, with the exception of the cell viability model at 50% conc.; indicating significant regression models have been realized for cell viability models produced at 25%, 75% and 100%. A tabulated comparison between observed and calculated behaviors of material compositions in the form of irregular particles versus beads is also presented in Table 20 (as based on the regression models using L-pseudo coding).

TABLE 20

Cell viability residuals for each glass.

PANEL B: Bead

| Glass Designation | 25% Conc. | | | 50% Conc. | | | 75% Conc. | | | 100% Conc. | | |
|---|---|---|---|---|---|---|---|---|---|---|---|---|
| | Pred. | Exp. | Resid. | Pred. | Exp. | Resid. | Pred. | Exp. | Resid. | Pred. | Exp. | Resid. |
| Occlu90Y1.1 | 91.174 ± 1.4 | 91.400 ± 5.9 | −0.226 | 88.352 ± 5 | 88.400 ± 5.5 | −0.048 | 87.203 ± 5 | 89.400 ± 4.2 | −2.197 | 77.813 ± 7 | 80.100 ± 3.4 | −2.287 |
| Occlu90Y1.2 | 91.029 ± 1.4 | 90.500 ± 5.4 | 0.529 | 88.104 ± 5 | 92.900 ± 0.7 | −4.796 | 86.816 ± 5 | 89.100 ± 2.1 | −2.284 | 76.601 ± 7 | 81.500 ± 0.4 | −4.899 |
| Occlu90Y1.4 | 97.984 ± 1.4 | 98.700 ± 5.7 | −0.716 | 85.045 ± 5 | 89.300 ± 4.6 | −4.255 | 68.340 ± 5 | 64.100 ± 5.7 | 4.24 | 47.864 ± 7 | 41.500 ± 0.6 | 6.364 |
| Occlu90Y1.5 | 90.953 ± 1.4 | 88.700 ± 0.3 | 2.253 | 84.616 ± 5 | 84.500 ± 1.7 | 0.116 | 77.848 ± 5 | 77.400 ± 4.2 | 0.448 | 68.121 ± 7 | 67.400 ± 2.9 | 0.721 |
| Occlu90Y1.6 | 91.029 ± 1.4 | 92.200 ± 2.1 | −1.171 | 88.104 ± 5 | 82.500 ± 3.9 | 5.604 | 86.816 ± 5 | 84.100 ± 3.0 | 2.716 | 76.601 ± 7 | 70.100 ± 3.1 | 6.501 |
| Occlu90Y1.7 | 97.984 ± 1.4 | 97.500 ± 4.9 | 0.484 | 85.045 ± 5 | 80.400 ± 4.8 | 4.645 | 68.340 ± 5 | 74.700 ± 3.6 | −6.36 | 47.864 ± 7 | 55.800 ± 8.5 | −7.936 |
| Occlu90Y1.11 | 99.777 ± 1.4 | 99.200 ± 3.9 | 0.577 | 88.781 ± 5 | 87.400 ± 7.5 | 1.381 | 96.403 ± 5 | 97.400 ± 1.9 | −0.997 | 86.098 ± 7 | 85.100 ± 7.6 | 0.998 |
| Occlu90Y1.12 | 90.515 ± 1.4 | 90.900 ± 0.9 | −0.385 | 74.641 ± 5 | 74.800 ± 4.5 | −0.159 | 36.849 ± 5 | 35.900 ± 4.8 | 0.949 | 15.473 ± 7 | 14.800 ± 1.4 | 0.673 |
| Occlu90Y1.15 | 95.189 ± 1.4 | 95.200 ± 5.5 | −0.011 | 88.869 ± 5 | 91.400 ± 6.5 | −2.531 | 92.473 ± 5 | 89.600 ± 3.8 | 2.873 | 81.420 ± 7 | 82.200 ± 2.3 | −0.780 |
| Occlu90Y1.16 | 93.565 ± 1.4 | 94.900 ± 3.3 | −1.335 | 99.342 ± 5 | 99.300 ± 14.39 | 0.042 | 97.312 ± 5 | 96.700 ± 4.5 | 0.612 | 75.245 ± 7 | 74.600 ± 7.2 | 0.645 |

Table 21 provides a ranked summary of the key compositional elements; which provide for key structure and property responses from the data.

TABLE 21

Summary of the top significant (positive and negative), individual and interaction effects (in terms of L-Pseudo co-efficients, as shown in parentheses) associated with compositional elements (order of significant effects: highest to lowest, ↑ represents positive effects, and ↓ represents negative effects).
PANEL B: Bead

| 25% Conc. | 50% Conc. | 75% Conc. | 100% Conc. |
|---|---|---|---|
| ↑ $Y_2O_3$ | ↑ SrO | ↑ SrO * $Ga_2O_3$ * (SrO—$Ga_2O_3$) | ↑ SrO * $Ga_2O_3$ * (SrO—$Ga_2O_3$) |
| ↑ $Ga_2O_3$ | ↑ $Y_2O_3$ | ↑ SrO * $Ga_2O_3$ | ↑ SrO * $Ga_2O_3$ |
| ↑ $SiO_2$ | ↑ $Ga_2O_3$ | ↓ SrO | ↓ SrO |
| ↑ SrO | ↑ $SiO_2$ | ↑ $Y_2O_3$ | ↑ $Y_2O_3$ |
| | | ↑ $SiO_2$ | ↑ $SiO_2$ |
| | | ↑ $Ga_2O_3$ | ↑ $Ga_2O_3$ |

No quantitative measures for cell viabilities relative to $Y_2O_3$—SrO—$Ga_2O_3$—$SiO_2$ glass systems currently exists in the literature.

The effect of the compositional elements on the cell viabilities at varying levels of material concentration is not predictive; since no significant models could be determined using either linear or quadratic modeling approaches.

To examine the complex relationships between the primary compositional elements, a cubic model was required to identify the substantive interaction effects between SrO and $Ga_2O_3$ to enhance the cell viabilities at high material concentrations (75% and 100%).

Surprisingly, no predictive relationship could be established for the cell viabilities at a concentration of 50% (Model p-value of 0.9750). Furthermore, while Occlu90Y 1.4, Occlu90Y 1.7 and Occlu90Y 1.12 denoted the top 3 compositions within the design space to yield maximum levels of cytotoxicity at all concentrations; the same compositions were also shown to yield the top 3 highest levels of CT radiopacity at a clinical level (120 kVp). Concurrent to this, Occlu90Y 1.15 and Occlu90Y 1.16 were shown to have slightly lower levels of CT radiopacity, yet exhibited the highest levels of cell viabilities for each concentration. The complex interaction between SrO and $Ga_2O_3$ could not have been predicted without the implementation of a design of experiments approach since such effects are currently unknown in the art.

TABLE 22

Summary table of the top 3 significant (positive and negative), interaction and/or individual effects (in terms of L-Pseudo co-efficients, as shown in parentheses) associated with compositional elements (order of significant effects: highest (left) to lowest (right)).

| Property | Compositional Effect |
|---|---|
| Density | SrO > $Y_2O_3$ > $Ga_2O_3$ |
| $T_g$ | $Y_2O_3$ > $SiO_2$ > $Ga_2O_3$ |
| Sphericity | SrO > $Y_2O_3$ > $Ga_2O_3$ |
| CT Radiopacity at 70 kVp | SrO > $Y_2O_3$ > $Ga_2O_3$ |
| CT Radiopacity at 70 kVp | SrO > $Y_2O_3$ > $Ga_2O_3$ |
| Cell Viability at 25% Conc. | $Y_2O_3$ > $Ga_2O_3$ > $SiO_2$ |
| Cell Viability at 75% Conc. | SrO * $Ga_2O_3$ * (SrO—$Ga_2O_3$) > SrO * $Ga_2O_3$ > SrO |
| Cell Viability at 100% Conc. | SrO * $Ga_2O_3$ * (SrO—$Ga_2O_3$) > SrO * $Ga_2O_3$ > SrO |
| Y Release, 3 d | $Y_2O_3$ * $Ga_2O_3$ > SrO > $Y_2O_3$ |
| Y Release, 7 d | $Y_2O_3$ * $Ga_2O_3$ > SrO > $Y_2O_3$ |
| Y Release, 21 d | $Y_2O_3$ * $Ga_2O_3$ > SrO > $Y_2O_3$ |

*Based on final product (ie. Beads) only.

The provision of an intrinsically radiopaque embolic material for TAE may enable (i) true spatial distribution of the embolic materials to be achieved and (ii) real-time intra-procedural feedback to be obtained by the physician during TAE. From a design standpoint, the current compositional design space was developed to enhance radiopacity, whilst retaining the therapeutic effect of $^{90}Y$.

Subsequently, $Al_2O_3$ was removed from the conventional YAS glass system, with replacement and augmentation of the compositional design space to include previously unknown and unexamined levels of SrO and $Ga_2O_3$ for a silicate based glass system. The primary concern with this approach is that both SrO and $Ga_2O_3$ whose roles in the glass network are to act as a network modifier and intermediate, respectively, may potentially reduce the overall network connectivity to result in enhanced levels of ion release (subsequently minimizing the chemical durability of the glass system). Such an approach may also adversely affect the process ability of the glass as a result of its thermodynamic instability, to result in crystallization.

As shown in Table 22, SrO and $Ga_2O_3$ were found to be the key compositional determinants for each of the critical properties for the $Y_2O_3$—$SiO_2$ glass system; and their impact with respect to each property is currently an unknown in the art.

Shown herein are durable quaternary glasses comprising Si, Ga, Sr and Y. These materials were observed to exhibit excellent durability, releasing <1 ppm of Y and <15 ppm for each of the other components under simulated physiological conditions. It was further noted, from a synthesis standpoint, that glasses with $SiO_2 \geq 0.667$ mol. fraction of the glass could not be produced; for all other elements, the minimum and maximum concentrations associated with the constraints were suitable for glass synthesis.

Materials Optimization

TABLE 23

Optimization design criterion

| Factor(s) | Goal | Lower Limit | Upper Limit | Lower Weight | Upper Weight | Importance |
|---|---|---|---|---|---|---|
| $Y_2O_3$ (mol. fraction) | Target: 0.17 | 0.1 | 0.17 | 1 | 1 | 5 |
| SrO (mol. fraction) | In range | 0.025 | 0.50 | 1 | 1 | 3 |
| $Ga_2O_3$ (mol. fraction) | In range | 0.1 | 0.3 | 1 | 1 | 3 |
| $SiO_2$ (mol. fraction) | In range | 0.50 | 0.75 | 1 | 1 | 3 |
| Bead density (g/cc) | Minimize | 3.56284 | 4.1293 | 1 | 1 | 3 |
| Sphericity (%) | Maximize | 90 | 98 | 1 | 1 | 3 |
| CT Radiopacity at 70 kVp (HU Value) | Maximize | 13,664 | 17,835 | 1 | 1 | 4 |
| CT Radiopacity at 120 kVp (HU Value) | Maximize | 7,341 | 9,790 | 1 | 1 | 4 |
| Cell Viability at 25% Conc. (%) | Maximize | 80 | 100 | 1 | 1 | 3 |
| Cell Viability at 75% Conc. (%) | Maximize | 80 | 100 | 1 | 1 | 3 |
| Cell Viability at 100% Conc. (%) | Maximize | 80 | 100 | 1 | 1 | 3 |
| Y Release, 3 d (ppm) | Minimize | 0.323 | 1.840 | 1 | 1 | 4 |
| Y Release, 7 d (ppm) | Minimize | 0.640 | 2.200 | 1 | 1 | 4 |
| Y Release, 21 d (ppm) | Minimize | 0.780 | 2.007 | 1 | 1 | 4 |

Table 23 defines the optimization design criterion within the ranges of the full compositional design space, whereby the loading of $Y_2O_3$ within the glass system is targeted at 0.17 mol. fraction at maximum importance (5). All other compositional elements and outputs such as, bead density and sphericity were kept within range at a lower level of importance (3). While cell viabilities for each concentration were annotated with a similar level of importance (3), their range was restricted to a minimum of 80% and a maximum of 100%. CT radiopacity and Yttrium release were also kept within range, yet annotated with an intermediary level of importance (4).

TABLE 24

Top 3 optimal compositional solutions

| | Optimal Solutions | | |
|---|---|---|---|
| Factor(s) | 1 | 2 | 3 |
| $Y_2O_3$ (mol. fraction) | 0.170 | 0.170 | 0.156 |
| SrO (mol. fraction) | 0.420 | 0.250 | 0.050 |
| $Ga_2O_3$ (mol. fraction) | 0.190 | 0.144 | 0.190 |
| $SiO_2$ (mol. fraction) | 0.598 | 0.661 | 0.603 |
| Bead density (g/cc) | 3.84326 | 3.62948 | 3.82811 |
| Sphericity (%) | 95.0207 | 91.3674 | 95.2829 |
| CT Radiopacity at 70 kVp (HU Value) | 16,556.0 | 14,812.2 | 16,616.1 |
| CT Radiopacity at 120 kVp (HU Value) | 9,789.9 | 23,150.8 | 9,790.02 |
| Cell Viability at 25% Conc. (%) | 94.5055 | 100.353 | 92.0986 |
| Cell Viability at 75% Conc. (%) | 95.3979 | 97.5618 | 97.5618 |
| Cell Viability at 100% Conc. (%) | 80.6409 | 84.4053 | 84.4053 |
| Y Release, 3 d (ppm) | 0.701392 | 0.54001 | 0.606567 |
| Y Release, 7 d (ppm) | 1.13399 | 1.12679 | 1.00927 |
| Y Release, 21 d (ppm) | 1.17047 | 1.37675 | 0.982523 |
| Desirability Ratio | 1 | 1 | 1 |

Table 24 lists the top 3 compositional variations, derived from the desirability analysis. Of the 3, it is noted that only 2 of the compositional variations satisfy the design criterion of a loading level of 0.17 mol. fraction for $Y_2O_3$. Of the remaining 2 variations, solution #2 predicts minimized density, yet also predicts minimal sphericity, CT radiopacity at 70 kVp and maximized Y release. Solution #1 predicts a higher density, albeit is also predicted to have desirable attributes in terms of its enhanced sphericity and minimized Y release over the 21 d period.

Examples 3 and 4

Microsphere Preparation

A linear screening mixture design was adopted to result in 15 $Y2O3$-SrO—$Ga2O3$-$MnO2$-$TiO2$-$SiO_2$ formulations (per Table 25) of radiopaque radioembolic particles, and will be analyzed using non-simplex algorithms through standard analysis of variance (ANOVA) using Design-Expert (Ver. 9. Stat-Ease Inc.). The ranges for the individual components investigated in Example 3 were set to the following constraints (in mol. fraction):

Constraint 1: $0.10 \leq Y2O3 \leq 0.17$
Constraint 2: $0.025 \leq SrO \leq 0.050$
Constraint 3: $0.10 \leq Ga2O3 \leq 0.30$ Constraint 4: $0.00 \leq TiO2 \leq 0.10$
Constraint 5: $0.00 \leq MnO \leq 0.05$
Constraint 6: $0.50 \leq SiO2 \leq 0.75$

*Where Y2O3+SrO+Ga2O3+TiO2+MnO2+SiO2=1.0

Example 4 describes further screening and optimization studies of the compositions comprising strontium described herein. A quadratic optimal mixture design was adopted to result in 11 SrO—Ga2O3-MnO2-TiO2-SiO$_2$ formulations (per Table 26) of radiopaque radioembolic particles, and shall be anlayzed using IV-Optimal algorithms through standard analysis of variance (ANOVA) using Design-Expert (Ver. 9. Stat-Ease Inc.). The ranges for the individual components investigated were set to the following constraints (in mol. fraction):
Constraint 1: $0.05 \leq SrO \leq 0.15$
Constraint 2: $0.10 \leq Ga2O3 \leq 0.30$
Constraint 3: $0.00 \leq TiO2 \leq 0.10$
Constraint 4: $0.00 \leq MnO \leq 0.05$
Constraint 5: $0.50 \leq SiO2 \leq 0.75$

*Where SrO+Ga2O3+TiO2+MnO2+SiO2=1.0

TABLE 25

15 compositions (in mol. fraction) formulated using a linear non-simplex screening mixture design #2.

| | Y2O3 | SrO | Ga2O3 | SiO2 | TiO2 | *MnO2 |
|---|---|---|---|---|---|---|
| Occlu90Y_2.1 | 0.100 | 0.025 | 0.100 | 0.670 | 0.100 | 0.005 |
| Occlu90Y_2.2 | 0.100 | 0.050 | 0.100 | 0.750 | 0.100 | 0.000 |
| Occlu90Y_2.3 | 0.100 | 0.050 | 0.250 | 0.500 | 0.100 | 0.000 |
| Occlu90Y_2.4 | 0.170 | 0.025 | 0.205 | 0.500 | 0.100 | 0.000 |
| Occlu90Y_2.5 | 0.100 | 0.050 | 0.300 | 0.500 | 0.045 | 0.005 |
| Occlu90Y_2.6 | 0.170 | 0.025 | 0.300 | 0.500 | 0.000 | 0.005 |
| Occlu90Y_2.7 | 0.100 | 0.025 | 0.120 | 0.750 | 0.000 | 0.005 |
| Occlu90Y_2.8 | 0.131 | 0.037 | 0.193 | 0.594 | 0.042 | 0.002 |
| Occlu90Y_2.9 | 0.131 | 0.037 | 0.193 | 0.594 | 0.042 | 0.002 |
| Occlu90Y_2.10 | 0.100 | 0.050 | 0.300 | 0.550 | 0.000 | 0.000 |
| Occlu90Y_2.11 | 0.170 | 0.050 | 0.100 | 0.680 | 0.000 | 0.000 |
| Occlu90Y_2.12 | 0.170 | 0.050 | 0.100 | 0.575 | 0.100 | 0.005 |
| Occlu90Y_2.13 | 0.131 | 0.037 | 0.193 | 0.594 | 0.042 | 0.002 |
| Occlu90Y_2.14 | 0.100 | 0.025 | 0.100 | 0.675 | 0.100 | 0.000 |
| Occlu90Y_2.15 | 0.170 | 0.025 | 0.300 | 0.500 | 0.005 | 0.000 |

Table 26 describes compositions formulated without yttrium, where Manganese and Titanium will provide the therapeutic effect.

TABLE 26

15 compositions (in mol. fraction) formulated using a quadratic IV-Optimal screening mixture design #4.

| | SrO | Ga2O3 | SiO2 | TiO2 | *MnO2 |
|---|---|---|---|---|---|
| Occlu89Sr_4.1 | 0.150 | 0.245 | 0.500 | 0.100 | 0.005 |
| Occlu89Sr_4.2 | 0.050 | 0.300 | 0.650 | 0.000 | 0.000 |
| Occlu89Sr_4.3 | 0.150 | 0.300 | 0.550 | 0.000 | 0.000 |
| Occlu89Sr_4.4 | 0.150 | 0.245 | 0.500 | 0.100 | 0.005 |
| Occlu89Sr_4.5 | 0.050 | 0.195 | 0.750 | 0.000 | 0.005 |
| Occlu89Sr_4.6 | 0.150 | 0.100 | 0.745 | 0.000 | 0.005 |
| Occlu89Sr_4.7 | 0.050 | 0.100 | 0.750 | 0.100 | 0.000 |
| Occlu89Sr_4.8 | 0.150 | 0.100 | 0.745 | 0.000 | 0.005 |
| Occlu89Sr_4.9 | 0.150 | 0.100 | 0.648 | 0.100 | 0.002 |
| Occlu89Sr_4.10 | 0.050 | 0.100 | 0.750 | 0.100 | 0.000 |
| Occlu89Sr_4.11 | 0.150 | 0.200 | 0.650 | 0.000 | 0.000 |

Material compositions denoted Occlu90Y 2.1 to Occlu90Y 2.15 and OccluSr89 4.1 to 4.11 (per Tables 25 and 26) were synthesized. Analytical grade reagents: strontium carbonate (Sigma-Aldrich, Milwaukee, US), yttrium oxide, gallium oxide and silicon dioxide (Sigma-Aldrich, Oakville, CAN) were weighed using an analytical balance (ABT 320-4M, Kern & Sohn GmbH, Germany) and homogeneously mixed in a rugged rotator (099A RD9912, Glas-Col, Atlanta, Ga., USA) for 1 h. Each composition was packed into 50 mL or 60 mL platinum crucibles (Alpha Aesar, USA), then fired (1550° C., 3 h) using a high temperature furnace (Carbolite RHF 1600, UK) and shock quenched into distilled water at ambient temperature. The resulting glass irregular particles was dried in an oven (100° C., 24 h), pulverized in an agate planetary mill (Pulverisette 7; Laval Labs Inc., Canada) and sieved to retrieve irregular particulates in the size range of 20-75 μm.

The particles retrieved were subsequently formed into glass microspheres by introducing the irregular particles into a gas/oxygen flame where they were melted and a spherical liquid droplet formed by surface tension. The droplet rapidly cooled before it touched any solid object so that its spherical shape was retained in the solid. Prior to spheroidization, the irregular particles were placed in a vibratory feeder located above the gas/oxygen burner and slowly vibrated into a vertical glass tube guiding the powder particles directly into the hot flame of the gas/oxygen burner at a powder feed rate 5 to 25 g/hr. The flame of the burner was directed into a stainless steel container, which collected the small glass beads as they were expelled from the flame, and subsequently screened with a sonic sifter.

X-Ray Diffraction

X-ray diffraction (XRD) measurements for each material composition in the form of both irregular particles and bead were performed using a Bruker D8 Advance XRD system with a high speed LynxEye™ detector coupled to an X-ray generator (40 kV, 40 mA) and equipped with a Cu target X-ray tube. Specimens of each experimental glass were prepared by pressing the materials (Ø8.5 mm) into Poly (methyl methacrylate) (PMMA) holder rings. The detector collected all scattered X-rays in the scan angle range $10° < 2\theta < 100°$. The handling station in the system allowed measurement and move operations to sequentially analyze up to nine different specimens in an automated, unattended manner.

Particle Size Analysis

The particle size distribution for each glass bead formulation (20-75 μm) was determined using the Mastersizer 3000 (Malvern, UK). Bead suspensions in deionized were prepared to get the obscuration value to range between 6-8%. Suspensions were then measured (n=5) using both a blue ($\lambda$=470 nm) and red ($\lambda$=632.8 nm) laser with values reported as the mean diameter d90, d50 and d10; representative of particle diameters at 90, 50 and 10% cumulative size, respectively.

Helium Pycnometry

The true density of each material composition (0.75 cc of glass in the particle size range of 20-75 μm) in the form of both irregular particles and beads were measured using helium pycnometry (AccuPyc 1340, Micromeritics) with results representative of an average of 10 measurements per composition.

Differential Scanning Calorimeter

A Differential Scanning calorimeter (DSC) 404 F1 Pegasus (404 F1 Pegasus, Netzsch) was used to measure the glass transition temperature ($T_g$) for each material composition in the form of both irregular particles and bead inside platinum crucibles over the temperature range of 20 to 1000° C. The heating profile used followed the order of heating to 500° C. at a heating rate of 30° C./min up to prior to heating from 500° C. to 1000° C. a rate of 10° C./min. Measurements were conducted under flowing argon (99.999%, Air Liquide, Canada) at a rate of 50 mL/min. The DSC was calibrated using melting points for pure In, Al, Sn, Au and Ag. $T_g$ at the inflection point for the step change in the heat flow curve was determined using Proteus Analysis software (Version 6.1).

Scanning Electron Microscope

Carbon coated morphologies for each bead composition was examined using a Hitachi S-4700 Scanning Electron Microscope (SEM), operating at an accelerating voltage of 3 KV accelerating voltage, 15.5 μA emission current, and 12.2 mm working distance.

One-way ANOVA was employed for density, $T_g$ and percentage sphericity followed by a Neuman-Keuls test to compare the mean values. Data was considered significant when p≤0.5. All calculations were done using Prism 6 for Mac OS X (GraphPad Software Inc., La Jolla, USA).

X-Ray Diffraction

Figure 12:
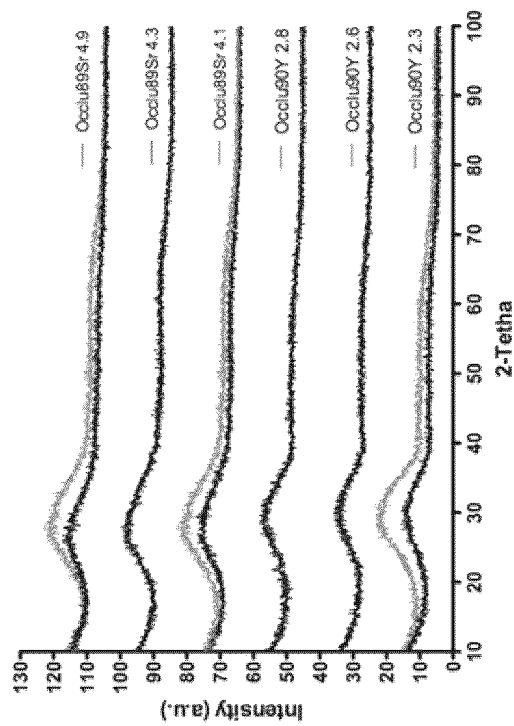
FIG. 12 shows XRD-spectra for each composition pre- (Irregular particles (grey colored spectra)) and post- (Bead) spherodization for Occlu90Y design space #2 and Occlu89Sr design space #4.

Three compositions from design space #2 comprising of (i) a high Ti and low Mn loading, (ii) median loadings for both Ti and Mn and (iii) a low Ti and high Mn loading were prepared herein. A further three compositions from design space #4 comprising of high, median and low loadings of Sr where prepared with all six compositions permitting 'ease of melt' and confirmed as amorphous with no evidence of any crystallinity based on their XRD spectra as shown in FIG. 12.

Table 27 shows the yttrium bead compositions in mole fractions.

| Formulation # | SrO | $Ga_2O_3$ | $Y_2O_3$ | $SiO_2$ |
|---|---|---|---|---|
| Formulation 1 | 0.05 | 0.21 | 0.10 | 0.64 |
| Formulation 2 | 0.05 | 0.14 | 0.17 | 0.64 |
| Formulation 3 | 0.14 | 0.05 | 0.17 | 0.64 |

Table 28 shows the ytrrium bead compositions in mass percentages by element.

| Formulation # | SrO | Ga2O3 | Y2O3 | SiO2 |
|---|---|---|---|---|
| Formulation 1 | 9.55 | 31.91 | 19.38 | 39.17 |
| Formulation 2 | 9.28 | 20.67 | 32.00 | 38.06 |
| Formulation 3 | 25.12 | 7.14 | 30.95 | 36.80 |

Formulation 1: 24 h Irradiation 100 mg of the composition of formulation 1 was irradiated for 24 h at 2E+14 n/cm·s. Table 29 shows the radioisotopes formed at different times after the end of irradiation (EOI). The $^{90}Y$ radionuclidic purity of the composition is also shown (percentage).

Table 29 shows radioisotopes formed from Formulation 1 after 24 h irradiation of 100 mg sample at 2E+14 n/cm$^2$ · s (all activities in MBq).

| EOI + h | Y-90 | Sr-85 | Sr-89 | Ga-70 | Ga-72 | Si-31 | % Y-90 |
|---|---|---|---|---|---|---|---|
| 0 | 7,687 | 0.0 | 1.013 | 91,740 | 3,547 | 556 | 7.42 |
| 12 | 6,750 | 0.0 | 1.006 | 0.00000518 | 1,966 | 23.29 | 77.23 |
| 36 | 5,205 | 0.0 | 0.993 | 0.0 | 604.4 | 0.0409 | 89.58 |
| 60 | 4,013 | 0.0 | 0.979 | 0.0 | 185.7 | 0.0000717 | 95.55 |
| 84 | 3,095 | 0.0 | 0.966 | 0.0 | 57.08 | 0.0 | 98.16 |
| 108 | 2,386 | 0.0 | 0.953 | 0.0 | 17.54 | 0.0 | 99.23 |
| 132 | 1,840 | 0.0 | 0.940 | 0.0 | 5.392 | 0.0 | 99.66 |
| 156 | 1,419 | 0.0 | 0.927 | 0.0 | 1.657 | 0.0 | 99.82 |
| 180 | 1,094 | 0.0 | 0.914 | 0.0 | 0.509 | 0.0 | 99.87 |
| 204 | 843.8 | 0.0 | 0.902 | 0.0 | 0.157 | 0.0 | 99.87 |
| 228 | 650.6 | 0.0 | 0.889 | 0.0 | 0.048 | 0.0 | 99.86 |
| 252 | 501.7 | 0.0 | 0.877 | 0.0 | 0.0148 | 0.0 | 99.82 |
| 276 | 386.9 | 0.0 | 0.865 | 0.0 | 0.0045 | 0.0 | 99.78 |
| 300 | 298.3 | 0.0 | 0.854 | 0.0 | 0.0014 | 0.0 | 99.71 |
| 324 | 230.0 | 0.0 | 0.842 | 0.0 | 0.0 | 0.0 | 99.64 |
| 348 | 177.3 | 0.0 | 0.830 | 0.0 | 0.0 | 0.0 | 99.53 | where EOI = End of Irradiation. Ex. "EOI + 12" is the activities present 12 h after EOI; % Y-90 and for radionuclidic purity of Y-90 (percentage); pale shading indicates radionuclidic purity >99.0% and brighter shading indicates data used for further analysis.

Helium Pycnometry and Differential Scanning Calorimeter

Figure 13:
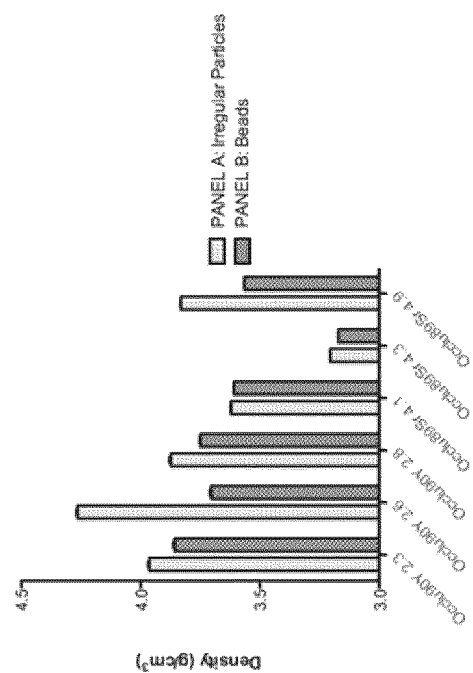
FIG. 13 shows summary of densities for irregular particles versus bead Occlu90Y compositions for design space #2 and Occlu89Sr compositions for design space #4.
Figure 14:
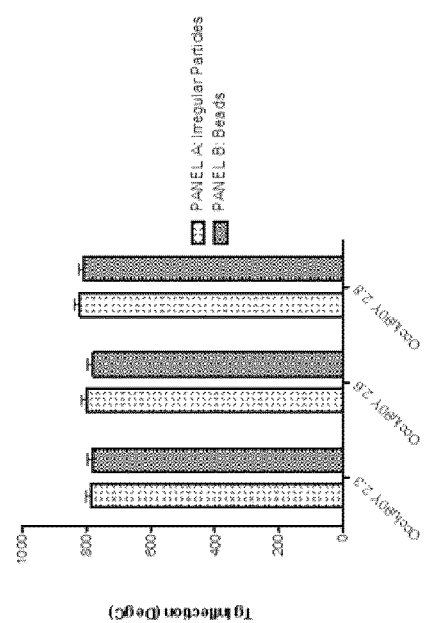
FIG. 14 shows summary of glass transition temperatures for irregular particles versus bead Occlu90Y compositions for design space #2 and Occlu89Sr compositions for design space #4.

The associated density for the materials prepared in each design space formed glass irregular particles with mean densities ranging from 3.2 to 4.3 g/cm$^3$, which were subsequently transformed to beads with mean densities ranging from 3.2 to 3.9 g/cm$^3$ (refer to FIG. 13). The associated $T_g$ for the Occlu$^{90}$Y design space #2 materials prepared formed glass irregular particles with mean $T_g$ ranging from 787 to 821° C., which were subsequently transformed to beads with mean $T_g$ ranging from 780 to 809° C. (refer FIG. 14).

Example 5

This example describes the projected theoretical radioisotope composition produced by irradiation of the compositions described herein.

Figure 15:
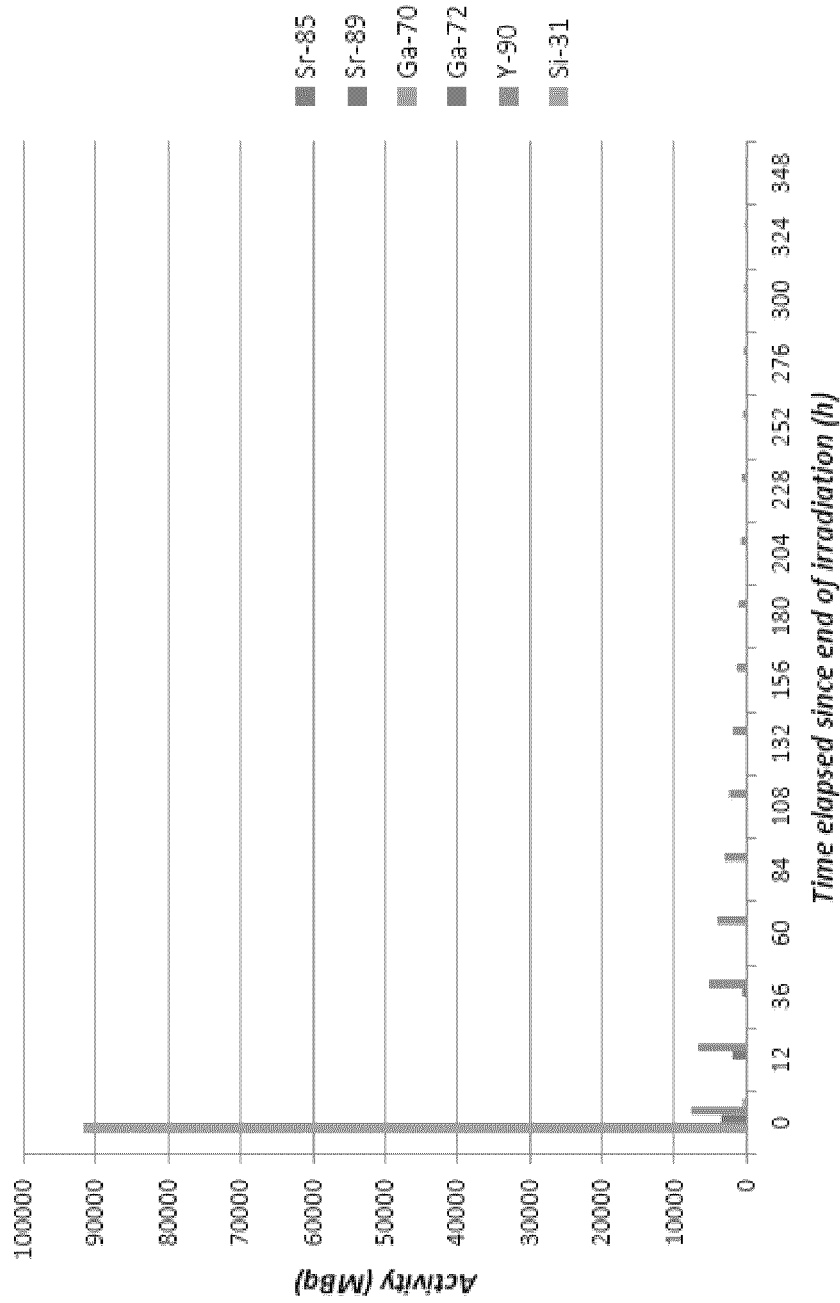
FIG. 15 shows total radioactivity present per 100 mg of Formulation 1 after 24 h irradiation of 100 mg sample at 2E+14 $n/cm^2 \cdot s$ (all activities in MBq). The x-axis shows time elapsed since end of irradiation (hours). The vertical bars show the activity for Sr-85, Sr-89, Ga-70, Ga-72, $^{90}Y$, and Si-31.
Figure 16:
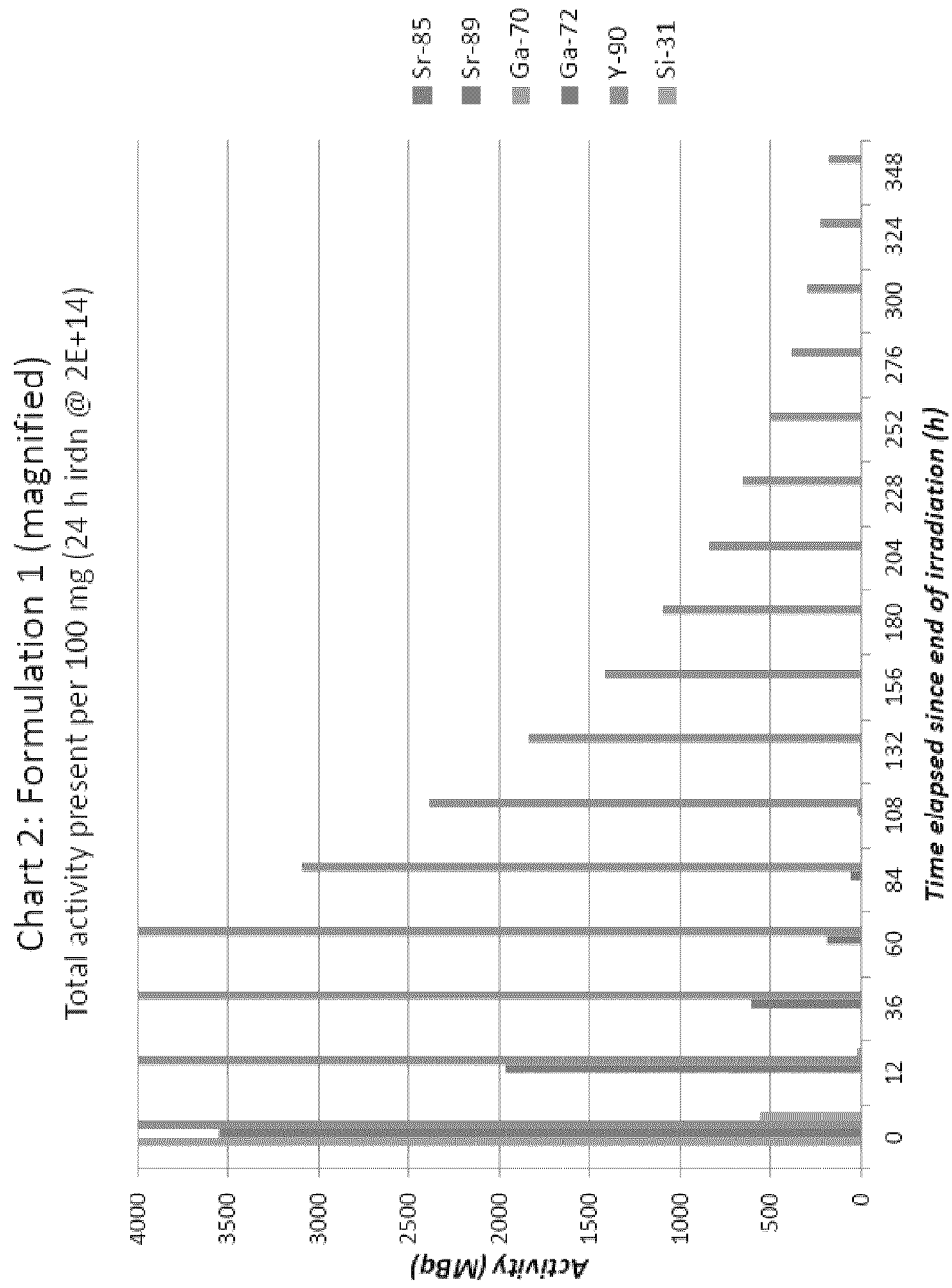
FIG. 16 shows the data from FIG. 15 with a different scale for the y-axis to more clearly show values of total radioactivity below 4000 MBq.
Figure 17:
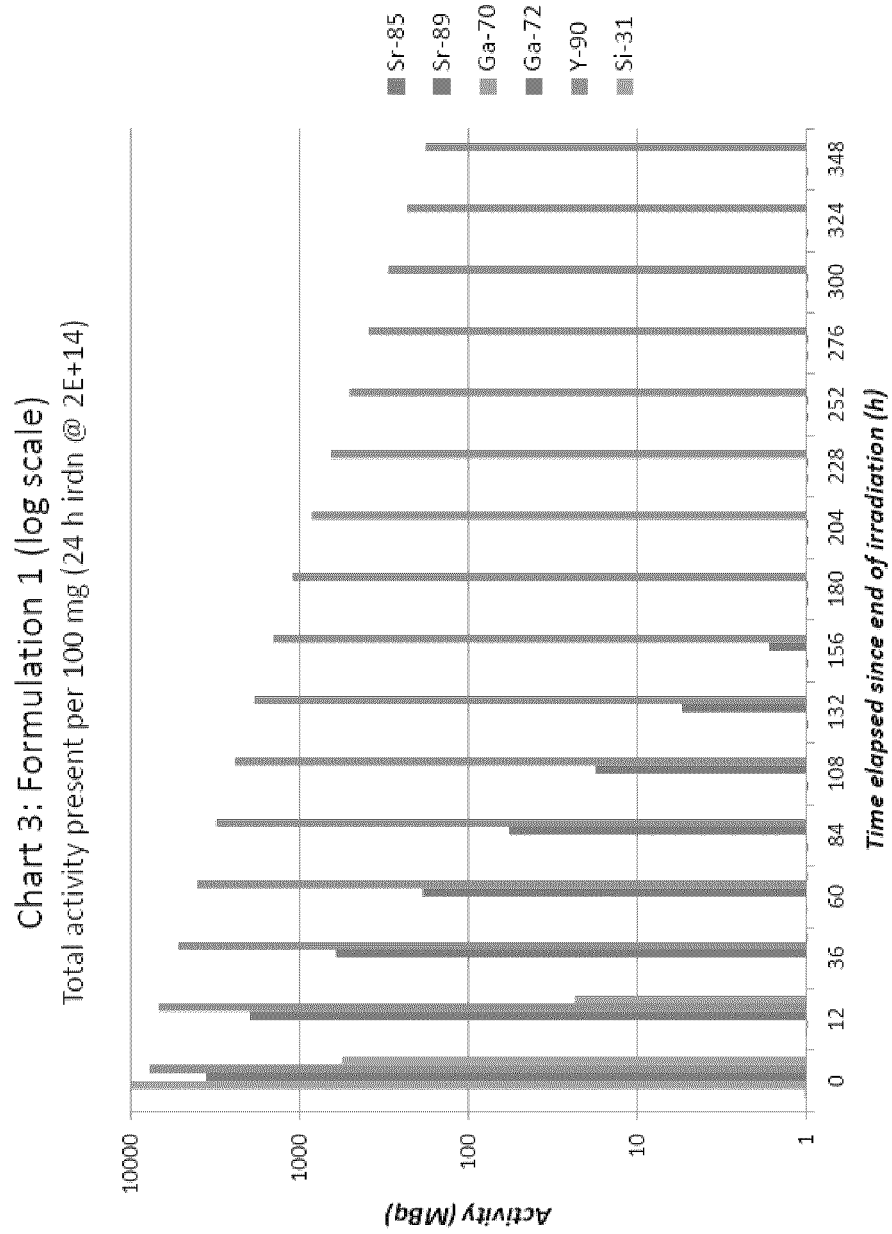
FIG. 17 shows the data from FIG. 15 with a log scale for the y-axis.
Figure 18:
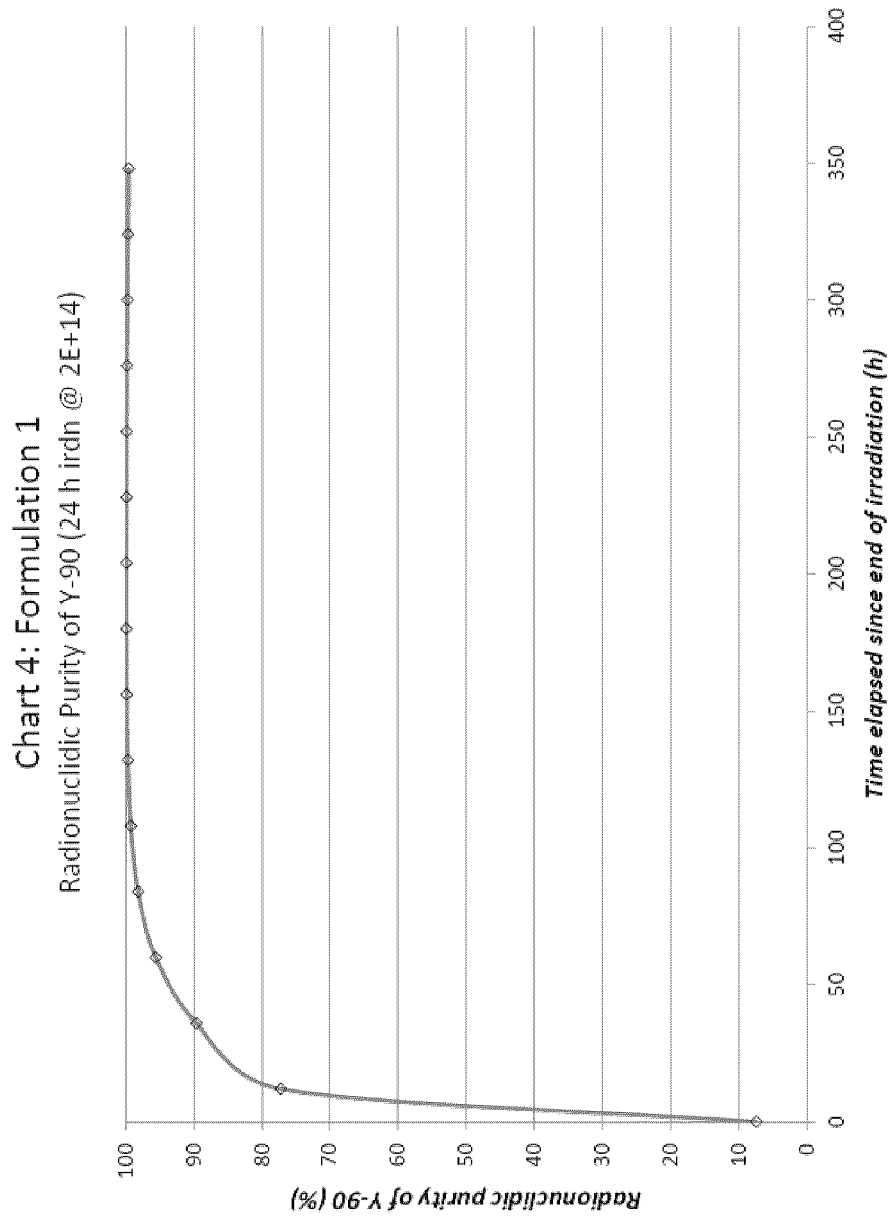
FIG. 18 shows the radionuclidic purity of $^{90}Y$ after irradiation under the conditions of FIG. 15. The x-axis shows time elapsed since end of irradiation (hours). The y-axis shows the radionuclidic purity of $^{90}Y$ as a percent of total radioactivity.

FIGS. 15 and 16 show the total activity for each isotope as bar graphs based on the data in Table 29, with different linear scales on the Y-axis. FIG. 17 shows the data where the Y-axis is a log scale. FIG. 18 shows the radionuclide purity of the Y-90 composition based on time elapsed since the EOI. By 108 h EOI, the purity was greater than 99.0%.

Formulation 1: 72 h Irradiation 100 mg of the composition of formulation 1 was irradiated for 72 h at 2E+14 n/cm·s. Table 30 shows the radioisotopes formed at different times after the end of irradiation (EIO). The $^{90}Y$ radionuclidic purity of the composition is also shown (percentage).

Table 30 shows radioisotopes formed from Formulation 1 after 24 h irradiation of 100 mg sample at 2E+14 n/cm$^2$ · s (all activities in MBq).

| EOI + h | Y-90 | Sr-85 | Sr-89 | Ga-70 | Ga-72 | Si-31 | % Y-90 |
|---|---|---|---|---|---|---|---|
| 0 | 18,180 | 0.0 | 2.998 | 91,730 | 4,972 | 557 | 15.75 |
| 12 | 15,960 | 0.0 | 2.978 | 0.00000518 | 2,756 | 23.33 | 85.15 |
| 36 | 12,310 | 0.0 | 2.937 | 0.0 | 847 | 0.04094 | 93.54 |
| 60 | 9,495 | 0.0 | 2.897 | 0.0 | 260 | 0.0000718 | 97.30 |
| 84 | 7,332 | 0.0 | 2.858 | 0.0 | 80 | 0.0 | 98.88 |
| 108 | 5,66 | 0.0 | 2.819 | 0.0 | 24.59 | 0.0 | 99.52 |
| 132 | 4,353 | 0.0 | 2.780 | 0.0 | 7.557 | 0.0 | 99.76 |
| 156 | 3,357 | 0.0 | 2.742 | 0.0 | 2.322 | 0.0 | 99.85 |
| 180 | 2,588 | 0.0 | 2.705 | 0.0 | 0.714 | 0.0 | 99.87 |
| 204 | 1,996 | 0.0 | 2.668 | 0.0 | 0.219 | 0.0 | 99.86 |
| 228 | 1,539 | 0.0 | 2.632 | 0.0 | 0.0674 | 0.0 | 99.82 |
| 252 | 1,186 | 0.0 | 2.596 | 0.0 | 0.0207 | 0.0 | 99.78 |
| 276 | 915.2 | 0.0 | 2.560 | 0.0 | 0.0064 | 0.0 | 99.72 |
| 300 | 705.7 | 0.0 | 2.526 | 0.0 | 0.00196 | 0.0 | 99.64 |
| 324 | 544.2 | 0.0 | 2.491 | 0.0 | 0.00006 | 0.0 | 99.54 |
| 348 | 419.6 | 0.0 | 2.457 | 0.0 | 0.000184 | 0.0 | 99.42 | where EOI = End of Irradiation. Ex. "EOI + 12" is the activities present 12 h after EOI; % Y-90 and for radionuclidic purity of Y-90 (percentage); pale shading indicates radionuclidic purity >99.0% and brighter shading indicates data used for further analysis.

Figure 19:
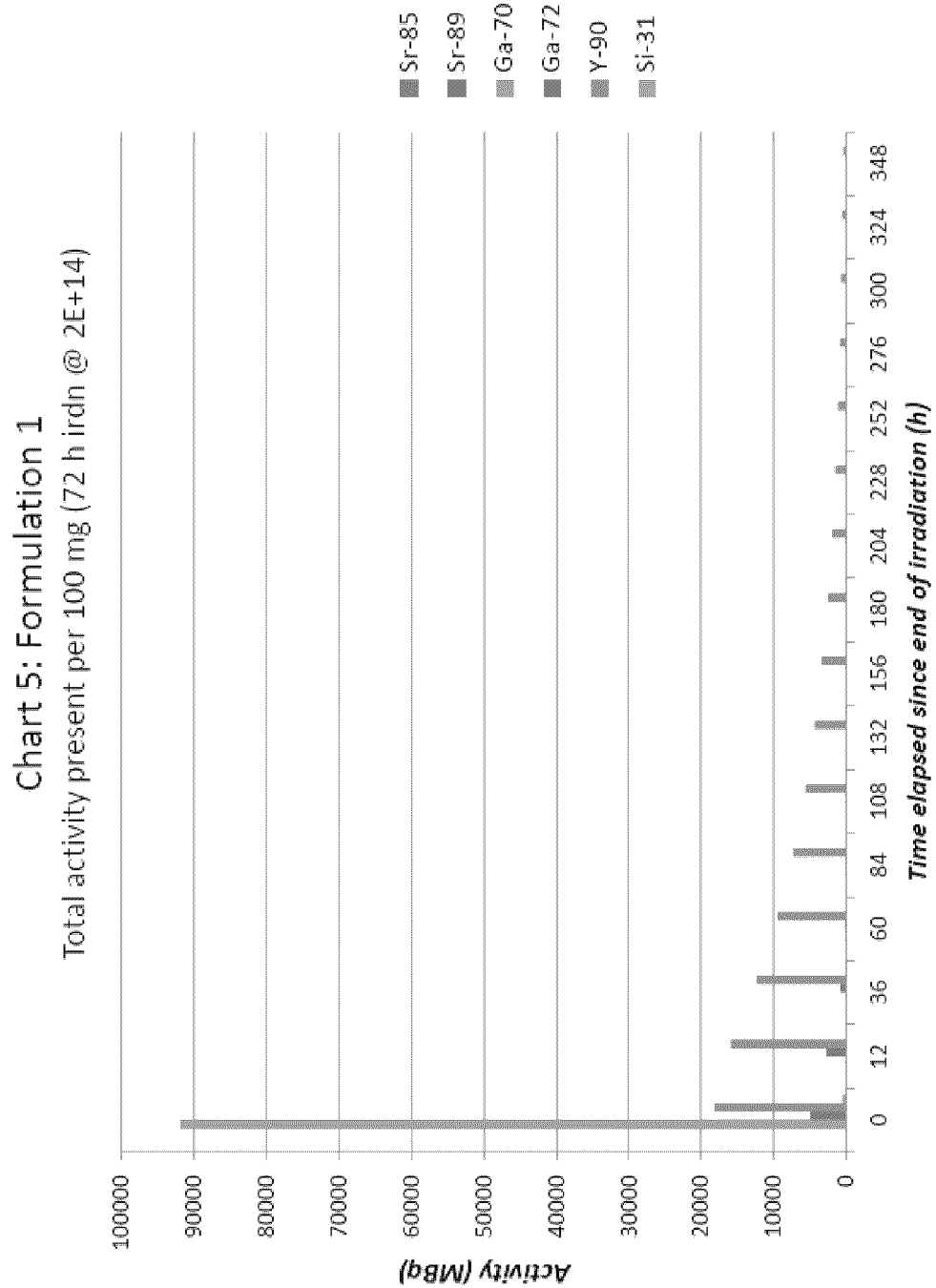
FIG. 19 shows total radioactivity present per 100 mg of Formulation 1 after 72 h irradiation of 100 mg sample at 2E+14 $n/cm^2 \cdot s$ (all activities in MBq). The x-axis shows time elapsed since end of irradiation (hours). The vertical bars show the activity for Sr-85, Sr-89, Ga-70, Ga-72, $^{90}Y$, and Si-31.
Figure 20:
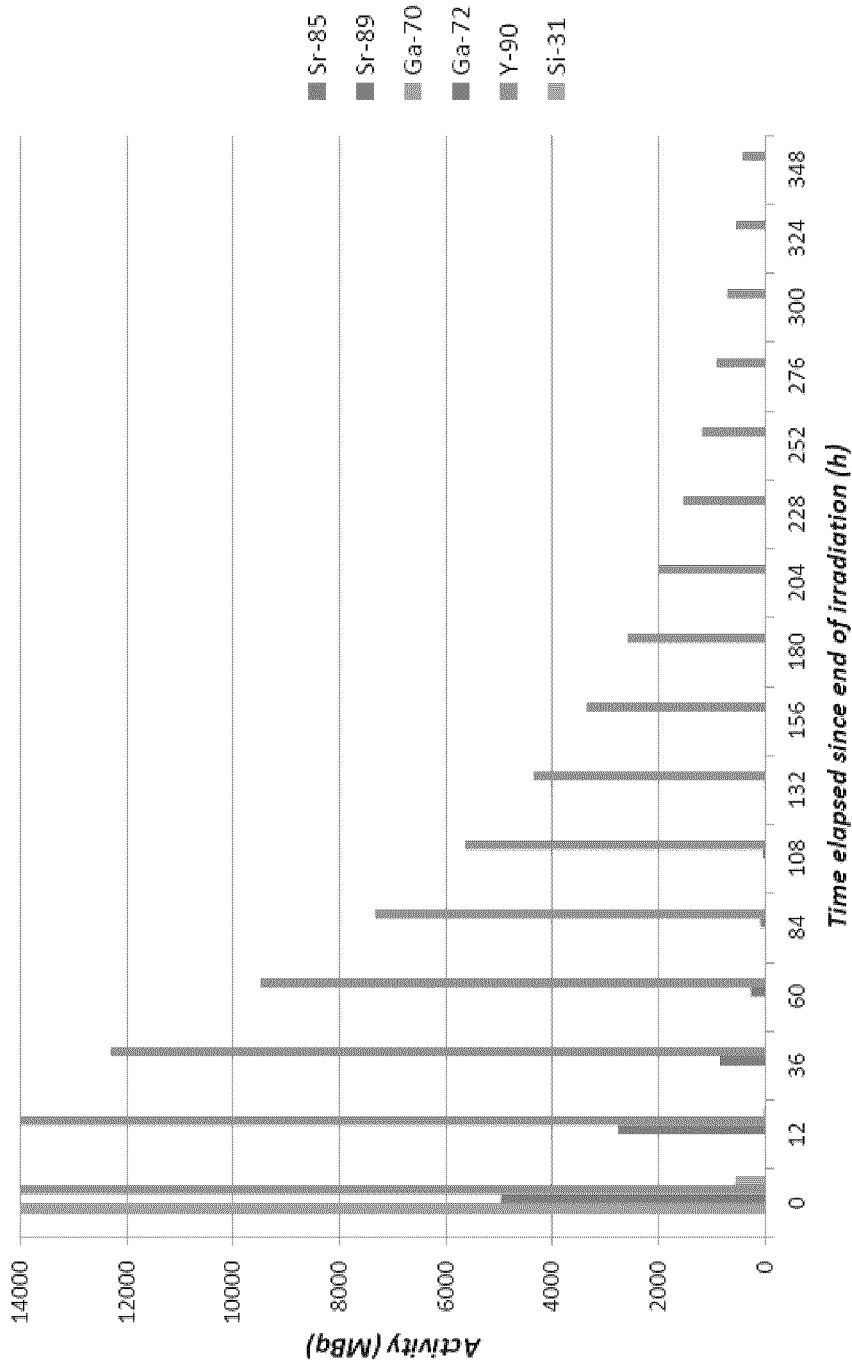
FIG. 20 shows the data from FIG. 19 with a different scale for the y-axis to more clearly show values of total radioactivity below 14000 MBq.
Figure 21:
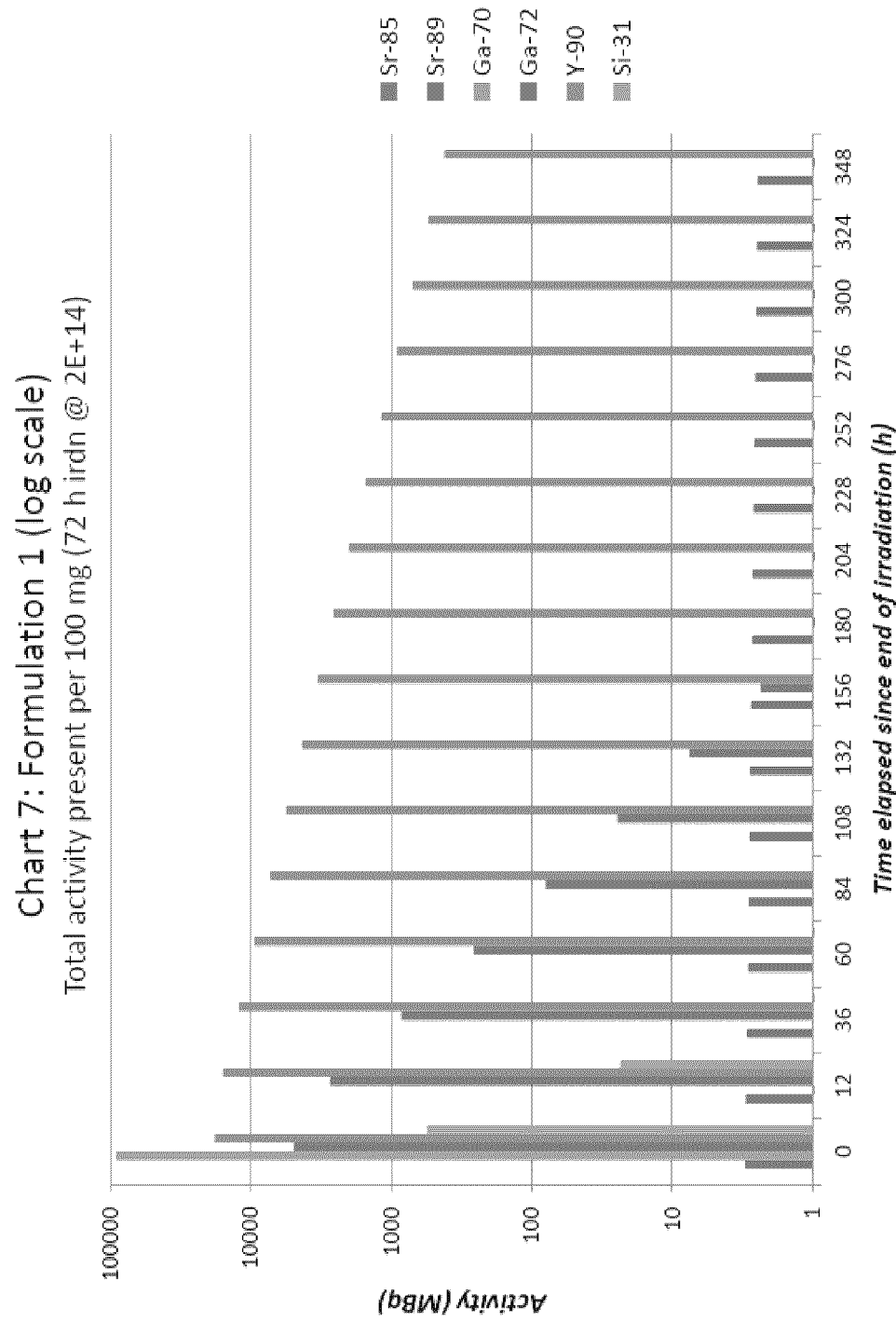
FIG. 21 shows the data from FIG. 19 with a log scale for the y-axis.
Figure 22:
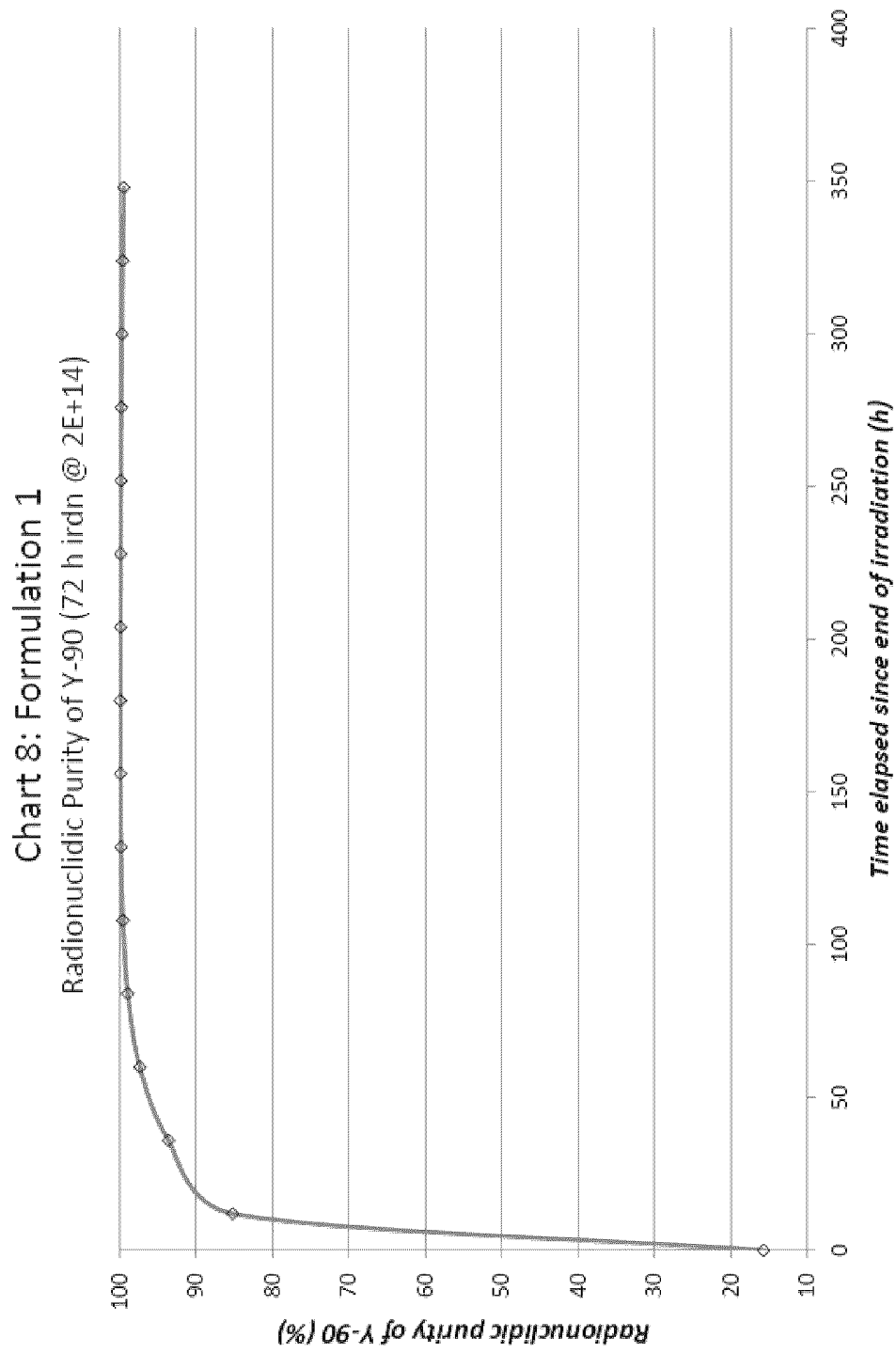
FIG. 22 shows the radionuclidic purity of $^{90}Y$ after irradiation under the conditions of FIG. 19. The x-axis shows time elapsed since end of irradiation (hours). The y-axis shows the radionuclidic purity of $^{90}Y$ as a percent of total radioactivity.

FIGS. 19 and 20 show the total activity for each isotope as bar graphs based on the data in Table 30, with different linear scales on the Y-axis. FIG. 21 shows the data where the Y-axis is a log scale. FIG. 22 shows the radionuclide purity of the $^{90}$Y composition based on time elapsed since the EOI. By 108 h EOI, the purity was greater than 99.0%.

Formulation 2: 24 h Irradiation 100 mg of the composition of formulation 2 was irradiated for 24 h at 2E+14 n/cm·s. Table 31 shows the radioisotopes formed at different times after the end of irradiation (EIO). The $^{90}$Y radionuclidic purity of the composition is also shown (percentage).

Figure 23:
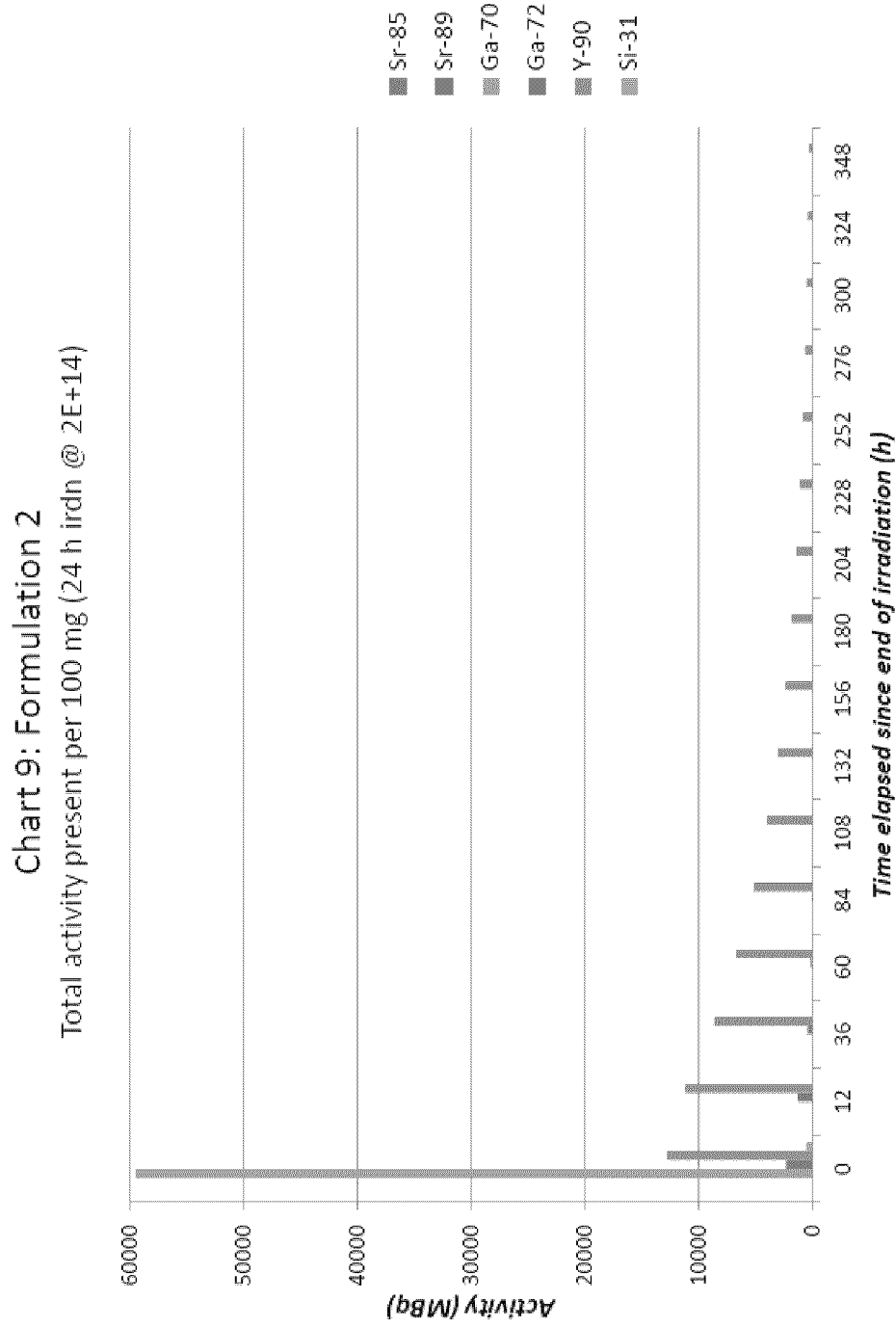
FIG. 23 shows total radioactivity present per 100 mg of Formulation 2 after 24 h irradiation of 100 mg sample at 2E+14 n/cm$^2$·s (all activities in MBq). The x-axis shows time elapsed since end of irradiation (hours). The vertical bars show the activity for Sr-85, Sr-89, Ga-70, Ga-72, $^{90}Y$, and Si-31.
Figure 24:
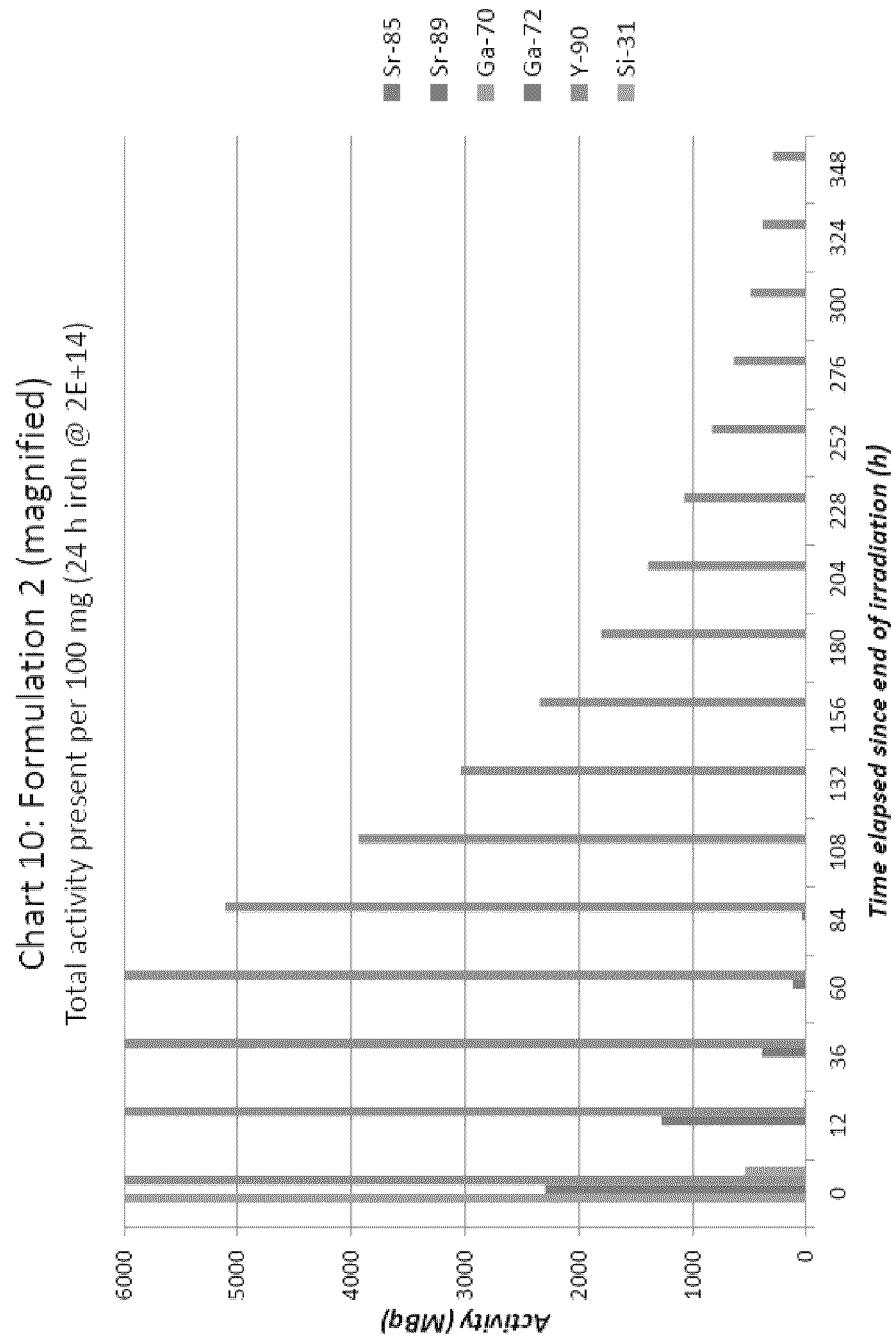
FIG. 24 shows the data from FIG. 23 with a different scale for the y-axis to more clearly show values of total radioactivity below 8000 MBq.
Figure 25:
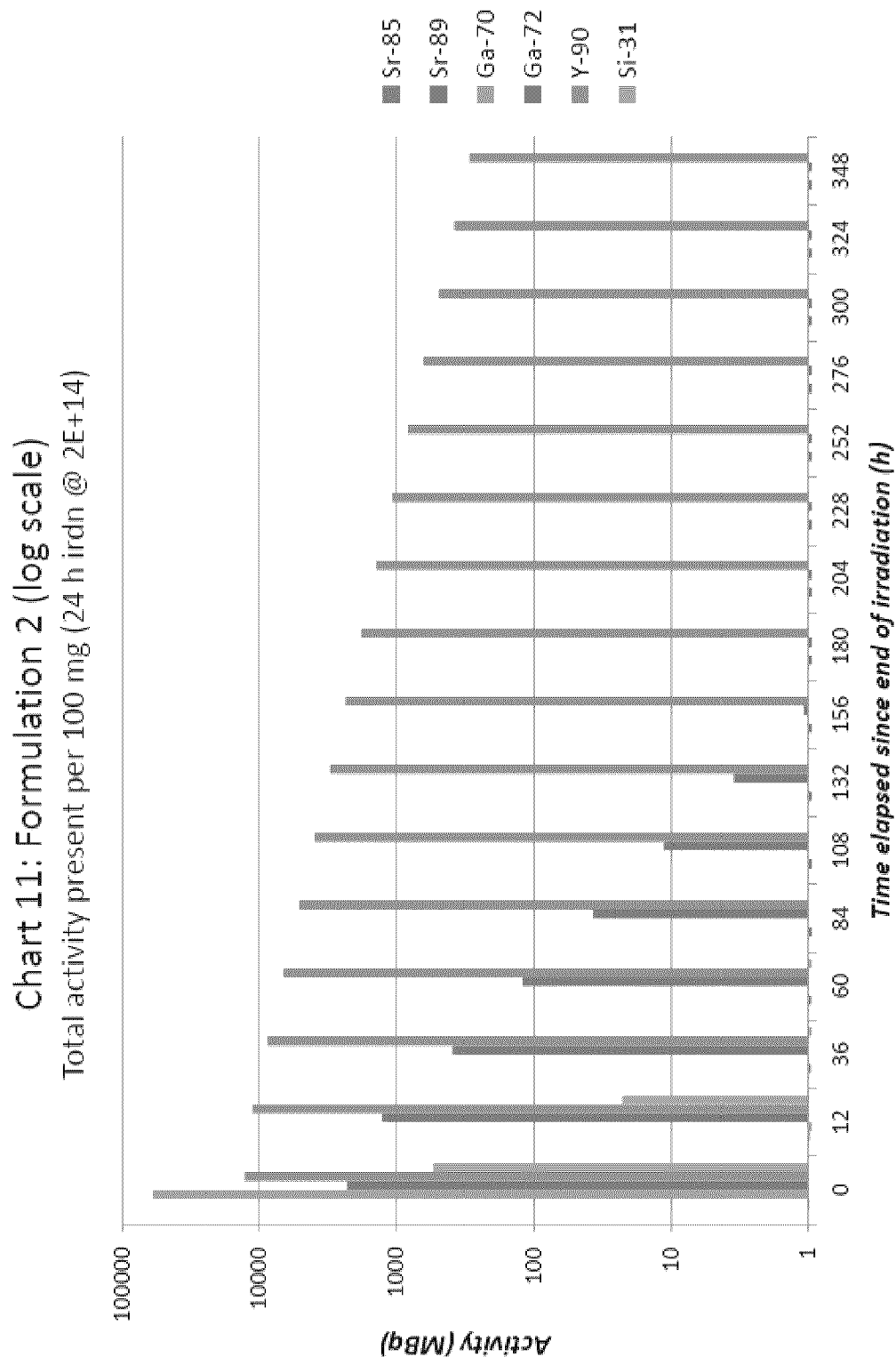
FIG. 25 shows the data from FIG. 23 with a log scale for the y-axis.
Figure 26:
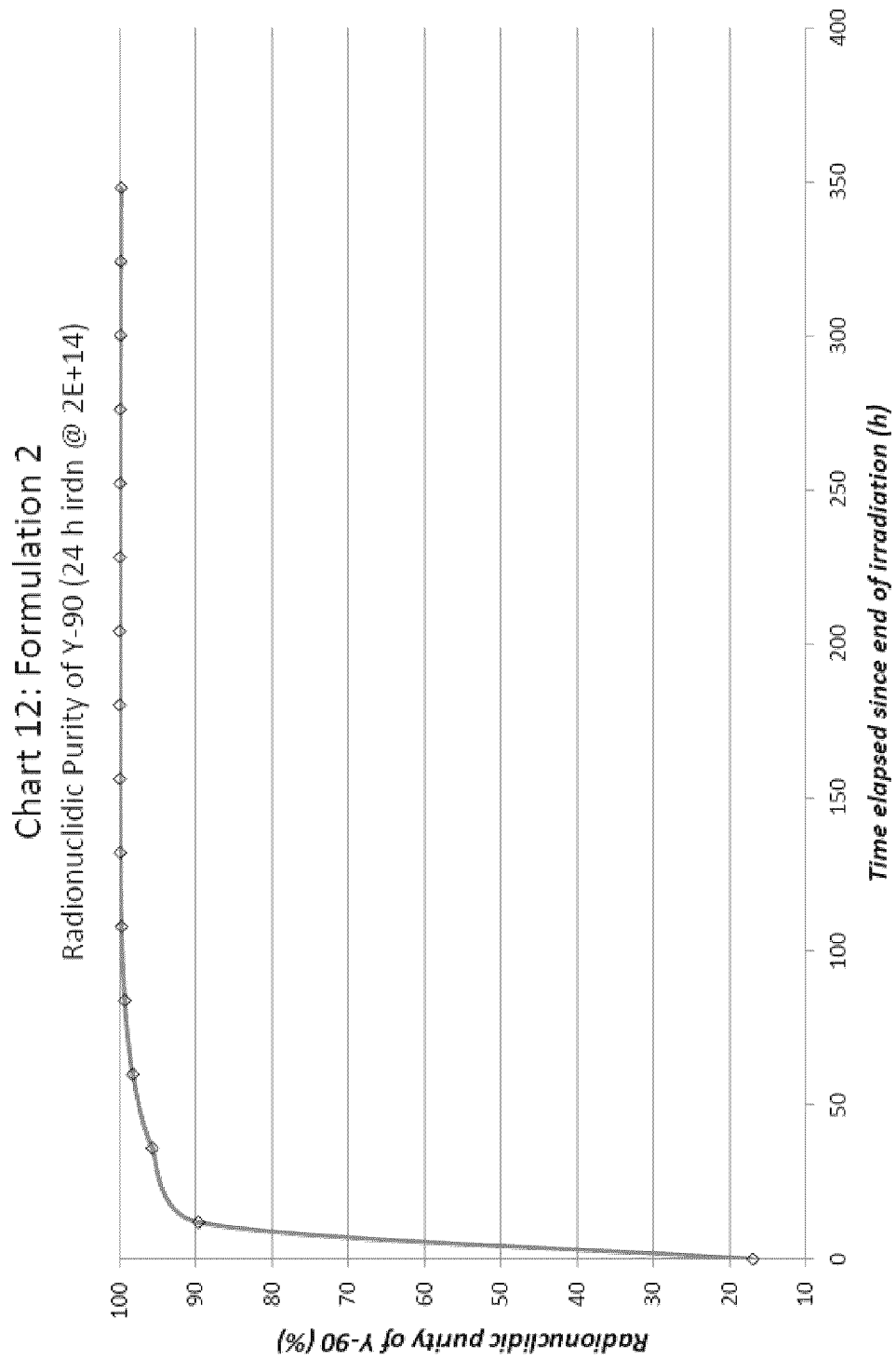
FIG. 26 shows the radionuclidic purity of $^{90}Y$ after irradiation under the conditions of FIG. 23. The x-axis shows time elapsed since end of irradiation (hours). The y-axis shows the radionuclidic purity of $^{90}Y$ as a percent of total radioactivity.

FIGS. 23 and 24 show the total activity for each isotope as bar graphs based on the data in Table 31, with different linear scales on the Y-axis. FIG. 25 shows the data where the Y-axis is a log scale. FIG. 26 shows the radionuclide purity of the $^{90}$Y composition based on time elapsed since the EOI. By 84 h EOI, the purity was greater than 99.0%.

Formulation 2: 72 h Irradiation 100 mg of the composition of formulation 2 was irradiated for 72 h at 2E+14 n/cm·s. Table 32 shows the radioisotopes formed at different times after the end of irradiation (EOI). The $^{90}$Y radionuclidic purity of the composition is also shown (percentage).

Table 31 shows radioisotopes formed from Formulation 2 after 24 h irradiation of 100 mg sample at 2E+14 n/cm$^2$ · s(all activities in MBq).

| EOI + h | Y-90 | Sr-85 | Sr-89 | Ga-70 | Ga-72 | Si-31 | % Y-90 |
|---|---|---|---|---|---|---|---|
| 0 | 12,960 | 0.0 | 0.984 | 59,430 | 2,296 | 540 | 16.93 |
| 12 | 11,140 | 0.0 | 0.977 | 0.000003 | 1,273 | 22.63 | 89.57 |
| 36 | 8,595 | 0.0 | 0.964 | 0.0 | 391 | 0.0397 | 95.64 |
| 60 | 6,627 | 0.0 | 0.951 | 0.0 | 120 | 0.00007 | 98.20 |
| 84 | 5,110 | 0.0 | 0.938 | 0.0 | 37 | 0.0 | 99.26 |
| 108 | 3,940 | 0.0 | 0.925 | 0.0 | 11 | 0.0 | 99.69 |
| 132 | 3,038 | 0.0 | 0.913 | 0.0 | 3 | 0.0 | 99.86 |
| 156 | 2,348 | 0.0 | 0.900 | 0.0 | 1.072 | 0.0 | 99.92 |
| 180 | 1,806 | 0.0 | 0.888 | 0.0 | 0.330 | 0.0 | 99.93 |
| 204 | 1,393 | 0.0 | 0.876 | 0.0 | 0.101 | 0.0 | 99.93 |
| 228 | 1,074 | 0.0 | 0.864 | 0.0 | 0.0311 | 0.0 | 99.92 |
| 252 | 828.4 | 0.0 | 0.852 | 0.0 | 0.0096 | 0.0 | 99.90 |
| 276 | 638.8 | 0.0 | 0.840 | 0.0 | 0.0029 | 0.0 | 99.87 |
| 300 | 492.6 | 0.0 | 0.829 | 0.0 | 0.00090 | 0.0 | 99.83 |
| 324 | 379.8 | 0.0 | 0.818 | 0.0 | 0.00028 | 0.0 | 99.79 |
| 348 | 292.9 | 0.0 | 0.807 | 0.0 | 0.000085 | 0.0 | 99.73 | where EOI = End of Irradiation. Ex. "EOI + 12" is the activities present 12 h after EOI; % Y-90 and for radionuclidic purity of Y-90 (percentage); pale shading indicates radionuclidic purity >99.0% and brighter shading indicates data used for further analysis.

Table 32 shows radioisotopes formed from Formulation 2 after 72 h irradiation of 100 mg sample at 2E+14 n/cm² · s (all activities in MBq).

| EOI + h | Y-90 | Sr-85 | Sr-89 | Ga-70 | Ga-72 | Si-31 | % Y-90 |
|---:|---:|---:|---:|---:|---:|---:|---:|
| 0 | 30,020 | 0.0 | 2.912 | 59,430 | 3,218 | 541 | 32.21 |
| 12 | 26,360 | 0.0 | 2.892 | 3.359E+00 | 1,784 | 22.67 | 93.57 |
| 36 | 20,330 | 0.0 | 2.852 | 0.0 | 58 | 0.0398 | 97.36 |
| 60 | 15,670 | 0.0 | 2.814 | 0.0 | 169 | 7.000E−05 | 98.92 |
| 84 | 12,090 | 0.0 | 2.775 | 0.0 | 52 | 0.0 | 99.55 |
| 108 | 9,332 | 0.0 | 2.737 | 0.0 | 15.91 | 0.0 | 99.80 |
| 132 | 7,188 | 0.0 | 2.700 | 0.0 | 4.892 | 0.0 | 99.89 |
| 156 | 5,543 | 0.0 | 2.663 | 0.0 | 1.503 | 0.0 | 99.92 |
| 180 | 4,274 | 0.0 | 2.627 | 0.0 | 0.462 | 0.0 | 99.93 |
| 204 | 3,296 | 0.0 | 2.591 | 0.0 | 0.142 | 0.0 | 99.92 |
| 228 | 2,541 | 0.0 | 2.556 | 0.0 | 0.0436 | 0.0 | 99.90 |
| 252 | 1,959 | 0.0 | 2.521 | 0.0 | 0.0134 | 0.0 | 99.87 |
| 276 | 1,511 | 0.0 | 2.487 | 0.0 | 0.00412 | 0.0 | 99.84 |
| 300 | 1,165 | 0.0 | 2.453 | 0.0 | 0.001266 | 0.0 | 99.79 |
| 324 | 898.6 | 0.0 | 2.419 | 0.0 | 0.00039 | 0.0 | 99.73 |
| 348 | 692.6 | 0.0 | 2.386 | 0.0 | 0.00012 | 0.0 | 99.66 | where EOI = End of Irradiation. Ex. "EOI + 12" is the activities present 12 h after EOI; % Y-90 and for radionuclidic purity of Y-90 (percentage); pale shading indicates radionuclidic purity >99.0% and brighter shading indicates data used for further analysis.

Figure 27:
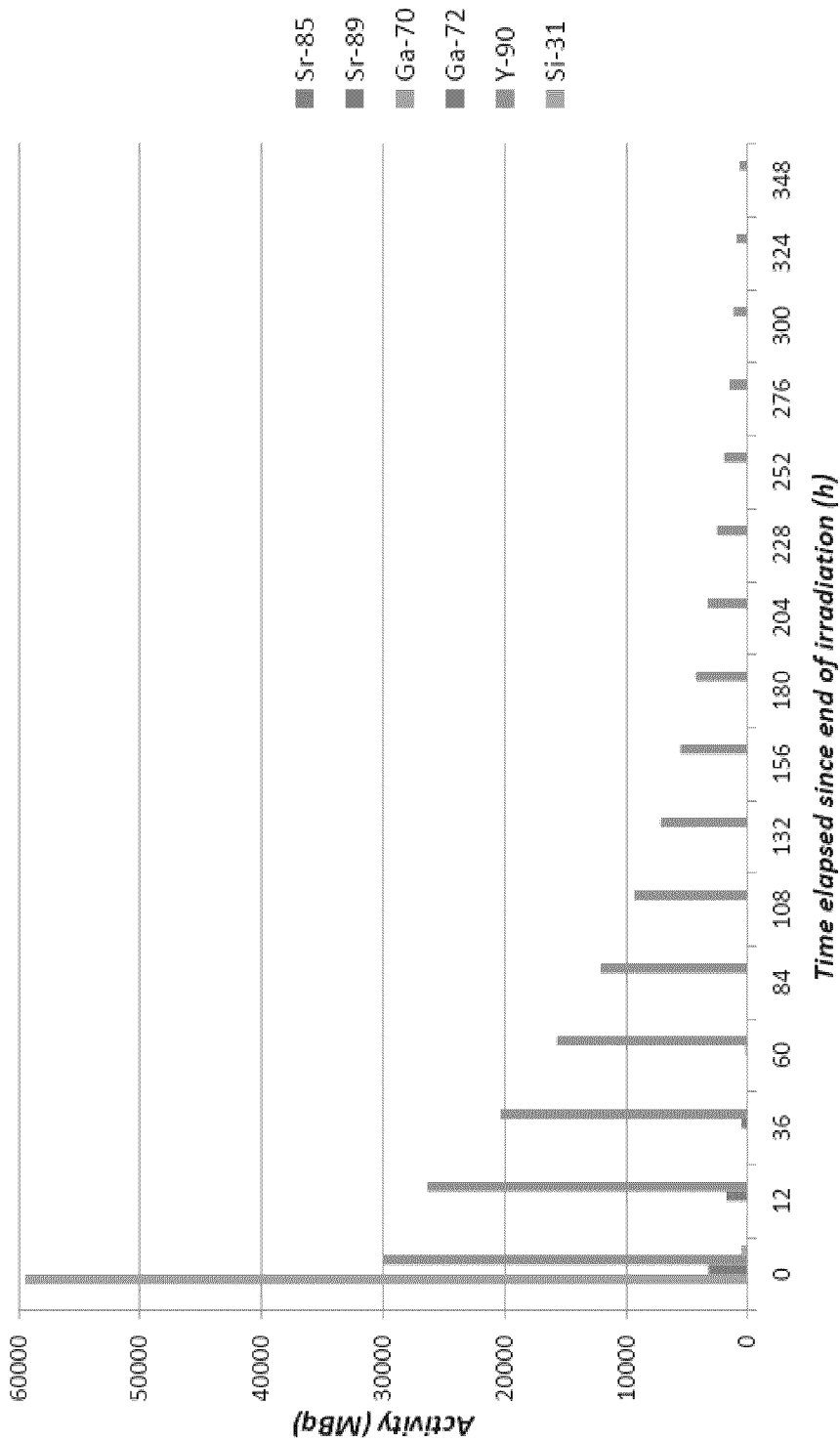
FIG. 27 shows total radioactivity present per 100 mg of Formulation 2 after 72 h irradiation of 100 mg sample at 2E+14 n/cm$^2$·s (all activities in MBq). The x-axis shows time elapsed since end of irradiation (hours). The vertical bars show the activity for Sr-85, Sr-89, Ga-70, Ga-72, $^{90}Y$, and Si-31.
Figure 28:
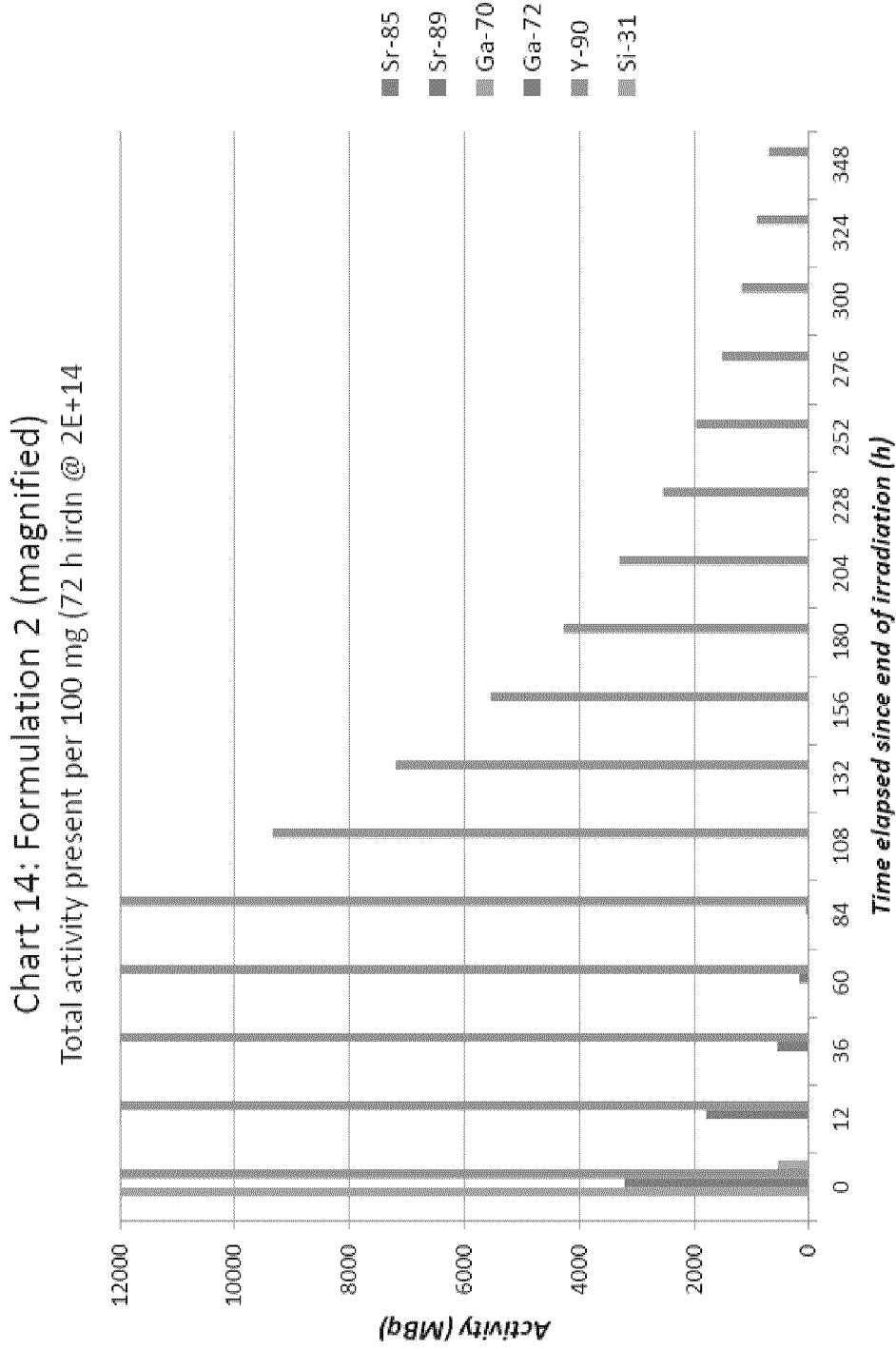
FIG. 28 shows the data from FIG. 27 with a different scale for the y-axis to more clearly show values of total radioactivity below 16000 MBq.
Figure 29:
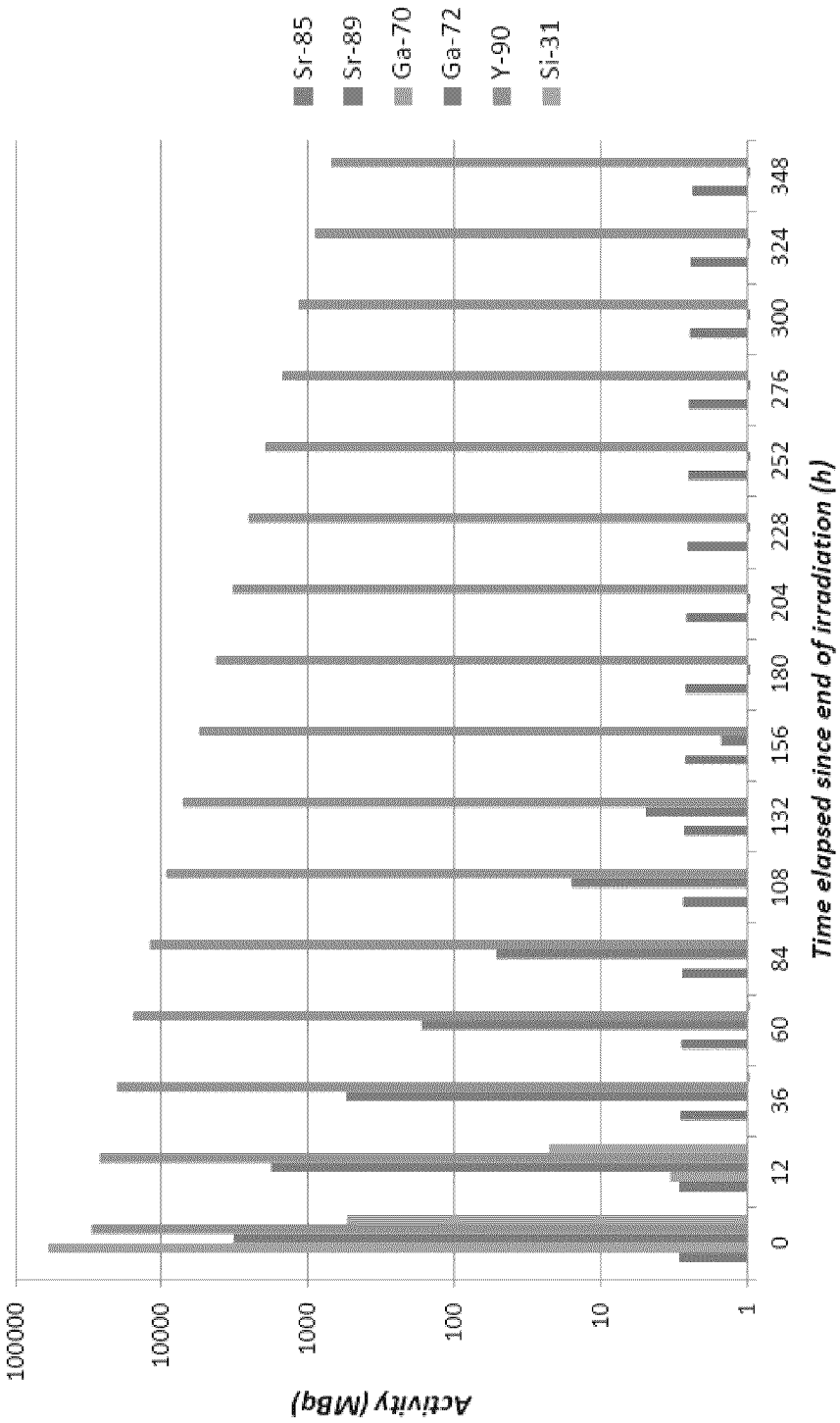
FIG. 29 shows the data from FIG. 27 with a log scale for the y-axis.
Figure 30:
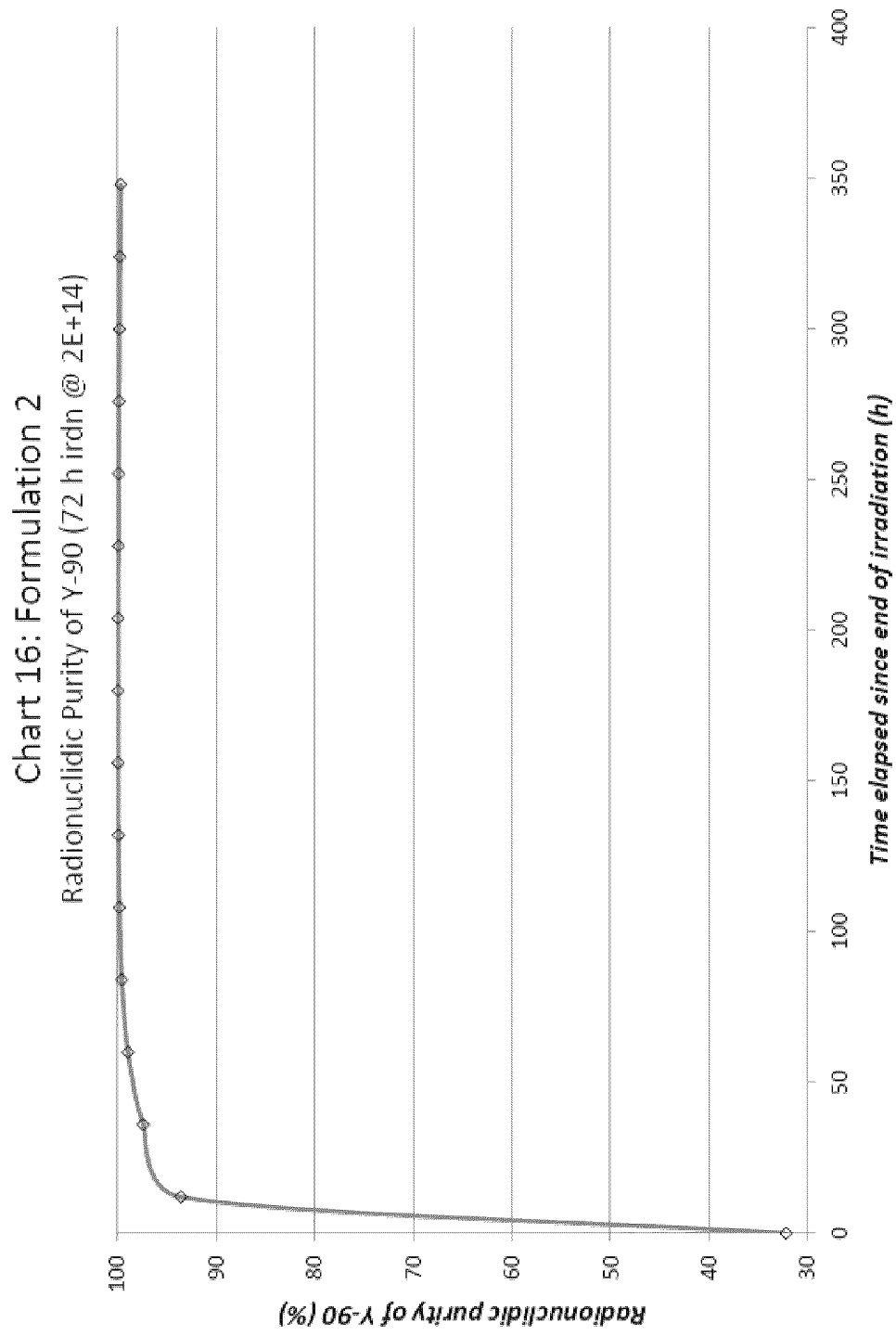
FIG. 30 shows the radionuclidic purity of $^{90}Y$ after irradiation under the conditions of FIG. 27. The x-axis shows time elapsed since end of irradiation (hours). The y-axis shows the radionuclidic purity of $^{90}Y$ as a percent of total radioactivity.

FIGS. 27 and 28 show the total activity for each isotope as bar graphs based on the data in Table 32, with different linear scales on the Y-axis. FIG. 29 shows the data where the Y-axis is a log scale. FIG. 30 shows the radionuclide purity of the $^{90}$Y composition based on time elapsed since the EOI. By 84 h EOI, the purity was greater than 99.0%.

Formulation 3: 24 h Irradiation 100 mg of the composition of formulation 3 was irradiated for 24 h at 2E+14 n/cm·s. Table 33 shows the radioisotopes formed at different times after the end of irradiation (EIO). The $^{90}$Y radionuclidic purity of the composition is also shown (percentage).

Figure 31:
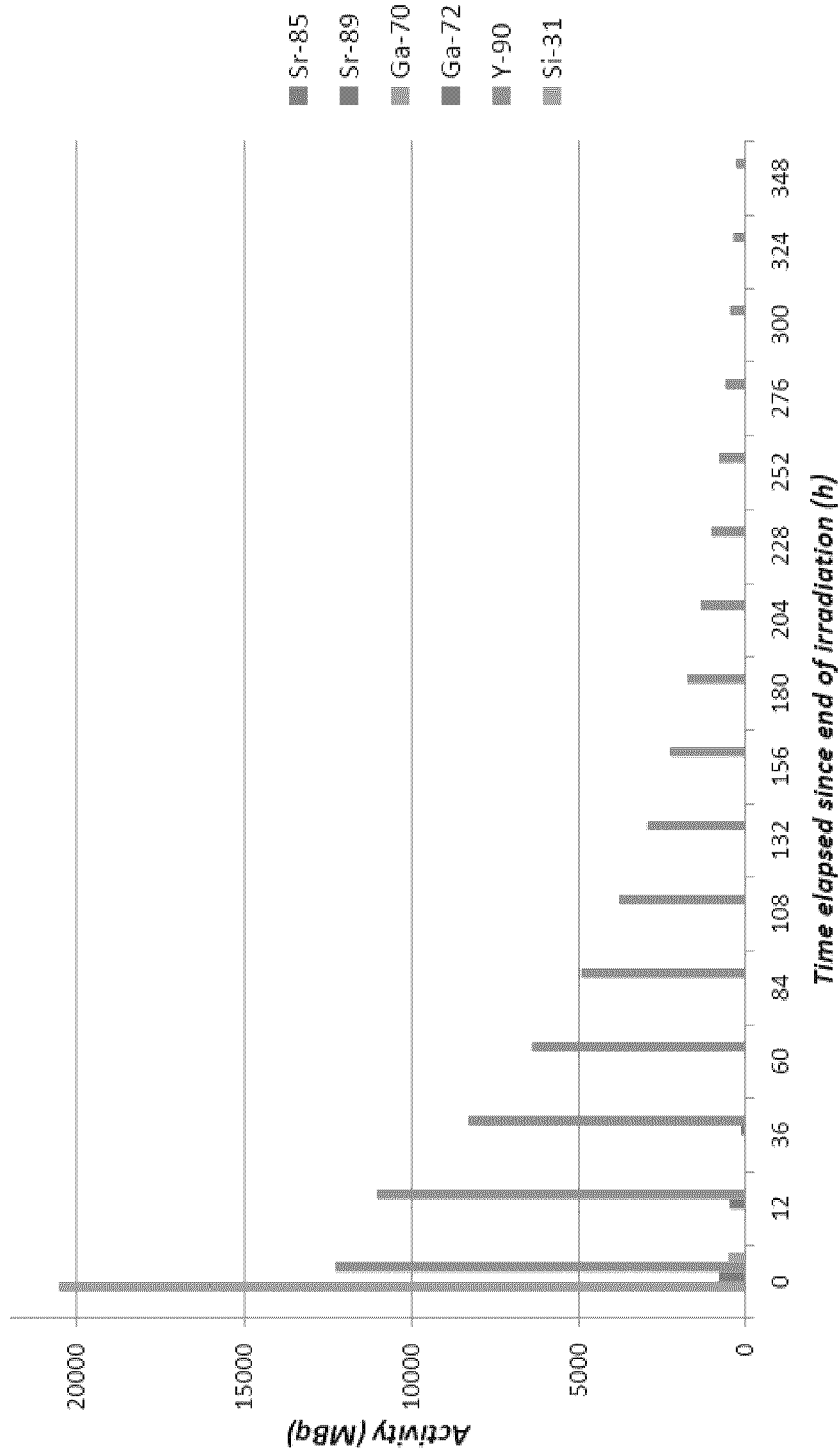
FIG. 31 shows total radioactivity present per 100 mg of Formulation 3 after 24 h irradiation of 100 mg sample at 2E+14 n/cm$^2$·s (all activities in MBq). The x-axis shows time elapsed since end of irradiation (hours). The vertical bars show the activity for Sr-85, Sr-89, Ga-70, Ga-72, $^{90}Y$, and Si-31.
Figure 32:
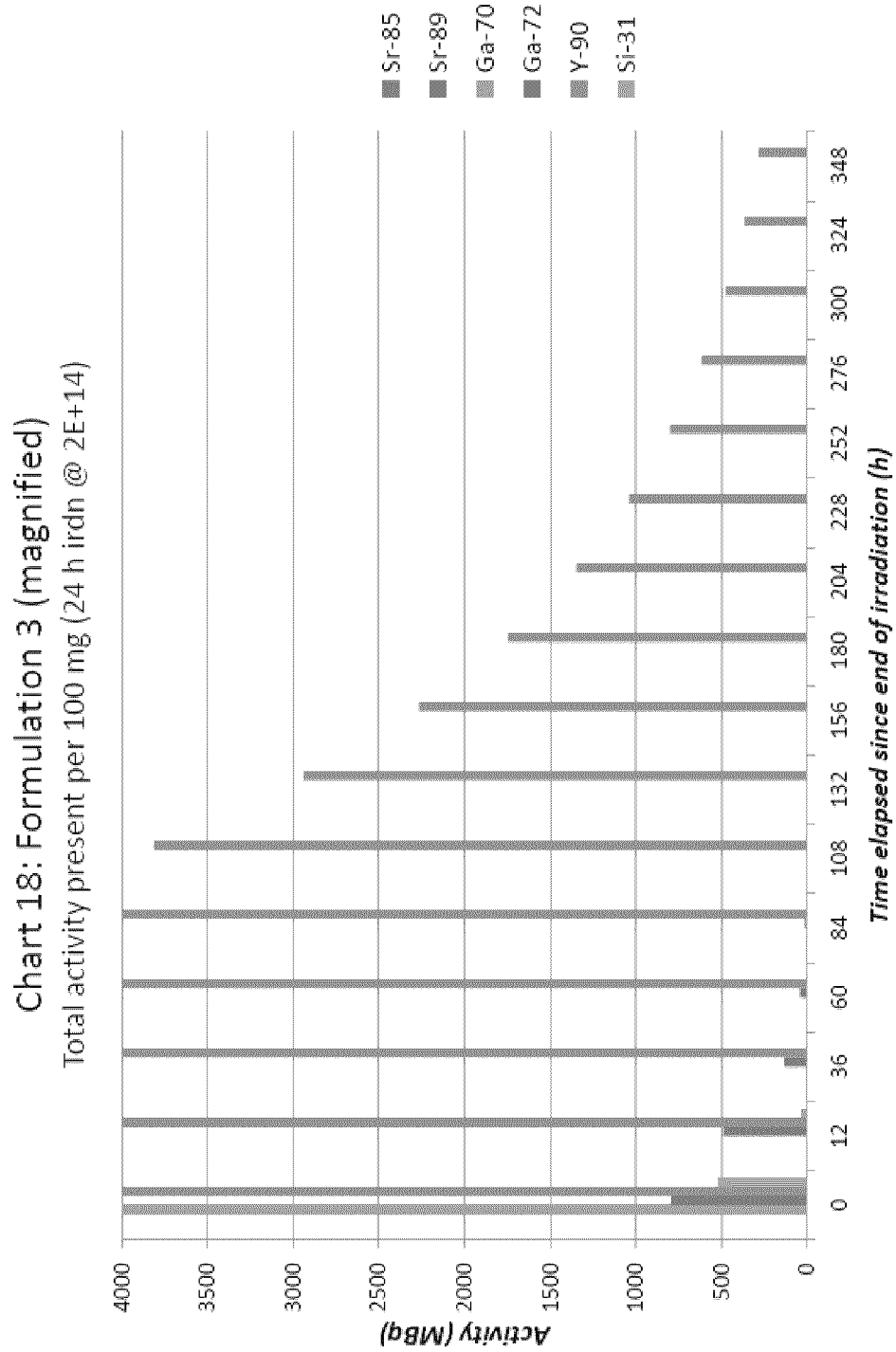
FIG. 32 shows the data from FIG. 31 with a different scale for the y-axis to more clearly show values of total radioactivity below 10000 MBq.
Figure 33:
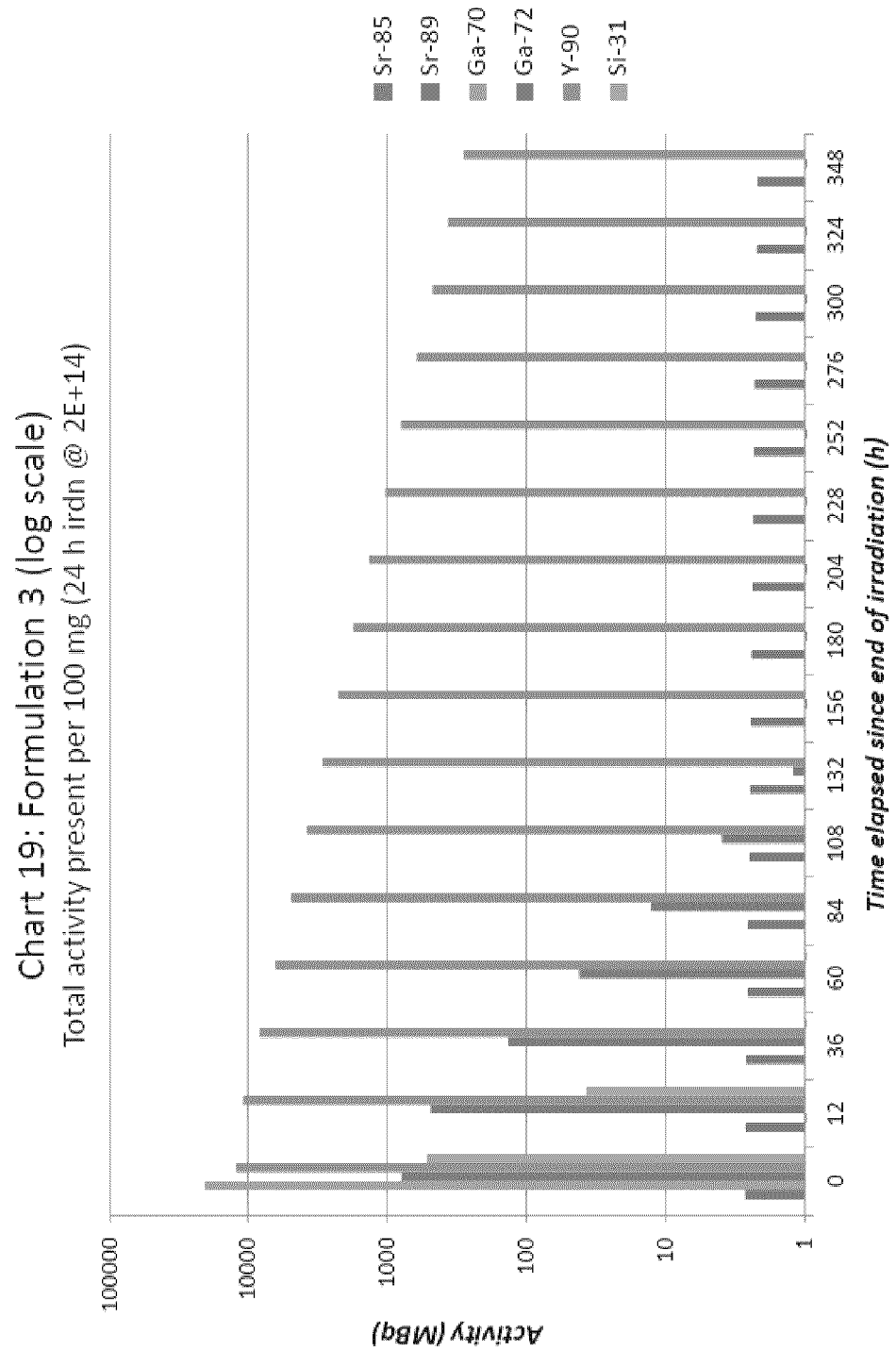
FIG. 33 shows the data from FIG. 31 with a log scale for the y-axis.
Figure 34:
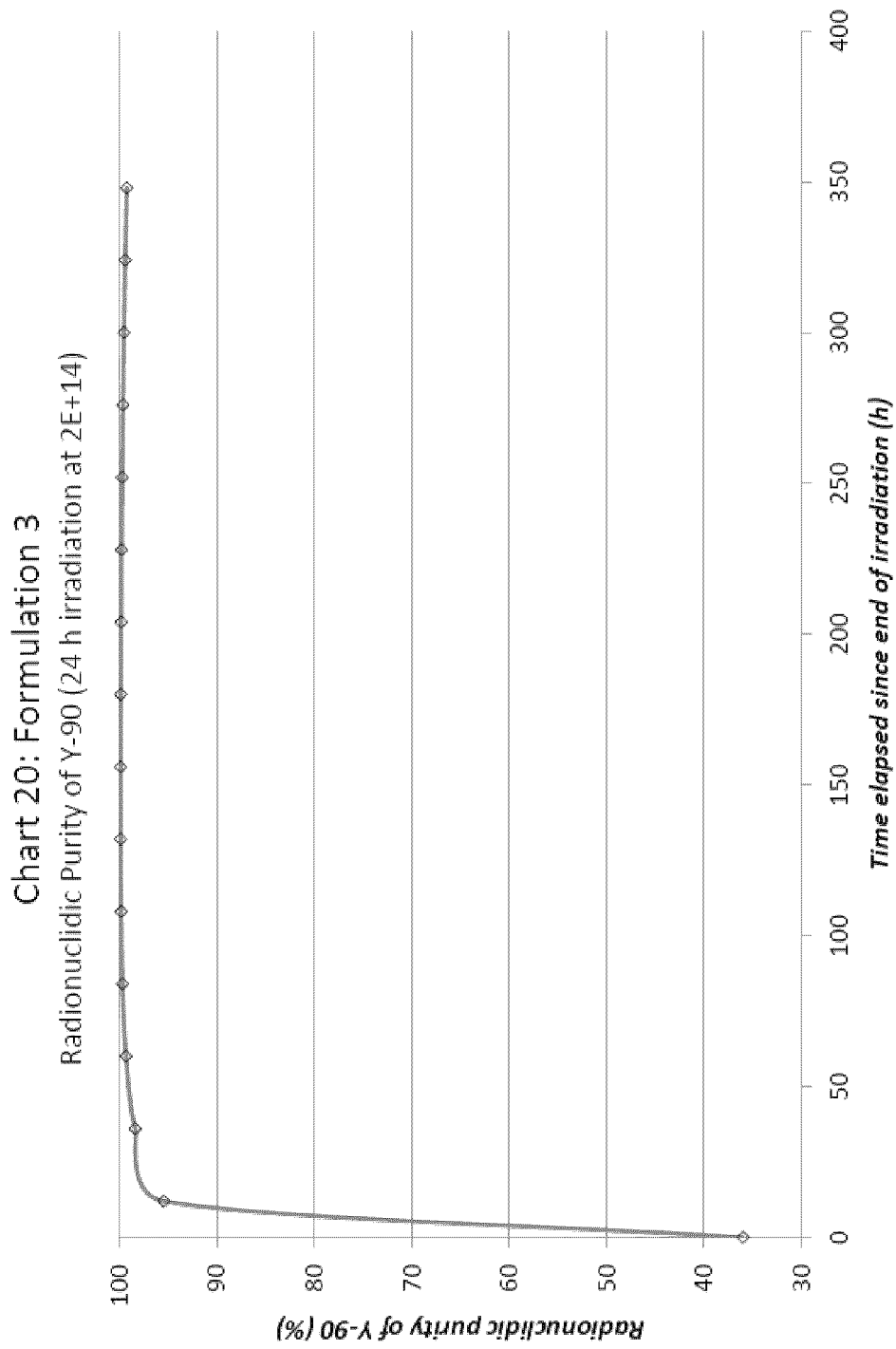
FIG. 34 shows the radionuclidic purity of $^{90}Y$ after irradiation under the conditions of FIG. 31. The x-axis shows time elapsed since end of irradiation (hours). The y-axis shows the radionuclidic purity of $^{90}Y$ as a percent of total radioactivity.

FIGS. 31 and 32 show the total activity for each isotope as bar graphs based on the data in Table 33, with different linear scales on the Y-axis. FIG. 33 shows the data where the Y-axis is a log scale. FIG. 34 shows the radionuclide purity of the $^{90}$Y composition based on time elapsed since the EOI. By 60 h EOI, the purity was greater than 99.0%.

Formulation 3: 72 h Irradiation 100 mg of the composition of formulation 3 was irradiated for 24 h at 2E+14 n/cm·s. Table 34 shows the radioisotopes formed at different times after the end of irradiation (EOI). The $^{90}$Y radionuclidic purity of the composition is also shown (percentage).

Table 33 shows radioisotopes formed from Formulation 3 after 24 h irradiation of 100 mg sample at 2E+14 n/cm² · s (all activities in MBq).

| EOI + h | Y-90 | Sr-85 | Sr-89 | Ga-70 | Ga-72 | Si-31 | % Y-90 |
|---:|---:|---:|---:|---:|---:|---:|---:|
| 0 | 12,270 | 0.0 | 2.665 | 20,520 | 795.1 | 522.3 | 35.97 |
| 12 | 11,010 | 0.0 | 2.650 | 0.00006 | 486.3 | 37.13 | 95.44 |
| 36 | 8,313 | 0.0 | 2.611 | 0.0 | 135.4 | 0.0384 | 98.37 |
| 60 | 6,410 | 0.0 | 2.575 | 0.0 | 41.63 | 6.70E−05 | 99.32 |
| 84 | 4,943 | 0.0 | 2.540 | 0.0 | 12.79 | 0.0 | 99.69 |
| 108 | 3,811 | 0.0 | 2.505 | 0.0 | 3.932 | 0.0 | 99.83 |
| 132 | 2,939 | 0.0 | 2.471 | 0.0 | 1.208 | 0.0 | 99.87 |
| 156 | 2,266 | 0.0 | 2.437 | 0.0 | 0.371 | 0.0 | 99.88 |
| 180 | 1,747 | 0.0 | 2.404 | 0.0 | 0.114 | 0.0 | 99.86 |
| 204 | 1,347 | 0.0 | 2.371 | 0.0 | 0.0351 | 0.0 | 99.82 |
| 228 | 1,039 | 0.0 | 2.339 | 0.0 | 0.0108 | 0.0 | 99.77 |
| 252 | 801.2 | 0.0 | 2.307 | 0.0 | 0.00331 | 0.0 | 99.71 |
| 276 | 617.8 | 0.0 | 2.276 | 0.0 | 0.001 | 0.0 | 99.63 |
| 300 | 476.4 | 0.0 | 2.245 | 0.0 | 0.00031 | 0.0 | 99.53 |
| 324 | 367.3 | 0.0 | 2.214 | 0.0 | 0.000096 | 0.0 | 99.40 |
| 348 | 283.3 | 0.0 | 2.184 | 0.0 | 0.00003 | 0.0 | 99.23 |

Table 34 shows radioisotopes formed from Formulation 3 after 24 h irradiation of 100 mg sample at 2E+14 n/cm² · s (all activities in MBq).

| EOI + h | Y-90 | Sr-85 | Sr-89 | Ga-70 | Ga-72 | Si-31 | % Y-90 |
|---|---|---|---|---|---|---|---|
| 0 | 29,040 | 0.0 | 7.887 | 20,520 | 1,114 | 523.2 | 56.71 |
| 12 | 25,500 | 0.0 | 7.834 | 0.000E+00 | 617.8 | 21.92 | 97.52 |
| 36 | 19,660 | 0.0 | 7.727 | 0.0 | 189.8 | 0.0385 | 99.01 |
| 60 | 15,160 | 0.0 | 7.621 | 0.0 | 58.53 | 6.700E−05 | 99.57 |
| 84 | 11,690 | 0.0 | 7.517 | 0.0 | 17.93 | 0.0 | 99.78 |
| 108 | 9,016 | 0.0 | 7.415 | 0.0 | 5.511 | 0.0 | 99.86 |
| 132 | 6,953 | 0.0 | 7.314 | 0.0 | 1.693 | 0.0 | 99.87 |
| 156 | 5,361 | 0.0 | 7.214 | 0.0 | 0.521 | 0.0 | 99.86 |
| 180 | 4,134 | 0.0 | 7.116 | 0.0 | 0.160 | 0.0 | 99.82 |
| 204 | 3,187 | 0.0 | 7.019 | 0.0 | 0.0492 | 0.0 | 99.78 |
| 228 | 2,458 | 0.0 | 6.923 | 0.0 | 0.0151 | 0.0 | 99.72 |
| 252 | 1,895 | 0.0 | 6.829 | 0.0 | 0.00464 | 0.0 | 99.64 |
| 276 | 1,461 | 0.0 | 6.736 | 0.0 | 0.00143 | 0.0 | 99.54 |
| 300 | 1,127 | 0.0 | 6.644 | 0.0 | 0.000439 | 0.0 | 99.41 |
| 324 | 869.1 | 0.0 | 6.553 | 0.0 | 0.000135 | 0.0 | 99.25 |
| 348 | 670.1 | 0.0 | 6.464 | 0.0 | 0.000041 | 0.0 | 99.04 | where EOI = End of Irradiation. Ex. "EOI + 12" is the activities present 12 h after EOI; % Y-90 and for radionuclidic purity of Y-90 (percentage); pale shading indicates radionuclidic purity >99.0% and brighter shading indicates data used for further analysis.

Figure 35:
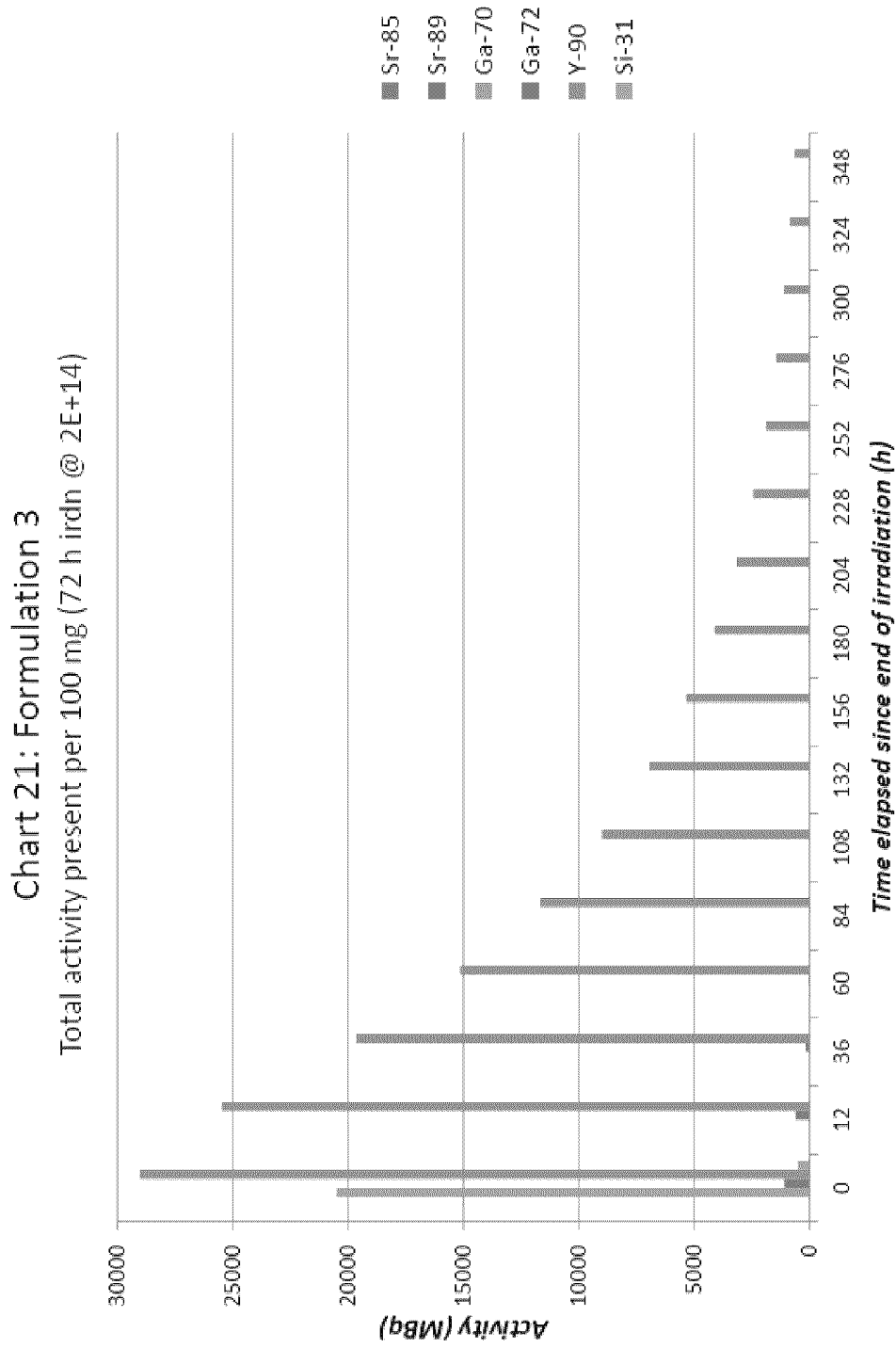
FIG. 35 shows total radioactivity present per 100 mg of Formulation 3 after 72 h irradiation of 100 mg sample at 2E+14 n/cm$^2$·s (all activities in MBq). The x-axis shows time elapsed since end of irradiation (hours). The vertical bars show the activity for Sr-85, Sr-89, Ga-70, Ga-72, $^{90}Y$, and Si-31.
Figure 36:
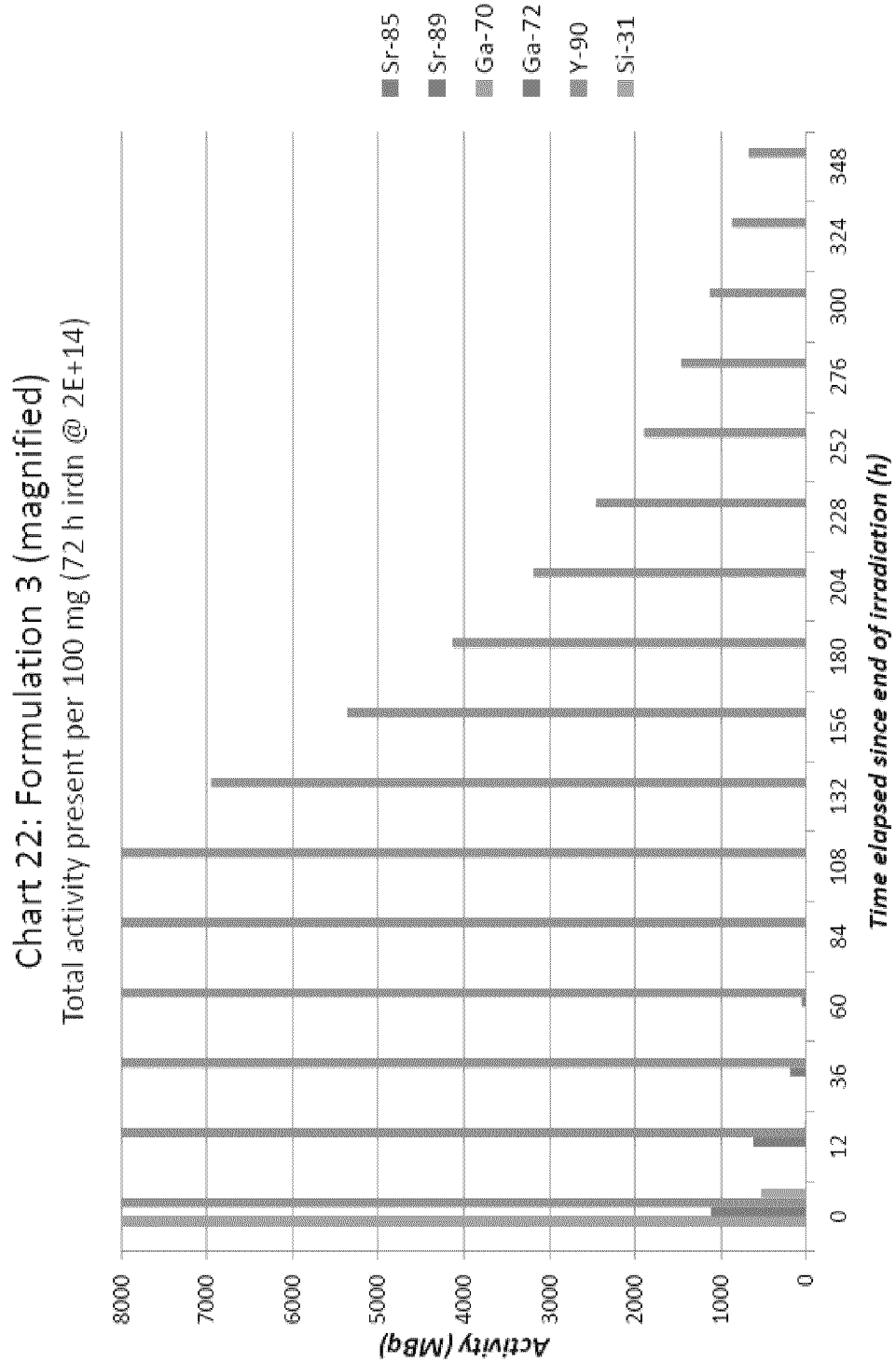
FIG. 36 shows the data from FIG. 35 with a different scale for the y-axis to more clearly show values of total radioactivity below 16000 MBq.
Figure 37:
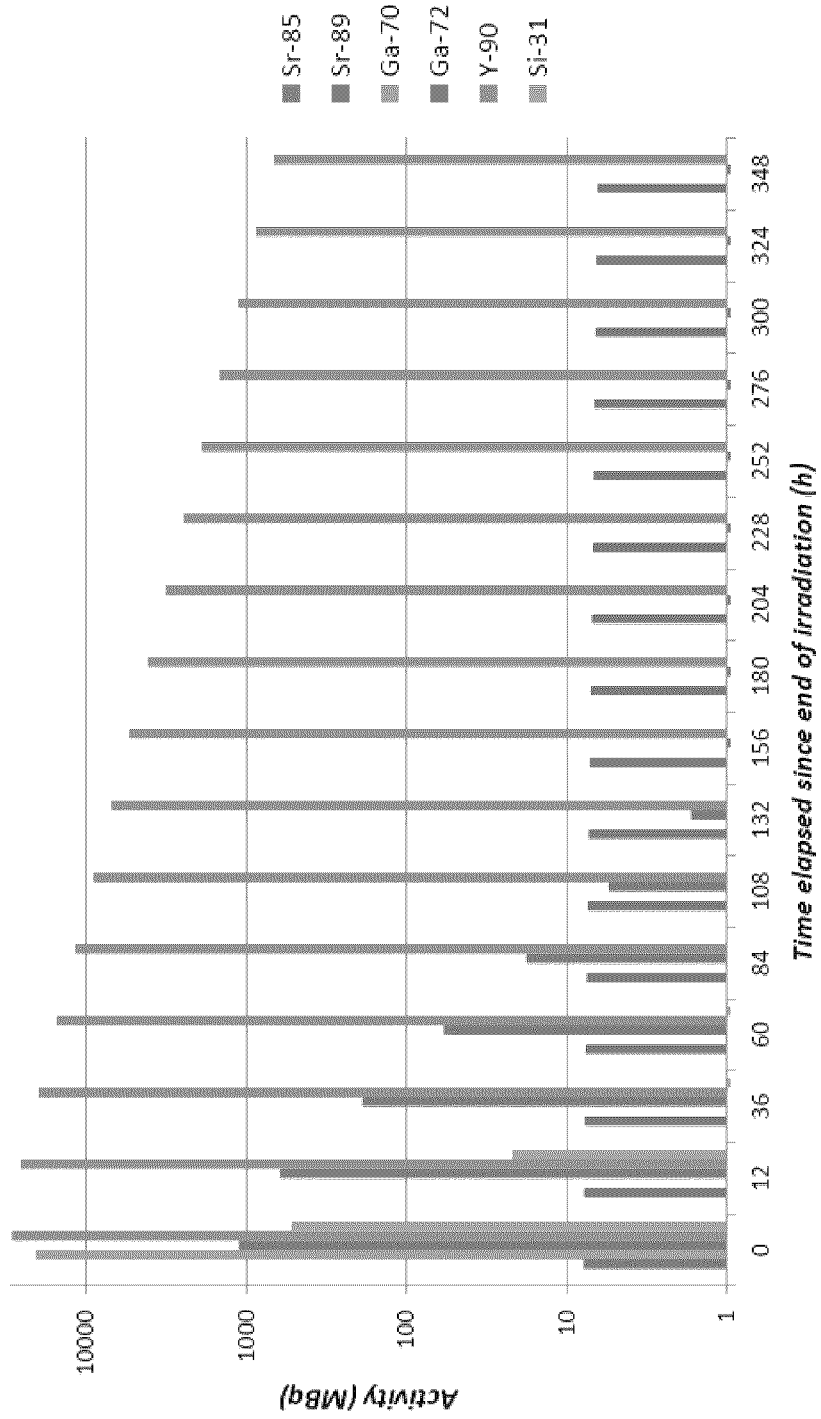
FIG. 37 shows the data from FIG. 35 with a log scale for the y-axis.
Figure 38:
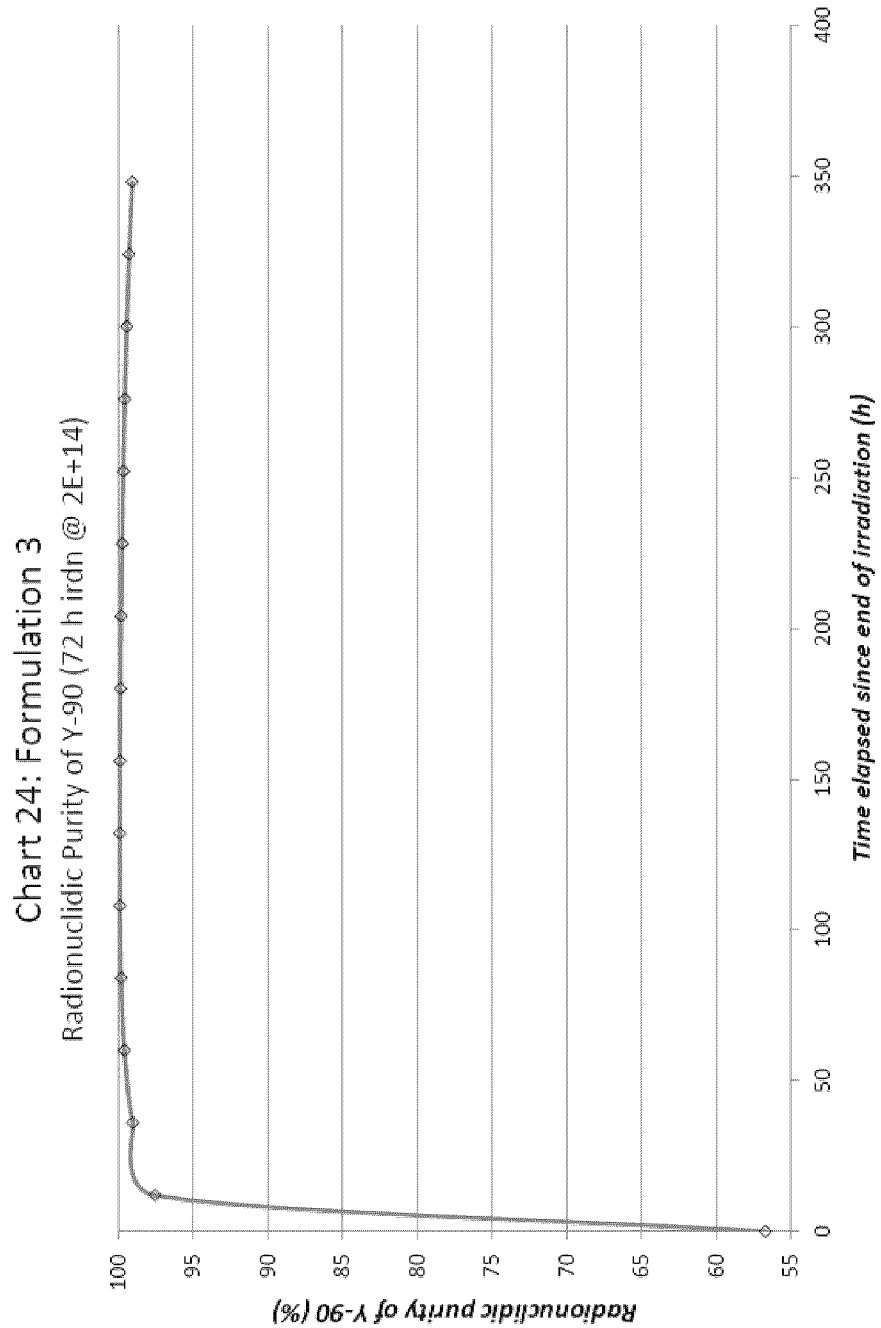
FIG. 38 shows the radionuclidic purity of $^{90}Y$ after irradiation under the conditions of FIG. 35. The x-axis shows time elapsed since end of irradiation (hours). The y-axis shows the radionuclidic purity of $^{90}Y$ as a percent of total radioactivity.

FIGS. 35 and 36 show the total activity for each isotope as bar graphs based on the data in Table 34, with different linear scales on the Y-axis. FIG. 37 shows the data where the Y-axis is a log scale. FIG. 38 shows the radionuclide purity of the $^{90}$Y composition based on time elapsed since the EOI. By 36 h EOI, the purity was greater than 99.0%.

Example 6

Projected Radioisotope Formulations Under Production Conditions Methodology

The compositions of the 10 bead formulations prepared in Occlu90Y design space #1 and 3 bead formulations prepared in Occlu90Y design space #2 were first converted from mole fractions into weight percentages of each element. These percentages were then combined with the natural abundances of all stable isotopes of yttrium, strontium, gallium, silicon, titanium, and manganese to create a master list of the weight percent of each stable isotope in each formulation. The Table of the Nuclides was consulted to determine which of these isotopes undergo neutron capture to produce radioisotopes; all isotopes that do not undergo neutron activation were discarded from further analysis.

A series of calculations was then carried out for each of the twelve bead compositions using a sample mass of 1 g in all cases. A thermal neutron flux value of 2×10" n/cm²·s was used for these calculations; this flux value is attainable at several radioisotope-producing research reactors around the world, including the NRU (Chalk River, Canada), MURR (University of Missouri), SAFARI (South Africa), OPAL (Australia), and BR-2 (Belgium). Three different irradiation times (24 h, 72 h, 168 h) were considered for each bead formulation, and the activities of the radioisotopes produced were tracked over a decay period of 384 h (approximately 8 weeks).

Complete data tables for all eleven formulations are presented in Tables 35 to 67. Highlighted portions of the data indicate yttrium-90 radionuclidic purity of greater than 95%; dark yellow is used to indicate the highest radionuclidic purity achievable for each irradiation scenario.

Three distinct production scenarios were considered for each of the bead formulations in order to highlight the impact of altering the irradiation time on the relative quantities of each radioisotope present at EOI. As a particular stable isotope with a non-zero neutron capture cross-section is exposed to a neutron flux, it will activate to form a radioisotope at a constant rate that is directly proportional to the cross-section, neutron flux, and mass of stable isotope present. However, as soon as the radioisotope forms, it begins to decay: in consequence, the amount of radioisotope present will not increase linearly over time although the activation continues at the same initial rate. In consequence, the maximum yield of a given radioisotope under continuous irradiation is reached after approximately five half-lives.

Gallium-70, with its 21-minute half-life, reaches a maximum yield after less than two hours irradiation, while the amount of Ga-72 ($t_{1/2}$=14 h) reaches a plateau after approximately 40 h of irradiation. In contrast, the long-lived strontium radioisotopes Sr-85 ($t_{1/2}$=64.9 d) and Sr-87 ($t_{1/2}$=50.5 d) continue to accumulate in a linear fashion over an irradiation period of months. The yttrium-90 ($t_{1/2}$=64 h) level stabilizes after approximately 300 h of irradiation, but its growth rate declines significantly beyond ~150 h. In consequence, the specific activity of the yttrium-containing beads—that is, the number of Bq of Y-90 per gram of beads—will not increase substantially by extending the irradiation time past 170 h (approximately one week). With this information in mind, three different irradiation times were considered for all eleven-bead formulations. The first and shortest irradiation time (24 h) has the advantage of creating the smallest amount of long-lived strontium radioisotopes, but the disadvantage of producing relatively low specific activity (Bq/g) yttrium-90. It will also feature the greatest ratio of Ga-72 to Y-90 at end of irradiation, as this 14 h gallium radioisotope will still be accumulating linearly throughout the 24 h period. All data generated using a 24 h irradiation period are labelled "Scenario 1" in the appended data tables. The second scenario employs a 72 h irradiation period, thereby staying within the linear growth period for yttrium-90; as such, it may be the most cost effective scenario of the three. Also, it will provide a slightly lower ratio of Ga-72 to Y-90 at end of irradiation which will be beneficial as slightly less time will be required for the Ga-72 to decay to acceptable levels. The ratio of long-lived strontium to yttrium-90 will be essentially unchanged from Scenario 1, as all three of these isotopes (Sr-85, Sr-87, and Y-90) are still accumulating in a linear fashion. All data generated using a 72 h irradiation period are labelled "Scenario 2" in Tables 35 to 67.

Finally, a 1 wk (168 h) irradiation was considered. This scenario was chosen in order to maximize the specific activity of the yttrium-90 produced without entering into the Y-90 plateau region (~180 h and onwards), while the formation of long-lived radiostrontiums continues unabated. Under these conditions, the ratio of Ga-72 to Y-90 will be substantially lower, as the Ga-72 yield will plateau after approximately 60 h; conversely, the proportion of Sr-85 and Sr-89 will be slightly higher. All data generated using a 168 h (7 d) irradiation period are labelled "Scenario 3" in the appended data tables. In all three scenarios, only thermal neutron capture reactions were considered: nuclear transformations due to fast neutron interactions were excluded, as their cross-sections are highly dependent on the flux characteristics of the particular irradiation site being used. Moreover, for design space #1, the presence of fast neutrons is not expected to significantly alter the radioisotope profiles generated. The components of these beads (Y, Sr, Ga, Si, 0) undergo a limited number of fast neutron reactions, and the radioisotopes generated from these reactions are generally short-lived: silicon-28 produces Al-28 ($t_{1/2}$=2.24 min), Si-29 produces Al-29 ($t_{1/2}$=6.5 min), and Sr-88 produces Rb-88 ($t_{1/2}$=15.2 min). The only exception to this is Y-89, which can undergo a (n,p) reaction to produce Sr-89, but the cross-section for this reaction is very low ($\sigma$=0.3 mb) and the contribution to the total amount of Sr-89 from this route, compared to thermal neutron activation of Sr-88, is expected to be negligible. Fast neutron reactions may be more problematic for certain formulations in design space #2, as titanium-46 is capable of undergoing a (n,p) reaction to yield scandium-46, which has an 84 d half-life. As with other fast neutron reactions, the cross-section for this transformation is very low: combined with the small amount of titanium present in Occlu90Y2.3 and 2.8, this should render the amount of Sc-46 generated negligible.

The results of the theoretical yield projections are presented in Tables 35 to 67. In general, the beads reach a radionuclidic purity (RNP) of >95% Y-90 at approximately 4-5 d after end of irradiation, at which time the major radionuclidic impurity is always gallium-72. Maximum radionuclidic purity is consistently achieved 4-6 d subsequent to this, or 10-12 d after EOI. The mass of beads required to formulate a patient dose of 4 GBq was shown to vary, not unexpectedly, as a function of both bead composition and irradiation time. This is illustrated in Table 68, which contains selected data for beads with diverse formulations: Occlu90Y1.4 is high in yttrium and gallium, while Occlu90Y1.16 contains a comparable amount of yttrium, only half the gallium, but substantially more strontium; Occlu90Y1.1 and 1.2 are both low in yttrium, but contain varying concentrations of strontium and gallium. Compounds from design space #2 are not included in this comparison, but their compositions with respect to strontium, gallium, and yttrium are quite similar to those of design space #1, and the addition of manganese and titanium does not significantly impact their radioactive decay patterns.

TABLE 35

Scenario 1: Continuous 24 h neutron irradiation of Occlu90Y1.1 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 66,002 | 227 | 222 | 1.6 | 3,688.5 | 2.9 | 487,956 | 613,848 | 2,241 | 5.62 |
| 12 | 58,063 | 16.7 | 0.1 | 1.6 | 191.1 | 2.9 | 0.0 | 340,302 | 93.7 | 14.56 |
| 18 | 54,459 | 4.5 | 0.0 | 1.6 | 43.5 | 2.9 | 0.0 | 253,377 | 19.2 | 17.69 |
| 24 | 51,079 | 1.2 | 0.0 | 1.6 | 9.9 | 2.9 | 0.0 | 188,655 | 3.9 | 21.30 |
| 36 | 44,934 | 0.1 | 0.0 | 1.6 | 0.5 | 2.9 | 0.0 | 104,586 | 0.2 | 30.05 |
| 48 | 39,529 | 0.0 | 0.0 | 1.6 | 0.0 | 2.9 | 0.0 | 57,980 | 0.0 | 40.54 |
| 72 | 30,591 | 0.0 | 0.0 | 1.6 | 0.0 | 2.8 | 0.0 | 17,819 | 0.0 | 63.19 |
| 96 | 23,674 | 0.0 | 0.0 | 1.6 | 0.0 | 2.8 | 0.0 | 5,476 | 0.0 | 81.20 |
| 120 | 18,321 | 0.0 | 0.0 | 1.5 | 0.0 | 2.7 | 0.0 | 1,683 | 0.0 | 91.57 |
| 144 | 14,179 | 0.0 | 0.0 | 1.5 | 0.0 | 2.7 | 0.0 | 517 | 0.0 | 96.45 |
| 168 | 10,973 | 0.0 | 0.0 | 1.5 | 0.0 | 2.7 | 0.0 | 159 | 0.0 | 98.53 |
| 192 | 8,492 | 0.0 | 0.0 | 1.5 | 0.0 | 2.6 | 0.0 | 48.9 | 0.0 | 99.38 |
| 216 | 6,572 | 0.0 | 0.0 | 1.5 | 0.0 | 2.6 | 0.0 | 15.0 | 0.0 | 99.71 |
| 240 | 5,086 | 0.0 | 0.0 | 1.5 | 0.0 | 2.6 | 0.0 | 4.6 | 0.0 | 99.83 |
| 264 | 3,936 | 0.0 | 0.0 | 1.4 | 0.0 | 2.5 | 0.0 | 1.4 | 0.0 | 99.86 |
| 288 | 3,046 | 0.0 | 0.0 | 1.4 | 0.0 | 2.5 | 0.0 | 0.4 | 0.0 | 99.86 |
| 312 | 2,357 | 0.0 | 0.0 | 1.4 | 0.0 | 2.5 | 0.0 | 0.1 | 0.0 | 99.83 |
| 336 | 1,824 | 0.0 | 0.0 | 1.4 | 0.0 | 2.4 | 0.0 | 0.0 | 0.0 | 99.79 |
| 360 | 1,412 | 0.0 | 0.0 | 1.4 | 0.0 | 2.4 | 0.0 | 0.0 | 0.0 | 99.73 |
| 384 | 1,093 | 0.0 | 0.0 | 1.4 | 0.0 | 2.4 | 0.0 | 0.0 | 0.0 | 99.66 |

Activity present (MBq) in 1 g of Occlu90Y1.1 at indicated time (h) after EOI.

TABLE 36

Scenario 2: Continuous 72 h neutron irradiation of Occlu90Y1.1 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 156,617 | 228 | 222 | 4.8 | 3,698.5 | 8.7 | 487,956 | 860,560 | 2,245 | 10.36 |
| 12 | 137,778 | 17 | 0.1 | 4.8 | 191.6 | 8.6 | 0.0 | 477,073 | 93.8 | 22.40 |
| 18 | 129,226 | 4.6 | 0.0 | 4.8 | 43.6 | 8.6 | 0.0 | 355,212 | 19.2 | 26.67 |
| 24 | 121,205 | 1.2 | 0.0 | 4.8 | 9.9 | 8.6 | 0.0 | 264,478 | 3.9 | 31.42 |
| 36 | 106,625 | 0.1 | 0.0 | 4.7 | 0.5 | 8.5 | 0.0 | 146,620 | 0.2 | 42.10 |
| 48 | 93,799 | 0.0 | 0.0 | 4.7 | 0.0 | 8.5 | 0.0 | 81,283 | 0.0 | 53.57 |
| 72 | 72,590 | 0.0 | 0.0 | 4.7 | 0.0 | 8.3 | 0.0 | 24,981 | 0.0 | 74.39 |

TABLE 36-continued

Scenario 2: Continuous 72 h neutron irradiation of Occlu90Y1.1 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 96 | 56,177 | 0.0 | 0.0 | 4.6 | 0.0 | 8.2 | 0.0 | 7,677 | 0.0 | 87.96 |
| 120 | 43,475 | 0.0 | 0.0 | 4.6 | 0.0 | 8.1 | 0.0 | 2,360 | 0.0 | 94.83 |
| 144 | 33,645 | 0.0 | 0.0 | 4.5 | 0.0 | 8.0 | 0.0 | 725 | 0.0 | 97.85 |
| 168 | 26,037 | 0.0 | 0.0 | 4.5 | 0.0 | 7.9 | 0.0 | 223 | 0.0 | 99.10 |
| 192 | 20,150 | 0.0 | 0.0 | 4.4 | 0.0 | 7.8 | 0.0 | 68.5 | 0.0 | 99.60 |
| 216 | 15,594 | 0.0 | 0.0 | 4.4 | 0.0 | 7.7 | 0.0 | 21.1 | 0.0 | 99.79 |
| 240 | 12,068 | 0.0 | 0.0 | 4.3 | 0.0 | 7.6 | 0.0 | 6.5 | 0.0 | 99.85 |
| 264 | 9,339 | 0.0 | 0.0 | 4.3 | 0.0 | 7.5 | 0.0 | 2.0 | 0.0 | 99.85 |
| 288 | 7,228 | 0.0 | 0.0 | 4.2 | 0.0 | 7.4 | 0.0 | 0.6 | 0.0 | 99.83 |
| 312 | 5,593 | 0.0 | 0.0 | 4.2 | 0.0 | 7.3 | 0.0 | 0.2 | 0.0 | 99.79 |
| 336 | 4,329 | 0.0 | 0.0 | 4.2 | 0.0 | 7.2 | 0.0 | 0.1 | 0.0 | 99.74 |
| 360 | 3,350 | 0.0 | 0.0 | 4.1 | 0.0 | 7.1 | 0.0 | 0.0 | 0.0 | 99.67 |
| 384 | 2,592 | 0.0 | 0.0 | 4.1 | 0.0 | 7.0 | 0.0 | 0.0 | 0.0 | 99.58 |

Activity present (MBq) in 1 g of Occlu90Y1.1 at indicated time (h) after End of Irradiation EOI.

TABLE 37

Scenario 3: Continuous 7 d (168 h) neutron irradiation of Occlu90Y1.1 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 243,403 | 228 | 222 | 11 | 3,698 | 20 | 487,956 | 886,077 | 2,245 | 14.99 |
| 12 | 214,124 | 16.8 | 0.1 | 11 | 192 | 20 | 0.0 | 491,220 | 93.8 | 30.34 |
| 18 | 200,833 | 4.6 | 0.0 | 11 | 43.6 | 20 | 0.0 | 365,745 | 19.2 | 35.44 |
| 24 | 188,367 | 1.2 | 0.0 | 11 | 9.9 | 19 | 0.0 | 272,320 | 3.9 | 40.88 |
| 36 | 165,708 | 0.1 | 0.0 | 11 | 0.5 | 19 | 0.0 | 150,968 | 0.2 | 52.32 |
| 48 | 145,775 | 0.0 | 0.0 | 11 | 0.0 | 19 | 0.0 | 83,693 | 0.0 | 63.52 |
| 72 | 112,814 | 0.0 | 0.0 | 11 | 0.0 | 19 | 0.0 | 25,722 | 0.0 | 81.42 |
| 96 | 87,306 | 0.0 | 0.0 | 11 | 0.0 | 19 | 0.0 | 7,905 | 0.0 | 91.67 |
| 120 | 67,565 | 0.0 | 0.0 | 10 | 0.0 | 18 | 0.0 | 2,429 | 0.0 | 96.49 |
| 144 | 52,288 | 0.0 | 0.0 | 10 | 0.0 | 18 | 0.0 | 747 | 0.0 | 98.54 |
| 168 | 40,465 | 0.0 | 0.0 | 10 | 0.0 | 18 | 0.0 | 229 | 0.0 | 99.37 |
| 192 | 31,315 | 0.0 | 0.0 | 10 | 0.0 | 18 | 0.0 | 70.5 | 0.0 | 99.69 |
| 216 | 24,235 | 0.0 | 0.0 | 10 | 0.0 | 17 | 0.0 | 21.7 | 0.0 | 99.80 |
| 240 | 18,755 | 0.0 | 0.0 | 9.9 | 0.0 | 17 | 0.0 | 6.7 | 0.0 | 99.82 |
| 264 | 14,514 | 0.0 | 0.0 | 9.8 | 0.0 | 17 | 0.0 | 2.0 | 0.0 | 99.80 |
| 288 | 11,232 | 0.0 | 0.0 | 9.7 | 0.0 | 17 | 0.0 | 0.6 | 0.0 | 99.76 |
| 312 | 8,693 | 0.0 | 0.0 | 9.6 | 0.0 | 17 | 0.0 | 0.2 | 0.0 | 99.70 |
| 336 | 6,727 | 0.0 | 0.0 | 9.5 | 0.0 | 16 | 0.0 | 0.1 | 0.0 | 99.62 |
| 360 | 5,206 | 0.0 | 0.0 | 9.4 | 0.0 | 16 | 0.0 | 0.0 | 0.0 | 99.51 |
| 384 | 4,029 | 0.0 | 0.0 | 9.3 | 0.0 | 16 | 0.0 | 0.0 | 0.0 | 99.38 |

Activity present (MBq) in 1 g of Occlu90Y1.1 at indicated time (h) after End of Irradiation EOI.

TABLE 38

Scenario 1: Continuous 24 h neutron irradiation of Occlu90Y1.2/1.6 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 59,547 | 205 | 131 | 0.96 | 2,176 | 1.7 | 629,492 | 791,900 | 1,836 | 4.01 |
| 12 | 52,384 | 15.1 | 0.1 | 0.95 | 113 | 1.7 | 0.0 | 439,010 | 76.7 | 10.66 |
| 18 | 49,133 | 4.1 | 0.0 | 0.95 | 25.7 | 1.7 | 0.0 | 326,871 | 15.7 | 13.07 |
| 24 | 46,083 | 1.1 | 0.0 | 0.95 | 5.8 | 1.7 | 0.0 | 243,377 | 3.2 | 15.92 |
| 36 | 40,540 | 0.1 | 0.0 | 0.94 | 0.3 | 1.7 | 0.0 | 134,922 | 0.1 | 23.10 |
| 48 | 35,663 | 0.0 | 0.0 | 0.94 | 0.0 | 1.7 | 0.0 | 74,798 | 0.0 | 32.29 |
| 72 | 27,599 | 0.0 | 0.0 | 0.93 | 0.0 | 1.7 | 0.0 | 22,988 | 0.0 | 54.56 |
| 96 | 21,359 | 0.0 | 0.0 | 0.92 | 0.0 | 1.6 | 0.0 | 7,065 | 0.0 | 75.14 |
| 120 | 16,529 | 0.0 | 0.0 | 0.91 | 0.0 | 1.6 | 0.0 | 2,171 | 0.0 | 88.38 |
| 144 | 12,792 | 0.0 | 0.0 | 0.90 | 0.0 | 1.6 | 0.0 | 667 | 0.0 | 95.02 |
| 168 | 9,900 | 0.0 | 0.0 | 0.89 | 0.0 | 1.6 | 0.0 | 205 | 0.0 | 97.95 |
| 192 | 7,661 | 0.0 | 0.0 | 0.88 | 0.0 | 1.6 | 0.0 | 63.0 | 0.0 | 99.15 |
| 216 | 5,929 | 0.0 | 0.0 | 0.87 | 0.0 | 1.5 | 0.0 | 19.4 | 0.0 | 99.63 |
| 240 | 4,588 | 0.0 | 0.0 | 0.86 | 0.0 | 1.5 | 0.0 | 6.0 | 0.0 | 99.82 |
| 264 | 3,551 | 0.0 | 0.0 | 0.85 | 0.0 | 1.5 | 0.0 | 1.8 | 0.0 | 99.88 |
| 288 | 2,748 | 0.0 | 0.0 | 0.84 | 0.0 | 1.5 | 0.0 | 0.6 | 0.0 | 99.90 |
| 312 | 2,127 | 0.0 | 0.0 | 0.83 | 0.0 | 1.4 | 0.0 | 0.2 | 0.0 | 99.88 |
| 336 | 1,646 | 0.0 | 0.0 | 0.83 | 0.0 | 1.4 | 0.0 | 0.1 | 0.0 | 99.86 |

TABLE 38-continued

Scenario 1: Continuous 24 h neutron irradiation of Occlu90Y1.2/1.6 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 360 | 1,274 | 0.0 | 0.0 | 0.82 | 0.0 | 1.4 | 0.0 | 0.0 | 0.0 | 99.82 |
| 384 | 986 | 0.0 | 0.0 | 0.81 | 0.0 | 1.4 | 0.0 | 0.0 | 0.0 | 99.78 |

Activity present (MBq) in 1 g of Occlu90Y1.2/1.6 at indicated time (h) after EOI.

TABLE 39

Scenario 2: Continuous 72 h neutron irradiation of Occlu90Y1.2/1.6 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 141,300 | 206 | 131 | 2.8 | 2,182 | 5.1 | 629,492 | 1,110,173 | 1,839 | 7.49 |
| 12 | 124,303 | 15.2 | 0.1 | 2.8 | 113 | 5.1 | 0.0 | 615,453 | 76.9 | 16.80 |
| 18 | 109,351 | 1.1 | 0.0 | 2.8 | 5.9 | 5.1 | 0.0 | 341,192 | 3.2 | 24.27 |
| 24 | 109,351 | 1.1 | 0.0 | 2.8 | 5.9 | 5.1 | 0.0 | 341,192 | 3.2 | 24.27 |
| 36 | 96,197 | 0.1 | 0.0 | 2.8 | 0.3 | 5.0 | 0.0 | 189,149 | 0.1 | 33.71 |
| 48 | 84,625 | 0.0 | 0.0 | 2.8 | 0.0 | 5.0 | 0.0 | 104,859 | 0.0 | 44.66 |
| 72 | 65,491 | 0.0 | 0.0 | 2.8 | 0.0 | 4.9 | 0.0 | 32,227 | 0.0 | 67.02 |
| 96 | 50,683 | 0.0 | 0.0 | 2.7 | 0.0 | 4.9 | 0.0 | 9,904 | 0.0 | 83.64 |
| 120 | 39,223 | 0.0 | 0.0 | 2.7 | 0.0 | 4.8 | 0.0 | 3,044 | 0.0 | 92.78 |
| 144 | 30,354 | 0.0 | 0.0 | 2.7 | 0.0 | 4.7 | 0.0 | 935 | 0.0 | 96.99 |
| 168 | 23,491 | 0.0 | 0.0 | 2.6 | 0.0 | 4.7 | 0.0 | 288 | 0.0 | 98.76 |
| 192 | 18,179 | 0.0 | 0.0 | 2.6 | 0.0 | 4.6 | 0.0 | 88.4 | 0.0 | 99.48 |
| 216 | 14,069 | 0.0 | 0.0 | 2.6 | 0.0 | 4.5 | 0.0 | 27.2 | 0.0 | 99.76 |
| 240 | 10,888 | 0.0 | 0.0 | 2.6 | 0.0 | 4.5 | 0.0 | 8.3 | 0.0 | 99.86 |
| 264 | 8,426 | 0.0 | 0.0 | 2.5 | 0.0 | 4.4 | 0.0 | 2.6 | 0.0 | 99.89 |
| 288 | 6,521 | 0.0 | 0.0 | 2.5 | 0.0 | 4.3 | 0.0 | 0.8 | 0.0 | 99.88 |
| 312 | 5,046 | 0.0 | 0.0 | 2.5 | 0.0 | 4.3 | 0.0 | 0.2 | 0.0 | 99.86 |
| 336 | 3,905 | 0.0 | 0.0 | 2.5 | 0.0 | 4.2 | 0.0 | 0.1 | 0.0 | 99.83 |
| 360 | 3,022 | 0.0 | 0.0 | 2.4 | 0.0 | 4.2 | 0.0 | 0.0 | 0.0 | 99.78 |
| 384 | 2,339 | 0.0 | 0.0 | 2.4 | 0.0 | 4.1 | 0.0 | 0.0 | 0.0 | 99.72 |

Activity present (MBq) in 1 g of Occlu90Y1.2/1.6 at indicated time (h) after EOI.

TABLE 40

Scenario 3: Continuous 7 d (168 h) neutron irradiation of Occlu90Y1.2/1.6 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 219,597 | 206 | 131 | 6.5 | 2,182 | 11.6 | 629,492 | 1,143,092 | 1,839 | 11.00 |
| 12 | 193,182 | 15.2 | 0.1 | 6.5 | 113 | 11.6 | 0.0 | 633,702 | 76.9 | 23.36 |
| 18 | 181,191 | 4.1 | 0.0 | 6.4 | 25.7 | 11.5 | 0.0 | 471,832 | 15.7 | 27.74 |
| 24 | 169,944 | 1.1 | 0.0 | 6.4 | 5.9 | 11.5 | 0.0 | 351,309 | 3.2 | 32.60 |
| 36 | 149,502 | 0.1 | 0.0 | 6.4 | 0.3 | 11.4 | 0.0 | 194,757 | 0.1 | 43.42 |
| 48 | 131,518 | 0.0 | 0.0 | 6.4 | 0.0 | 11.3 | 0.0 | 107,969 | 0.0 | 54.91 |
| 72 | 101,781 | 0.0 | 0.0 | 6.3 | 0.0 | 11.2 | 0.0 | 33,182 | 0.0 | 75.40 |
| 96 | 78,767 | 0.0 | 0.0 | 6.2 | 0.0 | 11.0 | 0.0 | 10,198 | 0.0 | 88.52 |
| 120 | 60,957 | 0.0 | 0.0 | 6.2 | 0.0 | 10.9 | 0.0 | 3,134 | 0.0 | 95.08 |
| 144 | 47,174 | 0.0 | 0.0 | 6.1 | 0.0 | 10.7 | 0.0 | 963 | 0.0 | 97.96 |
| 168 | 36,507 | 0.0 | 0.0 | 6.0 | 0.0 | 10.6 | 0.0 | 296 | 0.0 | 99.15 |
| 192 | 28,253 | 0.0 | 0.0 | 6.0 | 0.0 | 10.4 | 0.0 | 91.0 | 0.0 | 99.62 |
| 216 | 21,865 | 0.0 | 0.0 | 5.9 | 0.0 | 10.3 | 0.0 | 28.0 | 0.0 | 99.80 |
| 240 | 16,921 | 0.0 | 0.0 | 5.8 | 0.0 | 10.1 | 0.0 | 8.6 | 0.0 | 99.85 |
| 264 | 13,095 | 0.0 | 0.0 | 5.8 | 0.0 | 10.0 | 0.0 | 2.6 | 0.0 | 99.86 |
| 288 | 10,134 | 0.0 | 0.0 | 5.7 | 0.0 | 9.9 | 0.0 | 0.8 | 0.0 | 99.84 |
| 312 | 7,843 | 0.0 | 0.0 | 5.7 | 0.0 | 9.7 | 0.0 | 0.2 | 0.0 | 99.80 |
| 336 | 6,069 | 0.0 | 0.0 | 5.6 | 0.0 | 9.6 | 0.0 | 0.1 | 0.0 | 99.75 |
| 360 | 4,697 | 0.0 | 0.0 | 5.5 | 0.0 | 9.5 | 0.0 | 0.0 | 0.0 | 99.68 |
| 384 | 3,635 | 0.0 | 0.0 | 5.5 | 0.0 | 9.3 | 0.0 | 0.0 | 0.0 | 99.59 |

Activity present (MBq) in 1 g of Occlu90Y1.2/1.6 at indicated time (h) after EOI.

TABLE 41

Scenario 1: Continuous 24 h neutron irradiation of Occlu90Y1.4/1.7 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---:|---:|---:|---:|---:|---:|---:|---:|---:|---:|---:|
| 0 | 91,932 | 316.0 | 166.4 | 1.22 | 2,766.4 | 2.20 | 562,143 | 707,175 | 1,449.5 | 6.73 |
| 12 | 80,873 | 23.3 | 0.1 | 1.21 | 143.3 | 2.19 | 0.0 | 392,040 | 60.6 | 17.09 |
| 18 | 75,854 | 6.3 | 0.0 | 1.21 | 32.6 | 2.18 | 0.0 | 291,899 | 12.4 | 20.62 |
| 24 | 71,145 | 1.7 | 0.0 | 1.21 | 7.4 | 2.17 | 0.0 | 217,338 | 2.5 | 24.66 |
| 36 | 62,587 | 0.1 | 0.0 | 1.20 | 0.4 | 2.16 | 0.0 | 120,487 | 0.1 | 34.19 |
| 48 | 55,059 | 0.0 | 0.0 | 1.19 | 0.0 | 2.14 | 0.0 | 66,795 | 0.0 | 45.18 |
| 72 | 42,609 | 0.0 | 0.0 | 1.18 | 0.0 | 2.11 | 0.0 | 20,528 | 0.0 | 67.48 |
| 96 | 32,975 | 0.0 | 0.0 | 1.17 | 0.0 | 2.08 | 0.0 | 6,309 | 0.0 | 83.93 |
| 120 | 25,519 | 0.0 | 0.0 | 1.16 | 0.0 | 2.06 | 0.0 | 1,939 | 0.0 | 92.93 |
| 144 | 19,749 | 0.0 | 0.0 | 1.14 | 0.0 | 2.03 | 0.0 | 596 | 0.0 | 97.06 |
| 168 | 15,283 | 0.0 | 0.0 | 1.13 | 0.0 | 2.00 | 0.0 | 183 | 0.0 | 98.80 |
| 192 | 11,828 | 0.0 | 0.0 | 1.12 | 0.0 | 1.97 | 0.0 | 56.3 | 0.0 | 99.50 |
| 216 | 9,153 | 0.0 | 0.0 | 1.11 | 0.0 | 1.95 | 0.0 | 17.3 | 0.0 | 99.78 |
| 240 | 7,084 | 0.0 | 0.0 | 1.10 | 0.0 | 1.92 | 0.0 | 5.3 | 0.0 | 99.88 |
| 264 | 5,482 | 0.0 | 0.0 | 1.08 | 0.0 | 1.89 | 0.0 | 1.6 | 0.0 | 99.92 |
| 288 | 4,242 | 0.0 | 0.0 | 1.07 | 0.0 | 1.87 | 0.0 | 0.5 | 0.0 | 99.92 |
| 312 | 3,283 | 0.0 | 0.0 | 1.06 | 0.0 | 1.84 | 0.0 | 0.2 | 0.0 | 99.91 |
| 336 | 2,541 | 0.0 | 0.0 | 1.05 | 0.0 | 1.82 | 0.0 | 0.0 | 0.0 | 99.89 |
| 360 | 1,966 | 0.0 | 0.0 | 1.04 | 0.0 | 1.79 | 0.0 | 0.0 | 0.0 | 99.86 |
| 384 | 1,522 | 0.0 | 0.0 | 1.03 | 0.0 | 1.77 | 0.0 | 0.0 | 0.0 | 99.82 |

Activity present (MBq) in 1 g of Occlu90Y1.4/1.7 at indicated time (h) after EOI.

TABLE 42

Scenario 2: Continuous 72 h neutron irradiation of Occlu90Y1.4/1.7 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---:|---:|---:|---:|---:|---:|---:|---:|---:|---:|---:|
| 0 | 218,146 | 317.7 | 166.4 | 3.6 | 2,773.9 | 6.5 | 562,143 | 991,395 | 1,452.1 | 12.28 |
| 12 | 191,905 | 23.4 | 0.1 | 3.6 | 143.7 | 6.5 | 0.0 | 549,606 | 60.7 | 25.87 |
| 18 | 179,993 | 6.4 | 0.0 | 3.6 | 32.7 | 6.4 | 0.0 | 409,217 | 12.4 | 30.55 |
| 24 | 168,821 | 1.7 | 0.0 | 3.6 | 7.4 | 6.4 | 0.0 | 304,688 | 2.5 | 35.65 |
| 36 | 148,513 | 0.1 | 0.0 | 3.6 | 0.4 | 6.4 | 0.0 | 168,912 | 0.1 | 46.79 |
| 48 | 130,649 | 0.0 | 0.0 | 3.5 | 0.0 | 6.3 | 0.0 | 93,641 | 0.0 | 58.25 |
| 72 | 101,108 | 0.0 | 0.0 | 3.5 | 0.0 | 6.3 | 0.0 | 28,779 | 0.0 | 77.84 |
| 96 | 78,246 | 0.0 | 0.0 | 3.5 | 0.0 | 6.2 | 0.0 | 8,845 | 0.0 | 89.83 |
| 120 | 60,554 | 0.0 | 0.0 | 3.4 | 0.0 | 6.1 | 0.0 | 2,718 | 0.0 | 95.69 |
| 144 | 46,862 | 0.0 | 0.0 | 3.4 | 0.0 | 6.0 | 0.0 | 835 | 0.0 | 98.23 |
| 168 | 36,266 | 0.0 | 0.0 | 3.4 | 0.0 | 5.9 | 0.0 | 257 | 0.0 | 99.27 |
| 192 | 28,066 | 0.0 | 0.0 | 3.3 | 0.0 | 5.8 | 0.0 | 78.9 | 0.0 | 99.69 |
| 216 | 21,720 | 0.0 | 0.0 | 3.3 | 0.0 | 5.8 | 0.0 | 24.3 | 0.0 | 99.85 |
| 240 | 16,809 | 0.0 | 0.0 | 3.3 | 0.0 | 5.7 | 0.0 | 7.5 | 0.0 | 99.90 |
| 264 | 13,008 | 0.0 | 0.0 | 3.2 | 0.0 | 5.6 | 0.0 | 2.3 | 0.0 | 99.91 |
| 288 | 10,067 | 0.0 | 0.0 | 3.2 | 0.0 | 5.5 | 0.0 | 0.7 | 0.0 | 99.91 |
| 312 | 7,791 | 0.0 | 0.0 | 3.1 | 0.0 | 5.5 | 0.0 | 0.2 | 0.0 | 99.89 |
| 336 | 6,029 | 0.0 | 0.0 | 3.1 | 0.0 | 5.4 | 0.0 | 0.1 | 0.0 | 99.86 |
| 360 | 4,666 | 0.0 | 0.0 | 3.1 | 0.0 | 5.3 | 0.0 | 0.0 | 0.0 | 99.82 |
| 384 | 3,611 | 0.0 | 0.0 | 3.0 | 0.0 | 5.2 | 0.0 | 0.0 | 0.0 | 99.77 |

Activity present (MBq) in 1 g of Occlu90Y1.4/1.7 at indicated time (h) after EOI.

TABLE 43

Scenario 3: Continuous 7 d (168 h) neutron irradiation of Occlu90Y1.4/1.7 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---:|---:|---:|---:|---:|---:|---:|---:|---:|---:|---:|
| 0 | 339,025 | 318 | 166 | 8.3 | 2,774 | 14.8 | 562,143 | 1,020,792 | 1,452 | 17.60 |
| 12 | 298,244 | 23.4 | 0.1 | 8.2 | 144 | 14.7 | 0.0 | 565,903 | 60.7 | 34.50 |
| 18 | 279,731 | 6.4 | 0.0 | 8.2 | 32.7 | 14.6 | 0.0 | 421,351 | 12.4 | 39.90 |
| 24 | 262,368 | 1.7 | 0.0 | 8.2 | 7.4 | 14.6 | 0.0 | 313,723 | 2.5 | 45.54 |
| 36 | 230,808 | 0.1 | 0.0 | 8.1 | 0.4 | 14.5 | 0.0 | 173,920 | 0.1 | 57.02 |
| 48 | 203,044 | 0.0 | 0.0 | 8.1 | 0.0 | 14.4 | 0.0 | 96,417 | 0.0 | 67.80 |
| 72 | 157,134 | 0.0 | 0.0 | 8.0 | 0.0 | 14.2 | 0.0 | 29,632 | 0.0 | 84.12 |
| 96 | 121,604 | 0.0 | 0.0 | 7.9 | 0.0 | 14.0 | 0.0 | 9,107 | 0.0 | 93.02 |
| 120 | 94,108 | 0.0 | 0.0 | 7.8 | 0.0 | 13.8 | 0.0 | 2,799 | 0.0 | 97.09 |

TABLE 43-continued

Scenario 3: Continuous 7 d (168 h) neutron irradiation of Occlu90Y1.4/1.7 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 144 | 72,829 | 0.0 | 0.0 | 7.8 | 0.0 | 13.6 | 0.0 | 860 | 0.0 | 98.80 |
| 168 | 56,362 | 0.0 | 0.0 | 7.7 | 0.0 | 13.4 | 0.0 | 264 | 0.0 | 99.50 |
| 192 | 43,618 | 0.0 | 0.0 | 7.6 | 0.0 | 13.3 | 0.0 | 81.2 | 0.0 | 99.77 |
| 216 | 33,756 | 0.0 | 0.0 | 7.5 | 0.0 | 13.1 | 0.0 | 25.0 | 0.0 | 99.87 |
| 240 | 26,123 | 0.0 | 0.0 | 7.4 | 0.0 | 12.9 | 0.0 | 7.7 | 0.0 | 99.89 |
| 264 | 20,216 | 0.0 | 0.0 | 7.3 | 0.0 | 12.7 | 0.0 | 2.4 | 0.0 | 99.89 |
| 288 | 15,645 | 0.0 | 0.0 | 7.3 | 0.0 | 12.5 | 0.0 | 0.7 | 0.0 | 99.87 |
| 312 | 12,108 | 0.0 | 0.0 | 7.2 | 0.0 | 12.4 | 0.0 | 0.2 | 0.0 | 99.84 |
| 336 | 9,370 | 0.0 | 0.0 | 7.1 | 0.0 | 12.2 | 0.0 | 0.1 | 0.0 | 99.79 |
| 360 | 7,251 | 0.0 | 0.0 | 7.0 | 0.0 | 12.0 | 0.0 | 0.0 | 0.0 | 99.74 |
| 384 | 5,612 | 0.0 | 0.0 | 7.0 | 0.0 | 11.9 | 0.0 | 0.0 | 0.0 | 99.67 |

Activity present (MBq) in 1 g of Occlu90Y1.4/1.7 at indicated time (h) after EOI.

TABLE 44

Scenario 1: Continuous 24 h neutron irradiation of Occlu90Y1.5 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 81,925 | 282 | 242 | 1.8 | 4,020 | 3.2 | 513,445 | 645,913 | 1,769 | 6.57 |
| 12 | 72,070 | 20.8 | 0.2 | 1.8 | 208 | 3.2 | 0.0 | 358,078 | 74.0 | 16.74 |
| 18 | 67,597 | 5.6 | 0.0 | 1.8 | 47.4 | 3.2 | 0.0 | 266,612 | 15.1 | 20.22 |
| 24 | 63,401 | 1.5 | 0.0 | 1.8 | 10.8 | 3.2 | 0.0 | 198,510 | 3.1 | 24.21 |
| 36 | 55,774 | 0.1 | 0.0 | 1.7 | 0.6 | 3.1 | 0.0 | 110,049 | 0.1 | 33.63 |
| 48 | 49,065 | 0.0 | 0.0 | 1.7 | 0.0 | 3.1 | 0.0 | 61,009 | 0.0 | 44.57 |
| 72 | 37,971 | 0.0 | 0.0 | 1.7 | 0.0 | 3.1 | 0.0 | 18,750 | 0.0 | 66.94 |
| 96 | 29,385 | 0.0 | 0.0 | 1.7 | 0.0 | 3.0 | 0.0 | 5,762 | 0.0 | 83.59 |
| 120 | 22,741 | 0.0 | 0.0 | 1.7 | 0.0 | 3.0 | 0.0 | 1,771.0 | 0.0 | 92.76 |
| 144 | 17,599 | 0.0 | 0.0 | 1.7 | 0.0 | 2.9 | 0.0 | 544 | 0.0 | 96.98 |
| 168 | 13,620 | 0.0 | 0.0 | 1.6 | 0.0 | 2.9 | 0.0 | 167 | 0.0 | 98.75 |
| 192 | 10,540 | 0.0 | 0.0 | 1.6 | 0.0 | 2.9 | 0.0 | 51.4 | 0.0 | 99.47 |
| 216 | 8,157 | 0.0 | 0.0 | 1.6 | 0.0 | 2.8 | 0.0 | 15.8 | 0.0 | 99.75 |
| 240 | 6,313 | 0.0 | 0.0 | 1.6 | 0.0 | 2.8 | 0.0 | 4.9 | 0.0 | 99.85 |
| 264 | 4,885 | 0.0 | 0.0 | 1.6 | 0.0 | 2.8 | 0.0 | 1.5 | 0.0 | 99.88 |
| 288 | 3,781 | 0.0 | 0.0 | 1.6 | 0.0 | 2.7 | 0.0 | 0.5 | 0.0 | 99.88 |
| 312 | 2,926 | 0.0 | 0.0 | 1.5 | 0.0 | 2.7 | 0.0 | 0.1 | 0.0 | 99.85 |
| 336 | 2,264 | 0.0 | 0.0 | 1.5 | 0.0 | 2.6 | 0.0 | 0.0 | 0.0 | 99.81 |
| 360 | 1,752 | 0.0 | 0.0 | 1.5 | 0.0 | 2.6 | 0.0 | 0.0 | 0.0 | 99.77 |
| 384 | 1,356 | 0.0 | 0.0 | 1.5 | 0.0 | 2.6 | 0.0 | 0.0 | 0.0 | 99.70 |

Activity present (MBq) in 1 g of Occlu90Y1.5 at indicated time (h) after EOI.

TABLE 45

Scenario 2: Continuous 72 h neutron irradiation of Occlu90Y1.5 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 194,400 | 283 | 242 | 5.3 | 4,031 | 9.5 | 513,445 | 905,512 | 1,772 | 12.00 |
| 12 | 171,015 | 20.9 | 0.2 | 5.2 | 209 | 9.4 | 0.0 | 501,994 | 74.1 | 25.40 |
| 18 | 160,400 | 5.7 | 0.0 | 5.2 | 47.5 | 9.4 | 0.0 | 373,767 | 15.2 | 30.02 |
| 24 | 150,444 | 1.5 | 0.0 | 5.2 | 10.8 | 9.3 | 0.0 | 278,293 | 3.1 | 35.09 |
| 36 | 132,347 | 0.1 | 0.0 | 5.2 | 0.6 | 9.3 | 0.0 | 154,279 | 0.1 | 46.17 |
| 48 | 116,427 | 0.0 | 0.0 | 5.1 | 0.0 | 9.2 | 0.0 | 85,529 | 0.0 | 57.65 |
| 72 | 90,102 | 0.0 | 0.0 | 5.1 | 0.0 | 9.1 | 0.0 | 26,286 | 0.0 | 77.41 |
| 96 | 69,729 | 0.0 | 0.0 | 5.0 | 0.0 | 9.0 | 0.0 | 8,078 | 0.0 | 89.60 |
| 120 | 53,962 | 0.0 | 0.0 | 5.0 | 0.0 | 8.8 | 0.0 | 2,483 | 0.0 | 95.58 |
| 144 | 41,761 | 0.0 | 0.0 | 4.9 | 0.0 | 8.7 | 0.0 | 763 | 0.0 | 98.17 |
| 168 | 32,318 | 0.0 | 0.0 | 4.9 | 0.0 | 8.6 | 0.0 | 235 | 0.0 | 99.24 |
| 192 | 25,011 | 0.0 | 0.0 | 4.8 | 0.0 | 8.5 | 0.0 | 72.1 | 0.0 | 99.66 |
| 216 | 19,356 | 0.0 | 0.0 | 4.8 | 0.0 | 8.4 | 0.0 | 22.1 | 0.0 | 99.82 |
| 240 | 14,979 | 0.0 | 0.0 | 4.7 | 0.0 | 8.3 | 0.0 | 6.8 | 0.0 | 99.87 |
| 264 | 11,592 | 0.0 | 0.0 | 4.7 | 0.0 | 8.1 | 0.0 | 2.1 | 0.0 | 99.87 |
| 288 | 8,971 | 0.0 | 0.0 | 4.6 | 0.0 | 8.0 | 0.0 | 0.6 | 0.0 | 99.85 |
| 312 | 6,943 | 0.0 | 0.0 | 4.6 | 0.0 | 7.9 | 0.0 | 0.2 | 0.0 | 99.82 |

TABLE 45-continued

Scenario 2: Continuous 72 h neutron irradiation of Occlu90Y1.5 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 336 | 5,373 | 0.0 | 0.0 | 4.5 | 0.0 | 7.8 | 0.0 | 0.1 | 0.0 | 99.77 |
| 360 | 4,158 | 0.0 | 0.0 | 4.5 | 0.0 | 7.7 | 0.0 | 0.0 | 0.0 | 99.71 |
| 384 | 3,218 | 0.0 | 0.0 | 4.4 | 0.0 | 7.6 | 0.0 | 0.0 | 0.0 | 99.63 |

Activity present (MBq) in 1 g of Occlu90Y1.5 at indicated time (h) after EOI.

TABLE 46

Scenario 3: Continuous 7 d (168 h) neutron irradiation of Occlu90Y1.5 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 302,121 | 283 | 242 | 12.0 | 4,031 | 21.5 | 513,445 | 932,362 | 1,772 | 17.22 |
| 12 | 265,779 | 20.9 | 0.2 | 11.9 | 209 | 21.4 | 0.0 | 516,879 | 74.1 | 33.94 |
| 18 | 249,282 | 5.7 | 0.0 | 11.9 | 47.5 | 21.3 | 0.0 | 384,850 | 15.2 | 39.30 |
| 24 | 233,808 | 1.5 | 0.0 | 11.9 | 10.8 | 21.2 | 0.0 | 286,545 | 3.1 | 44.93 |
| 36 | 205,684 | 0.1 | 0.0 | 11.8 | 0.6 | 21.1 | 0.0 | 158,854 | 0.1 | 56.42 |
| 48 | 180,942 | 0.0 | 0.0 | 11.8 | 0.0 | 20.9 | 0.0 | 88,065 | 0.0 | 67.25 |
| 72 | 140,029 | 0.0 | 0.0 | 11.6 | 0.0 | 20.6 | 0.0 | 27,065 | 0.0 | 83.79 |
| 96 | 108,367 | 0.0 | 0.0 | 11.5 | 0.0 | 20.4 | 0.0 | 8,318 | 0.0 | 92.85 |
| 120 | 83,864 | 0.0 | 0.0 | 11.4 | 0.0 | 20.1 | 0.0 | 2,556 | 0.0 | 97.01 |
| 144 | 64,902 | 0.0 | 0.0 | 11.3 | 0.0 | 19.8 | 0.0 | 786 | 0.0 | 98.76 |
| 168 | 50,227 | 0.0 | 0.0 | 11.1 | 0.0 | 19.5 | 0.0 | 241 | 0.0 | 99.46 |
| 192 | 38,870 | 0.0 | 0.0 | 11.0 | 0.0 | 19.3 | 0.0 | 74.2 | 0.0 | 99.73 |
| 216 | 30,081 | 0.0 | 0.0 | 10.9 | 0.0 | 19.0 | 0.0 | 22.8 | 0.0 | 99.83 |
| 240 | 23,279 | 0.0 | 0.0 | 10.8 | 0.0 | 18.7 | 0.0 | 7.0 | 0.0 | 99.84 |
| 264 | 18,016 | 0.0 | 0.0 | 10.7 | 0.0 | 18.5 | 0.0 | 2.2 | 0.0 | 99.83 |
| 288 | 13,942 | 0.0 | 0.0 | 10.6 | 0.0 | 18.2 | 0.0 | 0.7 | 0.0 | 99.79 |
| 312 | 10,790 | 0.0 | 0.0 | 10.5 | 0.0 | 18.0 | 0.0 | 0.2 | 0.0 | 99.74 |
| 336 | 8,350 | 0.0 | 0.0 | 10.3 | 0.0 | 17.7 | 0.0 | 0.1 | 0.0 | 99.66 |
| 360 | 6,462 | 0.0 | 0.0 | 10.2 | 0.0 | 17.5 | 0.0 | 0.0 | 0.0 | 99.57 |
| 384 | 5,001 | 0.0 | 0.0 | 10.1 | 0.0 | 17.3 | 0.0 | 0.0 | 0.0 | 99.46 |

Activity present (MBq) in 1 g of Occlu90Y1.5 at indicated time (h) after EOI.

TABLE 47

Scenario 1: Continuous 24 h neutron irradiation of Occlu90Y1.11 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 99,679 | 343 | 143 | 1.0 | 2,381 | 1.9 | 348,950 | 438,979 | 2,340 | 11.16 |
| 12 | 87,689 | 25.3 | 0.1 | 1.0 | 123 | 1.9 | 0.0 | 243,359 | 97.8 | 26.47 |
| 18 | 82,246 | 6.9 | 0.0 | 1.0 | 28.1 | 1.9 | 0.0 | 181,196 | 20.0 | 31.21 |
| 24 | 77,141 | 1.9 | 0.0 | 1.0 | 6.4 | 1.9 | 0.0 | 134,912 | 4.1 | 36.38 |
| 36 | 67,861 | 0.1 | 0.0 | 1.0 | 0.3 | 1.9 | 0.0 | 74,792 | 0.2 | 47.57 |
| 48 | 59,698 | 0.0 | 0.0 | 1.0 | 0.0 | 1.8 | 0.0 | 41,463 | 0.0 | 59.01 |
| 72 | 46,200 | 0.0 | 0.0 | 1.0 | 0.0 | 1.8 | 0.0 | 12,743 | 0.0 | 78.38 |
| 96 | 35,754 | 0.0 | 0.0 | 1.0 | 0.0 | 1.8 | 0.0 | 3,916 | 0.0 | 90.12 |
| 120 | 27,669 | 0.0 | 0.0 | 1.0 | 0.0 | 1.8 | 0.0 | 1,203.6 | 0.0 | 95.82 |
| 144 | 21,413 | 0.0 | 0.0 | 1.0 | 0.0 | 1.7 | 0.0 | 370 | 0.0 | 98.29 |
| 168 | 16,571 | 0.0 | 0.0 | 1.0 | 0.0 | 1.7 | 0.0 | 114 | 0.0 | 99.30 |
| 192 | 12,824 | 0.0 | 0.0 | 1.0 | 0.0 | 1.7 | 0.0 | 34.9 | 0.0 | 99.71 |
| 216 | 9,925 | 0.0 | 0.0 | 1.0 | 0.0 | 1.7 | 0.0 | 10.7 | 0.0 | 99.87 |
| 240 | 7,681 | 0.0 | 0.0 | 0.9 | 0.0 | 1.7 | 0.0 | 3.3 | 0.0 | 99.92 |
| 264 | 5,934 | 0.0 | 0.0 | 0.9 | 0.0 | 1.7 | 0.0 | 1.4 | 0.0 | 99.94 |
| 288 | 4,600 | 0.0 | 0.0 | 0.9 | 0.0 | 1.6 | 0.0 | 0.3 | 0.0 | 99.94 |
| 312 | 3,560 | 0.0 | 0.0 | 0.9 | 0.0 | 1.6 | 0.0 | 0.1 | 0.0 | 99.93 |
| 336 | 2,755 | 0.0 | 0.0 | 0.9 | 0.0 | 1.6 | 0.0 | 0.0 | 0.0 | 99.91 |
| 360 | 2,132 | 0.0 | 0.0 | 0.9 | 0.0 | 1.5 | 0.0 | 0.0 | 0.0 | 99.89 |
| 384 | 1,650 | 0.0 | 0.0 | 0.9 | 0.0 | 1.5 | 0.0 | 0.0 | 0.0 | 99.85 |

Activity present (MBq) in 1 g of Occlu90Y1.11 at indicated time (h) after EOI.

TABLE 48

Scenario 2: Continuous 72 h neutron irradiation of Occlu90Y1.11 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 236,529 | 344 | 143 | 3.1 | 2,387 | 5.6 | 348,950 | 615,408 | 2,344 | 19.61 |
| 12 | 208,077 | 25.4 | 0.1 | 3.1 | 124 | 5.6 | 0.0 | 341,168 | 98.0 | 37.87 |
| 18 | 195,161 | 6.9 | 0.0 | 3.1 | 28.2 | 5.5 | 0.0 | 254,021 | 20.0 | 43.44 |
| 24 | 183,047 | 1.9 | 0.0 | 3.1 | 6.4 | 5.5 | 0.0 | 189,135 | 4.1 | 49.18 |
| 36 | 161,029 | 0.1 | 0.0 | 3.1 | 0.3 | 5.5 | 0.0 | 104,852 | 0.2 | 60.56 |
| 48 | 141,658 | 0.0 | 0.0 | 3.0 | 0.0 | 5.5 | 0.0 | 58,127 | 0.0 | 70.90 |
| 72 | 109,628 | 0.0 | 0.0 | 3.0 | 0.0 | 5.4 | 0.0 | 17,864 | 0.0 | 85.98 |
| 96 | 84,840 | 0.0 | 0.0 | 3.0 | 0.0 | 5.3 | 0.0 | 5,490 | 0.0 | 93.91 |
| 120 | 65,657 | 0.0 | 0.0 | 3.0 | 0.0 | 5.2 | 0.0 | 1,687 | 0.0 | 97.48 |
| 144 | 50,811 | 0.0 | 0.0 | 2.9 | 0.0 | 5.2 | 0.0 | 519 | 0.0 | 98.97 |
| 168 | 39,322 | 0.0 | 0.0 | 2.9 | 0.0 | 5.1 | 0.0 | 159 | 0.0 | 99.58 |
| 192 | 30,431 | 0.0 | 0.0 | 2.9 | 0.0 | 5.0 | 0.0 | 49.0 | 0.0 | 99.81 |
| 216 | 23,550 | 0.0 | 0.0 | 2.8 | 0.0 | 5.0 | 0.0 | 15.1 | 0.0 | 99.90 |
| 240 | 18,225 | 0.0 | 0.0 | 2.8 | 0.0 | 4.9 | 0.0 | 4.6 | 0.0 | 99.93 |
| 264 | 14,104 | 0.0 | 0.0 | 2.8 | 0.0 | 4.8 | 0.0 | 1.4 | 0.0 | 99.94 |
| 288 | 10,915 | 0.0 | 0.0 | 2.7 | 0.0 | 4.8 | 0.0 | 0.4 | 0.0 | 99.93 |
| 312 | 8,447 | 0.0 | 0.0 | 2.7 | 0.0 | 4.7 | 0.0 | 0.1 | 0.0 | 99.91 |
| 336 | 6,537 | 0.0 | 0.0 | 2.7 | 0.0 | 4.6 | 0.0 | 0.0 | 0.0 | 99.89 |
| 360 | 5,059 | 0.0 | 0.0 | 2.7 | 0.0 | 4.6 | 0.0 | 0.0 | 0.0 | 99.86 |
| 384 | 3,915 | 0.0 | 0.0 | 2.6 | 0.0 | 4.5 | 0.0 | 0.0 | 0.0 | 99.82 |

Activity present (MBq) in 1 g of Occlu90Y1.11 at indicated time (h) after EOI.

TABLE 49

Scenario 3: Continuous 7 d (168 h) neutron irradiation of Occlu90Y1.11 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 367,595 | 344 | 143 | 7.1 | 2,387 | 12.7 | 348,950 | 633,657 | 2,344 | 27.12 |
| 12 | 323,377 | 25.4 | 0.1 | 7.1 | 124 | 12.6 | 0.0 | 351,284 | 98.0 | 47.91 |
| 18 | 303,304 | 6.9 | 0.0 | 7.1 | 28.2 | 12.6 | 0.0 | 261,553 | 20.0 | 53.69 |
| 24 | 284,478 | 1.9 | 0.0 | 7.0 | 6.4 | 12.6 | 0.0 | 194,743 | 4.1 | 59.36 |
| 36 | 250,258 | 0.1 | 0.0 | 7.0 | 0.3 | 12.5 | 0.0 | 107,961 | 0.2 | 69.86 |
| 48 | 220,155 | 0.0 | 0.0 | 7.0 | 0.0 | 12.4 | 0.0 | 59,851 | 0.0 | 78.62 |
| 72 | 170,375 | 0.0 | 0.0 | 6.9 | 0.0 | 12.2 | 0.0 | 18,394 | 0.0 | 90.25 |
| 96 | 131,852 | 0.0 | 0.0 | 6.8 | 0.0 | 12.1 | 0.0 | 5,653 | 0.0 | 95.88 |
| 120 | 102,039 | 0.0 | 0.0 | 6.7 | 0.0 | 11.9 | 0.0 | 1,737 | 0.0 | 98.31 |
| 144 | 78,967 | 0.0 | 0.0 | 6.7 | 0.0 | 11.7 | 0.0 | 534 | 0.0 | 99.31 |
| 168 | 61,112 | 0.0 | 0.0 | 6.6 | 0.0 | 11.6 | 0.0 | 164 | 0.0 | 99.70 |
| 192 | 47,294 | 0.0 | 0.0 | 6.5 | 0.0 | 11.4 | 0.0 | 50.4 | 0.0 | 99.86 |
| 216 | 36,600 | 0.0 | 0.0 | 6.5 | 0.0 | 11.3 | 0.0 | 15.5 | 0.0 | 99.91 |
| 240 | 28,324 | 0.0 | 0.0 | 6.4 | 0.0 | 11.1 | 0.0 | 4.8 | 0.0 | 99.92 |
| 264 | 21,920 | 0.0 | 0.0 | 6.3 | 0.0 | 10.9 | 0.0 | 1.5 | 0.0 | 99.91 |
| 288 | 16,964 | 0.0 | 0.0 | 6.3 | 0.0 | 10.8 | 0.0 | 0.4 | 0.0 | 99.90 |
| 312 | 13,128 | 0.0 | 0.0 | 6.2 | 0.0 | 10.7 | 0.0 | 0.1 | 0.0 | 99.87 |
| 336 | 10,160 | 0.0 | 0.0 | 6.1 | 0.0 | 10.5 | 0.0 | 0.0 | 0.0 | 99.84 |
| 360 | 7,862 | 0.0 | 0.0 | 6.1 | 0.0 | 10.4 | 0.0 | 0.0 | 0.0 | 99.79 |
| 384 | 6,085 | 0.0 | 0.0 | 6.0 | 0.0 | 10.2 | 0.0 | 0.0 | 0.0 | 99.73 |

Activity present (MBq) in 1 g of Occlu90Y1.11 at indicated time (h) after EOI.

TABLE 50

Scenario 1: Continuous 24 h neutron irradiation of Occlu90Y1.12 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 71,552 | 246 | 248 | 1.8 | 4,117 | 3.3 | 595,590 | 749,251 | 1,580 | 5.03 |
| 12 | 62,945 | 18.1 | 0.2 | 1.8 | 213 | 3.3 | 0.0 | 415,367 | 66.0 | 13.15 |
| 18 | 59,038 | 4.9 | 0.0 | 1.8 | 48.6 | 3.2 | 0.0 | 309,267 | 13.5 | 16.03 |
| 24 | 55,373 | 1.3 | 0.0 | 1.8 | 11.1 | 3.2 | 0.0 | 230,269 | 2.8 | 19.38 |
| 36 | 48,713 | 0.1 | 0.0 | 1.8 | 0.6 | 3.2 | 0.0 | 127,656 | 0.1 | 27.62 |
| 48 | 42,853 | 0.0 | 0.0 | 1.8 | 0.0 | 3.2 | 0.0 | 70,769 | 0.0 | 37.71 |
| 72 | 33,163 | 0.0 | 0.0 | 1.8 | 0.0 | 3.1 | 0.0 | 21,750 | 0.0 | 60.39 |
| 96 | 25,665 | 0.0 | 0.0 | 1.7 | 0.0 | 3.1 | 0.0 | 6,684 | 0.0 | 79.32 |

TABLE 50-continued

Scenario 1: Continuous 24 h neutron irradiation of Occlu90Y1.12 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 120 | 19,862 | 0.0 | 0.0 | 1.7 | 0.0 | 3.1 | 0.0 | 2,054 | 0.0 | 90.61 |
| 144 | 15,371 | 0.0 | 0.0 | 1.7 | 0.0 | 3.0 | 0.0 | 631 | 0.0 | 96.03 |
| 168 | 11,895 | 0.0 | 0.0 | 1.7 | 0.0 | 3.0 | 0.0 | 194 | 0.0 | 98.36 |
| 192 | 9,206 | 0.0 | 0.0 | 1.7 | 0.0 | 2.9 | 0.0 | 59.6 | 0.0 | 99.31 |
| 216 | 7,124 | 0.0 | 0.0 | 1.6 | 0.0 | 2.9 | 0.0 | 18.3 | 0.0 | 99.68 |
| 240 | 5,513 | 0.0 | 0.0 | 1.6 | 0.0 | 2.9 | 0.0 | 5.6 | 0.0 | 99.82 |
| 264 | 4,267 | 0.0 | 0.0 | 1.6 | 0.0 | 2.8 | 0.0 | 1.7 | 0.0 | 99.86 |
| 288 | 3,302 | 0.0 | 0.0 | 1.6 | 0.0 | 2.8 | 0.0 | 0.5 | 0.0 | 99.85 |
| 312 | 2,555 | 0.0 | 0.0 | 1.6 | 0.0 | 2.7 | 0.0 | 0.2 | 0.0 | 99.82 |
| 336 | 1,978 | 0.0 | 0.0 | 1.6 | 0.0 | 2.7 | 0.0 | 0.1 | 0.0 | 99.78 |
| 360 | 1,530 | 0.0 | 0.0 | 1.5 | 0.0 | 2.7 | 0.0 | 0.0 | 0.0 | 99.72 |
| 384 | 1,184 | 0.0 | 0.0 | 1.5 | 0.0 | 2.6 | 0.0 | 0.0 | 0.0 | 99.65 |

Activity present (MBq) in 1 g of Occlu90Y1.12 at indicated time (h) after EOI.

TABLE 51

Scenario 2: Continuous 72 h neutron irradiation of Occlu90Y1.12 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 169,786 | 247 | 248 | 5.4 | 4,128 | 9.7 | 595,590 | 1,050,382 | 1,582 | 9.32 |
| 12 | 149,363 | 18.2 | 0.2 | 5.4 | 214 | 9.6 | 0.0 | 582,307 | 66.2 | 20.41 |
| 18 | 140,092 | 4.9 | 0.0 | 5.3 | 48.7 | 9.6 | 0.0 | 433,565 | 13.5 | 24.42 |
| 24 | 131,396 | 1.3 | 0.0 | 5.3 | 11.1 | 9.6 | 0.0 | 322,817 | 2.8 | 28.93 |
| 36 | 115,590 | 0.1 | 0.0 | 5.3 | 0.6 | 9.5 | 0.0 | 178,962 | 0.1 | 39.24 |
| 48 | 101,686 | 0.0 | 0.0 | 5.3 | 0.0 | 9.4 | 0.0 | 99,212 | 0.0 | 50.61 |
| 72 | 78,694 | 0.0 | 0.0 | 5.2 | 0.0 | 9.3 | 0.0 | 30,491 | 0.0 | 72.06 |
| 96 | 60,900 | 0.0 | 0.0 | 5.2 | 0.0 | 9.2 | 0.0 | 9,371 | 0.0 | 86.65 |
| 120 | 47,130 | 0.0 | 0.0 | 5.1 | 0.0 | 9.1 | 0.0 | 2,880 | 0.0 | 94.21 |
| 144 | 36,474 | 0.0 | 0.0 | 5.0 | 0.0 | 8.9 | 0.0 | 885 | 0.0 | 97.59 |
| 168 | 28,227 | 0.0 | 0.0 | 5.0 | 0.0 | 8.8 | 0.0 | 272 | 0.0 | 99.00 |
| 192 | 21,844 | 0.0 | 0.0 | 4.9 | 0.0 | 8.7 | 0.0 | 83.6 | 0.0 | 99.56 |
| 216 | 16,905 | 0.0 | 0.0 | 4.9 | 0.0 | 8.6 | 0.0 | 25.7 | 0.0 | 99.77 |
| 240 | 13,083 | 0.0 | 0.0 | 4.8 | 0.0 | 8.5 | 0.0 | 7.9 | 0.0 | 99.84 |
| 264 | 10,125 | 0.0 | 0.0 | 4.8 | 0.0 | 8.3 | 0.0 | 2.4 | 0.0 | 99.85 |
| 288 | 7,835 | 0.0 | 0.0 | 4.7 | 0.0 | 8.2 | 0.0 | 0.7 | 0.0 | 99.83 |
| 312 | 6,064 | 0.0 | 0.0 | 4.7 | 0.0 | 8.1 | 0.0 | 0.2 | 0.0 | 99.79 |
| 336 | 4,693 | 0.0 | 0.0 | 4.6 | 0.0 | 8.0 | 0.0 | 0.1 | 0.0 | 99.73 |
| 360 | 3,632 | 0.0 | 0.0 | 4.6 | 0.0 | 7.9 | 0.0 | 0.0 | 0.0 | 99.66 |
| 384 | 2,810 | 0.0 | 0.0 | 4.5 | 0.0 | 7.8 | 0.0 | 0.0 | 0.0 | 99.56 |

Activity present (MBq) in 1 g of Occlu90Y1.12 at indicated time (h) after EOI.

TABLE 52

Scenario 3: Continuous 7 d (168 h) neutron irradiation of Occlu90Y1.12 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 263,869 | 247 | 248 | 12.3 | 4,128 | 22.0 | 595,590 | 1,081,529 | 1,582 | 13.55 |
| 12 | 232,128 | 18.2 | 0.2 | 12.2 | 214 | 21.9 | 0.0 | 599,573 | 66.2 | 27.90 |
| 18 | 217,720 | 4.9 | 0.0 | 12.2 | 48.7 | 21.8 | 0.0 | 446,421 | 13.5 | 32.78 |
| 24 | 204,205 | 1.3 | 0.0 | 12.2 | 11.1 | 21.7 | 0.0 | 332,389 | 2.8 | 38.05 |
| 36 | 179,642 | 0.1 | 0.0 | 12.1 | 0.6 | 21.6 | 0.0 | 184,268 | 0.1 | 49.36 |
| 48 | 158,033 | 0.0 | 0.0 | 12.0 | 0.0 | 21.4 | 0.0 | 102,154 | 0.0 | 60.73 |
| 72 | 122,300 | 0.0 | 0.0 | 11.9 | 0.0 | 21.1 | 0.0 | 31,395 | 0.0 | 79.56 |
| 96 | 94,647 | 0.0 | 0.0 | 11.8 | 0.0 | 20.8 | 0.0 | 9,649 | 0.0 | 90.72 |
| 120 | 73,246 | 0.0 | 0.0 | 11.7 | 0.0 | 20.6 | 0.0 | 2,965 | 0.0 | 96.07 |
| 144 | 56,684 | 0.0 | 0.0 | 11.5 | 0.0 | 20.3 | 0.0 | 911 | 0.0 | 98.36 |
| 168 | 43,867 | 0.0 | 0.0 | 11.4 | 0.0 | 20.0 | 0.0 | 280 | 0.0 | 99.29 |
| 192 | 33,949 | 0.0 | 0.0 | 11.3 | 0.0 | 19.7 | 0.0 | 86.1 | 0.0 | 99.66 |
| 216 | 26,272 | 0.0 | 0.0 | 11.2 | 0.0 | 19.5 | 0.0 | 26.5 | 0.0 | 99.78 |
| 240 | 20,332 | 0.0 | 0.0 | 11.1 | 0.0 | 19.2 | 0.0 | 8.1 | 0.0 | 99.81 |
| 264 | 15,735 | 0.0 | 0.0 | 10.9 | 0.0 | 18.9 | 0.0 | 2.5 | 0.0 | 99.79 |
| 288 | 12,177 | 0.0 | 0.0 | 10.8 | 0.0 | 18.7 | 0.0 | 0.8 | 0.0 | 99.75 |

TABLE 52-continued

Scenario 3: Continuous 7 d (168 h) neutron irradiation of Occlu90Y1.12 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 312 | 9,424 | 0.0 | 0.0 | 10.7 | 0.0 | 18.4 | 0.0 | 0.2 | 0.0 | 99.69 |
| 336 | 7,293 | 0.0 | 0.0 | 10.6 | 0.0 | 18.2 | 0.0 | 0.1 | 0.0 | 99.61 |
| 360 | 5,644 | 0.0 | 0.0 | 10.5 | 0.0 | 17.9 | 0.0 | 0.0 | 0.0 | 99.50 |
| 384 | 4,368 | 0.0 | 0.0 | 10.4 | 0.0 | 17.7 | 0.0 | 0.0 | 0.0 | 99.36 |

Activity present (MBq) in 1 g of Occlu90Y1.12 at indicated time (h) after EOI.

TABLE 53

Scenario 1: Continuous 24 h neutron irradiation of Occlu90Y1.15 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 86,935 | 299 | 141 | 1.0 | 2,343 | 1.9 | 467,112 | 587,626 | 2,039 | 7.58 |
| 12 | 76,478 | 22.0 | 0.1 | 1.0 | 121 | 1.9 | 0.0 | 325,766 | 85.3 | 19.00 |
| 18 | 71,731 | 6.0 | 0.0 | 1.0 | 27.6 | 1.8 | 0.0 | 242,553 | 17.4 | 22.82 |
| 24 | 67,278 | 1.6 | 0.0 | 1.0 | 6.3 | 1.8 | 0.0 | 180,597 | 3.6 | 27.14 |
| 36 | 59,185 | 0.1 | 0.0 | 1.0 | 0.3 | 1.8 | 0.0 | 100,118 | 0.1 | 37.15 |
| 48 | 52,066 | 0.0 | 0.0 | 1.0 | 0.0 | 1.8 | 0.0 | 55,503 | 0.0 | 48.40 |
| 72 | 40,293 | 0.0 | 0.0 | 1.0 | 0.0 | 1.8 | 0.0 | 17,058 | 0.0 | 70.25 |
| 96 | 31,183 | 0.0 | 0.0 | 1.0 | 0.0 | 1.8 | 0.0 | 5,242 | 0.0 | 85.60 |
| 120 | 24,132 | 0.0 | 0.0 | 1.0 | 0.0 | 1.7 | 0.0 | 1,611 | 0.0 | 93.73 |
| 144 | 18,675 | 0.0 | 0.0 | 1.0 | 0.0 | 1.7 | 0.0 | 495 | 0.0 | 97.40 |
| 168 | 14,453 | 0.0 | 0.0 | 1.0 | 0.0 | 1.7 | 0.0 | 152 | 0.0 | 98.94 |
| 192 | 11,185 | 0.0 | 0.0 | 0.95 | 0.0 | 1.7 | 0.0 | 46.8 | 0.0 | 99.56 |
| 216 | 8,656 | 0.0 | 0.0 | 0.94 | 0.0 | 1.6 | 0.0 | 14.4 | 0.0 | 99.80 |
| 240 | 6,699 | 0.0 | 0.0 | 0.93 | 0.0 | 1.6 | 0.0 | 4.4 | 0.0 | 99.90 |
| 264 | 5,184 | 0.0 | 0.0 | 0.92 | 0.0 | 1.6 | 0.0 | 1.4 | 0.0 | 99.93 |
| 288 | 4,012 | 0.0 | 0.0 | 0.91 | 0.0 | 1.6 | 0.0 | 0.4 | 0.0 | 99.93 |
| 312 | 3,105 | 0.0 | 0.0 | 0.90 | 0.0 | 1.6 | 0.0 | 0.1 | 0.0 | 99.92 |
| 336 | 2,403 | 0.0 | 0.0 | 0.89 | 0.0 | 1.5 | 0.0 | 0.0 | 0.0 | 99.90 |
| 360 | 1,859 | 0.0 | 0.0 | 0.88 | 0.0 | 1.5 | 0.0 | 0.0 | 0.0 | 99.87 |
| 384 | 1,439 | 0.0 | 0.0 | 0.87 | 0.0 | 1.5 | 0.0 | 0.0 | 0.0 | 99.84 |

Activity present (MBq) in 1 g of Occlu90Y1.15 at indicated time (h) after EOI.

TABLE 54

Scenario 2: Continuous 72 h neutron irradiation of Occlu90Y1.15 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 206,288 | 300 | 141 | 3.1 | 2,349 | 5.5 | 467,112 | 823,799 | 2,043 | 13.73 |
| 12 | 181,474 | 22.1 | 0.1 | 3.0 | 122 | 5.5 | 0.0 | 456,694 | 85.4 | 28.43 |
| 18 | 170,210 | 6.0 | 0.0 | 3.0 | 27.7 | 5.5 | 0.0 | 340,038 | 17.5 | 33.35 |
| 24 | 159,644 | 1.6 | 0.0 | 3.0 | 6.3 | 5.4 | 0.0 | 253,180 | 3.6 | 38.67 |
| 36 | 140,441 | 0.1 | 0.0 | 3.0 | 0.3 | 5.4 | 0.0 | 140,357 | 0.1 | 50.01 |
| 48 | 123,547 | 0.0 | 0.0 | 3.0 | 0.0 | 5.4 | 0.0 | 77,810 | 0.0 | 61.35 |
| 72 | 95,612 | 0.0 | 0.0 | 3.0 | 0.0 | 5.3 | 0.0 | 23,914 | 0.0 | 79.99 |
| 96 | 73,993 | 0.0 | 0.0 | 2.9 | 0.0 | 5.2 | 0.0 | 7,349 | 0.0 | 90.96 |
| 120 | 57,263 | 0.0 | 0.0 | 2.9 | 0.0 | 5.2 | 0.0 | 2,259 | 0.0 | 96.19 |
| 144 | 44,315 | 0.0 | 0.0 | 2.9 | 0.0 | 5.1 | 0.0 | 694 | 0.0 | 98.44 |
| 168 | 34,295 | 0.0 | 0.0 | 2.8 | 0.0 | 5.0 | 0.0 | 213 | 0.0 | 99.36 |
| 192 | 26,540 | 0.0 | 0.0 | 2.8 | 0.0 | 4.9 | 0.0 | 65.6 | 0.0 | 99.72 |
| 216 | 20,539 | 0.0 | 0.0 | 2.8 | 0.0 | 4.9 | 0.0 | 20.2 | 0.0 | 99.86 |
| 240 | 15,895 | 0.0 | 0.0 | 2.8 | 0.0 | 4.8 | 0.0 | 6.2 | 0.0 | 99.91 |
| 264 | 12,301 | 0.0 | 0.0 | 2.7 | 0.0 | 4.7 | 0.0 | 1.9 | 0.0 | 99.92 |
| 288 | 9,520 | 0.0 | 0.0 | 2.7 | 0.0 | 4.7 | 0.0 | 0.6 | 0.0 | 99.92 |
| 312 | 7,367 | 0.0 | 0.0 | 2.7 | 0.0 | 4.6 | 0.0 | 0.2 | 0.0 | 99.90 |
| 336 | 5,701 | 0.0 | 0.0 | 2.6 | 0.0 | 4.6 | 0.0 | 0.1 | 0.0 | 99.87 |
| 360 | 4,412 | 0.0 | 0.0 | 2.6 | 0.0 | 4.5 | — | 0.0 | 0.0 | 99.84 |
| 384 | 3,415 | 0.0 | 0.0 | 2.6 | 0.0 | 4.4 | — | 0.0 | 0.0 | 99.79 |

Activity present (MBq) in 1 g of Occlu90Y1.15 at indicated time (h) after EOI.

TABLE 55

Scenario 3: Continuous 7 d (168 h) neutron irradiation of Occlu90Y1.15 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 320,597 | 300 | 141 | 7.0 | 2,349 | 12.5 | 467,112 | 848,226 | 2,043 | 19.54 |
| 12 | 282,033 | 22.1 | 0.1 | 7.0 | 122 | 12.4 | 0.0 | 470,236 | 85.4 | 37.48 |
| 18 | 264,527 | 6.0 | 0.0 | 6.9 | 27.7 | 12.4 | 0.0 | 350,121 | 17.5 | 43.03 |
| 24 | 248,107 | 1.6 | 0.0 | 6.9 | 6.3 | 12.4 | 0.0 | 260,688 | 3.6 | 48.76 |
| 36 | 218,262 | 0.1 | 0.0 | 6.9 | 0.3 | 12.3 | 0.0 | 144,519 | 0.1 | 60.16 |
| 48 | 192,008 | 0.0 | 0.0 | 6.9 | 0.0 | 12.2 | 0.0 | 80,118 | 0.0 | 70.55 |
| 72 | 148,593 | 0.0 | 0.0 | 6.8 | 0.0 | 12.0 | 0.0 | 24,623 | 0.0 | 85.78 |
| 96 | 114,994 | 0.0 | 0.0 | 6.7 | 0.0 | 11.9 | 0.0 | 7,567 | 0.0 | 93.81 |
| 120 | 88,993 | 0.0 | 0.0 | 6.6 | 0.0 | 11.7 | 0.0 | 2,326 | 0.0 | 97.43 |
| 144 | 68,871 | 0.0 | 0.0 | 6.6 | 0.0 | 11.5 | 0.0 | 715 | 0.0 | 98.95 |
| 168 | 53,298 | 0.0 | 0.0 | 6.5 | 0.0 | 11.4 | 0.0 | 220 | 0.0 | 99.56 |
| 192 | 41,247 | 0.0 | 0.0 | 6.4 | 0.0 | 11.2 | 0.0 | 67.5 | 0.0 | 99.79 |
| 216 | 31,921 | 0.0 | 0.0 | 6.4 | 0.0 | 11.1 | 0.0 | 20.7 | 0.0 | 99.88 |
| 240 | 24,703 | 0.0 | 0.0 | 6.3 | 0.0 | 10.9 | 0.0 | 6.4 | 0.0 | 99.90 |
| 264 | 19,118 | 0.0 | 0.0 | 6.2 | 0.0 | 10.8 | 0.0 | 2.0 | 0.0 | 99.90 |
| 288 | 14,795 | 0.0 | 0.0 | 6.2 | 0.0 | 10.6 | 0.0 | 0.6 | 0.0 | 99.88 |
| 312 | 11,450 | 0.0 | 0.0 | 6.1 | 0.0 | 10.5 | 0.0 | 0.2 | 0.0 | 99.85 |
| 336 | 8,861 | 0.0 | 0.0 | 6.0 | 0.0 | 10.3 | 0.0 | 0.1 | 0.0 | 99.81 |
| 360 | 6,857 | 0.0 | 0.0 | 6.0 | 0.0 | 10.2 | 0.0 | 0.0 | 0.0 | 99.76 |
| 384 | 5,307 | 0.0 | 0.0 | 5.9 | 0.0 | 10.1 | 0.0 | 0.0 | 0.0 | 99.70 |

Activity present (MBq) in 1 g of Occlu90Y1.15 at indicated time (h) after EOI.

TABLE 56

Scenario 1: Continuous 24 h neutron irradiation of Occlu90Y1.16 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 104,030 | 358 | 269 | 2.0 | 4,472 | 3.6 | 360,107 | 453,014 | 2,011 | 11.26 |
| 12 | 91,516 | 26.4 | 0.2 | 2.0 | 232 | 3.5 | 0.0 | 251,140 | 84.1 | 26.68 |
| 18 | 85,835 | 7.2 | 0.0 | 2.0 | 52.7 | 3.5 | 0.0 | 186,990 | 17.2 | 31.45 |
| 24 | 80,508 | 1.9 | 0.0 | 1.9 | 12.0 | 3.5 | 0.0 | 139,226 | 3.5 | 36.63 |
| 36 | 70,823 | 0.1 | 0.0 | 1.9 | 0.6 | 3.5 | 0.0 | 77,184 | 0.1 | 47.85 |
| 48 | 62,304 | 0.0 | 0.0 | 1.9 | 0.0 | 3.5 | 0.0 | 42,789 | 0.0 | 59.28 |
| 72 | 48,216 | 0.0 | 0.0 | 1.9 | 0.0 | 3.4 | 0.0 | 13,150 | 0.0 | 78.56 |
| 96 | 37,314 | 0.0 | 0.0 | 1.9 | 0.0 | 3.4 | 0.0 | 4,042 | 0.0 | 90.22 |
| 120 | 28,877 | 0.0 | 0.0 | 1.9 | 0.0 | 3.3 | 0.0 | 1,242 | 0.0 | 95.86 |
| 144 | 22,348 | 0.0 | 0.0 | 1.8 | 0.0 | 3.3 | 0.0 | 382 | 0.0 | 98.30 |
| 168 | 17,295 | 0.0 | 0.0 | 1.8 | 0.0 | 3.2 | 0.0 | 117 | 0.0 | 99.30 |
| 192 | 13,384 | 0.0 | 0.0 | 1.8 | 0.0 | 3.2 | 0.0 | 36.1 | 0.0 | 99.69 |
| 216 | 10,358 | 0.0 | 0.0 | 1.8 | 0.0 | 3.1 | 0.0 | 11.1 | 0.0 | 99.85 |
| 240 | 8,016 | 0.0 | 0.0 | 1.8 | 0.0 | 3.1 | 0.0 | 3.4 | 0.0 | 99.90 |
| 264 | 6,203 | 0.0 | 0.0 | 1.8 | 0.0 | 3.1 | 0.0 | 1.0 | 0.0 | 99.91 |
| 288 | 4,801 | 0.0 | 0.0 | 1.7 | 0.0 | 3.0 | 0.0 | 0.3 | 0.0 | 99.89 |
| 312 | 3,715 | 0.0 | 0.0 | 1.7 | 0.0 | 3.0 | 0.0 | 0.1 | 0.0 | 99.87 |
| 336 | 2,875 | 0.0 | 0.0 | 1.7 | 0.0 | 2.9 | 0.0 | 0.0 | 0.0 | 99.84 |
| 360 | 2,225 | 0.0 | 0.0 | 1.7 | 0.0 | 2.9 | 0.0 | 0.0 | 0.0 | 99.79 |
| 384 | 1,722 | 0.0 | 0.0 | 1.7 | 0.0 | 2.9 | 0.0 | 0.0 | 0.0 | 99.74 |

Activity present (MBq) in 1 g of Occlu90Y1.16 at indicated time (h) after EOI.

TABLE 57

Scenario 2: Continuous 72 h neutron irradiation of Occlu90Y1.16 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 246,852 | 360 | 269 | 5.8 | 4,484 | 10.5 | 360,107 | 635,085 | 2,015 | 19.76 |
| 12 | 217,158 | 26.5 | 0.2 | 5.8 | 232 | 10.5 | 0.0 | 352,076 | 84.2 | 38.13 |
| 18 | 203,679 | 7.2 | 0.0 | 5.8 | 52.9 | 10.4 | 0.0 | 262,143 | 17.2 | 43.72 |
| 24 | 191,037 | 2.0 | 0.0 | 5.8 | 12.0 | 10.4 | 0.0 | 195,182 | 3.5 | 49.46 |
| 36 | 168,057 | 0.1 | 0.0 | 5.8 | 0.6 | 10.3 | 0.0 | 108,204 | 0.1 | 60.83 |
| 48 | 147,841 | 0.0 | 0.0 | 5.7 | 0.0 | 10.2 | 0.0 | 59,986 | 0.0 | 71.13 |
| 72 | 114,413 | 0.0 | 0.0 | 5.7 | 0.0 | 10.1 | 0.0 | 18,436 | 0.0 | 86.11 |
| 96 | 88,543 | 0.0 | 0.0 | 5.6 | 0.0 | 10.0 | 0.0 | 5,666 | 0.0 | 93.97 |

TABLE 57-continued

Scenario 2: Continuous 72 h neutron irradiation of Occlu90Y1.16 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 120 | 68,523 | 0.0 | 0.0 | 5.5 | 0.0 | 9.8 | 0.0 | 1,741 | 0.0 | 97.50 |
| 144 | 53,029 | 0.0 | 0.0 | 5.5 | 0.0 | 9.7 | 0.0 | 535 | 0.0 | 98.97 |
| 168 | 41,039 | 0.0 | 0.0 | 5.4 | 0.0 | 9.6 | 0.0 | 164 | 0.0 | 99.56 |
| 192 | 31,759 | 0.0 | 0.0 | 5.4 | 0.0 | 9.4 | 0.0 | 50.5 | 0.0 | 99.79 |
| 216 | 24,578 | 0.0 | 0.0 | 5.3 | 0.0 | 9.3 | 0.0 | 15.5 | 0.0 | 99.88 |
| 240 | 19,021 | 0.0 | 0.0 | 5.3 | 0.0 | 9.2 | 0.0 | 4.8 | 0.0 | 99.90 |
| 264 | 14,720 | 0.0 | 0.0 | 5.2 | 0.0 | 9.1 | 0.0 | 1.5 | 0.0 | 99.89 |
| 288 | 11,392 | 0.0 | 0.0 | 5.1 | 0.0 | 8.8 | 0.0 | 0.5 | 0.0 | 99.87 |
| 312 | 8,816 | 0.0 | 0.0 | 5.1 | 0.0 | 8.8 | 0.0 | 0.1 | 0.0 | 99.84 |
| 336 | 6,823 | 0.0 | 0.0 | 5.0 | 0.0 | 8.7 | 0.0 | 0.0 | 0.0 | 99.80 |
| 360 | 5,280 | 0.0 | 0.0 | 5.0 | 0.0 | 8.6 | 0.0 | 0.0 | 0.0 | 99.74 |
| 384 | 4,086 | 0.0 | 0.0 | 4.9 | 0.0 | 8.5 | 0.0 | 0.0 | 0.0 | 99.67 |

Activity present (MBq) in 1 g of Occlu90Y1.16 at indicated time (h) after EOI.

TABLE 58

Scenario 3: Continuous 7 d (168 h) neutron irradiation of Occlu90Y1.16 at 2E+14 n/cm2 · s

| Time (h) | Y-90 | Y-90m | Sr-85m | Sr-85 | Sr-87m | Sr-89 | Ga-70 | Ga-72 | Si-31 | % Y-90 |
|---|---|---|---|---|---|---|---|---|---|---|
| 0 | 383,639 | 360 | 269 | 13.4 | 4,484 | 23.9 | 360,107 | 653,917 | 2,015 | 27.31 |
| 12 | 337,491 | 26.5 | 0.2 | 13.3 | 232 | 23.8 | 0.0 | 362,516 | 84.2 | 48.19 |
| 18 | 316,542 | 7.2 | 0.0 | 13.3 | 52.9 | 23.7 | 0.0 | 269,916 | 17.2 | 53.96 |
| 24 | 296,894 | 2.0 | 0.0 | 13.2 | 12.0 | 23.6 | 0.0 | 200,970 | 3.5 | 59.63 |
| 36 | 261,181 | 0.1 | 0.0 | 13.1 | 0.6 | 23.4 | 0.0 | 111,413 | 0.1 | 70.09 |
| 48 | 229,763 | 0.0 | 0.0 | 13.1 | 0.0 | 23.3 | 0.0 | 61,765 | 0.0 | 78.80 |
| 72 | 177,812 | 0.0 | 0.0 | 12.9 | 0.0 | 23.0 | 0.0 | 18,982 | 0.0 | 90.34 |
| 96 | 137,607 | 0.0 | 0.0 | 12.8 | 0.0 | 22.6 | 0.0 | 5,834 | 0.0 | 95.91 |
| 120 | 106,492 | 0.0 | 0.0 | 12.7 | 0.0 | 22.3 | 0.0 | 1,793 | 0.0 | 98.31 |
| 144 | 82,413 | 0.0 | 0.0 | 12.5 | 0.0 | 22.0 | 0.0 | 551 | 0.0 | 99.29 |
| 168 | 63,779 | 0.0 | 0.0 | 12.4 | 0.0 | 21.7 | 0.0 | 169 | 0.0 | 99.68 |
| 192 | 49,358 | 0.0 | 0.0 | 12.3 | 0.0 | 21.4 | 0.0 | 52.0 | 0.0 | 99.83 |
| 216 | 38,198 | 0.0 | 0.0 | 12.1 | 0.0 | 21.1 | 0.0 | 16.0 | 0.0 | 99.87 |
| 240 | 29,561 | 0.0 | 0.0 | 12.0 | 0.0 | 20.9 | 0.0 | 4.9 | 0.0 | 99.87 |
| 264 | 22,877 | 0.0 | 0.0 | 11.9 | 0.0 | 20.6 | 0.0 | 1.5 | 0.0 | 99.85 |
| 288 | 17,704 | 0.0 | 0.0 | 11.8 | 0.0 | 20.3 | 0.0 | 0.5 | 0.0 | 99.82 |
| 312 | 13,701 | 0.0 | 0.0 | 11.6 | 0.0 | 20.0 | 0.0 | 0.1 | 0.0 | 99.77 |
| 336 | 10,603 | 0.0 | 0.0 | 11.5 | 0.0 | 19.7 | 0.0 | 0.0 | 0.0 | 99.71 |
| 360 | 8,206 | 0.0 | 0.0 | 11.4 | 0.0 | 19.5 | 0.0 | 0.0 | 0.0 | 99.63 |
| 384 | 6,350 | 0.0 | 0.0 | 11.3 | 0.0 | 19.2 | 0.0 | 0.0 | 0.0 | 99.52 |

Activity present (MBq) in 1 g of Occlu90Y1.16 at indicated time (h) after EOI.

TABLE 59

Scenario 1: Continuous 24 h neutron irradiation of Occlu90Y2.3 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 60,689 | 209 | 267 | 2.0 | 4,435 | 3.5 | 534,632 | 672,566 | 1,627 | 932 | — | 4.76 |
| 12 | 53,388 | 15.4 | 0.2 | 1.9 | 230 | 3.5 | 0.0 | 372,854 | 68.0 | 0.0 | — | 12.52 |
| 18 | 50,075 | 4.2 | 0.0 | 1.9 | 52.3 | 3.5 | 0.0 | 277,614 | 13.9 | 0.0 | — | 15.28 |
| 24 | 46,966 | 1.1 | 0.0 | 1.9 | 11.9 | 3.5 | 0.0 | 206,701 | 2.8 | 0.0 | — | 18.51 |
| 36 | 41,317 | 0.1 | 0.0 | 1.9 | 0.6 | 3.5 | 0.0 | 114,590 | 0.1 | 0.0 | — | 26.50 |
| 48 | 36,347 | 0.0 | 0.0 | 1.9 | 0.0 | 3.4 | 0.0 | 63,526 | 0.0 | 0.0 | — | 36.39 |
| 72 | 28,128 | 0.0 | 0.0 | 1.9 | 0.0 | 3.4 | 0.0 | 19,524 | 0.0 | 0.0 | — | 59.02 |
| 96 | 21,768 | 0.0 | 0.0 | 1.9 | 0.0 | 3.3 | 0.0 | 6,000 | 0.0 | 0.0 | — | 78.38 |
| 120 | 16,846 | 0.0 | 0.0 | 1.9 | 0.0 | 3.3 | 0.0 | 1,844 | 0.0 | 0.0 | — | 90.11 |
| 144 | 13,037 | 0.0 | 0.0 | 1.8 | 0.0 | 3.3 | 0.0 | 567 | 0.0 | 0.0 | — | 95.80 |
| 168 | 10,089 | 0.0 | 0.0 | 1.8 | 0.0 | 3.2 | 0.0 | 174 | 0.0 | 0.0 | — | 98.25 |
| 192 | 7,808 | 0.0 | 0.0 | 1.8 | 0.0 | 3.2 | 0.0 | 53.5 | 0.0 | 0.0 | — | 99.26 |
| 216 | 6,043 | 0.0 | 0.0 | 1.8 | 0.0 | 3.1 | 0.0 | 16.5 | 0.0 | 0.0 | — | 99.65 |
| 240 | 4,676 | 0.0 | 0.0 | 1.8 | 0.0 | 3.1 | 0.0 | 5.1 | 0.0 | 0.0 | — | 99.79 |
| 264 | 3,619 | 0.0 | 0.0 | 1.7 | 0.0 | 3.0 | 0.0 | 1.6 | 0.0 | 0.0 | — | 99.83 |
| 288 | 2,801 | 0.0 | 0.0 | 1.7 | 0.0 | 3.0 | 0.0 | 0.5 | 0.0 | 0.0 | — | 99.82 |
| 312 | 2,167 | 0.0 | 0.0 | 1.7 | 0.0 | 3.0 | 0.0 | 0.1 | 0.0 | 0.0 | — | 99.78 |
| 336 | 1,677 | 0.0 | 0.0 | 1.7 | 0.0 | 2.9 | 0.0 | 0.0 | 0.0 | 0.0 | — | 99.72 |

TABLE 59-continued

Scenario 1: Continuous 24 h neutron irradiation of Occlu90Y2.3 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 360 | 1,298 | 0.0 | 0.0 | 1.7 | 0.0 | 2.9 | 0.0 | 0.0 | 0.0 | 0.0 | — | 99.65 |
| 384 | 1,005 | 0.0 | 0.0 | 1.6 | 0.0 | 2.8 | 0.0 | 0.0 | 0.0 | 0.0 | — | 99.56 |

Activity present (MBq) in 1 g of Occlu90Y2.3 at indicated time (h) after EOI.

TABLE 60

Scenario 2: Continuous 72 h neutron irradiation of Occlu90Y2.3 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 144,008 | 210 | 267 | 5.8 | 4,447 | 10.4 | 534,632 | 942,877 | 1,630 | 932 | — | 8.84 |
| 12 | 126,686 | 15.5 | 0.2 | 5.8 | 230 | 10.4 | 0.0 | 522,708 | 68.1 | 0.0 | — | 19.50 |
| 18 | 118,822 | 4.2 | 0.0 | 5.8 | 52.5 | 10.3 | 0.0 | 389,190 | 13.9 | 0.0 | — | 23.39 |
| 24 | 111,447 | 1.1 | 0.0 | 5.7 | 11.9 | 10.3 | 0.0 | 289,777 | 2.8 | 0.0 | — | 27.77 |
| 36 | 98,041 | 0.1 | 0.0 | 5.7 | 0.6 | 10.2 | 0.0 | 160,645 | 0.1 | 0.0 | — | 37.90 |
| 48 | 86,247 | 0.0 | 0.0 | 5.7 | 0.0 | 10.2 | 0.0 | 89,058 | 0.0 | 0.0 | — | 49.19 |
| 72 | 66,746 | 0.0 | 0.0 | 5.6 | 0.0 | 10.0 | 0.0 | 27,370 | 0.0 | 0.0 | — | 70.91 |
| 96 | 51,654 | 0.0 | 0.0 | 5.6 | 0.0 | 9.9 | 0.0 | 8,412 | 0.0 | 0.0 | — | 85.97 |
| 120 | 39,975 | 0.0 | 0.0 | 5.5 | 0.0 | 9.8 | 0.0 | 2,585 | 0.0 | 0.0 | — | 93.89 |
| 144 | 30,936 | 0.0 | 0.0 | 5.4 | 0.0 | 9.6 | 0.0 | 795 | 0.0 | 0.0 | — | 97.45 |
| 168 | 23,941 | 0.0 | 0.0 | 5.4 | 0.0 | 9.5 | 0.0 | 244 | 0.0 | 0.0 | — | 98.93 |
| 192 | 18,528 | 0.0 | 0.0 | 5.3 | 0.0 | 9.4 | 0.0 | 75.0 | 0.0 | 0.0 | — | 99.52 |
| 216 | 14,338 | 0.0 | 0.0 | 5.3 | 0.0 | 9.2 | 0.0 | 23.1 | 0.0 | 0.0 | — | 99.74 |
| 240 | 11,096 | 0.0 | 0.0 | 5.2 | 0.0 | 9.1 | 0.0 | 7.1 | 0.0 | 0.0 | — | 99.81 |
| 264 | 8,587 | 0.0 | 0.0 | 5.2 | 0.0 | 9.0 | 0.0 | 2.2 | 0.0 | 0.0 | — | 99.81 |
| 288 | 6,646 | 0.0 | 0.0 | 5.1 | 0.0 | 8.9 | 0.0 | 0.7 | 0.0 | 0.0 | — | 99.78 |
| 312 | 5,143 | 0.0 | 0.0 | 5.0 | 0.0 | 8.7 | 0.0 | 0.2 | 0.0 | 0.0 | — | 99.73 |
| 336 | 3,980 | 0.0 | 0.0 | 5.0 | 0.0 | 8.6 | 0.0 | 0.1 | 0.0 | 0.0 | — | 99.66 |
| 360 | 3,080 | 0.0 | 0.0 | 4.9 | 0.0 | 8.5 | 0.0 | 0.0 | 0.0 | 0.0 | — | 99.56 |
| 384 | 2,384 | 0.0 | 0.0 | 4.9 | 0.0 | 8.4 | 0.0 | 0.0 | 0.0 | 0.0 | — | 99.45 |

Activity present (MBq) in 1 g of Occlu90Y2.3 at indicated time (h) after EOI.

TABLE 61

Scenario 3: Continuous 7 d (168 h) neutron irradiation of Occlu90Y2.3 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 223,807 | 210 | 267 | 13.2 | 4,447 | 23.7 | 534,632 | 970,835 | 1,630 | 932 | — | 12.89 |
| 12 | 196,885 | 15.5 | 0.2 | 13.2 | 230 | 23.6 | 0.0 | 538,208 | 68.1 | 0.0 | — | 26.77 |
| 18 | 184,664 | 4.2 | 0.0 | 13.1 | 52.5 | 23.5 | 0.0 | 400,730 | 13.9 | 0.0 | — | 31.54 |
| 24 | 173,202 | 1.1 | 0.0 | 13.1 | 11.9 | 23.4 | 0.0 | 298,369 | 2.8 | 0.0 | — | 36.72 |
| 36 | 152,367 | 0.1 | 0.0 | 13.0 | 0.6 | 23.2 | 0.0 | 165,409 | 0.1 | 0.0 | — | 47.94 |
| 48 | 134,039 | 0.0 | 0.0 | 13.0 | 0.0 | 23.1 | 0.0 | 91,699 | 0.0 | 0.0 | — | 59.37 |
| 72 | 103,731 | 0.0 | 0.0 | 12.8 | 0.0 | 22.8 | 0.0 | 28,182 | 0.0 | 0.0 | — | 78.61 |
| 96 | 80,277 | 0.0 | 0.0 | 12.7 | 0.0 | 22.5 | 0.0 | 8,661 | 0.0 | 0.0 | — | 90.23 |
| 120 | 62,125 | 0.0 | 0.0 | 12.6 | 0.0 | 22.1 | 0.0 | 2,662 | 0.0 | 0.0 | — | 95.84 |
| 144 | 48,078 | 0.0 | 0.0 | 12.4 | 0.0 | 21.8 | 0.0 | 818 | 0.0 | 0.0 | — | 98.26 |
| 168 | 37,207 | 0.0 | 0.0 | 12.3 | 0.0 | 21.5 | 0.0 | 251 | 0.0 | 0.0 | — | 99.24 |
| 192 | 28,794 | 0.0 | 0.0 | 12.2 | 0.0 | 21.3 | 0.0 | 77.3 | 0.0 | 0.0 | — | 99.62 |
| 216 | 22,284 | 0.0 | 0.0 | 12.0 | 0.0 | 21.0 | 0.0 | 23.7 | 0.0 | 0.0 | — | 99.75 |
| 240 | 17,245 | 0.0 | 0.0 | 11.9 | 0.0 | 20.7 | 0.0 | 7.3 | 0.0 | 0.0 | — | 99.77 |
| 264 | 13,346 | 0.0 | 0.0 | 11.8 | 0.0 | 20.4 | 0.0 | 2.2 | 0.0 | 0.0 | — | 99.74 |
| 288 | 10,328 | 0.0 | 0.0 | 11.7 | 0.0 | 20.1 | 0.0 | 0.7 | 0.0 | 0.0 | — | 99.69 |
| 312 | 7,993 | 0.0 | 0.0 | 11.5 | 0.0 | 19.8 | 0.0 | 0.2 | 0.0 | 0.0 | — | 99.61 |
| 336 | 6,186 | 0.0 | 0.0 | 11.4 | 0.0 | 19.6 | 0.0 | 0.1 | 0.0 | 0.0 | — | 99.50 |
| 360 | 4,787 | 0.0 | 0.0 | 11.3 | 0.0 | 19.3 | 0.0 | 0.0 | 0.0 | 0.0 | — | 99.36 |
| 384 | 3,705 | 0.0 | 0.0 | 11.2 | 0.0 | 19.0 | 0.0 | 0.0 | 0.0 | 0.0 | — | 99.19 |

Activity present (MBq) in 1 g of Occlu90Y2.3 at indicated time (h) after EOI.

TABLE 62

Scenario 1: Continuous 24 h neutron irradiation of Occlu90Y2.6 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 92,006 | 316 | 119 | 0.87 | 1,978 | 1.6 | 572,134 | 719,743 | 1,451 | — | 64.7 | 6.63 |
| 12 | 80,939 | 23.3 | 0.1 | 0.87 | 102 | 1.6 | 0.0 | 399,008 | 60.6 | — | 2.6 | 16.86 |
| 18 | 75,915 | 6.3 | 0.0 | 0.86 | 23.3 | 1.6 | 0.0 | 297,087 | 12.4 | — | 0.5 | 20.35 |
| 24 | 71,203 | 1.7 | 0.0 | 0.86 | 5.3 | 1.6 | 0.0 | 221,200 | 2.5 | — | 0.1 | 24.35 |
| 36 | 62,638 | 0.1 | 0.0 | 0.86 | 0.3 | 1.5 | 0.0 | 122,628 | 0.1 | — | 0.0 | 33.81 |
| 48 | 55,103 | 0.0 | 0.0 | 0.85 | 0.0 | 1.5 | 0.0 | 67,982 | 0.0 | — | 0.0 | 44.77 |
| 72 | 42,644 | 0.0 | 0.0 | 0.84 | 0.0 | 1.5 | 0.0 | 20,893 | 0.0 | — | 0.0 | 67.11 |
| 96 | 33,002 | 0.0 | 0.0 | 0.83 | 0.0 | 1.5 | 0.0 | 6,421 | 0.0 | — | 0.0 | 83.71 |
| 120 | 25,540 | 0.0 | 0.0 | 0.83 | 0.0 | 1.5 | 0.0 | 1,973 | 0.0 | — | 0.0 | 92.82 |
| 144 | 19,765 | 0.0 | 0.0 | 0.82 | 0.0 | 1.4 | 0.0 | 606 | 0.0 | — | 0.0 | 97.01 |
| 168 | 15,296 | 0.0 | 0.0 | 0.81 | 0.0 | 1.4 | 0.0 | 186 | 0.0 | — | 0.0 | 98.78 |
| 192 | 11,837 | 0.0 | 0.0 | 0.80 | 0.0 | 1.4 | 0.0 | 57.3 | 0.0 | — | 0.0 | 99.50 |
| 216 | 9,161 | 0.0 | 0.0 | 0.79 | 0.0 | 1.4 | 0.0 | 17.6 | 0.0 | — | 0.0 | 99.78 |
| 240 | 7,089 | 0.0 | 0.0 | 0.78 | 0.0 | 1.4 | 0.0 | 5.4 | 0.0 | — | 0.0 | 99.89 |
| 264 | 5,486 | 0.0 | 0.0 | 0.77 | 0.0 | 1.4 | 0.0 | 1.7 | 0.0 | — | 0.0 | 99.93 |
| 288 | 4,246 | 0.0 | 0.0 | 0.77 | 0.0 | 1.3 | 0.0 | 0.5 | 0.0 | — | 0.0 | 99.94 |
| 312 | 3,286 | 0.0 | 0.0 | 0.76 | 0.0 | 1.3 | 0.0 | 0.2 | 0.0 | — | 0.0 | 99.93 |
| 336 | 2,543 | 0.0 | 0.0 | 0.75 | 0.0 | 1.3 | 0.0 | 0.0 | 0.0 | — | 0.0 | 99.92 |
| 360 | 1,968 | 0.0 | 0.0 | 0.74 | 0.0 | 1.3 | 0.0 | 0.0 | 0.0 | — | 0.0 | 99.90 |
| 384 | 1,523 | 0.0 | 0.0 | 0.73 | 0.0 | 1.3 | 0.0 | 0.0 | 0.0 | — | 0.0 | 99.87 |

Activity present (MBq) in 1 g of Occlu90Y2.6 at indicated time (h) after EOI.

TABLE 63

Scenario 2: Continuous 72 h neutron irradiation of Occlu90Y2.6 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 218,322 | 318 | 119 | 2.6 | 1,983 | 4.7 | 572,134 | 1,009,015 | 1,453 | — | 64.8 | 12.11 |
| 12 | 192,060 | 23.4 | 0.1 | 2.6 | 103 | 4.6 | 0.0 | 559,373 | 60.8 | — | 2.6 | 25.55 |
| 18 | 180,139 | 6.4 | 0.0 | 2.6 | 23.4 | 4.6 | 0.0 | 416,489 | 12.4 | — | 0.5 | 30.19 |
| 24 | 168,957 | 1.7 | 0.0 | 2.6 | 5.3 | 4.6 | 0.0 | 310,103 | 2.5 | — | 0.1 | 35.27 |
| 36 | 148,634 | 0.1 | 0.0 | 2.5 | 0.3 | 4.6 | 0.0 | 171,914 | 0.1 | — | 0.0 | 46.37 |
| 48 | 130,754 | 0.0 | 0.0 | 2.5 | 0.0 | 4.5 | 0.0 | 95,305 | 0.0 | — | 0.0 | 57.84 |
| 72 | 101,190 | 0.0 | 0.0 | 2.5 | 0.0 | 4.5 | 0.0 | 29,290 | 0.0 | — | 0.0 | 77.55 |
| 96 | 78,310 | 0.0 | 0.0 | 2.5 | 0.0 | 4.4 | 0.0 | 9,002 | 0.0 | — | 0.0 | 89.68 |
| 120 | 60,603 | 0.0 | 0.0 | 2.5 | 0.0 | 4.3 | 0.0 | 2,767 | 0.0 | — | 0.0 | 95.62 |
| 144 | 46,900 | 0.0 | 0.0 | 2.4 | 0.0 | 4.3 | 0.0 | 850 | 0.0 | — | 0.0 | 98.21 |
| 168 | 36,295 | 0.0 | 0.0 | 2.4 | 0.0 | 4.2 | 0.0 | 261 | 0.0 | — | 0.0 | 99.27 |
| 192 | 28,089 | 0.0 | 0.0 | 2.4 | 0.0 | 4.2 | 0.0 | 80.3 | 0.0 | — | 0.0 | 99.69 |
| 216 | 21,738 | 0.0 | 0.0 | 2.3 | 0.0 | 4.1 | 0.0 | 24.7 | 0.0 | — | 0.0 | 99.86 |
| 240 | 16,822 | 0.0 | 0.0 | 2.3 | 0.0 | 4.1 | 0.0 | 7.6 | 0.0 | — | 0.0 | 99.92 |
| 264 | 13,019 | 0.0 | 0.0 | 2.3 | 0.0 | 4.0 | 0.0 | 2.3 | 0.0 | — | 0.0 | 99.93 |
| 288 | 10,075 | 0.0 | 0.0 | 2.3 | 0.0 | 4.0 | 0.0 | 0.7 | 0.0 | — | 0.0 | 99.93 |
| 312 | 7,797 | 0.0 | 0.0 | 2.3 | 0.0 | 3.9 | 0.0 | 0.2 | 0.0 | — | 0.0 | 99.92 |
| 336 | 6,034 | 0.0 | 0.0 | 2.2 | 0.0 | 3.8 | 0.0 | 0.1 | 0.0 | — | 0.0 | 99.90 |
| 360 | 4,670 | 0.0 | 0.0 | 2.2 | 0.0 | 3.8 | 0.0 | 0.0 | 0.0 | — | 0.0 | 99.87 |
| 384 | 3,614 | 0.0 | 0.0 | 2.2 | 0.0 | 3.7 | 0.0 | 0.0 | 0.0 | — | 0.0 | 99.84 |

Activity present (MBq) in 1 g of Occlu90Y2.6 at indicated time (h) after EOI.

TABLE 64

Scenario 3: Continuous 7 d (168 h) neutron irradiation of Occlu90Y2.6 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 339,300 | 318 | 119 | 5.9 | 1,983 | 10.6 | 572,134 | 1,038,935 | 1,453 | — | 64.8 | 17.36 |
| 12 | 298,485 | 23.4 | 0.1 | 5.9 | 103 | 10.5 | 0.0 | 575,960 | 60.8 | — | 2.6 | 34.13 |
| 18 | 279,958 | 6.4 | 0.0 | 5.9 | 23.4 | 10.5 | 0.0 | 428,839 | 12.4 | — | 0.5 | 39.49 |
| 24 | 262,581 | 1.7 | 0.0 | 5.8 | 5.3 | 10.4 | 0.0 | 319,298 | 2.5 | — | 0.1 | 45.12 |
| 36 | 230,995 | 0.1 | 0.0 | 5.8 | 0.3 | 10.4 | 0.0 | 177,011 | 0.1 | — | 0.0 | 56.61 |
| 48 | 203,208 | 0.0 | 0.0 | 5.8 | 0.0 | 10.3 | 0.0 | 98,131 | 0.0 | — | 0.0 | 67.43 |
| 72 | 157,261 | 0.0 | 0.0 | 5.7 | 0.0 | 10.2 | 0.0 | 30,159 | 0.0 | — | 0.0 | 83.90 |
| 96 | 121,703 | 0.0 | 0.0 | 5.7 | 0.0 | 10.0 | 0.0 | 9,269 | 0.0 | — | 0.0 | 92.91 |
| 120 | 94,184 | 0.0 | 0.0 | 5.6 | 0.0 | 9.9 | 0.0 | 2,849 | 0.0 | — | 0.0 | 97.05 |
| 144 | 72,888 | 0.0 | 0.0 | 5.5 | 0.0 | 9.7 | 0.0 | 875 | 0.0 | — | 0.0 | 98.79 |
| 168 | 56,408 | 0.0 | 0.0 | 5.5 | 0.0 | 9.6 | 0.0 | 269 | 0.0 | — | 0.0 | 99.50 |

TABLE 64-continued

Scenario 3: Continuous 7 d (168 h) neutron irradiation of Occlu90Y2.6 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 192 | 43,653 | 0.0 | 0.0 | 5.4 | 0.0 | 9.5 | 0.0 | 82.7 | 0.0 | — | 0.0 | 99.78 |
| 216 | 33,783 | 0.0 | 0.0 | 5.4 | 0.0 | 9.3 | 0.0 | 25.4 | 0.0 | — | 0.0 | 99.88 |
| 240 | 26,144 | 0.0 | 0.0 | 5.3 | 0.0 | 9.2 | 0.0 | 7.8 | 0.0 | — | 0.0 | 99.91 |
| 264 | 20,233 | 0.0 | 0.0 | 5.3 | 0.0 | 9.1 | 0.0 | 2.4 | 0.0 | — | 0.0 | 99.92 |
| 288 | 15,658 | 0.0 | 0.0 | 5.2 | 0.0 | 9.0 | 0.0 | 0.7 | 0.0 | — | 0.0 | 99.90 |
| 312 | 12,117 | 0.0 | 0.0 | 5.1 | 0.0 | 8.8 | 0.0 | 0.2 | 0.0 | — | 0.0 | 99.88 |
| 336 | 9,378 | 0.0 | 0.0 | 5.1 | 0.0 | 8.7 | 0.0 | 0.1 | 0.0 | — | 0.0 | 99.85 |
| 360 | 7,257 | 0.0 | 0.0 | 5.0 | 0.0 | 8.6 | 0.0 | 0.0 | 0.0 | — | 0.0 | 99.81 |
| 384 | 5,616 | 0.0 | 0.0 | 5.0 | 0.0 | 8.5 | 0.0 | 0.0 | 0.0 | — | 0.0 | 99.76 |

Activity present (MBq) in 1 g of Occlu90Y2.6 at indicated time (h) after EOI.

TABLE 65

Scenario 1: Continuous 24 h neutron irradiation of Occlu90Y2.8 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 82,680 | 284 | 205 | 1.5 | 3,413 | 2.7 | 429,231 | 539,972 | 2,010 | 407 | 28,963 | 7.61 |
| 12 | 72,734 | 20.9 | 0.1 | 1.5 | 177 | 2.7 | 0.0 | 299,347 | 84.0 | 0.00 | 1,153 | 19.47 |
| 18 | 68,219 | 5.7 | 0.0 | 1.5 | 40.3 | 2.7 | 0.0 | 222,883 | 17.2 | 0.00 | 230 | 23.41 |
| 24 | 63,985 | 1.5 | 0.0 | 1.5 | 9.2 | 2.7 | 0.0 | 165,951 | 3.5 | 0.00 | 45.9 | 27.82 |
| 36 | 56,288 | 0.1 | 0.0 | 1.5 | 0.5 | 2.7 | 0.0 | 91,999 | 0.1 | 0.00 | 1.8 | 37.96 |
| 48 | 49,517 | 0.0 | 0.0 | 1.5 | 0.0 | 2.6 | 0.0 | 51,002 | 0.0 | 0.00 | 0.1 | 49.26 |
| 72 | 38,321 | 0.0 | 0.0 | 1.5 | 0.0 | 2.6 | 0.0 | 15,675 | 0.0 | 0.00 | 0.0 | 70.97 |
| 96 | 29,656 | 0.0 | 0.0 | 1.4 | 0.0 | 2.6 | 0.0 | 4,817 | 0.0 | 0.00 | 0.0 | 86.02 |
| 120 | 22,951 | 0.0 | 0.0 | 1.4 | 0.0 | 2.5 | 0.0 | 1,481 | 0.0 | 0.00 | 0.0 | 93.92 |
| 144 | 17,761 | 0.0 | 0.0 | 1.4 | 0.0 | 2.5 | 0.0 | 455 | 0.0 | 0.00 | 0.0 | 97.48 |
| 168 | 13,745 | 0.0 | 0.0 | 1.4 | 0.0 | 2.5 | 0.0 | 140 | 0.0 | 0.00 | 0.0 | 98.97 |
| 192 | 10,637 | 0.0 | 0.0 | 1.4 | 0.0 | 2.4 | 0.0 | 43.0 | 0.0 | 0.00 | 0.0 | 99.56 |
| 216 | 8,232 | 0.0 | 0.0 | 1.4 | 0.0 | 2.4 | 0.0 | 13.2 | 0.0 | 0.00 | 0.0 | 99.79 |
| 240 | 6,371 | 0.0 | 0.0 | 1.4 | 0.0 | 2.4 | 0.0 | 4.1 | 0.0 | 0.00 | 0.0 | 99.88 |
| 264 | 4,930 | 0.0 | 0.0 | 1.3 | 0.0 | 2.3 | 0.0 | 1.2 | 0.0 | 0.00 | 0.0 | 99.90 |
| 288 | 3,815 | 0.0 | 0.0 | 1.3 | 0.0 | 2.3 | 0.0 | 0.4 | 0.0 | 0.00 | 0.0 | 99.90 |
| 312 | 2,953 | 0.0 | 0.0 | 1.3 | 0.0 | 2.3 | 0.0 | 0.1 | 0.0 | 0.00 | 0.0 | 99.87 |
| 336 | 2,285 | 0.0 | 0.0 | 1.3 | 0.0 | 2.2 | 0.0 | 0.0 | 0.0 | 0.00 | 0.0 | 99.84 |
| 360 | 1,768 | 0.0 | 0.0 | 1.3 | 0.0 | 2.2 | 0.0 | 0.0 | 0.0 | 0.00 | 0.0 | 99.80 |
| 384 | 1,369 | 0.0 | 0.0 | 1.3 | 0.0 | 2.2 | 0.0 | 0.0 | 0.0 | 0.00 | 0.0 | 99.75 |

Activity present (MBq) in 1 g of Occlu90Y2.8 at indicated time (h) after EOI.

TABLE 66

Scenario 2: Continubus 72 h neutron irradiation of Occlu90Y2.8 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 196,190 | 286 | 205 | 4.5 | 3,422 | 8.0 | 429,231 | 756,992 | 2,013 | 407 | 29,009 | 13.84 |
| 12 | 172,591 | 21.1 | 0.1 | 4.4 | 177 | 8.0 | 0.0 | 419,658 | 84.2 | 0.00 | 1,154 | 29.07 |
| 18 | 161,878 | 5.7 | 0.0 | 4.4 | 40.4 | 8.0 | 0.0 | 312,462 | 17.2 | 0.00 | 230 | 34.10 |
| 24 | 151,830 | 1.6 | 0.0 | 4.4 | 9.2 | 7.9 | 0.0 | 232,648 | 3.5 | 0.00 | 45.9 | 39.48 |
| 36 | 133,566 | 0.1 | 0.0 | 4.4 | 0.5 | 7.9 | 0.0 | 128,974 | 0.1 | 0.00 | 1.8 | 50.87 |
| 48 | 117,500 | 0.0 | 0.0 | 4.4 | 0.0 | 7.8 | 0.0 | 71,500 | 0.0 | 0.00 | 0.1 | 62.17 |
| 72 | 90,932 | 0.0 | 0.0 | 4.3 | 0.0 | 7.7 | 0.0 | 21,974 | 0.0 | 0.00 | 0.0 | 80.53 |
| 96 | 70,371 | 0.0 | 0.0 | 4.3 | 0.0 | 7.6 | 0.0 | 6,753 | 0.0 | 0.00 | 0.0 | 91.23 |
| 120 | 54,460 | 0.0 | 0.0 | 4.2 | 0.0 | 7.5 | 0.0 | 2,076 | 0.0 | 0.00 | 0.0 | 96.31 |
| 144 | 42,146 | 0.0 | 0.0 | 4.2 | 0.0 | 7.4 | 0.0 | 638 | 0.0 | 0.00 | 0.0 | 98.48 |
| 168 | 32,616 | 0.0 | 0.0 | 4.1 | 0.0 | 7.3 | 0.0 | 196 | 0.0 | 0.00 | 0.0 | 99.37 |
| 192 | 25,241 | 0.0 | 0.0 | 4.1 | 0.0 | 7.2 | 0.0 | 60.3 | 0.0 | 0.00 | 0.0 | 99.72 |
| 216 | 19,534 | 0.0 | 0.0 | 4.1 | 0.0 | 7.1 | 0.0 | 18.5 | 0.0 | 0.00 | 0.0 | 99.85 |
| 240 | 15,117 | 0.0 | 0.0 | 4.0 | 0.0 | 7.0 | 0.0 | 5.7 | 0.0 | 0.00 | 0.0 | 99.89 |
| 264 | 11,699 | 0.0 | 0.0 | 4.0 | 0.0 | 6.9 | 0.0 | 1.7 | 0.0 | 0.00 | 0.0 | 99.89 |
| 288 | 9,054 | 0.0 | 0.0 | 3.9 | 0.0 | 6.8 | 0.0 | 0.5 | 0.0 | 0.00 | 0.0 | 99.88 |
| 312 | 7,007 | 0.0 | 0.0 | 3.9 | 0.0 | 6.7 | 0.0 | 0.2 | 0.0 | 0.00 | 0.0 | 99.85 |
| 336 | 5,422 | 0.0 | 0.0 | 3.8 | 0.0 | 6.6 | 0.0 | 0.1 | 0.0 | 0.00 | 0.0 | 99.81 |

TABLE 66-continued

Scenario 2: Continuous 72 h neutron irradiation of Occlu90Y2.8 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 360 | 4,196 | 0.0 | 0.0 | 3.8 | 0.0 | 6.5 | 0.0 | 0.0 | 0.0 | 0.00 | 0.0 | 99.75 |
| 384 | 3,247 | 0.0 | 0.0 | 3.8 | 0.0 | 6.5 | 0.0 | 0.0 | 0.0 | 0.00 | 0.0 | 99.69 |

Activity present (MBq) in 1 g of Occlu90Y2.8 at indicated time (h) after EOI.

TABLE 67

Scenario 3: Continuous 7 d (168 h) neutron irradiation of Occlu90Y2.8 at 2E+14 n/cm2 · s

| Time (h) | Y-90 | Y-90m | Sr-85m | Sr-85 | Sr-87m | Sr-89 | Ga-70 | Ga-72 | Si-31 | Ti-51 | Mn-56 | % Y-90 |
|---|---|---|---|---|---|---|---|---|---|---|---|---|
| 0 | 304,904 | 286 | 205 | 10.2 | 3,422 | 18.3 | 429,231 | 779,438 | 2,013 | 407 | 29009 | 19.68 |
| 12 | 268,227 | 21.1 | 0.1 | 10.1 | 177 | 18.1 | 0.0 | 432,102 | 84.2 | 0.0 | 1154 | 38.22 |
| 18 | 251,578 | 5.7 | 0.0 | 10.1 | 40.4 | 18.1 | 0.0 | 321,727 | 17.2 | 0.0 | 230 | 43.86 |
| 24 | 235,962 | 1.6 | 0.0 | 10.1 | 9.2 | 18.0 | 0.0 | 239,547 | 3.5 | 0.00 | 45.9 | 49.61 |
| 36 | 207,578 | 0.1 | 0.0 | 10.0 | 0.5 | 17.9 | 0.0 | 132,799 | 0.1 | 0.00 | 1.8 | 60.98 |
| 48 | 182,609 | 0.0 | 0.0 | 10.0 | 0.0 | 17.8 | 0.0 | 73,620 | 0.0 | 0.00 | 0.1 | 71.26 |
| 72 | 141,319 | 0.0 | 0.0 | 9.9 | 0.0 | 17.5 | 0.0 | 22,626 | 0.0 | 0.00 | 0.0 | 86.18 |
| 96 | 109,365 | 0.0 | 0.0 | 9.8 | 0.0 | 17.3 | 0.0 | 6,954 | 0.0 | 0.00 | 0.0 | 94.00 |
| 120 | 84,637 | 0.0 | 0.0 | 9.7 | 0.0 | 17.0 | 0.0 | 2,137 | 0.0 | 0.00 | 0.0 | 97.51 |
| 144 | 65,500 | 0.0 | 0.0 | 9.6 | 0.0 | 16.8 | 0.0 | 657 | 0.0 | 0.00 | 0.0 | 98.97 |
| 168 | 50,689 | 0.0 | 0.0 | 9.5 | 0.0 | 16.6 | 0.0 | 202 | 0.0 | 0.00 | 0.0 | 99.55 |
| 192 | 39,228 | 0.0 | 0.0 | 9.4 | 0.0 | 16.4 | 0.0 | 62.0 | 0.0 | 0.00 | 0.0 | 99.78 |
| 216 | 30,358 | 0.0 | 0.0 | 9.3 | 0.0 | 16.1 | 0.0 | 19.1 | 0.0 | 0.00 | 0.0 | 99.85 |
| 240 | 23,494 | 0.0 | 0.0 | 9.2 | 0.0 | 15.9 | 0.0 | 5.9 | 0.0 | 0.00 | 0.0 | 99.87 |
| 264 | 18,182 | 0.0 | 0.0 | 9.1 | 0.0 | 15.7 | 0.0 | 1.8 | 0.0 | 0.00 | 0.0 | 99.85 |
| 288 | 14,071 | 0.0 | 0.0 | 9.0 | 0.0 | 15.5 | 0.0 | 0.6 | 0.0 | 0.00 | 0.0 | 99.82 |
| 312 | 10,889 | 0.0 | 0.0 | 8.9 | 0.0 | 15.3 | 0.0 | 0.2 | 0.0 | 0.00 | 0.0 | 99.78 |
| 336 | 8,427 | 0.0 | 0.0 | 8.8 | 0.0 | 15.1 | 0.0 | 0.1 | 0.0 | 0.00 | 0.0 | 99.72 |
| 360 | 6,522 | 0.0 | 0.0 | 8.7 | 0.0 | 14.9 | 0.0 | 0.0 | 0.0 | 0.00 | 0.0 | 99.64 |
| 384 | 5,047 | 0.0 | 0.0 | 8.6 | 0.0 | 14.7 | 0.0 | 0.0 | 0.0 | 0.00 | 0.0 | 99.54 |

Activity present (MBq) in 1 g of Occlu90Y2.8 at indicated time (h) after EOI.

Consistent with the principles discussed earlier, longer irradiations result in higher specific activity of Y-90, resulting in smaller masses of beads required to formulate a patient dose when moving from Scenario 1 through Scenario 3 for a particular formulation. Also as described above, the 7 d irradiations considered in "Scenario 3" result in a substantially larger amount of Sr-85 and Sr-89 being present in a 4 GBq dose. However, it should be noted that absolute quantity of radiostrontiums present is generally quite low, at less than 0.1% of the Y-90 activity in the cases considered in Table 68. The impact of using higher yttrium-content beads is illustrated by comparing the bead masses in the top two rows (low yttrium) to those in the bottom two (high yttrium) of any given column: increasing the mole fraction of yttrium oxide from 0.1 to 0.17 decreases the total mass of beads required for a 4 GBq dose by a factor of approximately two. Based on the limited data presented in Table 68, Occlu90Y1.16 appears to have a near-ideal combination of characteristics: the mass of beads required to deliver a therapeutic quantity of Y-90 is quite low, and the Sr-85/87 burden is lower than two of the other three formulations under the same irradiation scenarios. This is initially surprising, as Occlu90Y1.16 contains a larger mole fraction of strontium oxide (0.05) than any of the other bead formulations, and logically, a larger quantity of Sr-85/87 would be anticipated. Additionally, while the mole fraction of yttrium oxide (0.17) in Occlu90Y1.16 is quite large and will therefore give rise to large amounts of Y-90 per gram of beads, is it is no different from that of Occlu90Y1.4. A closer examination of the data reveals that the key difference between these two formulations is the lower gallium oxide mole fraction in Occlu90Y1.16 than Occlu90Y1.4 (0.167 vs. 0.295). The resultant lower burden of Ga-72 produced in Occlu90Y1.16 means that these beads do not require as much decay time to achieve a radionuclidic purity of >99%, and can therefore be used closer to end of irradiation, when the Y-90 activity per gram of beads is higher. Finally, it must be noted that the data included in Table 35 and discussed here consider bead formulations in which the radionuclidic purity of the yttrium-90 is greater than 99%—typically 168-192 h after EOI. It is possible that lower radionuclidic purity (perhaps 97-98%) may be acceptable. If that is the case, all the bead formulations can be used closer to end of irradiation, which would decrease, in some cases dramatically, the mass of beads required to deliver a 4 GBq patient dose, and the amount of Sr-85/87 in that patient dose.

TABLE 68

Mass of ABK bead formulations required for 4 GBq patient dose at >99% RNP. Total amount of Sr-85/87 in parentheses.

| Composition | Scenario 1 | Scenario 2 | Scenario 3 |
|---|---|---|---|
| Occlu90Y 1.1 | 470 mg (1.9 MBq) | 155 mg (1.9 MBq) | 100 mg (2.8 MBq) |
| Occlu90Y 1.2/1.6 | 520 mg (1.6 MBq) | 220 mg (1.6 MBq) | 110 mg (1.8 MBq) |

TABLE 68-continued

Mass of ABK bead formulations required for 4 GBq patient dose at >99% RNP. Total amount of Sr-85/87 in parentheses.

| Composition | Scenario 1 | Scenario 2 | Scenario 3 |
|---|---|---|---|
| Occlu90Y 1.4/1.7 | 340 mg (1.0 MBq) | 110 mg (1.0 MBq) | 70 mg (1.5 MBq) |
| Occlu90Y 1.16 | 230 mg (1.2 MBq) | 95 mg (1.5 MBq) | 50 mg (1.6 MBq) |

Example 7

Short-Lived Neutron Activation Analysis
Methodology

Samples were prepared for neutron activation by weighing approximately 100 mg of each bead formulation into a labeled polyethylene vial, recording the exact mass of the sample to four decimal places, and heat-sealing the vial. Duplicate samples of each formulation were prepared. Each polyethylene vial was then encapsulated in a larger vial, which was subsequently heat-sealed.

Standards were prepared from TraceCERT Certified Reference Materials (Fluka)—aqueous solutions of precisely known concentrations of yttrium, gallium, strontium, titanium, and manganese. Precise volumes ranging from 0.100 mL (Mn standard) to 3.000 mL (Ga standard) were pipetted into separate polyethylene bulbs, which were heat-sealed, then encapsulated in larger polyethylene vials (also heat-sealed). Each of these standard samples was prepared in duplicate. See Table 69 for exact volumes and analyte masses of standards.

employed, spanning an energy window from 0-2116 keV. Spectra were recorded using GammaVision for Windows Version 5.31 (ORTEC, Oak Ridge, Tenn., 2001) and analyzed using Aptec MCA Application Version 7.04 (Canberra Co., 2002).

Element compositions of the Occlu90Y formulations were determined empirically by comparing the count rate (counts per second, cps) of a selected gamma emission in the spectrum of the standard samples with the count rate of the corresponding emission in the spectrum of the bead samples. This is expressed mathematically in the simple proportionality below, where the $cps_{sample}$ and $cps_{standard}$ terms are the count rates for a particular gamma line in a bead sample and standard, respectively, and the mass terms refer to the mass of the analyte (e.g. yttrium, gallium, etc) present in the standard ($mass_{standard}$, from Table 2) and the sample ($mass_{sample}$, empirically determined).

$$cps_{sample}/mass_{sample} = cps_{standard}/mass_{standard}$$

Rearranging to isolate the "$mass_{sample}$" term yields the total mass of that analyte in the bead sample; dividing by the

TABLE 69

Standards used in NAA.

| | Yttrium | Strontium | Gallium | Titanium | Manganese |
|---|---|---|---|---|---|
| Concentration of CRM | 9.846 g/L | 0.989 g/L | 0.973 g/L | 1.000 g/L | 1.040 g/L |
| Volume used | 2.000 mL | 2.000 mL | 3.000 mL | 1.000 mL | 0.100 mL |
| Mass analyte | 19.692 mg | 1.978 mg | 2.919 mg | 1.000 mg | 0.104 mg |

The samples and standards were irradiated in a thermal neutron flux of $4.2 \times 10^{12}$ n/cm²·s in site RAB-4 at the McMaster Nuclear Reactor (MNR) while the reactor was operating at a nominal power of 2.5 MW. Irradiation-delay-count times (in seconds) of 600-25-600 were initially used for all samples. After a delay of 4 (design space #1) or 5 (design space #2) days, samples and standards were reanalyzed using shorter irradiation and count times (60-30-60).

All gamma emission spectra were recorded using a GMX 30% efficiency, 70 mm endcap high purity germanium (HPGe) detector (ORTEC, Oak Ridge, Tenn.); samples were placed approximately 32.5 cm from the detector face in "Position 9". A total of 16,383 energy channels were total mass of the sample and multiplying by 100% (as indicated below) yields the weight percent of analyte in the bead sample.

$$Wt. \% = mass_{sample}/mass_{total\ sample} * 100\%$$

Since duplicate samples of each bead formulation were prepared and analyzed, the value of the weight percent for each element is reported as an average of the two duplicates. Refer to Table 70 for a list of radioisotopes generated during these analyses, and the major gamma lines that were used to identify and quantify the five analytes (Y, Sr, Ga, Ti, Mn).

TABLE 70

Radioisotopes & key emissions used in NAA. Lines used to generate quantitative data in bold.

| | Y-89m | Y-90m | Sr-85m | Sr-87m | Ga-70 | Ga-72 | Ti-51 | Mn-56 |
|---|---|---|---|---|---|---|---|---|
| Half-life | 16.06 s | 3.19 h | 67.63 min | 2.803 h | 21.14 min | 14.10 h | 5.76 min | 2.58 h |
| Gamma energy (keV) | 908.96 | 202.53<br>479.51 | 231.86 | 388.53 | 176.17<br>1039.2 | 600.95<br>629.96<br>834.20<br>894.25 | 320.08 | 846.75 |

To determine appropriate neutron activation parameters for the Occlu90Y formulations, the mole fraction compositions were converted into weight percentages (see Table 71) in order to identify the expected concentration ranges of the five analytes (Y, Sr, Ga, Ti and Mn). Activation yield calculations were then carried out using these mass percentages to determine the rates at which radioisotopes of these five elements would form.

TABLE 71

Compositions from Tables 2 and 25 expressed in wt. %.

|  | Y2O3 | SrO | Ga2O3 | TiO2 | MnO2 |
|---|---|---|---|---|---|
| Occlu90Y1.1 | 16.84 | 3.17 | 27.70 | — | — |
| Occlu90Y1.2 | 15.19 | 1.87 | 35.74 | — | — |
| Occlu90Y1.4 | 23.45 | 2.38 | 31.92 | — | — |
| Occlu90Y1.5 | 20.90 | 3.46 | 29.15 | — | — |
| Occlu90Y1.6 | 15.19 | 1.87 | 35.74 | — | — |
| Occlu90Y1.7 | 23.45 | 2.38 | 31.92 | — | — |
| Occlu90Y1.11 | 25.43 | 2.05 | 19.81 | — | — |
| Occlu90Y1.12 | 18.25 | 3.54 | 33.81 | — | — |
| Occlu90Y1.15 | 22.18 | 2.02 | 26.52 | — | — |
| Occlu90Y1.16 | 26.5 | 3.85 | 20.45 | — | — |
| Occlu90Yr2.3 | 15.48 | 3.81 | 30.35 | 4.17 | — |
| Occlu90Yr2.6 | 23.47 | 1.70 | 32.48 | — | 0.213 |
| Occlu90Y2.8 | 21.09 | 2.94 | 24.37 | 1.82 | 0.100 |

The sample of approximately 100 mg, strontium, which activates only poorly, would require activation times of several minutes in order for its short-lived activation products Sr-85m and Sr-87m (see Table 70) to be detectable. Also, despite the substantially larger quantities of yttrium in the beads as compared to strontium, similar irradiation parameters were required to quantify yttrium due to the small cross section of the nuclear reaction leading to the formation of metastable Y-90m.

While the quantities of the desired activation products could also be increased either by extending the irradiation time into tens of minutes, or by increasing the mass of sample used, further calculations indicated that this would generate the gallium radioisotopes Ga-70 and Ga-72 in quantities too large for the detector to analyze. In consequence, an irradiation time of 600 s was chosen for initial experiments, followed by a short delay (25 s) prior to the start of the gamma counting, during which the sample was physically removed from the irradiation system and placed in front of the detector. A relatively long count time of 600 s was selected to obtain the best possible counting statistics for Sr-85m, Sr-87m, and Y-90m, without losing significant portions of these radioisotopes through decay.

Figure 39:
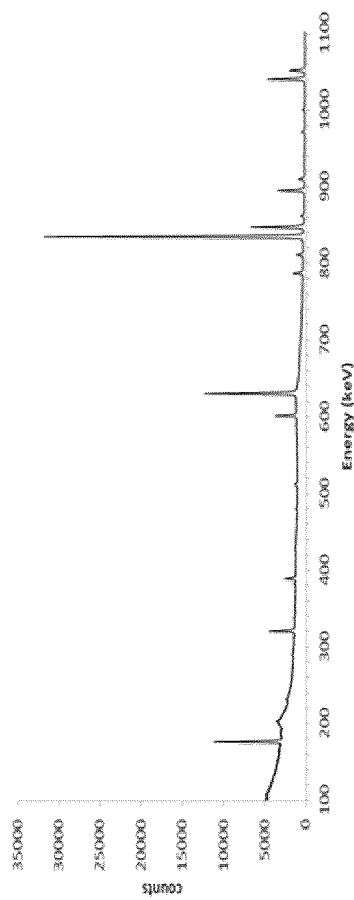
FIG. 39 shows gamma spectrum of Occlu90Y2.8 using 600-25-600 irradiation-delay-count time.

A typical gamma spectrum of one of the bead formulations—Occlu90Y2.8—is shown in FIG. 39. The spectrum is dominated by Ga-72 lines at 176, 610, 630 and 834 keV, but the single photon emissions of manganese and titanium are also readily discernible at 846 keV and 320 keV, respectively. These three elements (Ga, Ti, Mn) were readily quantified based on these NAA parameters (600-25-600).

Figure 40:
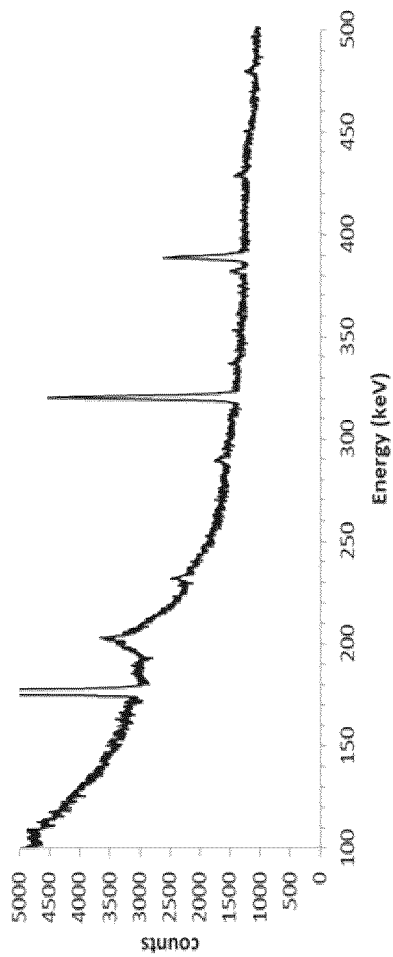
FIG. 40 shows gamma spectrum of Occlu90Y2.8: magnification of low energy region.

Looking more closely at the low energy region of this spectrum (FIG. 40), gamma emissions from Sr-85m (232 keV) and Sr-87m (388.53 keV) can be identified, but the signal to noise ratio of the former is too low to generate accurate quantitative data. In consequence, the weight percent of strontium in the bead formulations was calculated solely based on the Sr-87m line; even so, errors in strontium mass may be as high as 5-10%. The strontium content in the bead formulations are best determined by long-lived neutron activation analysis using the 514.0 keV gamma emission of Sr-85 ($t_{1/2=64.8}$ d), which will be carried out following in-core irradiation of the beads.

The quantification of yttrium based on Y-90m gamma emissions was also hampered by poor counting statistics (low signal to noise ratio). Referring again to FIG. 40, one of the expected Y-90m gamma lines (202.5 keV) is completely buried in the baseline, and while the 479.5 keV emission is discernible, this small "bump" in the spectrum's baseline lacks the sharp, well-defined line-shape of the more intense emissions in this spectrum. Moreover, the error associated with the net count rate for this line ranged from 20% up to 60% in some samples: such a large uncertainty would render analyses based on this gamma emission semi-quantitative, at best. Thus the weight percent of yttrium in the bead formulations could not be determined on the basis of the Y-90m radioisotope.

Figure 41:
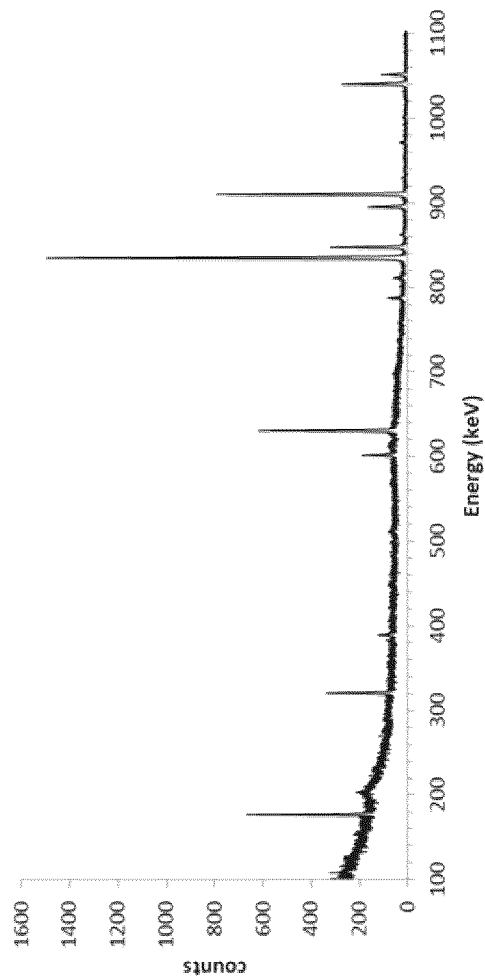
FIG. 41 shows gamma spectrum of Occlu90Y2.8 using 60-30-60 irradiation-delay-count.

In consequence, a second set of NAA parameters was selected, focusing this time on the quantification of the extremely short-lived metastable radioisotope Y-89m ($t_{1/2=16}$ s). As the yield of this isotope reaches a maximum after less than a minute of irradiation, each sample was irradiated 60 s, then counted for another 60 s—long enough to generate good quality counting statistics without losing all the Y-89m through radioactive decay. The gamma spectrum of Occlu90Y2.8 treated in this way is shown in FIG. 41. In contrast to FIG. 39, a prominent Y-89m peak is now evident at 908.96 keV, enabling the quantification of yttrium in the bead formulations. Note that using this short an irradiation time, the Sr-85m, Sr-87m, and Y-90m gamma emissions are not detectable at all: only gamma lines due to gallium radioisotopes are present in addition to the Y-89 peak. Thus, by utilizing two different sets of parameters, all five key analytes—yttrium, strontium, gallium, titanium, and manganese—in Occlu90Y design spaces #1 and #2 were quantified by short-lived Neutron Activation Analysis.

Example 8

In-Core Neutron Irradiation: Identification and Quantification of Long-Lived Activation Products
Methodology A portion of each bead sample was weighed into a quartz tube, which was subsequently plugged with quartz wool, then wrapped in aluminum foil. Four of these samples—including the two duplicate formulations Occlu90Y1.2 and Occlu90Y1.6—were placed inside an aluminum irradiation capsule along with a sample of the reference material strontium oxide. The capsule was assigned the unique identifier MNR159845 which was engraved on the capsule before it was cold-welded, leak-tested, and inserted into the reactor core. A complete list of samples contained in this capsule is listed under the heading "Capsule 1" in Table 72.

Quartz tubes containing five additional bead formulations—including the two duplicate formulations Occlu90Y1.4 and Occlu90Y1.7—were placed inside another capsule that was assigned the designation MNR159846 prior to being engraved, cold-welded and leak-tested. The contents of this capsule are listed under the heading "Capsule 2" in Table 72.

Because two capsules can be inserted into a single irradiation site while maintaining a homogenous neutron flux distribution over the length of the stacked capsules, only a single sample of reference material (Capsule 1) was required to confirm the total neutron flux experienced during this irradiation. Capsules 1 and 2 were inserted into in-core position 2A at the start of operation on Monday, Sep. 21, 2015, and were removed from this site at the end of the operating day on Friday, Oct. 9, 2015. During this period, the reactor was operated for approximately 14 h per day on weekdays, as well as on two Saturdays (September 26 and October 3). The capsules were stored in an underwater storage rack until they could be safely retrieved on Monday, October 26. The remaining four bead samples were prepared for irradiation in a similar manner, and placed in an irradiation canister along with a sample of the reference material strontium oxide. This capsule was assigned the unique identifier of MNR159877; its contents are listed under the heading "Capsule 3" in Table 72.

TABLE 72

Distribution of beads and reference materials in irradiation capsules.

|  | Capsule 1 (MNR 159845) | Capsule 2 (MNR 159846) | Capsule 3 (MNR 159847) |
|---|---|---|---|
| Occlu90Y1.1 | 1.9964 g | — | — |
| Occlu90Y1.2 | 1.9525 g | — | — |
| Occlu90Y1.4 | — | 1.8405 g | — |
| Occlu90Y1.5 | — | — | 1.9751 g |
| Occlu90Y1.6 | 1.8800 g | — | — |
| Occlu90Y1.7 | — | 1.7841 g | — |
| Occlu90Y1.11 | — | — | 0.9456 g |
| Occlu90Y1.12 | — | — | 1.4377 g |
| Occlu90Y1.15 | — | — | 1.5284 g |
| Occlu90Y1.16 | 1.9639 g | — | — |
| Occlu90Y2.3 | — | 1.2018 g | — |
| Occlu90Y2.6 | — | 1.1810 g | — |
| Occlu90Y2.8 | — | 1.6384 g | — |
| SrO std | 0.0720 g | — | 0.0778 g |

The core position 2A experiences a neutron flux that is approximately 50% higher than the flux in other in-core irradiation sites at MNR ($2.5 \times 10^{13}$ n/cm$^2$·s compared to $1.6 \times 10^{13}$ n/cm$^2$·s at 3 MW). In consequence, it is the preferred site for irradiations attempting to mimic conditions in higher power nuclear reactors. However, inserting a third capsule into a single irradiation site cannot be done without creating an unequal neutron flux distribution over the length of the three capsules. This would necessitate the use of computational modeling to estimate the flux experienced by each of the three samples and introduce uncertainty into any quantitative data obtained. To avoid this, Capsule 3 was inserted into another in-core position (8B) and irradiated from Monday, September 28 through Friday, October 9 at a lower neutron flux. Once Capsules 1 and 2 had been removed from the reactor core, Capsule 3 was placed in site 2A for an additional two weeks of irradiation (Tuesday October 13 through Saturday October 24), then stored underwater until Monday, November 9.

Each capsule was opened on the date indicated above, and the aluminum foil-wrapped tubes were transported to a radioisotope laboratory containing a fumehood. The samples were placed behind appropriate shielding, and the foil and quartz wool were discarded. Each sample was transferred into a pre-labelled cylindrical polyethylene vial (5.5 cm×1.8 cm, h×d) with a snap-lid for further analysis.

All gamma emission spectra were recorded using a GMX 30% efficiency, 70 mm endcap high purity germanium (HPGe) detector (ORTEC, Oak Ridge, Tenn.); samples were placed at a distance of 32.5 cm from the detector face ("Position 9"). A total of 16,383 energy channels were employed, spanning an energy window from 0-2116 keV. Spectra were recorded using GammaVision for Windows Version 5.31 (ORTEC, Oak Ridge, Tenn., 2001) and analyzed using Aptec MCA Application Version 7.04 (Canberra Co., 2002). The efficiency of the detector over the energy range 60-1408 keV was determined using a Eu-152/154/155 multi gamma standard (MGS) disc source (Canberra).

The strontium content of the beads was quantified by comparing the intensity of the 514.0 keV emission of Sr-85 in the strontium standard (of known mass) with the corresponding line in the gamma spectra of the beads. The Sr-85 content of the standard materials was verified using the detector efficiency curve that was created using the europium MGS source.

Radionuclidic impurities were identified based on gamma lines, and quantified using the detector efficiency curve generated previously. Whenever possible, radioisotope identifications were confirmed by the presence of at least two gamma emissions in the expected relative intensities. Exceptions to this were Sc-47, Cr-51, Zn-65, Sr-85, and Ce-141, all of which have only a single gamma line.

Stable trace and ultra-trace impurities were identified based on the most plausible production routes to the observed radioisotopes. The activity of each radioisotope was decay corrected to EOI, and a series of neutron activation equations were solved for mass and summed to accurately capture the neutron irradiation conditions experienced by each capsule. For samples in Capsules 1 and 2, this involved summing the results of 27 individual activation calculations to account for the 17 operating days and 10 on-line changes in operating power; for samples in Capsule 3, 35 calculations were used to account for 22 operating days and with 13 on-line changes in operating power. These calculations indicated the total mass of stable precursor isotope present in the sample; this mass was then corrected to account for the relative natural abundance of the isotope, thereby revealing the total mass of that chemical element present. This final step was not required for lanthanum, tantalum, or terbium, all of which are essentially monoisotopic.

Dose rate measurements were made using a Victoreen 451B Ion Chamber Survey Meter equipped with a beta slide shield (0.3 mm thick; 0.44 mg/cm$^2$). Each sample was laid on its side and four readings were taken: two at contact with the vial (~1.5 cm from the beads) with the beta slide alternately open and closed, and two at a distance of 8.0 cm from the top of the vial (~9.5 cm from the beads), with the beta slide alternately open and closed. Measurements were recorded at 20 d (Capsules 1 & 2) and 19 d (Capsule 3) after EOI, and are considered accurate within 10%.

The total neutron exposure experienced by the three capsules was determined by recording the exact reactor operating hours and power between September 21 and October 24, and multiplying the operating time by the neutron flux in that site at that power. For example, Capsule 3 was in site 8B during 17.0 h of operation at 2.0 MW and 129.5 h of operation at 2.5 MW; it was then irradiated in 2A for 19.0 h at 2.0 MW and 125.3 h at 2.5 MW. The total flux experienced by Capsule 3 is therefore given by the following sum:

$$\text{Total neutron exposure} = (17.0\text{h} \cdot 3{,}600\text{s} \cdot 1.07 \times 10^{13} \text{n/cm}^2\text{xs}) + (129.5 \text{ h} \cdot 3{,}600\text{s} \cdot 1.33 \times 10^{13} \text{n/cm}^2\text{xs}) + (19.0\text{h} \cdot 3{,}600\text{s} \cdot 1.67 \times 10^{13} \text{n/cm}^2\text{xs}) + (125.3\text{h} \cdot 3{,}600\text{s} \cdot 2.08 \times 10^{13} \text{n/cm}^2\text{xs})$$

which sums to $1.74 \times 10^{19}$ n/cm$^2$ over the duration of the irradiation. Capsules 1 and 2 were exposed to a total of $1.66 \times 10^{19}$ n/cm$^2$, or 5% less than Capsule 3. This was corroborated by quantifying the yields of Sr-85 in the strontium oxide reference materials that were included in Capsules 1 and 3.

The total neutron exposure created by these irradiations can readily be related to irradiation conditions that would plausibly be used in a production scenario. For example, a sample exposed to a neutron flux of $2.0 \times 10^{14}$ n/cm$^2$×s at a facility such as the National Research Universal (NRU) reactor in Chalk River would experience the same total neutron exposure as Capsules 1/2 and Capsule 3 in 23.1 h and 24.1 h, respectively. Thus the radionuclidic impurity profiles resulting from the neutron irradiations described here provide a realistic estimate of the impurity profiles that will be obtained from production-type scenarios.

Strontium Activation Analysis

Gamma spectra of the bead samples acquired 17-20 d after EOI were dominated by an intense emission at 514 keV, indicating that the major gamma emitting radioisotope present was strontium-85 ($t_{1/2}$, =64.8 d), noting that yttrium-90 cannot be detected by gamma spectrometry. Despite the low natural abundance of the precursor Sr-84 (0.56%) and its relatively small neutron capture cross-section (0.87b), this was not unexpected since the bead formulations were expected to contain 1.7-3.9% strontium by weight. The mass of strontium present in each sample was determined by comparing the intensity of its 514 keV gamma line with the corresponding line in the spectrum of the strontium oxide reference material (see Table 73).

The experimentally determined strontium weight percentages compared well with the predicted compositions of the beads. This is consistent with the short-lived neutron activation results reported previously, which demonstrated close correlations between theoretical (Example 7) and experimentally determined quantities of gallium, titanium, manganese and yttrium. The strontium content of the two duplicate formulations Occlu90Y1.2 and Occlu90Y1.6 agreed within 7%, and even closer agreement observed between the Occlu90Y1.4/Occlu90Y1.7 pair (<3% variance), indicating good reproducibility in the process used to fabricate these beads.

TABLE 73

Strontium content of ABK bead formulations from long-lived neutron activation analysis (LL NAA) based on Sr-85.

|  | net cps (514 keV) | mass Sr present | total mass sample | wt % Sr LL NAA | wt % Sr (theor.) |
|---|---|---|---|---|---|
| Occlu90Y1.1 | 1,691.4 | 0.0680 g | 1.9964 g | 3.41 | 3.17 |
| Occlu90Y1.2 | 1,069.6 | 0.0430 g | 1.9525 g | 2.20 | 1.87 |
| Occlu90Y1.4 | 1,162.2 | 0.0467 g | 1.8405 g | 2.54 | 2.38 |
| Occlu90Y1.5 | 1,737.5 | 0.0730 g | 1.9751 g | 3.70 | 3.46 |
| Occlu90Y1.6 | 953.8 | 0.0383 g | 1.8800 g | 2.04 | 1.87 |
| Occlu90Y1.7 | 1,098.3 | 0.0441 g | 1.7841 g | 2.47 | 2.38 |
| Occlu90Y1.11 | 435.8 | 0.0183 g | 0.9456 g | 1.94 | 2.05 |
| Occlu90Y1.12 | 1,220.3 | 0.0513 g | 1.4377 g | 3.57 | 3.54 |
| Occlu90Y1.15 | 722.8 | 0.0304 g | 1.5284 g | 1.99 | 2.02 |
| Occlu90Y1.16 | 2,007.7 | 0.0807 g | 1.9639 g | 4.11 | 3.85 |
| Occlu90Y2.3 | 1,262.4 | 0.0507 g | 1.2018 g | 4.22 | 3.81 |
| Occlu90Y2.6 | 585.1 | 0.0235 g | 1.1810 g | 1.99 | 1.70 |
| Occlu90Y2.8 | 1,214.4 | 0.0488 g | 1.6384 g | 2.98 | 2.94 |

Major Radionuclidic Impurities

Figure 43:
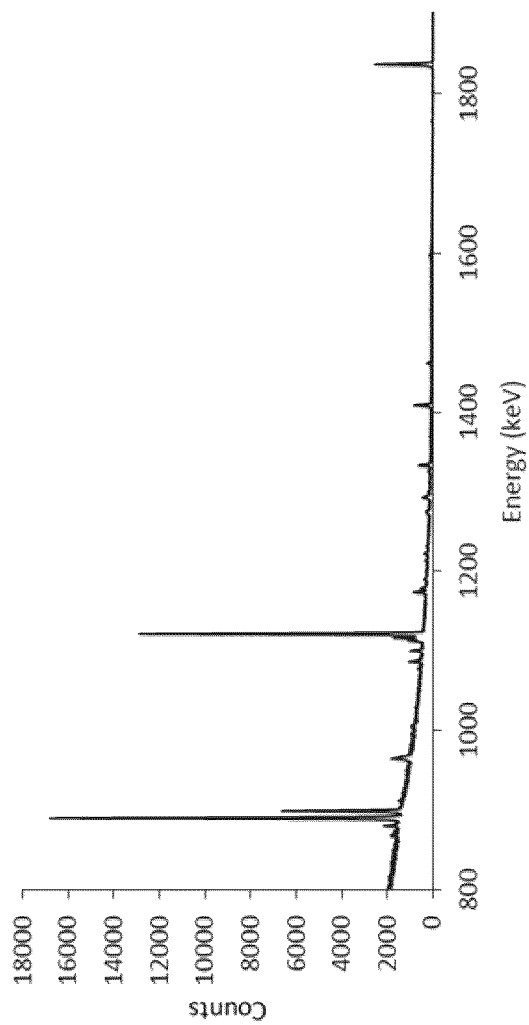
FIG. 43 shows gamma spectrum of Occlu90Y1.6 after in-core irradiation (expanded).

In addition to the Sr-85 emission, four major lines were observed in the gamma spectra of all thirteen-bead samples (see FIG. 43 and Table 74). Re-counting a given sample on subsequent days produced identical spectra with no detectable decrease in energy intensities, indicating that the radioisotopes producing these lines had half-lives well in excess of one week. Based on this information and the relative intensities of the emissions, these gamma emissions were unambiguously assigned to scandium-46 ($t_{1/2}$, =83.4 d) and yttrium-88 ($t_{1/2}$, =106.7 d).

TABLE 74

Major gamma emissions in ABK bead samples 17-20 d after EOI (net counts per second).

|  | 514.0 keV Sr-85 | 889.3 keV Sc-46 | 898.5 keV Y-88 | 1120.5 keV Sc-46 | 1827.1 keV Y-88 |
|---|---|---|---|---|---|
| Occlu90Y1.1 | 1,691.4 | 98.3 | 31.3 | 83.8 | 19.6 |
| Occlu90Y1.2 | 1,069.6 | 91.2 | 29.4 | 78.4 | 18.6 |
| Occlu90Y1.4 | 1,162.2 | 56.7 | 39.6 | 50.0 | 25.1 |
| Occlu90Y1.5 | 1,737.5 | 71.7 | 35.1 | 57.0 | 22.7 |
| Occlu90Y1.6 | 953.8 | 78.5 | 26.4 | 67.0 | 16.8 |
| Occlu90Y1.7 | 1,098.3 | 51.8 | 37.3 | 44.5 | 23.3 |
| Occlu90Y1.11 | 435.8 | 45.7 | 18.3 | 39.0 | 11.6 |
| Occlu90Y1.12 | 1,220.3 | 45.1 | 21.1 | 37.7 | 13.4 |
| Occlu90Y1.15 | 722.8 | 62.9 | 27.3 | 51.3 | 17.4 |
| Occlu90Y1.16 | 2,007.7 | 81.6 | 47.4 | 70.8 | 30.1 |
| Occlu90Y2.3 | 1,262.4 | 105.6 | 18.0 | 89.8 | 11.3 |
| Occlu90Y2.6 | 585.1 | 41.3 | 27.9 | 34.9 | 17.6 |
| Occlu90Y2.8 | 1,214.4 | 106.3 | 33.1 | 95.5 | 20.7 |

An examination of the Table of the Nuclides indicated that the only plausible precursor to scandium-46 is the stable isotope scandium-45. This seemed reasonable, as scandium and yttrium are both Group 3 elements, and as such, share many chemical properties. It was assumed that the scandium was present as a minor impurity in the yttrium oxide used to manufacture the beads. However, quantitative analysis of the scandium content of the bead formulations did not support this hypothesis (see Table 75).

The activity of Sc-46 present in each sample was determined based on the net counts per second of its 889 keV line, combined with knowledge of the detector efficiency at this energy. A series of neutron activation equations were solved for mass and summed to yield the total mass of natural scandium (100% Sc-45) required to produce the observed activities under the conditions experienced by Capsules 1-3. The scandium content of the beads in parts per million (ppm) was then calculated by dividing each experimentally determined mass of scandium by the mass of the corresponding bead sample. As with the strontium long lived neutron activation analysis (LL NAA), reasonably close agreement in scandium content was observed in the two pairs of duplicate formulations, again with closer agreement between the Occlu90Y1.2/Occlu90Y1.6 pair than between the Occlu90Y1.4/Occlu90Y1.7 replicates.

A comparison of scandium content with the theoretical weight percent of yttrium (Table 75) did not indicate a correlative relationship between the two elements. There was also no obvious correlation between the empirical scandium content and either the gallium or strontium content. However, a loose correlation could be detected between scandium content and the weight percent of silicon in the beads.

Formulations Occlu90Y2.3 and Occlu90Y2.8 exhibited significantly higher scandium contents than the other eleven samples. Comparing Occlu90Y2.3 to other bead formulations with similar silicon contents, one would expect it to have a scandium content of 0.20-0.25 ppm, not the observed 0.60 ppm. Similarly, Occlu90Y2.8 would be expected to contain 0.26-0.30 ppm scandium, not 0.44 ppm. This finding suggests that silicon is not the sole source of scandium in these two samples.

TABLE 75

Scandium content of ABK bead formulations from long-lived neutron activation analysis (LN NAA) using 889.3 keV line of Sc-46. Key values in bold.

| | Sc-46 (mCi) | mass Sc (mg) | Sc content (ppm) | theor. wt % Si | theor. wt % Ti | theor. wt % Y |
|---|---|---|---|---|---|---|
| Occlu90Y1.1 | 8.38 | 0.672 | 0.337 | 16.8 | 0 | 16.8 |
| Occlu90Y1.2 | 7.77 | 0.623 | 0.319 | 13.8 | 0 | 15.2 |
| Occlu90Y1.4 | 4.83 | 0.387 | 0.210 | 10.9 | 0 | 23.5 |
| Occlu90Y1.5 | 6.11 | 0.473 | 0.239 | 13.3 | 0 | 20.9 |
| Occlu90Y1.6 | 6.69 | 0.536 | 0.285 | 13.8 | 0 | 15.2 |
| Occlu90Y1.7 | 4.42 | 0.354 | 0.198 | 10.9 | 0 | 23.5 |
| Occlu90Y1.11 | 3.89 | 0.301 | 0.318 | 17.6 | 0 | 25.4 |
| Occlu90Y1.12 | 3.84 | 0.297 | 0.207 | 11.9 | 0 | 18.3 |
| Occlu90Y1.15 | 5.36 | 0.415 | 0.272 | 15.3 | 0 | 22.2 |
| Occlu90Y1.16 | 6.95 | 0.557 | 0.284 | 15.1 | 0 | 26.5 |
| Occlu90Y2.3 | 9.00 | 0.722 | 0.601 | 12.2 | 4.17 | 15.5 |
| Occlu90Y2.6 | 3.52 | 0.282 | 0.239 | 10.9 | 0 | 23.5 |
| Occlu90Y2.8 | 9.06 | 0.727 | 0.444 | 15.1 | 1.82 | 21.1 |

Occlu90Y2.3 and Occlu90Y2.8 are the only two bead formulations that contain titanium: moreover, the observed discrepancies between "expected" and observed scandium content are directly proportional to the relative titanium contents of these two formulations (Occlu90Y2.3: 4=0.35-0.40 ppm, Ti=4.17%; Occlu90Y2.8: 4=0.14-0.18 ppm, Ti=1.82%). It is therefore reasonable to conclude that the titanium dioxide used to create Occlu90Y2.3 and Occlu90Y2.8 is the other source of the scandium contaminant in these two formulations. However, silicon dioxide remains the most probable source of the low levels of scandium that are found throughout the other eleven bead samples. It should therefore be possible to decrease the amount of the major radionuclidic impurity Sc-46 through the use of ultra-pure silicon and titanium dioxide in the bead fabrication process.

In addition to Sr-85 and Sc-46, gamma spectra of the bead samples indicated the presence of the long-lived yttrium isotope Y-88. The only neutron-based nuclear transformation that results in generation of this radioisotope is the fast neutron-induced 89Y(n,2n')88Y reaction. The conclusion that yttrium is the source of the Y-88 is corroborated by the data shown in Table 76, which shows a correlation between yttrium weight percent and the activity of Y-88 present per gram of beads.

Since the Y-88 is not caused by a chemical contaminant however, it is not possible to decrease the amount of this radionuclidic impurity through the use of higher purity reagents. However, an examination of the cross-section of the 89Y(n,2n')88Y transformation reveals that the energy threshold of this reaction is 11.5 MeV—several orders of magnitude higher than the energy of the thermal neutrons that are typical present in research reactors (~0.025 eV). At still higher neutron energies, the reaction cross-section increases exponentially from 0.0019b (En=11.7 MeV) to 1.2b (En=16.0 MeV). The formation of Y-88 can therefore be minimized by conducting production irradiations in a highly thermalized neutron flux: that is, by employing an irradiation site that has a very low fraction of high energy neutrons, particularly neutrons with an energy greater than 12 MeV.

TABLE 76

Yttrium-88 present in ABK bead formulations (using 898.5 keV line): normalized activity compared to theoretical and empirical Y-89 weight percent.

| | Total Y-88 (uCi) | norm. Y-88 (uCi/g) | Weight % Y SL NAA | Weight % Y Theor. |
|---|---|---|---|---|
| Occlu90Y1.1 | 2.87 | 1.44 | 18.6 | 16.8 |
| Occlu90Y1.2 | 2.69 | 1.38 | 16.7 | 15.2 |
| Occlu90Y1.4 | 3.63 | 1.97 | 25.7 | 23.5 |
| Occlu90Y1.5 | 3.21 | 1.62 | 22.2 | 20.9 |
| Occlu90Y1.6 | 2.42 | 1.29 | 15.5 | 15.9 |
| Occlu90Y1.7 | 3.42 | 1.91 | 24.0 | 23.5 |
| Occlu90Y1.11 | 1.68 | 1.77 | 23.4 | 25.4 |
| Occlu90Y1.12 | 1.93 | 1.34 | 18.2 | 18.3 |
| Occlu90Y1.15 | 2.14 | 1.40 | 22.6 | 22.2 |
| Occlu90Y1.16 | 4.34 | 2.21 | 29.1 | 26.5 |
| Occlu90Y2.3 | 1.65 | 1.37 | 17.0 | 15.5 |
| Occlu90Y2.6 | 2.56 | 2.16 | 25.3 | 23.5 |
| Occlu90Y2.8 | 3.03 | 1.85 | 21.3 | 21.1 |

It may be possible to completely eliminate formation of Y-88 by wrapping the sample in a lead sheet prior to irradiation. One may therefore postulate that yttrium-based devices currently on the market contain small quantities of Y-88. In that case, the total elimination of Y-88 is unnecessary to produce beads of comparable quality to existing yttrium-90 based therapeutics.

Figure 42:
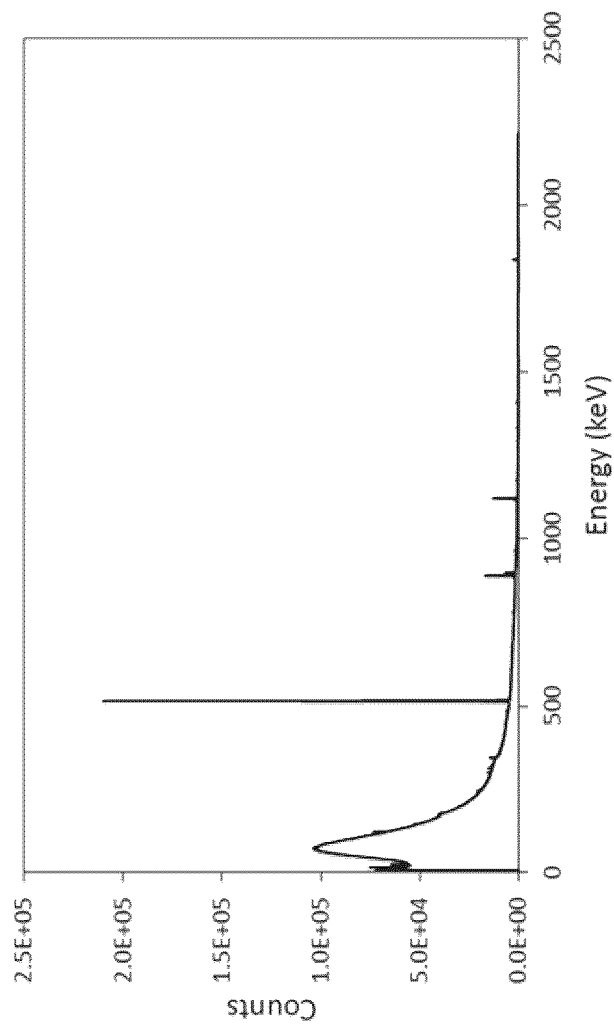
FIG. 42 shows gamma spectrum of Occlu90Y1.6 after in-core irradiation.

Finally, yttrium-88 and scandium-46 are both present in very small quantities compared to strontium-85 (see Table 74 and FIGS. 42 and 43). In consequence, they will decay to background levels at least as quickly as the Sr-85 despite their longer half-lives. This suggests that their presence will only be problematic if their high-energy gamma rays cause an adverse effect on dose rate to either the patient or bystanders. To aid in this determination, the dose rates of all thirteen-bead samples were measured both with and without a beta slide shield in place. The resulting data, shown in Table 77, indicate that the majority of the radiation fields are due to beta particles, not gamma rays, even at 17-20 d (7-8 half-lives of Y-90) after EOI.

TABLE 77

Dose rates (R/h) per gram of bead. Measurements taken 19 d (Capsule 3) and 20 d (Capsules 1 & 2) after EOI.

| | Near Contact | | At 8.0 cm | |
|---|---|---|---|---|
| | Slide Open | Slide Closed | Slide Open | Slide Closed |
| Occlu90Y1.1 | 10.5 | 0.54 | 1.65 | 0.11 |
| Occlu90Y1.2 | 9.90 | 0.49 | 2.15 | 0.14 |
| Occlu90Y1.4 | 12.5 | 0.67 | 3.42 | 0.20 |
| Occlu90Y1.5 | 13.7 | 0.64 | 2.89 | 0.15 |
| Occlu90Y1.6 | 10.4 | 0.56 | 1.86 | 0.12 |
| Occlu90Y1.7 | 14.0 | 0.73 | 2.58 | 0.16 |
| Occlu90Y1.11 | 19.2 | 1.10 | 2.96 | 0.19 |
| Occlu90Y1.12 | 13.9 | 0.70 | 2.64 | 0.19 |
| Occlu90Y1.15 | 16.4 | 0.78 | 2.81 | 0.16 |
| Occlu90Y1.16 | 17.3 | 1.01 | 4.33 | 0.31 |
| Occlu90Y2.3 | 13.1 | 0.62 | 2.83 | 0.20 |
| Occlu90Y2.6 | 18.6 | 0.99 | 3.05 | 0.21 |
| Occlu90Y2.8 | 12.2 | 0.70 | 3.78 | 0.24 |

Minor Radionuclidic Impurities

In addition to the five prominent lines due to Sc-46, Sr-85, and Y-88, as many as thirty minor lines could be observed in the gamma spectra of some of the bead samples. The energies and relative intensities of these emissions were used to identify the presence of eleven trace and ultra-trace elements (see Table 78). The limit of detection (LOD) of each radioisotope was defined as the minimum activity necessary to generate a signal to noise ratio of at least 3:1 for at least one of its characteristic gamma emissions. Limits of detection vary substantially from element to element due to a number of factors, including:

The natural abundance of the stable precursor isotope;
The magnitude of its neutron capture cross-section;
The half-life of the radioisotope being detected;
The delay time between end of irradiation and start of gamma counting;
The relative intensity of the radioisotope's characteristic gamma line;
The need to detect a secondary, less intense, gamma line in order to unambiguously identify the radioisotope;
The presence of any interfering species at this energy; and finally
The efficiency of the detector at that energy.

The Limit of Quantification (LOQ) for each radioisotope was defined as the minimum activity necessary to generate reliable counting statistics (<8% error) for at least one characteristic gamma emission. Limits of quantification are inherently dependent on LOD values, but also vary due to practical concerns such as the highly variable background count-rates across a gamma spectrum. The variance in magnitude between the LOD and LOQ for a given radioisotope therefore differs from one radioisotope to another.

The LOD and LOQ values for each of the eleven radioisotopes were inputted into a series of activation yield equations; the equations were solved for mass, revealing the amounts of the stable precursor isotope required to generate the LOD and LOQ activities. These mass values were corrected to account for the relative natural abundance of the stable precursor isotope, generating LOD and LOQ values of the parent chemical elements. These values are presented in Table 8, along with the radioisotopes and key gamma emissions used to quantify their activation products. Due to the short half-life of the La-140 ($t_{1/2}$, =40.3 h), the LOD and LOQ values for lanthanum vary depending on how long after end of irradiation a particular sample was analyzed.

TABLE 78

Limits of Quantification (LOQs) and Limits of Detection (LODs) of trace and ultra-trace impurities in ABK bead formulations.

|  | Isotope | Half-life | Energy (intensity) | LOD | LOQ |
| --- | --- | --- | --- | --- | --- |
| Cerium | Ce-141 | 32.5 d | 145 keV (48%) | 1.2 mg | 8.1 mg |
| Chromium | Cr-51 | 27.7 d | 320 keV (9.9%) | 0.96 mg | 4.0 mg |
| Cobalt | Co-60 | 5.27 y | 1,174 keV (100%) | 21 ng | 0.42 mg |
| Europium | Eu-152 | 12.7 y | 345 keV (26.5%) | 40 ng | 0.10 mg |
| Hafnium | Hf-181 | 42.5 d | 133 keV (42.5%) | 0.22 mg | 1.4 mg |
| Iridium | Ir-192 | 74.2 d | 468 keV (50%) | 4.0 ng | 9.2 ng |
| Iron | Fe-59 | 44.6 d | 1,099 keV (56.5%) | 55 mg | 0.17 mg |
| Lanthanum | La-140 | 40.2 h | 1,597 keV (95%) | 2-6 mg | 10-20 mg |
| Tantalum | Ta-182 | 115.1 d | 1,189 keV (16%) | 0.32 mg | 1.3 mg |
| Terbium | Tb-160 | 72.1 d | 879 keV (30%) | 0.12 mg | 0.26 mg |

Of the eleven chemical elements listed in Table 78, only europium and terbium have radioisotopes that were present in quantities above the LOQ in all thirteen-bead samples. Two more elements—iron and zinc—have radioisotopes that could be accurately quantified in the majority of the samples. The radioisotope activities were used to calculate the total mass of the chemical element present as described previously; the concentrations of the four elements in the bead samples were then determined. Quantitative data for europium, iron, terbium, and zinc are presented in Table 79, expressed as either parts per thousand (ppt, mg/g) or parts per million (ppm, mg/g) of analyte in each of the thirteen bead formulations. Elements that were present in detectable (>LOD) but not quantifiable (<LOQ) amounts are presented as the range of concentrations that would result from their presence at the LOD and LOQ quantities.

The concentrations of europium, terbium, and zinc in the beads are all in the very low parts per million ranges, and are comparable to the quantities of scandium identified earlier (Table 5). In contrast to the scandium data, there are no obvious correlations between the concentrations of these three elements and any of the bulk elements present by design in the bead formulations (see Table 1)—instead, these trace impurities appear to have a random distribution throughout the samples. Further analysis in an attempt to identify the source of these contaminants would be of limited validity due to the low number of significant digits associated with the values in Table 79.

TABLE 79

Quantifiable trace and ultra-trace impurities in ABK bead formulations in parts per thousand (ppt) and parts per million (ppm).

|  | Europium (ppm) | Iron (ppt) | Terbium (ppm) | Zinc (ppm) |
| --- | --- | --- | --- | --- |
| Occlu90Y1.1 | 0.32 | 0.12 | 0.18 | 5.5 |
| Occlu90Y1.2 | 0.32 | 0.15 | 0.16 | 14 |
| Occlu90Y1.4 | 0.35 | 0.18 | 0.07-0.14 | 14 |
| Occlu90Y1.5 | 0.16 | 0.10 | 0.12 | 0.4-4.0 |
| Occlu90Y1.6 | 0.27 | 0.13 | 0.15 | 15 |
| Occlu90Y1.7 | 0.34 | 0.083 | 0.13 | 0.5-5.0 |
| Occlu90Y1.11 | 0.23 | 0.13 | 0.15 | 32 |
| Occlu90Y1.12 | 0.13 | 0.073 | 0.12 | 16 |
| Occlu90Y1.15 | 0.20 | 0.17 | 0.11 | 0.55-5.5 |
| Occlu90Y1.16 | 0.41 | 0.10 | 0.17 | 0.45-4.5 |
| Occlu90Y2.3 | 0.15 | 0.11 | 0.11-0.22 | 0.74-7.4 |
| Occlu90Y2.6 | 0.20 | 0.20 | 0.12 | 21 |
| Occlu90Y2.8 | 0.20 | 0.16 | 0.16 | 0.54-5.4 |

The much larger concentration of iron in the bead samples is not entirely surprising due to the near-ubiquitous nature of that element. As with the other three elements in Table 79, drawing further conclusions regarding potential source(s) of this contaminant is not advisable due to the limited number of significant figures in the calculated values.

Seven additional elements were detected in the bead samples, namely cerium (Ce), chromium (Cr), cobalt (Co), hafnium (Hf), iridium (Ir), lanthanum (La), and tantalum (Ta). In many cases the amounts of radioisotope present fell in between the limits of detection and quantification; such cases are indicated by a range of values. In other instances, a given radioisotope could only be detected in a fraction of the samples examined. The concentration of the analyte in such samples is stated as less than the LOD, indicated by the notation "<X.XX". See Table 80 for numerical data.

TABLE 80

Semi-quantifiable ultra-trace impurities in ABK bead formulations in parts per million (ppm) and parts per billion (ppb).

| | Cerium (ppm) | Chromium (ppm) | Cobalt (ppm) | Hafnium (ppm) | Iridium (ppb) | Lanthanum (ppm) |
|---|---|---|---|---|---|---|
| Occlu90Y1.1  | 0.62-4.1 | 0.48-2.0 | 0.011-0.22 | 0.11-0.74 | <2.0    | 7.6     |
| Occlu90Y1.2  | 0.64-4.2 | 0.55     | 0.011-0.22 | 0.11-0.76 | <2.0    | 9.1     |
| Occlu90Y1.4  | 0.68-4.5 | 0.62     | 0.012-0.23 | <0.12     | 2.2-5.1 | 2.0-8.9 |
| Occlu90Y1.5  | 0.61-4.1 | <0.49    | 0.010-0.21 | 0.11-0.73 | <2.0    | 8.6     |
| Occlu90Y1.6  | 0.66-4.4 | 0.68     | 0.011-0.23 | 0.12-0.79 | <2.1    | 3.9-18  |
| Occlu90Y1.7  | 0.70-4.5 | 0.54-2.2 | 0.012-0.24 | 0.12-0.83 | 2.2-5.2 | 2.6-12  |
| Occlu90Y1.11 | 1.3-8.7  | <1.0     | <0.022     | <0.23     | 4.1-9.5 | 1.5-6.9 |
| Occlu90Y1.12 | 0.84-5.7 | <0.67    | 14-290     | <0.15     | <2.7    | 1.2-5.4 |
| Occlu90Y1.15 | <0.79    | <0.63    | <13        | 0.14-0.94 | <2.5    | 2.0-8.8 |
| Occlu90Y1.16 | 0.63-4.1 | <0.49    | 11-210     | <0.11     | <2.0    | 13      |
| Occlu90Y2.3  | <1.0     | <0.80    | <17        | <0.18     | <3.3    | 3.1-14  |
| Occlu90Y2.6  | 1.1-7.0  | 0.81-3.4 | 18-360     | <0.19     | 3.4-7.9 | 22      |
| Occlu90Y2.8  | 0.76-5.0 | 0.59-2.4 | 13-260     | 0.14-0.90 | <2.4    | 2.3-10  |

Note that the limit of detection of a given element expressed as a concentration will vary with the mass of the sample being analyzed. For example, the limit of detection for tantalum is 0.32 µg (see Table 78): this is an absolute value that holds true for any sample exposed to the same neutron irradiation conditions as Capsules 1-3. When this number (0.32 µg) is divided by the mass of the Occlu90Y1.1 bead sample (1.9964 g), the limit of detection of tantalum in this particular sample emerges as 0.17 ppm. However, when the same mass of tantalum (0.32 µg) is divided by the mass of the much smaller Occlu90Y1.11 bead sample (0.9456 g), a limit of detection of 0.34 ppm is attained.

Figure 44:
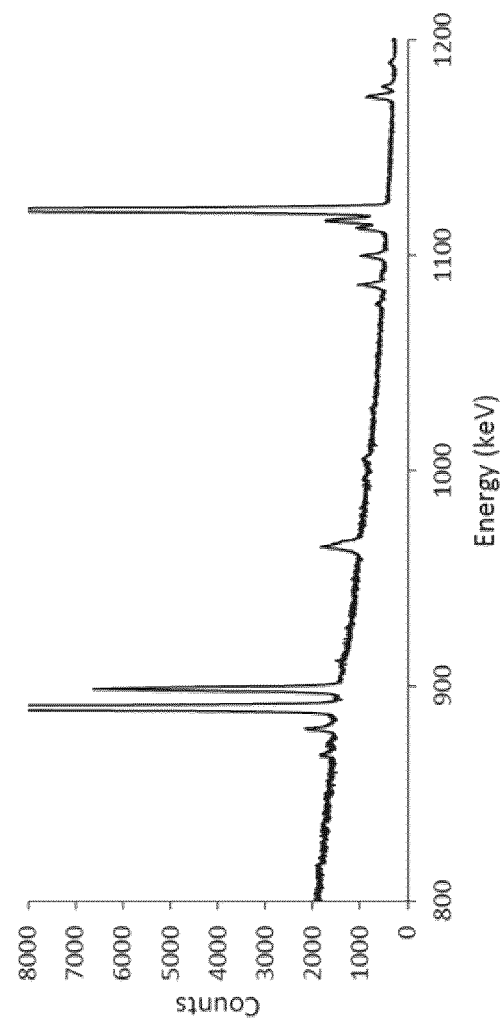
FIG. 44 shows gamma spectrum of Occlu90Y1.6 after in-core irradiation (expanded). Major lines are due to Sc-46 (889 keV, 1,121 keV)) and Y-88 (899 keV).

Though the presence of no fewer than eleven chemical contaminants in the bead samples may initially appear to be cause for alarm, the levels at which these elements and radioisotopes are present are extremely low. Referring back to the gamma spectra in FIG. 42, it is not possible to distinguish any of the radioisotopes listed in Table 78 when the y-axis (net counts) is displayed at full range. It is only with substantial magnification, as in FIG. 44, that the gamma emissions of Co-60 (1,174 keV), Fe-59 (1,099 keV) and other radioisotopes can be observed. This suggests that they will have a negligible impact on the clinical properties of the present bead formulations.

To explore this hypothesis further, two sets of "production scenario" activation yield calculations were carried out on the eleven distinct bead compositions, considering irradiation times of 24 h and 7 d at a neutron flux of $2.0 \times 10^{14}$ n/cm$^2$×s. Unlike the predictive calculations reported previously, these calculations ignored the bulk chemical components of the beads (Ga, Y, Sr, Ti, Si) and instead used the empirically determined concentrations of contaminants to semi-quantitatively estimate the radionuclidic impurities expected at end of irradiation. Only the chemical elements impurities that could be accurately quantified—namely europium, iron, scandium, and terbium—were considered. The results of this work are compiled in Table 81.

TABLE 81

Radionuclidic impurities expected per gram of beads following a 24 h (left) or 7 d (right) neutron irradiation at $2.0 \times 10^{14}$ n/cm$^2$ × s.

| | Europium-152 (mCi/g) | | Iron-59 (mCi/g) | | Scandium-46 (mCi/g) | | Terbium-160 (mCi/g) | |
|---|---|---|---|---|---|---|---|---|
| | 24 h | 7 d | 24 h | 7 d | 24 h | 7 d | 24 h | 7 d |
| Occlu90Y1.1     | 2.1 | 9.6  | 0.42 | 2.8 | 5.5 | 37 | 0.82 | 5.6 |
| Occlu90Y1.2/1.6 | 2.1 | 9.6  | 0.53 | 3.5 | 5.2 | 35 | 0.73 | 4.9 |
| Occlu90Y1.4/1.7 | 2.4 | 11   | 0.63 | 4.2 | 3.4 | 23 | 0.46 | 3.1 |
| Occlu90Y1.5     | 2.0 | 9.1  | 0.35 | 2.3 | 3.9 | 26 | 0.45 | 3.1 |
| Occlu90Y1.11    | 2.9 | 13   | 0.46 | 3.0 | 5.2 | 35 | 0.68 | 4.6 |
| Occlu90Y1.12    | 1.6 | 7.4  | 0.26 | 1.7 | 3.4 | 23 | 0.55 | 3.7 |
| Occlu90Y1.15    | 2.5 | 11   | 0.60 | 4.0 | 4.4 | 30 | 0.50 | 3.4 |
| Occlu90Y1.16    | 5.1 | 23   | 0.35 | 2.3 | 4.6 | 31 | 0.77 | 5.3 |
| Occlu90Y2.3     | 1.9 | 8.5  | 0.39 | 2.6 | 4.6 | 31 | <2.7 | <18 |
| Occlu90Y2.6     | 2.5 | 11   | 0.70 | 4.7 | 3.9 | 26 | 0.55 | 3.7 |
| Occlu90Y2.8     | 2.5 | 11   | 0.56 | 3.8 | 7.2 | 49 | 0.73 | 4.9 |

When the values in Table 80 are compared with the quantities of incidental activation products expected due to the presence of elements such as gallium and strontium, it becomes clear that their overall contribution to the radioisotope profile of the bead formulations is negligible. It should be noted that two bead samples, Occlu90Y2.3 and Occlu90Y2.8, also contained small quantities of the shorter-lived radioscandium Sc-47 ($t_{1/2}$, =3.42 d, Ey=159.5 keV).

This isotope is formed from the fast neutron reaction $^{47}$Ti(n,p)$^{47}$Sc—its presence is therefore explained by the inclusion of titanium in these two bead formulations. The rate of formation of any fast neutron activation product is highly dependent on the neutron energy profile of the irradiation site used, so it is not possible to predict the quantities of Sc-47 that would occur in a production scenario without additional information.

Expected Contaminants

The bead fabrication process involves the use of numerous materials that could potentially introduce contaminants into the beads themselves. These elements include chromium, iron, platinum, ruthenium, tungsten, and zirconium. Iron was found to be present at low parts per thousand levels in all of the bead samples (see Table 79), while chromium was identified in 7 of the 13 samples (see Table 80). However, the other anticipated impurities (Pt, Ru, W, Zr) were not observed. While this is not to say that these elements are entirely absent, it is conclusive proof that they are present below the limits of detection indicated in Table 82.

TABLE 82

LODs of elements not observed but plausibly present in beads.

| | Isotope | Half-life | Energy (intensity) | LOD |
|---|---|---|---|---|
| Platinum | Pt-105m | 4.1 d | 129.8 keV (2.8%) | 15 mg |
| Ruthenium | Ru-103 | 39.4 d | 318.9 keV (19%) | 7.1 µg |
| Tungsten | W-187 | 23.9 h | 497.6 keV (22%) | 5-10 mg |
| | | | 685.7 keV (27%) | |
| Zirconium | Zr-95s | 64.0 d | 756.7 keV (55%) | 0.13 mg |

Platinum has a particularly high limit of detection due to the low cross-section for the $194Pt(n,\gamma)^{195m}Pt$ reaction ($\sigma$=0.09b), as well as the low intensity of its characteristic gamma emission. The limit of detection for tungsten is also rather high; this is due to its short half-life and the necessity of waiting at least two weeks after end of irradiation to safely unencapsulate and analyze the bead samples. Because the bead samples were counted over a period of 2 d, the LOD for tungsten is presented as a range.

REFERENCES

N. Kilcup, E. Tonkopi, R. J. Abraham, D. Boyd, S. Kehoe. Composition-property relationships for radiopaque composite materials: pre-loaded drug-eluting beads for transarterial chemoembolization. Journal of Biomaterials Applications 30(1), 2015, 93-103. doi:10.1177/0885328215572196.

INDUSTRIAL APPLICABILITY

The compositions described herein are useful in the following industrial applications: medical procedures such as radioembolization and TAE to treat tumors in a human or animal subject.

It is understood that the examples and embodiments described herein are for illustrative purposes only and that various modifications or changes in light thereof will be suggested to persons skilled in the art and are to be included within the spirit and purview of this application and scope of the appended claims. All publications, issued patents, and patent applications cited herein are hereby incorporated by reference in their entirety for all purposes.

What is claimed is:

1. A composition comprising:
   more than 0.10 and up to about 0.17 mole fraction of $Y_2O_3$;
   at least 0.10 and up to about 0.30 mole fraction of $Ga_2O_3$;
   more than 0.5 and up to about 0.8 mole fraction of $SiO_2$; and
   about 0.02 to about 0.15 mole fraction of SrO.

2. The composition of claim 1, further comprising $MnO_2$, and $TiO_2$.

3. The composition of claim 2, comprising:
   more than 0.10 and up to about 0.17 mole fraction of $Y_2O_3$;
   about 0.02 to about 0.15 mole fraction of SrO;
   at least 0.10 and up to about 0.30 mole fraction of $Ga_2O_3$;
   more than 0.5 and up to about 0.8 mole fraction of $SiO_2$;
   up to about 0.350 mole fraction of $MnO_2$; and
   up to about 0.10 mole fraction of $TiO_2$.

4. The composition of claim 3, comprising:
   more than 0.10 and up to to about 0.17 mole fraction of $Y_2O_3$;
   about 0.025 to about 0.05 mole fraction of SrO;
   at least 0.10 and up to about 0.30 mole fraction of $Ga_2O_3$;
   more than 0.5 and up to about 0.75 mole fraction of $SiO_2$;
   up to about 0.05 mole fraction of $MnO_2$; and
   up to about 0.10 mole fraction of $TiO_2$.

5. The composition of claim 1, wherein the composition is radiopaque.

6. The composition of claim 1, wherein the composition comprises particles having a particle size from about 15 to about 80 microns.

7. A composition of claim 1 wherein the SrO comprises radioisotope Sr-89, the $Ga_2O_3$ comprises radioisotope Ga-72, and the $Y_2O_3$ comprises radioisotope $^{90}Y$.

8. A method of treating a disease or medical condition in a subject in need thereof, comprising:
   administering the composition of claim 7, via injection of the composition into a blood vessel of the subject.

9. The method of claim 8, wherein the disease is a tumor.

10. The composition of claim 1, wherein the composition comprises:
    at least 0.10 and up to about 0.30 mole fraction of $Ga_2O_3$;
    from 0.52 to about 0.8 mole fraction of $SiO_2$;
    more than 0.10 and up to about 0.17 mole fraction of $Y_2O_3$; and
    about 0.02 to about 0.15 mole fraction of SrO.

11. The composition of claim 1, wherein the composition comprises:
    about 0.170 mole fraction of $Y_2O_3$;
    about 0.050 mole fraction of SrO;
    about 0.167 mole fraction of $Ga_2O_3$; and
    about 0.613 mole fraction of $SiO_2$.

12. The composition according to claim 11, wherein the composition comprises particles having a particle size from about 15 to about 80 microns.

13. An irradiated composition produced by the irradiation of a composition of claim 12.

14. A method of treating a disease or medical condition in a subject in need thereof, comprising:
    administering the composition of claim 13 via injection of the composition into a blood vessel of the subject.

15. The composition of claim 1, wherein the composition consists essentially of:
    0.170 mole fraction of $Y_2O_3$;
    0.050 mole fraction of SrO;
    0.167 mole fraction of $Ga_2O_3$; and
    0.613 mole fraction of $SiO_2$.

* * * * *

UNITED STATES PATENT AND TRADEMARK OFFICE
CERTIFICATE OF CORRECTION

Page 1 of 1

PATENT NO. : 11,083,806 B2
APPLICATION NO. : 15/528264
DATED : August 10, 2021
INVENTOR(S) : Boyd et al.

It is certified that error appears in the above-identified patent and that said Letters Patent is hereby corrected as shown below:

On the Title Page

Item (73), Line 1, should read --ABK Biomedical Inc--

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*